US012612653B2

(12) United States Patent
Wang et al.

(10) Patent No.: US 12,612,653 B2
(45) Date of Patent: Apr. 28, 2026

(54) POLYPEPTIDES FOR PRODUCING ALBICANOL AND/OR DRIMENOL COMPOUNDS

(71) Applicant: FIRMENICH SA, Satigny (CH)

(72) Inventors: Qi Wang, Shanghai (CN); Michel Schalk, Satigny (CH)

(73) Assignee: FIRMENICH SA, Satigny (CH)

(*) Notice: Subject to any disclaimer, the term of this patent is extended or adjusted under 35 U.S.C. 154(b) by 807 days.

(21) Appl. No.: 17/760,705

(22) PCT Filed: Nov. 25, 2020

(86) PCT No.: PCT/EP2020/083408
§ 371 (c)(1),
(2) Date: Mar. 15, 2022

(87) PCT Pub. No.: WO2021/105236
PCT Pub. Date: Jun. 3, 2021

(65) Prior Publication Data
US 2024/0376502 A1 Nov. 14, 2024

(30) Foreign Application Priority Data

Nov. 27, 2019 (WO) ................ PCT/CN2019/121244
Jan. 22, 2020 (EP) ..................................... 20153128

(51) Int. Cl.
*C12P 7/22* (2006.01)
*C12N 9/14* (2006.01)
*C12P 5/00* (2006.01)

(52) U.S. Cl.
CPC .................. *C12P 7/22* (2013.01); *C12N 9/14* (2013.01); *C12P 5/005* (2013.01)

(58) Field of Classification Search
None
See application file for complete search history.

(56) References Cited

U.S. PATENT DOCUMENTS 11,293,037 B2 * 4/2022 Schalk ..................... C12N 9/88

FOREIGN PATENT DOCUMENTS

WO 2018220113 A1 12/2018

OTHER PUBLICATIONS

UniProt F8PUX1: https://www.uniprot.org/uniprotkb/F8PUX1/entry (Year: 2011).*

(Continued)

*Primary Examiner* — Robert J Yamasaki
*Assistant Examiner* — Charles Zoltan Constantine
(74) *Attorney, Agent, or Firm* — Armstrong Teasdale LLP

(57) ABSTRACT

Described herein are plant-derived haloacid dehalogenase-like (HAD-like) polypeptides having cyclic terpene synthase (TPS) activity, in particular suitable for use in biochemical methods of producing drimane-type sesquiterpenes, encompassing drimenol and/or albicanol and related compounds, like phosphorylated drimane-type sesquiterpene alcohols, in particular phosphorylated drimenol and/or albicanol compounds and derivatives. Also described herein are the coding nucleotide sequences of the TPS activity, corresponding expression constructs, recombinant hosts, and methods of preparing such polypeptides and mutants and variants thereof. Also described herein is a method of using such polypeptides, the method including using the polypeptides in the production of odorants, flavours and fragrance ingredients.

4 Claims, 21 Drawing Sheets
Specification includes a Sequence Listing.

(56) References Cited

OTHER PUBLICATIONS

Akita ("A convenient synthesis of (+)-albicanol based on enzymatic function: total synthesis of (+)-albicanyl acetate, (−)-albicanyl 3,4-dihydroxycinnamate, (−)-drimenol, (−)-drimenin and (−)-ambrox", Tetrahedron: Asymmetry, (2000), 11, 1375-1388). (Year: 2000).*

Shinohara ("Identification of a novel sesquiterpene biosynthetic machinery involved in astellolide biosynthesis", Scientific Reports, 6: 32865, 2016, 1-11 and Supplementary information). (Year: 2016).*

Banks J.A., "Uniprot:D8SXJ4", Oct. 5, 2010 (Oct. 5, 2010), Retrieved from the Internet: URL:http://ibis.internal.epo.org/exam/dbfetch.jsp?id=Uniprot:D8SXJ4 [retrieved on Jun. 30, 2020].

Banks J.A., "Uniprot:D8RNR3", Oct. 5, 2010 (Oct. 5, 2010), Retrieved from the Internet: URL:http://ibis.internal.epo.org/exam/dbfetch.jsp?id=Uniprot:D8RNR3 [retrieved on Jun. 30, 2020].

Yasutomo Shinohara et al, "Identification of a novel sesquiterpene biosynthetic machinery involved in astellolide biosynthesis", Scientific Reports,vol. 6, No. 1, Sep. 15, 2016 (Sep. 15, 2016).

Knapp D.G., "Uniprot:A0A2V1ECS9", Sep. 12, 2018 (Sep. 12, 2018), Retrieved from the Internet: URL:http://ibis.internal.epo.org/exam/dbfetch.jsp?id=Uniprot:A0A2V1ECS9 [retrieved on Jun. 30, 2020].

Warmers U et al, "Sesquiterpene constituents of the liverwort Bazzania trilobata", Phytochemistry, Elsevier, Amsterdam, NL, vol. 52, No. 1, Sep. 1, 1999 (Sep. 1, 1999), pp. 99-104.

"SubName: Full=Uncharacterized protein {ECO:0000313|EMBL:TFY83564.1};", UniProt; Sep. 18, 2019 (Sep. 18, 2019), retrieved from EBI accession No. Uniprot:A0A4Z0ABD3Database accession No. A0A4Z0ABD3.

"Sequence 63 from Patent WO2018220113.", EPO Proteins, Feb. 11, 2019 (Feb. 11, 2019), retrieved from EBI accession No. EPOP:MP025737Database accession No. MP025737.

International Search Report and Written Opinion for corresponding PCT/EP2020/083408 mailed Jun. 9, 2021; 20 pages.

* cited by examiner (4aR,5S,6S,8aS)-1,1,4a,5,6-pentamethyldecahydronaphthalene

FIG. 1a drimane structure

FIG. 1b

(+)-albicanol          (-)-drimenol

FIG. 2

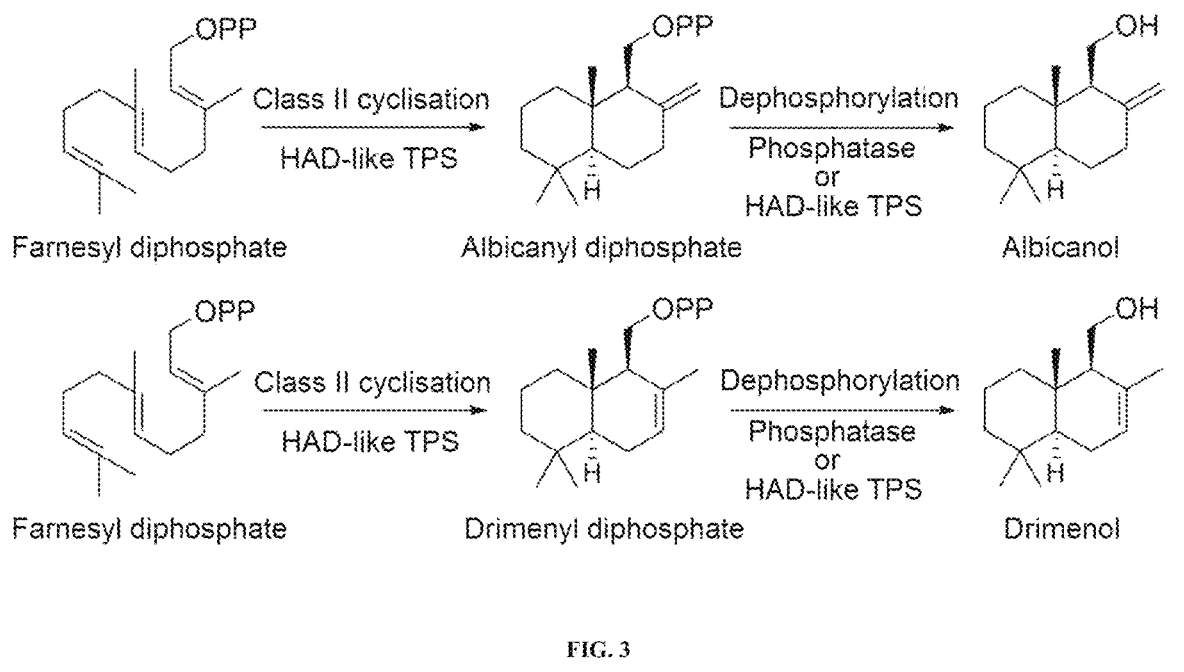

Farnesyl diphosphate — Class II cyclisation / HAD-like TPS → Albicanyl diphosphate — Dephosphorylation / Phosphatase or HAD-like TPS → Albicanol Farnesyl diphosphate — Class II cyclisation / HAD-like TPS → Drimenyl diphosphate — Dephosphorylation / Phosphatase or HAD-like TPS → Drimenol

FIG. 3

Abundance

TIC: Bazz HAD3M ev TBL21B_190111_TWZD\data.ms

Time →

Abundance

Scan 6472 (31.666 min): EFJ10816 pETD uetMev TBL21A_180601_TWZD\data.ms m/z ⟶

Abundance

Scan 6539 (31.993 min): EFJ10816 pETD uetMev TBL21A_180601_TWZD\data.ms

Abundance

Scan 6474 (31.676 min): EFJ26126 pETD uetMev TBL21A_180601_TWZD\data.ms

```
BazzHAD1        MAPPFGFIGGNATSVTTSPDVLDYNYDGGPPTGQYKSLILDIGGVLLQPNLDRSYGTIVP  60
BazzHAD2        ------------------------MERPHFDTLIMDLGGVIVDFSLQTST-STSV  30
BazzHAD3        ---------------------MPALSSHMEPPNFDTLILDLGDVLVGGSLQGSY-ALAM  37
BtHAD           MAPPFGYIGGNESSVTTSPDVLDYSYDGGPPTGQYKSMLDIGGVLLQPNLDRSYGTIVP  60
SmHAD1          -----------------------------------MIIISFACLLKFGCGDNG---PR  20
SmHAD2          -----------------------------------MIIISFACLLKFGCGDSG---PR  20
EMD37666.1      --------------------------MSAAAQYTTLILDLGDVLFTWSPKTKT-SIPP  31
XP_007369631.1  --------------------------MASIHRRYTTLILDLGDVLFRWSPKTET-AIPP  32

BazzHAD1        PVQFIRMLRSHILFNYSMGKMSAEEVFRQLSVKSG---YPAEDMRSFGRKFRESLVPITII  118
BazzHAD2        K-SLIFVLRSATAAIECGHMSESDCYAAVAKDLGSSANASQIGEAISEFRKSLQVNEIL  89
BazzHAD3        KRILILSLRTPTIGKYECGQLSELDCYDAVAEDLGNSTSSAQIGEVVSEFRKSLQVNEIL  97
BtHAD           PVQFIRMLRSHILFNYSMGKVSAEEVFRQLSVKSG---YPAEDIRSFARKFRESLVPITII  118
SmHAD1          GDLLIRALQHSSILAYSCGELDRTAAISTISRKFK-LTDPALIDSMLLEIASSCEVDKIL  79
SmHAD2          GDLLIRALQHSSILAYSCGELDRAAAISTISRKFK-LKEPALIDSMLLEIASSCEVDEIL  79
EMD37666.1      R-TLIEILNSATIYEYERGRISQDECYERVGTEFG---IAPSEIDNAFKQIRDSMESNDIL  88
XP_007369631.1  Q-QLIDILSSVTIFEYERGRLSQEACYERCAEEFK--IEASVIAEAFKQIRGSLRPNEIF  89
                           Lxxxx(W/F)xxYxxG  (conserved sequence motif 1)

BazzHAD1        TDIIFKLSKESK--VRIFCMTICPAEDFEYLSQAYPKLFGLFIRIITSASTGMRIPNRNF  176
BazzHAD2        IGIRELKAQNG--LRIYVMSIIPQPDFDAVKAKSASWG-VFIGMIPSYAVGTHIPDLAF  146
BazzHAD3        IKIQELKAENN--LRIYVMSIIPKPDLAVVKAKSVNWG-VIIGWIPSYAVGFHIPDLAF  154
BtHAD           TDIIVKLSKESK--IRIFCMTICPAEDFAYLSQAYPNLFGLFIRIITSASTGMRIPNRNF  176
SmHAD1          LSIIQSTR------QQILGWIIIPPQ--------------EWIRVISLFPVSLWINFATI  119
SmHAD2          LSIIQSTR------QQILGWIIIPPQ--------------EWIRVINLFPWSLWINFATI  119
EMD37666.1      IAIIRELKTQLDGELIIFALSIISLPDYEVVLTKPADWS-IFIKVIPSALVGERIPHLGV  147
XP_007369631.1  IAIIRDLRREMHGDLTILALSIISLPDYEYIMSLSSDWTTVFIRVIPSALVGERIPHLGC  149

BazzHAD1        FIHILQETGIRASETIFVDDLIPNIMAAEALDFTIIHVSPESPAETVRLIMFHLRKIEER  236
BazzHAD2        YIHILEETNTDPLKAIFVDDSIQNIIAARSFGLTIIIYN--DTVNAARTIRNLLGDI----  201
BazzHAD3        YIHILEETNTDPLKAIFVDDKIQNIIVARSFGMTIIVFK--DTKSTTKEIKNLLGDI---  209
BtHAD           FIHILQETGISATETIFVDDLIPNIMAAEALDFTIIHVSPESPAETVRLIMFHLRKIEER  236
SmHAD1          SIDIDSLLGDIRSHAIIVDKSIEMIALHAFESLLIIPYASPNKKACQDFIKRRFLLIR-A  178
SmHAD2          SIDIDSLLGDIRFHAIIVDKSIEMIALHAFESLLIIPYASPNKKACQDFIKRRFLLIR-A  178
EMD37666.1      YIHIIAETGIDPRTTIFVDDKIDNILSARSVGMHIIVFE--KQEDVMRAIRNIFGDI---  202
XP_007369631.1  YIKIISEMNLEPQTTIFVDDKIDNIASARSLGMHIIVFD---NQANVFRQIRNIFGDI----  204
                          DDxx(D/E)  (class I motif location)

BazzHAD1        AAIRDYILRNRGVDKILISLTSDGVRVQVYFDHFIVAEVLNDERFLPITAAPESGTMIFF  296
BazzHAD2        LRIEQYISSH--AGQILISISDTGTPFPDNFSQLIILDATGNRDLVVLENPQR--TWIYF  257
BazzHAD3        KRIEHFISAH--AKQIESIVCGDGTTFLDNFAQLIILHDTGNSDLVARQHHGR--TWIYF  265
BtHAD           AAIRDYILRNRGVDKILISLTSDGVRVQVYFDHFIVAEVLNDERFLPITAAPKSGTMIFF  296
SmHAD1          KLIMDRIKEEVRSKQIKSLYLLDNGRHE-LVSEIFFPCVAAWCLPEIIIPLGWMKYLIVL  237
SmHAD2          KLIMDRIKEEVRSKQIKSLYLLDNGRQE-LVSEIFFPCVAAWCLPEIIIPLGWMESLIVL  237
EMD37666.1      RRIREYIRRN--AMRIESIVTDHGVAFGENFTQLIILELTNDPSLVTLPDRPR--TWIFF  258
XP_007369631.1  RRIQEYIRGH--AGKIESISTDNGLIFEENFTQLIIYELTQDRTLISLSECPR--TWIFF  260

BazzHAD1        PKEERKATRDITTNAVTHVDLIPDDIDITSVAISVIYKFSKVGMETIQRVLIMIEKRVDDI  356
BazzHAD2        IG---------KPVLTSETFIPDDIDITSIAIMAIN----VDLEVINSVMIPILEFRNSI  303
BazzHAD3        IG---------KPMGTTDTFIPNDIDITSIAILTIN----VDSEVIRSVLIEILLYTSSI  311
BtHAD           PKEERNATRDMTTNAVTHVDLIPDDIDITSVAISVIYKFSKVAMETIQRVLIMIEKRVDDI  356
SmHAD1          IKRGHPFG----YFGADVSRYIPDIDIMSTCISTIFDLSLVTSAQIMHFLIILENVNDI  293
SmHAD2          IERGHPFG----YFGADVSRYIPDIDIMSTCISTIFDLSLVTSAQIMHFLIILENVNDI  293
EMD37666.1      RGNGGRPS-----KPLFS-EAFIPDDIDITSLAITVLQ-----RDPGVISSVMIEILNYRDPI  309
XP_007369631.1  RG---------EPLFS-ETFIPDDIDITSVAITVLQ----PDRALINSVLIEILEYVDAI  305
                          PxDxD(T/S)(T/M)S  (class II motif location)

BazzHAD1        GIFQTYIFIPLRLRVIPVIATNTIYLFHLGGRPGP--TQQTEQFISKLIEKRSILRGILIY  414
BazzHAD2        GLFLTYIFIETRPRVIAVINVNVIRLFHRERERE--AQQPLEWITNVITHRAIVDGILIY  361
BazzHAD3        GLVEVYIFIKTRPRVIPVICVNVIRLFSKYGRELQ--LQKTLDWITEVIVHRAIIDGILIY  369
BtHAD           GIFQTYIFIPLRLRVIPVIATNTIYLFHLGGRPGP--TQQTEQFISKLIEKRSIVRGILIY  414
SmHAD1          NQLLTYILIDVERPRVIPVIIANVIYLAYALSMEDHPVVRHNENLIQRYILSGGIVYGIRIY  353
SmHAD2          NQLLTYILIERPRVIPVIIANVIYFAYALSMEDHPVVRHNENLIQRYILSGGIVYGIRIY  353
EMD37666.1      GIMQTYIFIDGRPLIPFINVNVITFFYTNGRGHE--LDQCLTWIREVILYRAILGGIRIY  367
```

POLYPEPTIDES FOR PRODUCING ALBICANOL AND/OR DRIMENOL COMPOUNDS

CROSS-REFERENCE TO RELATED APPLICATIONS

This application is a U.S. National Phase application of International Patent Application No. PCT/EP2020/083408, filed Nov. 25, 2020, which claims priority to International Patent Application No. PCT/CN2019/121244, filed Nov. 27, 2019, and which claims priority to European Patent Application No. 20153128.2, filed Jan. 22, 2020, the entire contents of which are hereby incorporated by reference herein.

REFERENCE TO AN ELECTRONIC SEQUENCE LISTING

The contents of the electronic sequence listing (Sequence-Listing_36803-244.txt; Size: 136,113 bytes; and Date of Creation: Mar. 15, 2022) is herein incorporated by reference in its entirety.

TECHNICAL FIELD

The present invention relates to novel plant-derived haloacid dehalogenase-like (HAD-like) polypeptides having cyclic terpene synthase (TPS) activity, in particular suitable for use in biochemical methods of producing drimane-type sesquiterpenes, encompassing drimenol and/or albicanol and related compounds, like phosphorylated drimane-type sesquiterpene alcohols, in particular phosphorylated drimenol and/or albicanol compounds and derivatives. The invention also provides the coding nucleotide sequences of said novel TPS activity, corresponding expression constructs, recombinant hosts, method of preparing such novel polypeptides and mutants and variants thereof. The invention also relates to the use of such novel polypeptides in the production of odorants, flavours and fragrance ingredients.

BACKGROUND

Terpenes are found in most organisms (microorganisms, animals and plants). These compounds are made up of isoprene units and are classified by the number of these units present in their structure, which may comprise cyclic structural elements. Thus hemiterpenes, monoterpenes, sesquiterpenes and diterpenes are terpenes containing 5, 10, 15 and 20 carbon atoms (i. e. 1, 2, 3 and 4 isoprene units), respectively. Monoterpenes are derived from geranyl diphosphate (GPP, $C_{10}$), sesquiterpenes from farnesyl diphosphate (FPP, $C_{15}$), and diterpenes from geranylgeranyl diphosphate (GGPP, $C_{20}$). Sesquiterpenes, for example, are widely found in the plant kingdom. Many sesquiterpene molecules are known for their flavour and fragrance properties and their cosmetic, medicinal and antimicrobial effects. Numerous sesquiterpene hydrocarbons and sesquiterpenoids have been identified. Chemical synthesis approaches have been developed but are still complex and not always cost-effective.

The biosynthetic production of terpenes involves enzymes called terpene synthases. There are numerous sesquiterpene synthases present in the plant kingdom, all using the same substrate (famesyl diphosphate, FPP), but having different product profiles. Genes and cDNAs encoding sesquiterpene synthases have been cloned and the corresponding recombinant enzymes characterized.

Many of the main sources for sesquiterpenes, for example, compounds with a drimane structure, like albicanol or drimenol compounds, are from plants; however, the content of sesquiterpenes in these natural sources can be low. There remains a need for the identification and characterization of new terpene synthases optionally characterized by a particular drimane-type product profile and/or drimane-type product yield and/or more cost-effective methods of producing drimane-type compounds, such as drimenol and/or albicanol, the potential building blocks for the preparation of highly valuable perfumery ingredients, such as Ambrox.

SUMMARY

The above-mentioned problem could be solved by providing several new enzymes having cyclic terpene synthase (TPS) activity, in particular cyclic sesquiterpene synthase activity, and which more particularly show drimenyl and/or albicanyl diphosphate synthase activity and produce drimenyl and/or albicanyl diphosphate with surprisingly high selectivity from FPP. In particular, novel drimenyl and/or albicanyl diphosphate synthase genes were identified from plants of the genus *Bazzania* sp. such as *Bazzania trilobata* and from the plant *Selaginella moellendorffii*. These new synthase enzymes are designated BazzHAD1, BazzHAD2, BazzHAD3, BtHAD, SmHAD1 and SmHAD2.

The protein sequences of SmHAD1 and SmHAD2 have a very low identity with all other known HAD-like TPSs (~14-20%) but show high homology between themselves (>96%), BtHAD and BazzHAD1 show a slightly higher homology to fern and fungal HAD-like TPSs (~22-30%) and 96% identity between themselves, whereas BazzHAD2 and BazzHAD3 show an intermediate homology to fern and fungal HAD-like TPSs (~22-43%) and 67% identity between themselves (see Table 2 in experimental section).

All the HAD-like TPSs described herein contain a class II motif PxDxD(T/S)(T/M)S (SEQ ID NO:46), and more C-terminally shifted thereto a QW motif QxxDGx(W/F) (SEQ ID NO:51), mainly characteristics of diterpene synthases. Mutations performed on said class II motif cause full loss of the activity, mutation on said QW motif cause 90% loss of the activity. An class I motif (DDxx(D/E) (SEQ ID NO:45) is missing in all these six newly identified TPS of the present invention.

DESCRIPTION OF THE DRAWINGS

FIG. 1*a*. Drimane structure.

FIG. 1*b*. More generic drimane-type structure; the dotted line in the formula indicates that a single C═C double bond may be present in anyone the indicated positions.

FIG. 2. Structural formula of (+)-albicanol and (−)-drimenol.

FIG. 3. Mechanism of cyclization of farnesyl diphosphate (FPP) by a HAD-like TPS containing class II motif and dephosphorylation of drimenyl and/or albicanyl diphosphate by the same HAD-like TPS or other phosphatase.

FIG. 21*a*. Amino acid sequences alignment of HAD-like TPSs: BazzHAD1 (SEQ ID NO: 3), BazzHAD2 (SEQ ID NO: 6), BazzHAD3 (SEQ ID NO: 9), BtHAD (SEQ ID NO: 12), SmHAD1 (SEQ ID NO: 19), SmHAD2 (SEQ ID NO: 26); EMD37666.1 (SEQ ID NO: 32) and XP_007369631.1 (SEQ ID NO: 36) as previously described in WO 2018/220113. The class I motif (DDxx(D/E); SEQ ID NO: 45) and class II motif (PxDxD(T/S)(T/M)S; SEQ ID NOs: 46) as well as three other conserved sequence motifs 1-3 (Lxxxx (W/F)xxYxxG; SEQ ID NO: 56, YxDxxRxRVD(P/A)V(V/A)xxN; SEQ ID NO: 62, GTx(Y/F)YxxxExFL(Y/F); SEQ ID NO: 69) are identified in the Figure.

Figure 4:
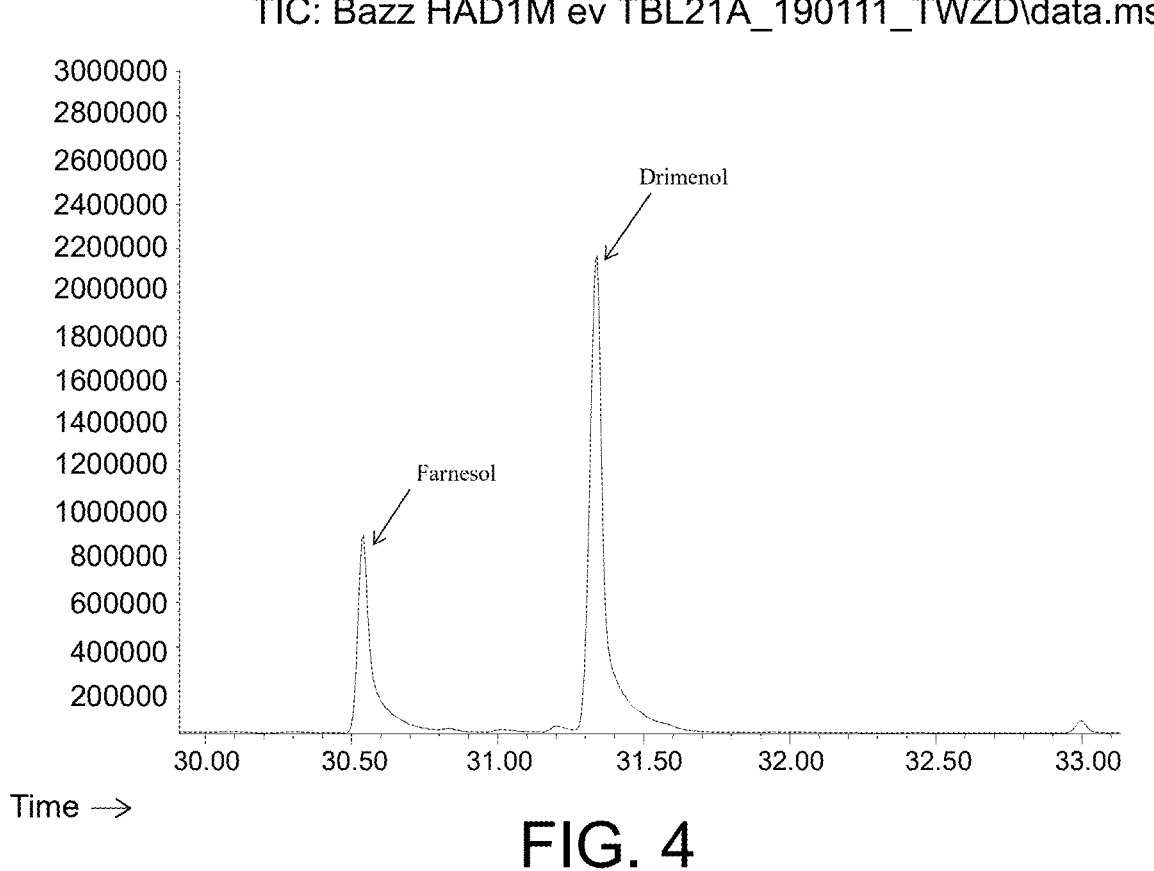
FIG. 4. GC/MS chromatogram of samples from the in vivo biochemical assay of BazzHAD1. Farnesol results from the dephosphorylation of the precursor FPP, whereas drimenol is presumably the product of the dephosphorylation of drimenyl diphosphate.
Figure 5:
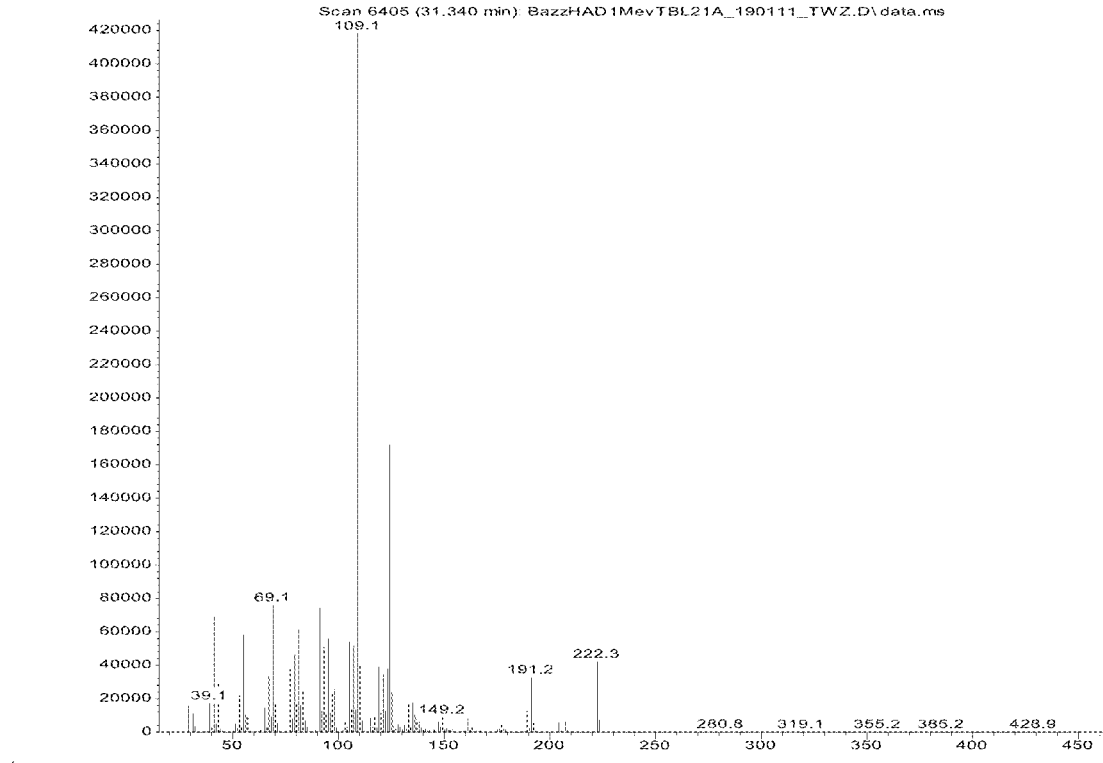
FIG. 5. Mass spectrum of the drimenol peak in FIG. 4.
Figure 6:
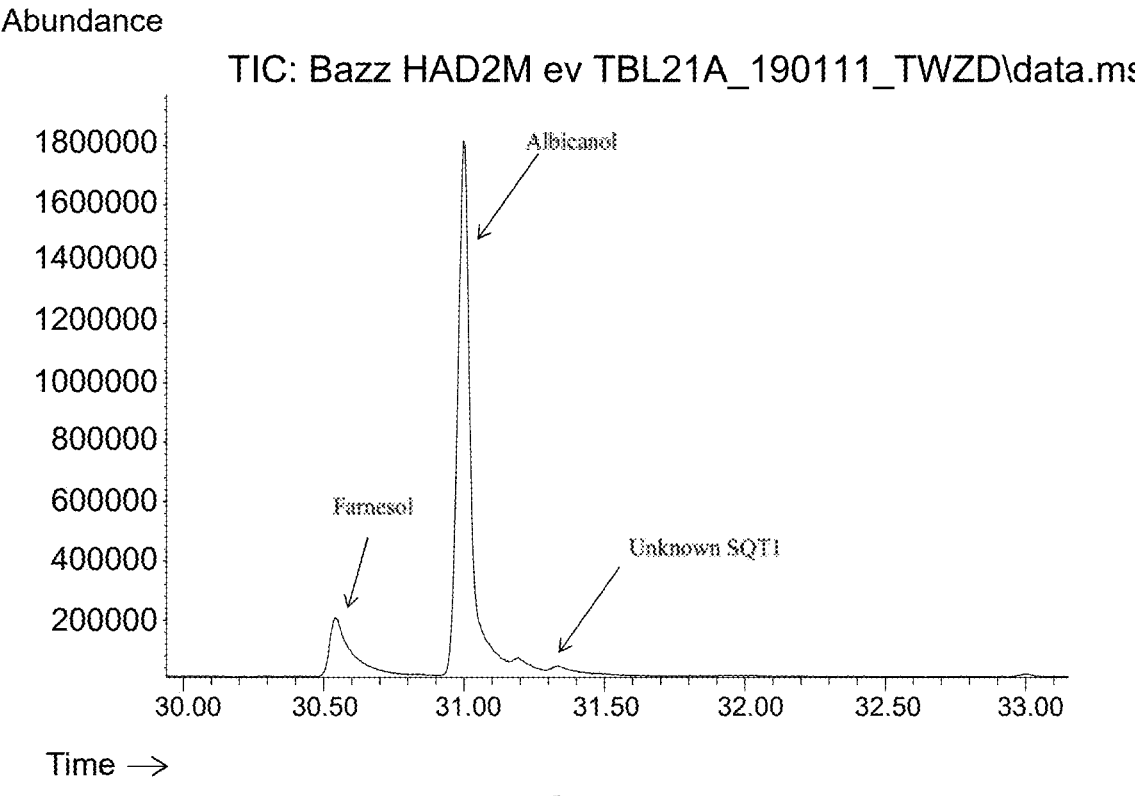
FIG. 6. GC/MS chromatogram of samples from the in vivo biochemical assay of BazzHAD2. Farnesol results from the dephosphorylation of the precursor FPP, whereas albicanol and unknown compound SQT1 are presumably the products of the dephosphorylation of albicanyl diphosphate and an unknown diphosphate, respectively.
Figure 7:
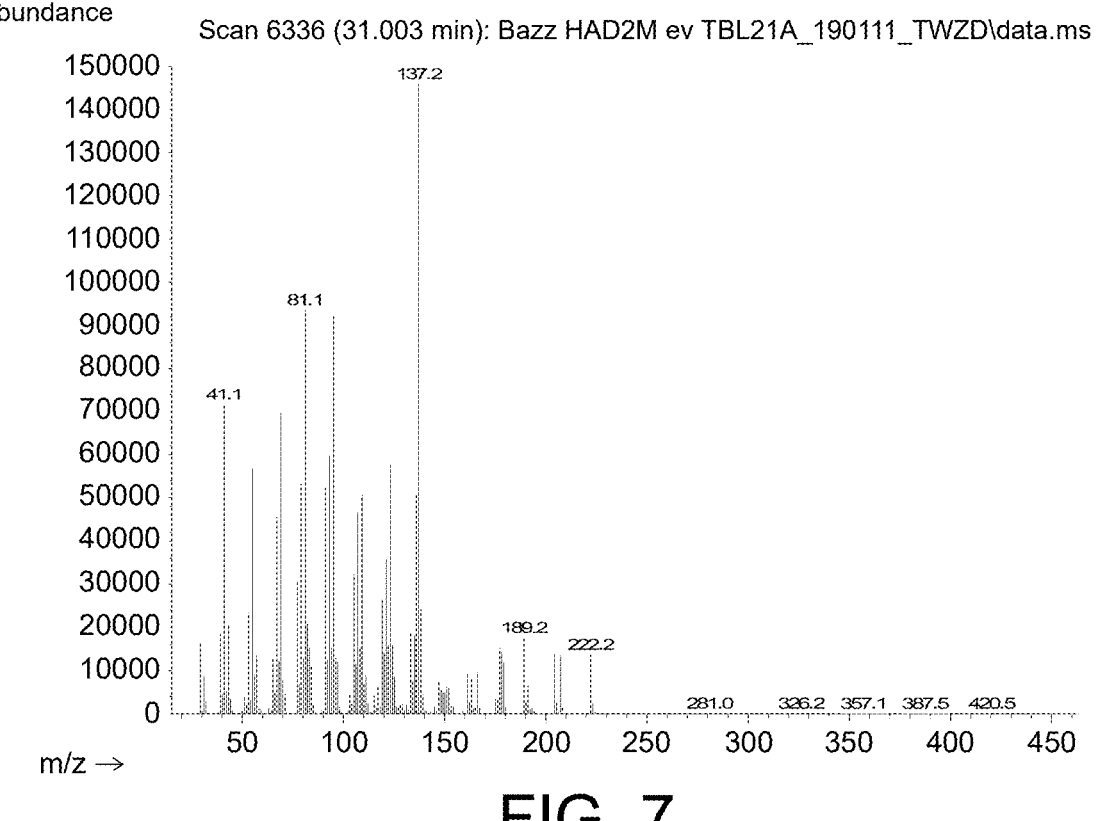
FIG. 7. Mass spectrum of the albicanol peak in FIG. 4.
Figure 8:
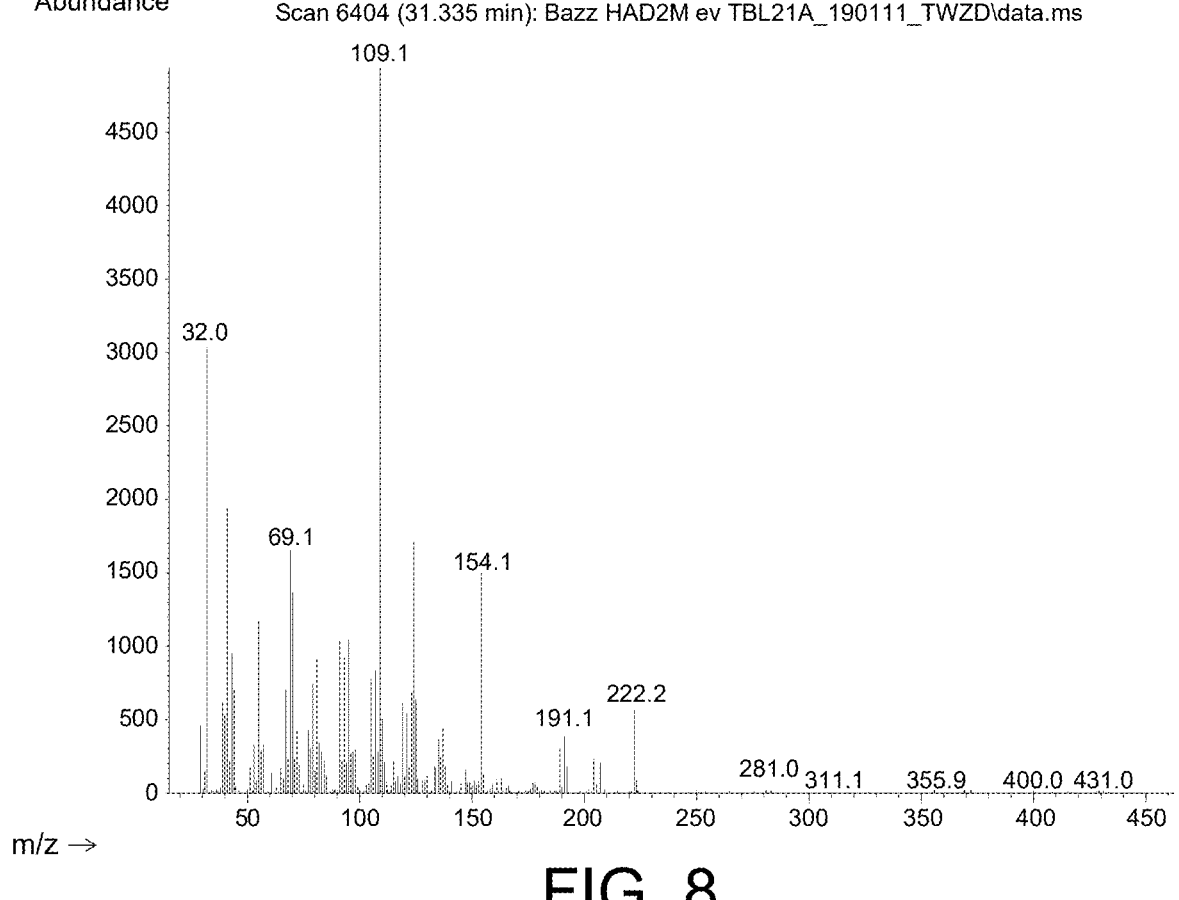
FIG. 8. Mass spectrum of the unknown SQT1 peak in FIG. 4.
Figure 9:
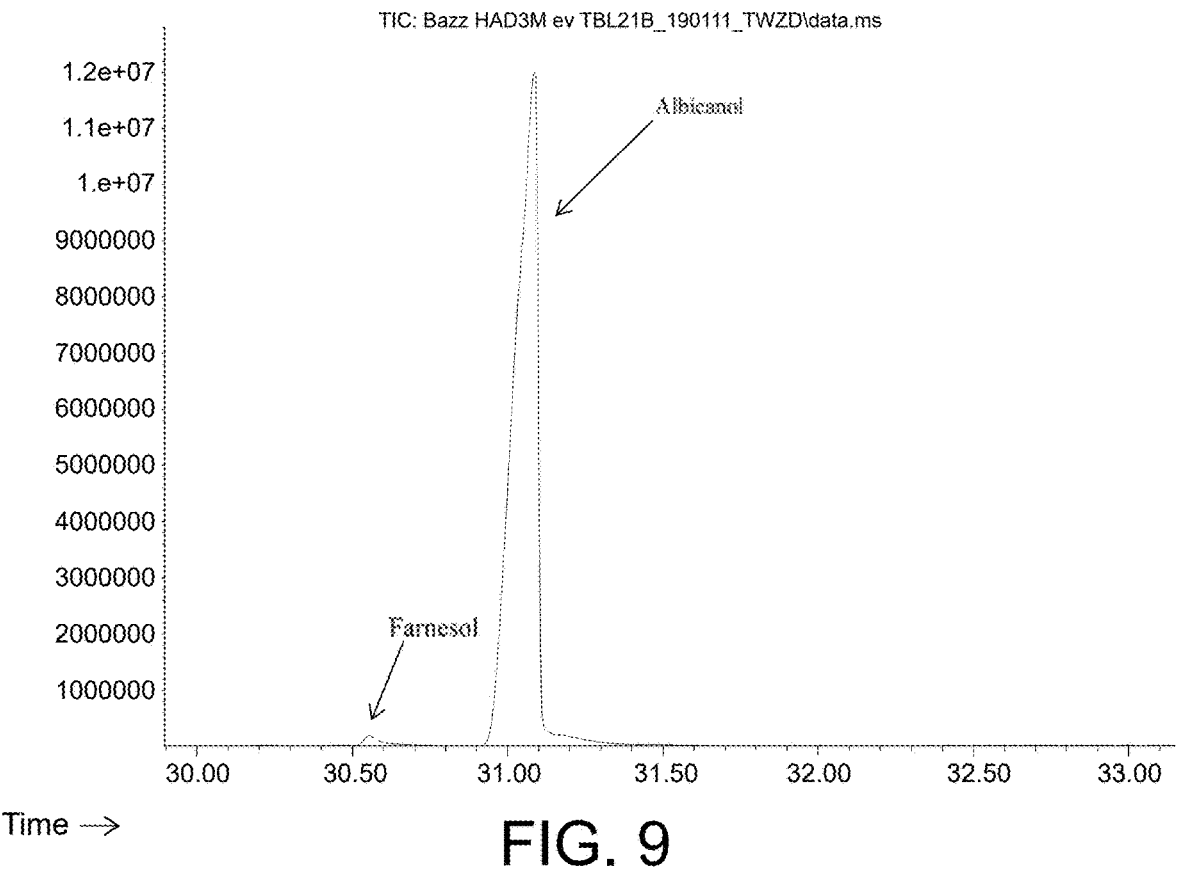
FIG. 9. GC/MS chromatogram of samples from the in vivo biochemical assay of BazzHAD3. Farnesol results from the dephosphorylation of the precursor FPP, whereas albicanol is presumably the product of the dephosphorylation of albicanyl diphosphate.
Figure 10:
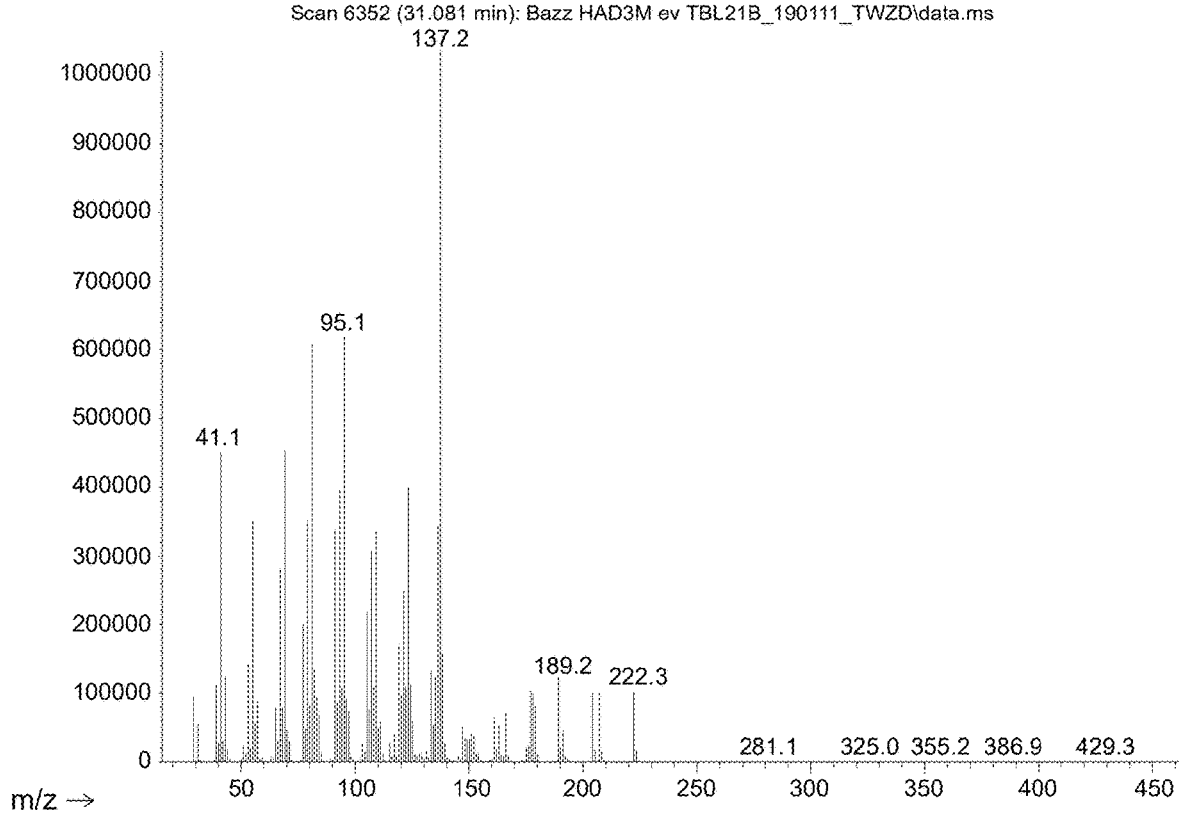
FIG. 10. Mass spectrum of the albicanol peak in FIG. 7.
Figure 11:
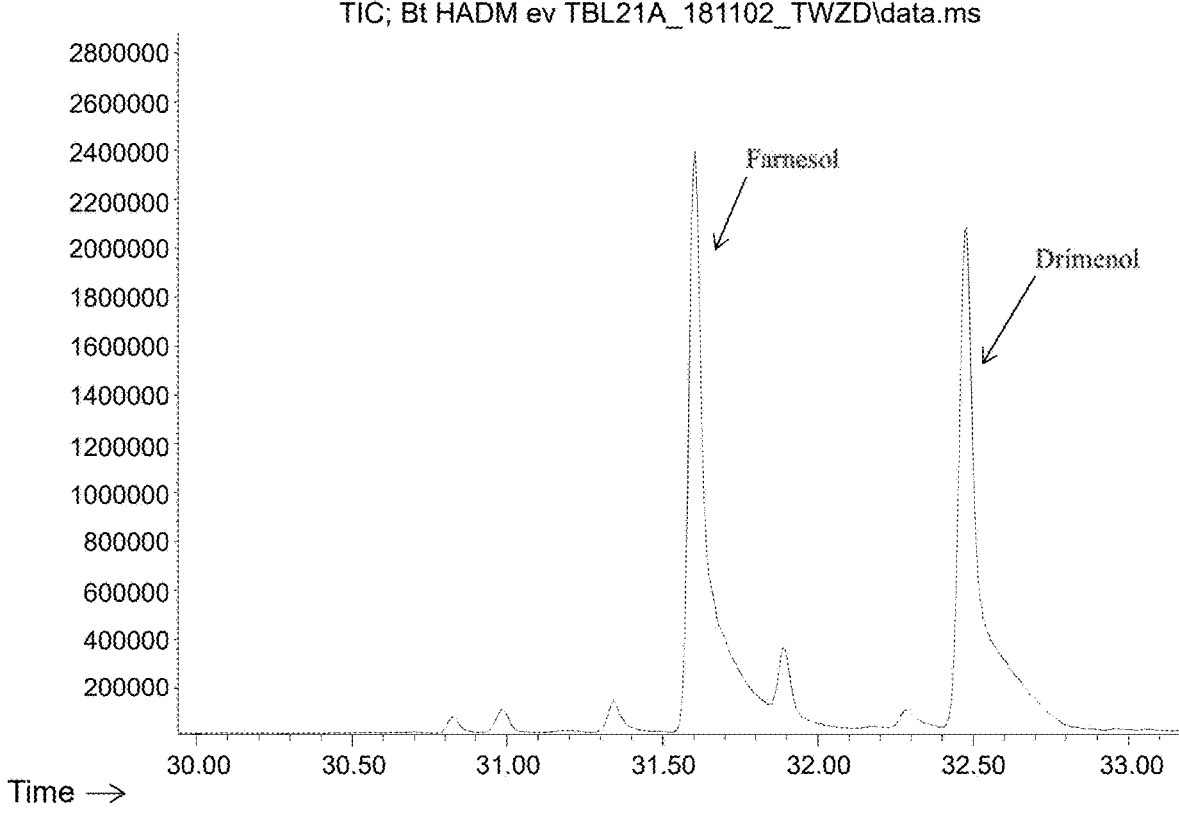
FIG. 11. GC/MS chromatogram of samples from the in vivo biochemical assay of BtHAD. Farnesol results from the dephosphorylation of the precursor FPP, whereas drimenol is presumably the product of the dephosphorylation of drimenyl diphosphate.
Figure 12:
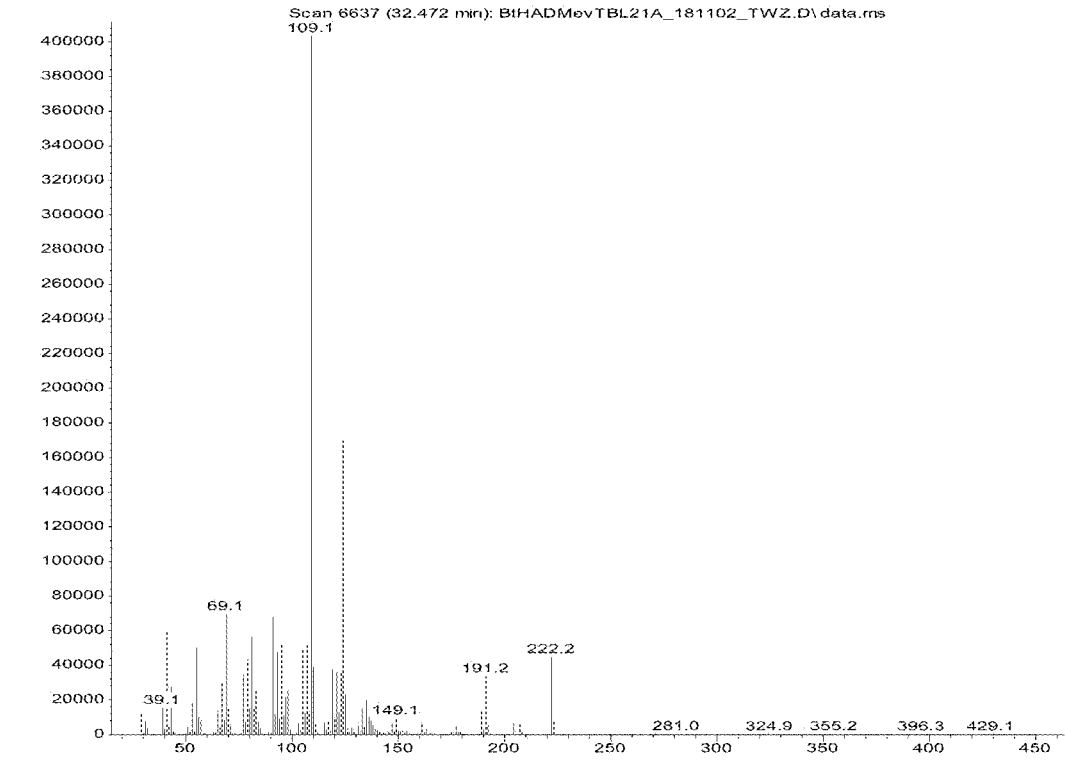
FIG. 12. Mass spectrum of the drimenol peak in FIG. 10.
Figure 13:
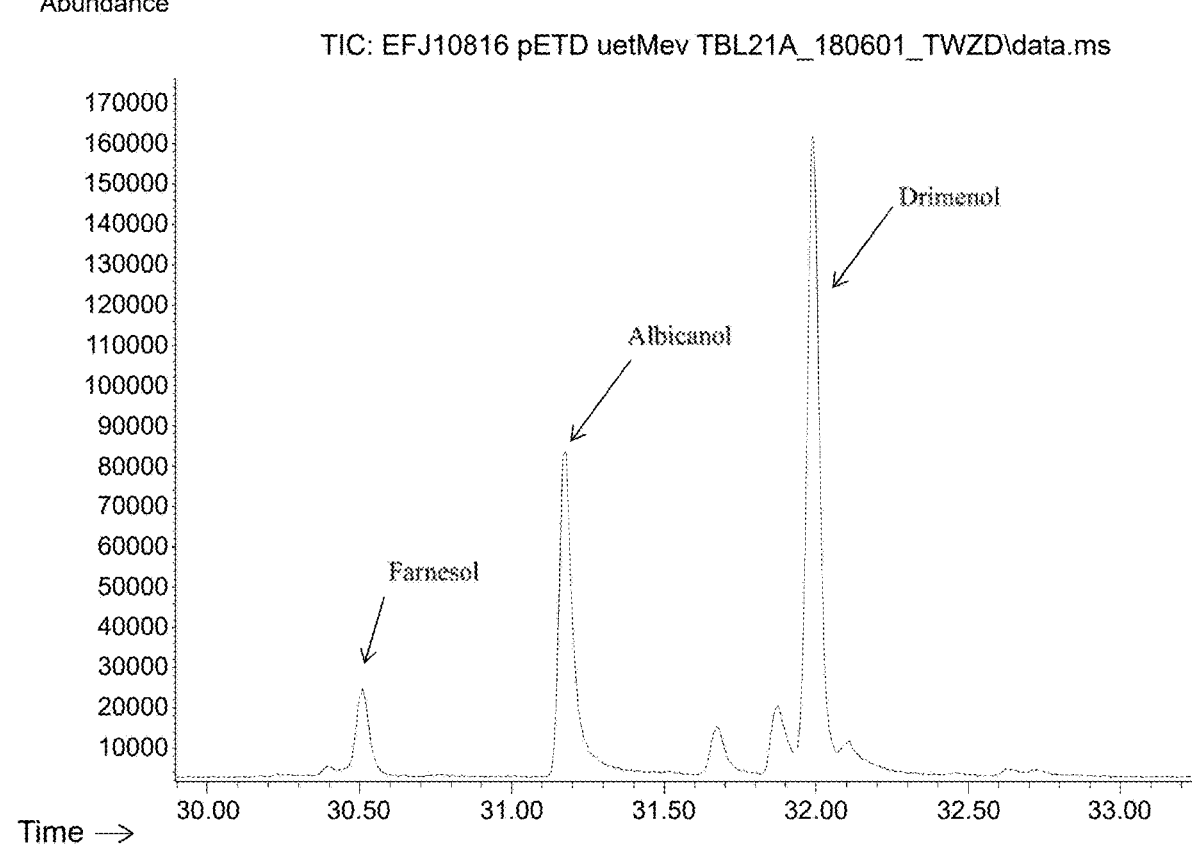
FIG. 13. GC/MS chromatogram of samples from the in vivo biochemical assay of SmHAD1 (EFJ10816.1). Farnesol results from the dephosphorylation of the precursor FPP, whereas drimenol and albicanol are presumably the products of the dephosphorylation of drimenyl and albicanyl diphosphates, respectively.
Figure 14:
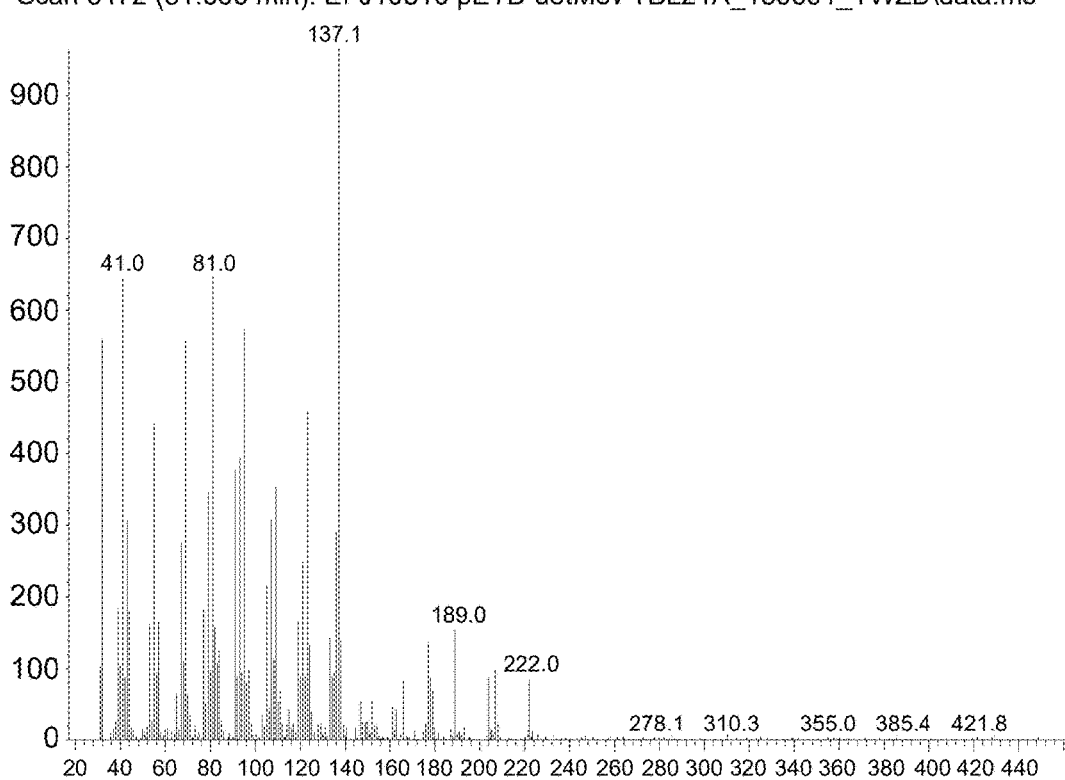
FIG. 14. Mass spectrum of the albicanol peak in FIG. 11.
Figure 15:
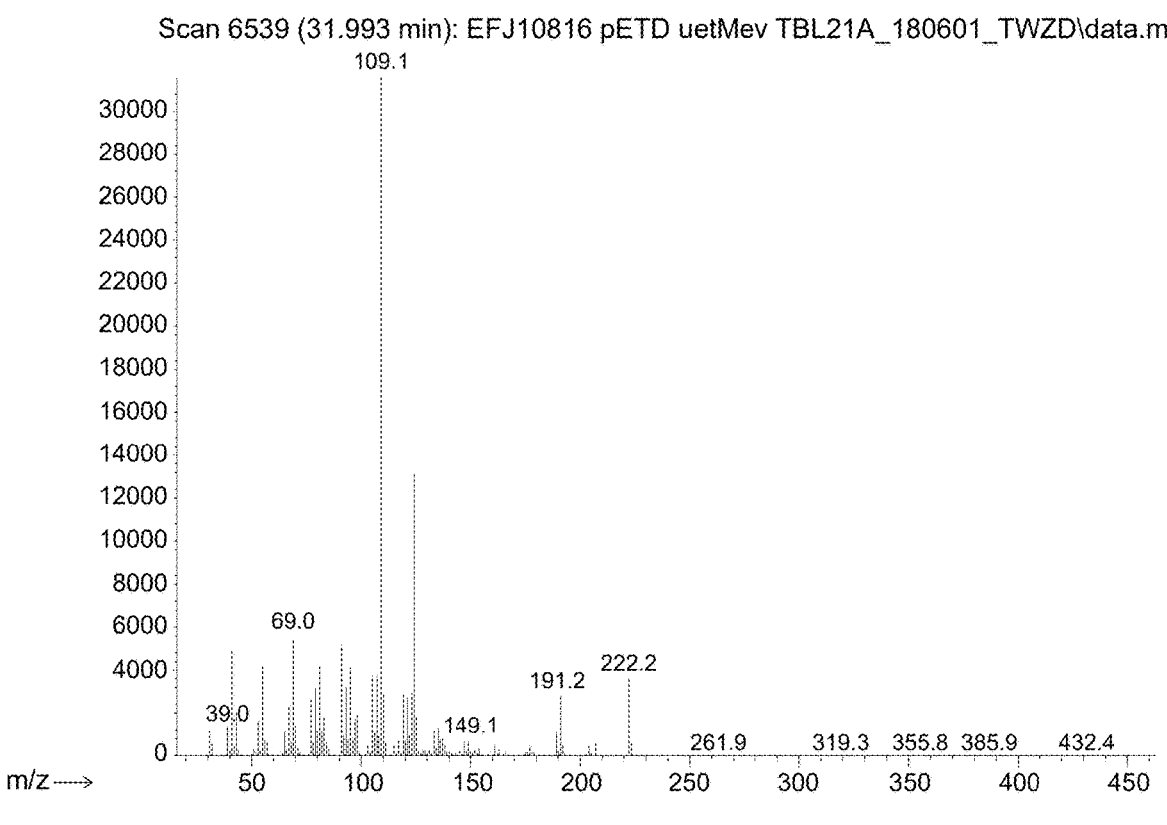
FIG. 15. Mass spectrum of the drimenol peak in FIG. 11.
Figure 16:
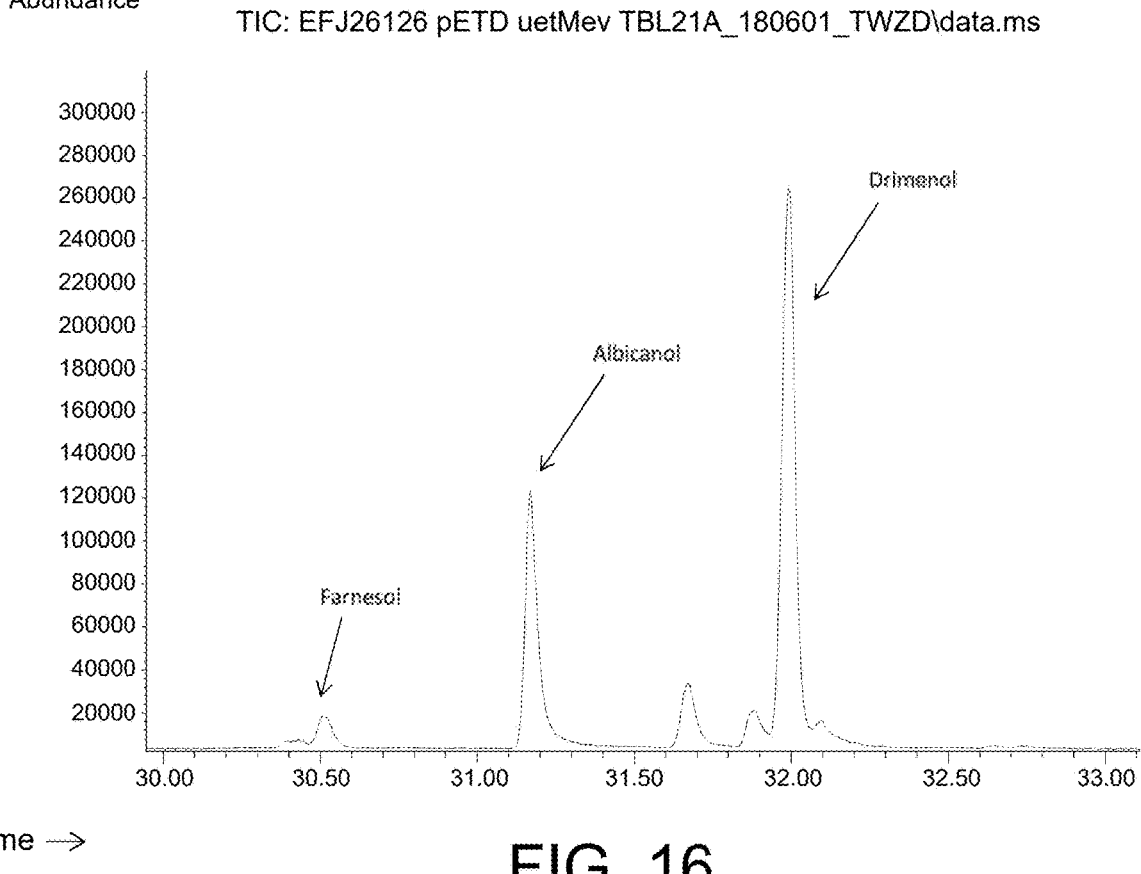
FIG. 16. GC/MS chromatogram of samples from the in vivo biochemical assay of SmHAD2 (EFJ26126.1). Farnesol results from the dephosphorylation of the precursor FPP, whereas drimenol and albicanol are presumably the products of the dephosphorylation of drimenyl and albicanyl diphosphates, respectively.
Figure 17:
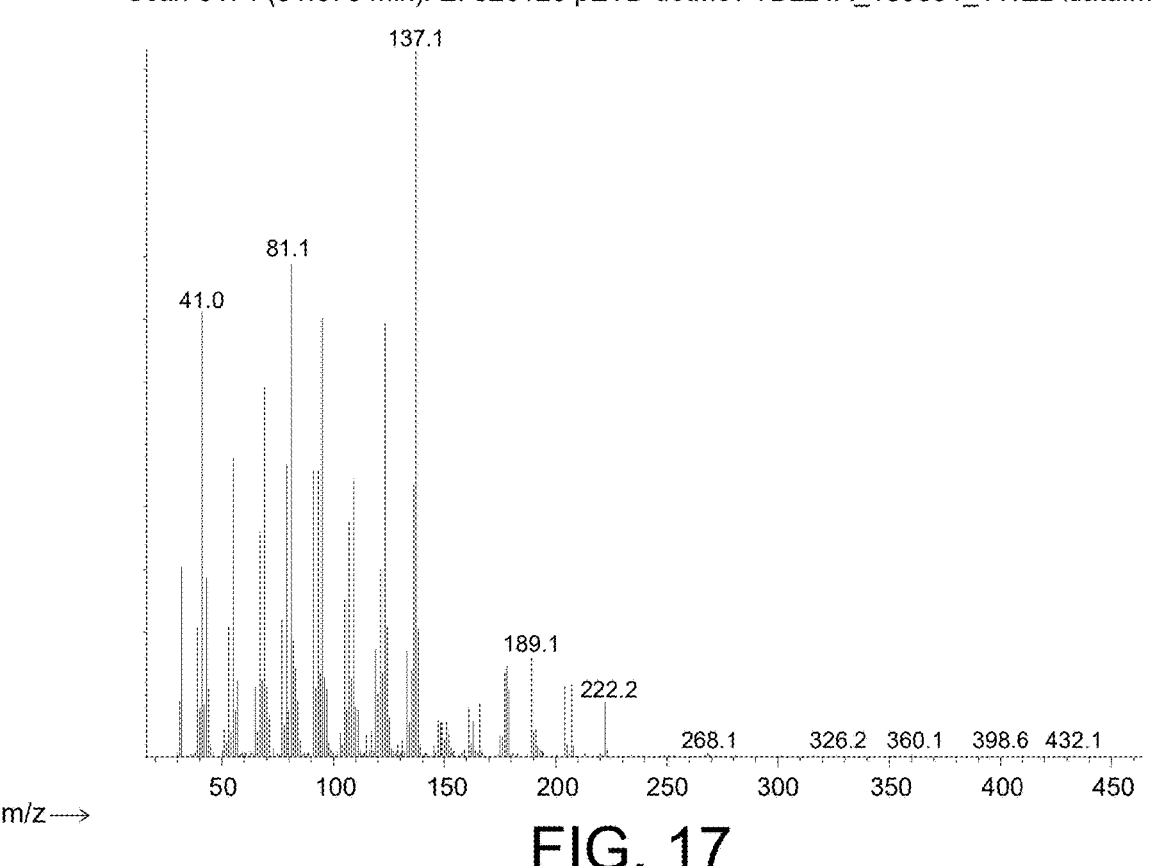
FIG. 17. Mass spectrum of the albicanol peak in FIG. 14.
Figure 18:
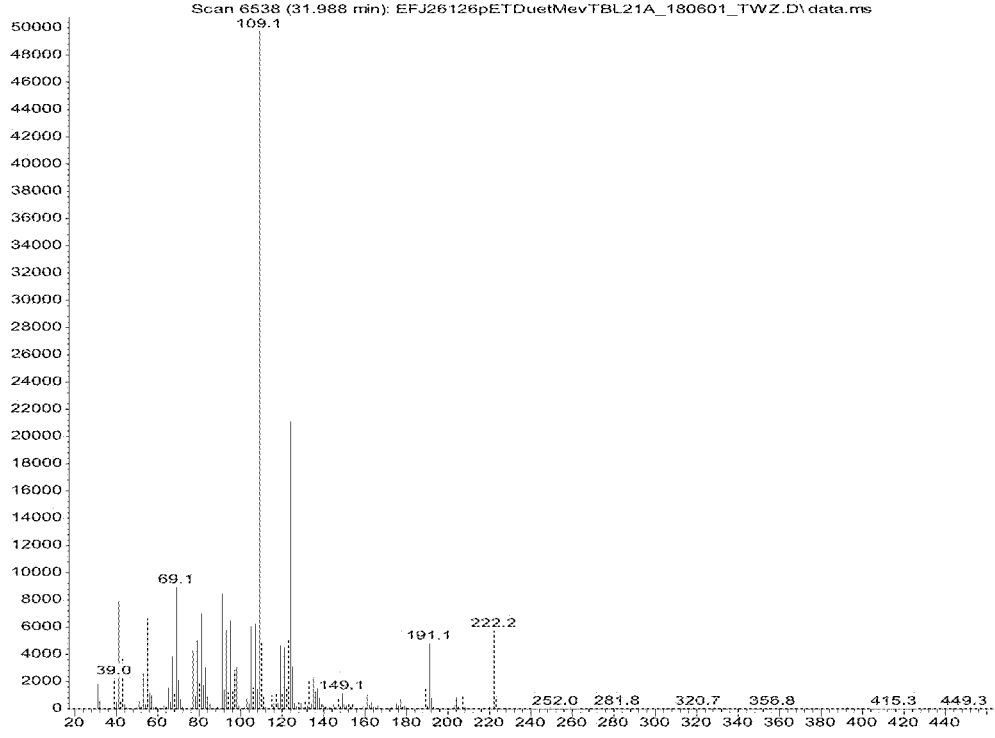
FIG. 18. Mass spectrum of the drimenol peak in FIG. 14.

ABBREVIATIONS USED bp base pair
BAP bacterial alkaline phosphatase
BSA bovine serum albumin
DNA deoxyribonucleic acid
cDNA complementary DNA
DTT dithiothreitol
FPP farnesyl diphosphate
GC gas chromatograph
HAD haloacid dehalogenase
IPTG isopropyl-D-thiogalacto-pyranoside
LB lysogeny broth
MS mass spectrometer/mass spectrometry
MVA mevalonic acid
PCR polymerase chain reaction
PP diphosphate or pyrophosphate
RNA ribonucleic acid
mRNA messenger ribonucleic acid
miRNA micro RNA
siRNA small interfering RNA
rRNA ribosomal RNA
tRNA transfer RNA
sp. Species
TPS Terpene Synthase

DETAILED DESCRIPTION a. Definitions

"Terpenes" are a large and diverse class of organic compounds, produced by a variety of plants, particularly conifers, and by some insects. Terpenes are hydrocarbons. Although sometimes used interchangeably with "terpenes", "terpenoids" or "isoprenoids" are modified terpenes as they contain additional functional groups, usually oxygen-containing.

"Terpenoids" ("isoprenoids") are a large and diverse class of naturally occurring organic chemicals derived from terpenes. Although sometimes used interchangeably with the term "terpenes", "terpenoids" contain additional functional groups, usually 0-containing groups, like for example hydroxyl, carbonyl or carboxyl groups. Most are multicyclic structures with oxygen-containing functional groups. Unless stated otherwise, in the context of the present description the term "terpene" and the term "terpenoid" may be used interchangeably.

Terpenes (and terpenoids) may be classified by the number of isoprene units in the molecule; a prefix in the name indicates the number of terpene units needed to assemble the molecule. Hemiterpenes consist of a single isoprene unit. Monoterpenes consist of two isoprene units and have the molecular formula $C_{10}H_{16}$. Sesquiterpenes consist of three isoprene units and have the molecular formula $C_{15}H_{24}$. Diterpenes are composed of four isoprene units and have the molecular formula $C_{20}H_{32}$.

Figures 1A, 1B, 2:
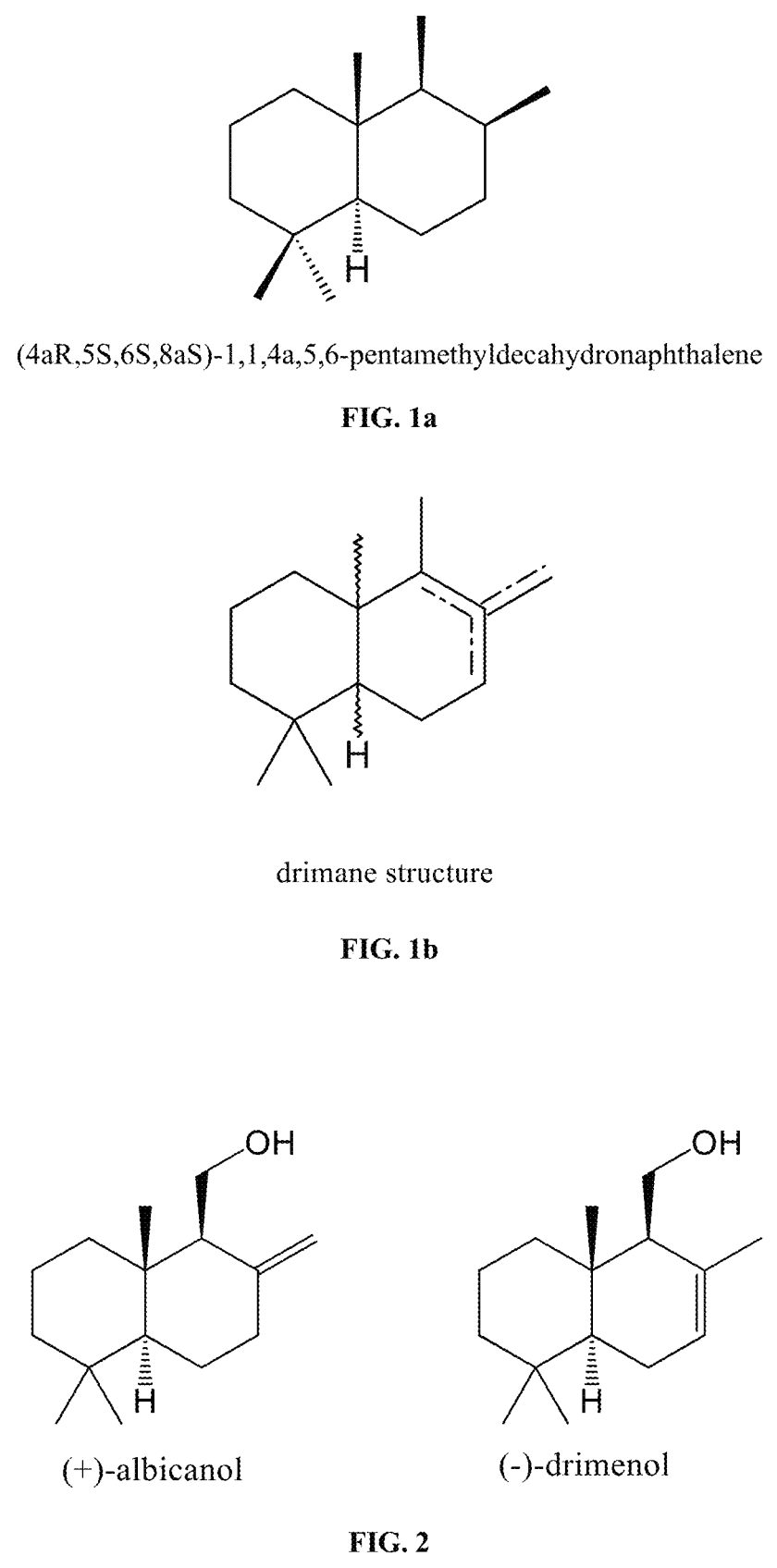

"Drimane" or "drimane sesquiterpene" is a bicyclic sesquiterpene and is the parent structure of many natural products with various biological activities (FIG. 1a). According to IUPAC its systematic chemical name is (4aR, 5S,6S,8aS)-1,1,4a,5,6-pentamethyldecahydronaphthalene. For purposes of this application the term "drimane" has to be understood more broadly, and is also referred to as "drimane-type", and covers bicyclic sesquiterpenes having the general structures as depicted in FIG. 1b. It is not limited to a particular stereochemistry and may contain a single C=C-double bond at certain positions of the drimane skeleton. Particular drimane structures are those as contained in drimenol and albicanol.

"Drimane alcohol" or "drimane sesquiterpene alcohol" refer to a "Drimane" or "drimane sesquiterpene" carrying a hydroxyl group; particular examples are drimenol and albicanol. The term relates in particular to a cyclic terpene (terpenoid) having a drimane-like carbon skeleton structure as depicted in FIG. 1b.

"Albicanol" for the purpose of this application relates to (+)-albicanol (CAS: 54632-04-1) (FIG. 2).

"Albicanol derivatives" include, for example, compounds derived from albicanol by one or more steps of esterification, hydroxylation, oxidation, acylation, isomerization, dimethylation and the like. Suitable derivatives may be selected from a hydrocarbon, alcohol, diol, triol, acetal, ketal, aldehyde, acid, ether, amide, ketone, lactone, epoxide, acetate, glycoside and/or an ester.

"Drimenol" for purposes of this application relates to (−)-drimenol (CAS: 468-68-8) (FIG. 2).

"Drimenol derivatives" include, for example, compounds derived from drimenol by or more steps of esterification, hydroxylation, oxidation, acylation, isomerization, dimethylation and the likes. Suitable derivatives may be selected from a hydrocarbon, alcohol, diol, triol, acetal, ketal, aldehyde, acid, ether, amide, ketone, lactone, epoxide, acetate, glycoside and/or an ester.

"Ambrox" for purposes of this application relates to IUPAC Name: (−)-(3aR,5aS,9aS,9bR)-3a,6,6,9a-tetramethyldodecahydronaphto[2,1-b]furan (CAS: 6790-58-5).

A "precursor" molecule of a target compound as described herein is converted to said target compound, preferably through the enzymatic action of a suitable polypeptide performing at least one structural change on said precursor molecule. For example a "diphosphate precursor" (as for example a "terpenyl diphosphate precursor") is converted to said target compound (as for example a terpene alcohol) via enzymatic removal of the diphosphate moiety, for example by removal of mono- or diphosphate groups by a phosphatase enzyme. For example a "non-cyclic precursor" (like a "non-cyclic terpenyl precursor") may be converted to the cyclic target molecule (like a cyclic terpene compound) through the action of a cyclase or synthase enzyme, irrespective of the particular enzymatic mechanism of such enzyme, in one or more steps.

The terms "cyclic terpene synthase" or "polypeptide having cyclic terpene synthase activity" are used as synonyms to the terms "terpene cyclase" or "polypeptide having terpene cyclase activity". The term "TPS" is used as abbreviation to the term "terpene synthase". A cyclic terpene synthase as described herein belongs to the haloacid dehalogenase-like (HAD-like) hydrolase superfamily which comprises domains corresponding to Pfam domains PF13419 (pfam.xfam.org/family/PF13419) and/or PF00702 (pfam.xfam.org/family/PF00702.26). Some cyclic terpene synthases herein which don't have a significant Pfam domains PF13419 and/or PF00702 remain considered as from HAD-like hydrolase as harboring modified conserved motifs of the above mentioned HAD-like hydrolase superfamily, e.g. class I motif location, class II motif location and QW motif location (SEQ ID: 45, SEQ ID: 46, SEQ ID: 51). A HAD-like hydrolase domain is a portion of a polypeptide having amino acid sequence similarities with the members of the HAD-like hydrolase family and related function. A HAD-like hydrolase domain can be identified in a polypeptide by searching for amino acid motifs or signatures characteristic of this protein family. Tools for performing such searches are available, for example, at the following web sites: www.ebi.ac.uk/interpro/or www.ebi.ac.uk/Tools/hmmer/. Proteins are generally composed of one or more functional regions or domains. Different combinations of domains give rise to the diverse range of proteins found in nature. The identification of domains that occur within proteins can therefore provide insights into their function. A polypeptide which comprises a HAD-like hydrolase domain and/or characteristic HAD-like hydrolase motifs functions in binding and cleavage of phosphate or diphosphate groups of a ligand. An polypeptide of the haloacid dehalogenase-like (HAD-like) hydrolase superfamily, comprising cyclic terpene synthase activity could be defined as HAD-like TPS.

The term "class I terpene synthase" relates to a terpene synthase that catalyzes ionization-initiated reactions, for example, monoterpene and sesquiterpene synthases.

The term "class I terpene synthase motif", "class I terpene synthase-like motif", "class I synthase(-like) motif", "class I synthase motif" or "class I motif" relates to an active site of a terpene synthase that comprises the conserved DDxx (D/E) motif (SEQ ID NO: 45). The aspartic acid residues of this class I motif bind, for example, a divalent metal ion (most often Mg 2+) involved in the binding of the diphosphate group and catalyze the ionization and cleavage of the allylic diphosphate bond of the substrate.

The term "class II terpene synthase" or "class II synthase" relates to a terpene synthase that catalyzes protonation-initiated cyclization reaction, for example, typically involved in the biosynthesis of triterpenes and labdane diterpenes. In class II terpene synthases, the protonation-initiated reaction may involve, for example, acidic amino acids donating a proton to the terminal double-bond.

The term "(modified) class II terpene synthase motif", "(modified) class II terpene synthase-like motif", "(modified) class II synthase(-like) motif", "(modified) class II synthase motif" or "(modified) class II motif" relates to an active site of a terpene synthase that comprises the conserved DxDxxS (SEQ ID NO: 75) motif, e.g. PxDxD(T/S) (T/M)S motif (SEQ ID NO: 46) herein.

The term "QW motif" herein relates to an active site of a terpene synthase that comprises the conserved QxxxxxW (SEQ ID NO: 76) motif, e.g. QxxDGxW motif (SEQ ID NO: 50) herein.

The terms "albicanyl diphosphate synthase" or "polypeptide having albicanyl diphosphate synthase activity" or "albicanyl diphosphate synthase protein" or "having the ability to produce albicanyl diphosphate" relate to a polypeptide capable of catalyzing the synthesis of albicanyl diphosphate, in the form of any of its stereoisomers or a mixture thereof, starting from an acyclic terpene pyrophosphate, particularly farnesyl diphosphate (FPP). Albicanyl diphosphate may be the only product or may be part of a mixture of sesquiterpenes. Said mixture may comprise albicanyl monophosphate and/or albicanol.

The terms "albicanol synthase" or "polypeptide having a albicanol synthase activity" or "albicanol synthase protein" relate to a polypeptide capable of catalyzing the synthesis of albicanol, in the form of any of its stereoisomers or a mixture thereof, starting from an acyclic terpene pyrophosphate, particularly farnesyl diphosphate (FPP). Albicanol may be the only product or may be part of a mixture of sesquiterpenes.

"Albicanyl diphosphate synthase activity" is determined under "standard conditions" as described herein below: They can be determined using recombinant albicanyl diphosphate synthase expressing host cells, disrupted albicanyl diphosphate synthase expressing cells, fractions of these or enriched or purified albicanyl diphosphate synthase enzyme, in a culture medium or reaction medium, preferably buffered, having a pH in the range of 6 to 11, preferably 7 to 9, at a temperature in the range of about 20 to 45° C., like about 25 to 40° C., preferably 25 to 32° C. and in the presence of a reference substrate, here in particular FPP, either added at an initial concentration in the range of 1 to 100 μM, preferably 5 to 50 μM, in particular 30 to 40 μM, or endogenously produced by the host cell. The conversion reaction to form of albicanyl diphosphate is conducted form 10 min to 5 h, preferably about 1 to 2 h. If no endogenous alkaline phosphatase is present, one or more exogenous phosphatase is added to the reaction mixture to convert albicanyl diphosphate as formed by the synthase. Albicanol may then be determined in conventional manner, for example after extraction with an organic solvent, like ethyl acetate. Particular examples of suitable standard conditions are applied in the Experimental Part below, like in Example 4 below, which conditions also shall form part of the general disclosure of the invention.

The terms "drimenyl diphosphate synthase" or "polypeptide having drimenyl diphosphate synthase activity" or "drimenyl diphosphate synthase protein" or "having the ability to produce drimenyl diphosphate" relate to a polypeptide capable of catalyzing the synthesis of drimenyl diphosphate, in the form of any of its stereoisomers or a mixture thereof, starting from an acyclic terpene pyrophosphate, particularly farnesyl diphosphate (FPP). Drimenyl diphosphate may be the only product or may be part of a mixture of sesquiterpenes. Said mixture may comprise drimenyl monophosphate and/or drimenol.

The terms "drimenol synthase" or "polypeptide having a drimenol synthase activity" or "drimenol synthase protein" relate to a polypeptide capable of catalyzing the synthesis of drimenol, in the form of any of its stereoisomers or a mixture thereof, starting from an acyclic terpene pyrophosphate, particularly farnesyl diphosphate (FPP). Drimenol may be the only product or may be part of a mixture of sesquiterpenes.

"Drimenyl diphosphate synthase activity" is determined under "standard conditions" as described herein below: They can be determined using recombinant drimenyl diphosphate synthase expressing host cells, disrupted drimenyl diphosphate synthase expressing cells, fractions of these or enriched or purified drimenyl diphosphate synthase enzyme, in a culture medium or reaction medium, preferably buffered, having a pH in the range of 6 to 11, preferably 7 to 9, at a temperature in the range of about 20 to 45° C., like about 25 to 40° C., preferably 25 to 32° C. and in the presence of a reference substrate, here in particular FPP, either added at an initial concentration in the range of 1 to 100 μM, preferably 5 to 50 μM, in particular 30 to 40 μM, or endogenously produced by the host cell. The conversion reaction to form of drimenyl diphosphate is conducted form 10 min to 5 h, preferably about 1 to 2 h. If no endogenous alkaline phosphatase is present, one or more exogenous phosphatase is added to the reaction mixture to convert drimenyl diphosphate as formed by the synthase. Drimenol may then be determined in conventional manner, for example after extraction with an organic solvent, like ethyl acetate. Particular examples of suitable standard conditions are applied in the Experimental Part below, like in Example 4 below, which conditions also shall form part of the general disclosure of the invention.

The terms "biological function", "function", "biological activity", or "activity" refer to the ability of the terpene synthases as described herein to catalyze the formation of drimenyl diphosphate and/or drimenol, and/or albicanyl diphosphate and/or albicanol; or a mixture of compounds comprising drimenyl diphosphate and/or drimenyl monophosphate and/or drimenol, and/or albicanyl diphosphate and/or albicanyl monophosphate and/or albicanol, and/or and one or more other terpenes, in particular drimenyl diphosphate and/or albicanyl diphosphate.

The terms "mixture of terpenes" or "mixture of sesquiterpenes" refer to a mixture of terpenes or of sesquiterpenes that comprises drimenyl diphosphate and/or drimenyl monophosphate and/or drimenol, and/or albicanyl diphosphate and/or albicanyl monophosphate and/or albicanol and may also comprise one or more additional terpenes, like one or more additional sesquiterpenes.

The "mevalonate pathway" also known as the "isoprenoid pathway" or "HMG-CoA reductase pathway" is an essential metabolic pathway present in eukaryotes, archaea, and some bacteria. The mevalonate pathway begins with acetyl-CoA and produces two five-carbon building blocks called isopentenyl pyrophosphate (IPP) and dimethylallyl pyrophosphate (DMAPP). Key enzymes are acetoacetyl-CoA thiolase (atoB), HMG-CoA synthase (mvaS), HMG-CoA reductase (mvaA), mevalonate kinase (MvaK1), phosphomevalonate kinase (MvaK2), a mevalonate diphosphate decarboxylase (MvaD), and an isopentenyl diphosphate isomerase (idi). Combining the mevalonate pathway with enzyme activity to generate the terpene precursors GPP, FPP or GGPP, like in particular FPP synthase (ERG20), allows the recombinant cellular production of terpenes. As used herein, the term "recombinant host cell/organism", "genetically altered (modified) cell/organism" or "transformed cell/organism" refers to a cell or organism altered to harbor at least one nucleic acid molecule, for instance, a recombinant gene encoding a desired protein or nucleic acid sequence which upon transcription yields a functional polypeptide of the present invention, in particular a drimenyl diphosphate synthase protein useful to produce drimenyl diphosphate and/or drimenyl monophosphate and/or drimenol or corresponding mixtures of terpenes containing drimenyl diphosphate and/or drimenyl monophosphate and/or drimenol, and/or an albicanyl diphosphate synthase protein useful to produce albicanyl diphosphate and/or albicanyl monophosphate and/or albicanol or corresponding mixtures of terpenes containing albicanyl diphosphate and/or albicanyl monophosphate and/or albicanol. The host cell is particularly a bacterial cell, a fungal cell, a yeast cell or a plant cell, or plants. The host cell may contain a recombinant gene which has been integrated into the nuclear or organelle genomes of the host cell. Alternatively, the host may contain the recombinant gene extra-chromosomally.

The term "organism" refers to any non-human multicellular or unicellular organisms such as a plant, or a microorganism. Particularly, a microorganism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

A particular organism or cell is meant to be "capable of producing FPP" when it produces FPP naturally or when it does not produce FPP naturally but is (genetically) modified, such as transformed, to produce FPP with a nucleic acid as described herein. Organisms or cells transformed to produce a higher or lower, in particular higher amount of FPP than the naturally occurring organism or cell are also encompassed by the "organisms or cells capable of producing FPP".

A particular organism or cell is meant to be "capable of producing albicanyl diphosphate" when it produces albicanyl diphosphate naturally or when it does not produce albicanyl diphosphate naturally but is transformed to produce albicanyl diphosphate with a nucleic acid as described herein. Organisms or cells transformed to produce a higher or lower, in particular higher amount of albicanyl diphosphate than the naturally occurring organism or cell are also encompassed by the "organisms or cells capable of producing albicanyl diphosphate".

A particular organism or cell is meant to be "capable of producing albicanol" when it produces albicanol naturally or when it does not produce albicanol naturally but is transformed to produce albicanyl diphosphate with a nucleic acid as described herein, and optionally further transformed with a nucleic acid to produce enzyme activity converting albicanyl diphosphate to albicanol. Organisms or cells transformed to produce a higher or lower, in particular higher amount of albicanol than the naturally occurring organism or cell are also encompassed by the "organisms or cells capable of producing albicanol".

A particular organism or cell is meant to be "capable of producing drimenyl diphosphate" when it produces drimenyl diphosphate naturally or when it does not produce drimenyl diphosphate naturally but is transformed to produce drimenyl diphosphate with a nucleic acid as described herein. Organisms or cells transformed to produce a higher or lower, in particular higher amount of drimenyl diphosphate than the naturally occurring organism or cell are also encompassed by the "organisms or cells capable of producing drimenyl diphosphate".

A particular organism or cell is meant to be "capable of producing drimenol" when it produces drimenol naturally or when it does not produce drimenol naturally but is transformed to produce drimenol diphosphate with a nucleic acid as described herein, and optionally further transformed with a nucleic acid to produce enzyme activity converting drimenyl diphosphate to drimenol. Organisms or cells transformed to produce a higher or lower, in particular higher amount of drimenol than the naturally occurring organism or cell are also encompassed by the "organisms or cells capable of producing drimenol".

The terms "purified", "substantially purified", and "isolated" as used herein refer to the state of being free of other, dissimilar compounds with which a compound of the invention is normally associated in its natural state, so that the "purified", "substantially purified", and "isolated" subject comprises at least 0.5%, 1%, 5%, 10%, or 20%, or at least 50% or 75% of the mass, by weight, of a given sample. In one embodiment, these terms refer to the compound of the invention comprising at least 95, 96, 97, 98, 99 or 100%, of the mass, by weight, of a given sample. As used herein, the terms "purified", "substantially purified", and "isolated" when referring to a nucleic acid or protein, of nucleic acids or proteins, also refers to a state of purification or concentration different than that which occurs naturally, for example in an prokaryotic or eukaryotic environment, like, for example in a bacterial or fungal cell, or in the mammalian organism, especially human body. Any degree of purification or concentration greater than that which occurs naturally, including (i) the purification from other associated structures or compounds or (ii) the association with structures or compounds to which it is not normally associated in said prokaryotic or eukaryotic environment, are within the meaning of "isolated". The nucleic acid or protein or classes of nucleic acids or proteins, described herein, may be isolated, or otherwise associated with structures or compounds to which they are not normally associated in nature, according to a variety of methods and processes known to those of skill in the art.

The term "about" indicates a potential variation of ±25% of the stated value, in particular ±15%, ±10%, more particularly ±50%, ±2% or ±1%.

The term "substantially" describes a range of values of from about 80 to 100%, such as, for example, 85-99.9%, in particular 90 to 99.9%, more particularly 95 to 99.9%, or 98 to 99.9% and especially 99 to 99.9%.

"Predominantly" refers to a proportion in the range of above 50%, as for example in the range of 51 to 100%, particularly in the range of 75 to 99.9%; more particularly 85 to 98.5%, like 95 to 99%.

A "main product" in the context of the present invention designates a single compound or a group of at least 2 compounds, like 2, 3, 4, 5 or more, particularly 2 or 3 compounds, which single compound or group of compounds is "predominantly" prepared by a reaction as described herein, and is contained in said reaction in a predominant proportion based on the total amount of the constituents of the product formed by said reaction. Said proportion may be a molar proportion, a weight proportion or, preferably based on chromatographic analytics, an area proportion calculated from the corresponding chromatogram of the reaction products.

A "side product" in the context of the present invention designates a single compound or a group of at least 2 compounds, like 2, 3, 4, 5 or more, particularly 2 or 3 compounds, which single compound or group of compounds is not "predominantly" prepared by a reaction as described herein.

Because of the reversibility of enzymatic reactions, the present invention relates, unless otherwise stated, to the enzymatic or biocatalytic reactions described herein in both directions of reaction.

"Functional mutants" of herein described polypeptides include the "functional equivalents" of such polypeptides as defined below.

The term "stereoisomers" includes in particular conformational isomers.

Included in general are, according to the invention, all "stereoisomeric forms" of the compounds described herein, such as "constitutional isomers" and, in particular, "stereoisomers".

"Stereoisomeric forms" encompass in particular, "stereoisomers" and mixtures thereof, e.g. configuration isomers (optical isomers), such as enantiomers, or geometric isomers (diastereomers), such as E- and Z-isomers, and combinations thereof. If one or more asymmetric centers are present in one molecule, the invention encompasses all combinations of different conformations of these asymmetry centers, e.g. enantiomeric pairs.

"Stereoselectivity" describes the ability to produce a particular stereoisomer of a compound in a stereoisomerically pure form or to specifically convert a particular stereoisomer in an enzyme catalyzed method as described herein out of a plurality of stereoisomers. More specifically, this means that a product of the invention is enriched with respect to a specific stereoisomer, or an educt may be depleted with respect to a particular stereoisomer. This may be quantified via the purity % ee-parameter calculated according to the formula:

$$\% \ ee = [XA-XB]/[XA+XB]*100,$$

wherein XA and XB represent the molar ratio (Molenbruch) of the stereoisomers A and B.

The terms "selectively converting" or "increasing the selectivity" in general means that a particular stereoisomeric form, as for example the E-form, of an unsaturated hydrocarbon, is converted in a higher proportion or amount (compared on a molar basis) than the corresponding other stereoisomeric form, as for example Z-form, either during the entire course of said reaction (i.e. between initiation and termination of the reaction), at a certain point of time of said reaction, or during an "interval" of said reaction. In particular, said selectivity may be observed during an "interval" corresponding to 1 to 99%, 2 to 95%, 3 to 90%, 5 to 85%, 10 to 80%, 15 to 75%, 20 to 70%, 25 to 65%, 30 to 60%, or 40 to 50% conversion of the initial amount of the substrate. Said higher proportion or amount may, for example, be expressed in terms of:

a higher maximum yield of an isomer observed during the entire course of the reaction or said interval thereof;

a higher relative amount of an isomer at a defined % degree of conversion value of the substrate; and/or an identical relative amount of an isomer at a higher % degree of conversion value;

each of which preferably being observed relative to a reference method, said reference method being performed under otherwise identical conditions with known chemical or biochemical means.

Generally also comprised in accordance with the invention are all "isomeric forms" of the compounds described herein, such as constitutional isomers and in particular stereoisomers and mixtures of these, such as, for example, optical isomers or geometric isomers, such as E- and Z-isomers, and combinations of these. If several centers of asymmetry are present in a molecule, then the invention comprises all combinations of different conformations of these centers of asymmetry, such as, for example, pairs of enantiomers, or any mixtures of stereoisomeric forms.

For the descriptions herein and the appended claims, the use of "or" means "and/or" unless stated otherwise. Similarly, "comprise", "comprises", "comprising", "include", "includes", and "including" are interchangeable and not intended to be limiting.

It is to be further understood that where descriptions of various embodiments use the term "comprising", those skilled in the art would understand that in some specific instances an embodiment can be alternatively described using language "consisting essentially of" or "consisting of".

If the present disclosure refers to features, parameters and ranges thereof of different degree of preference (including general, not explicitly preferred features, parameters and ranges thereof) then, unless otherwise stated, any combination of two or more of such features, parameters and ranges thereof, irrespective of their respective degree of preference, is encompassed by the disclosure of the present description.

b. Particular Embodiments of the Invention

The present invention relates to the following embodiments:

1. An isolated polypeptide of the haloacid dehalogenase-like (HAD-like) hydrolase superfamily, comprising cyclic terpene synthase activity, wherein said polypeptide is selected from a. BazzHAD1 comprising an amino acid sequence of SEQ ID NO: 3, or a mutant or natural variant thereof comprising an amino acid sequence having at least 40%, 45%, 50%, 55%, 60%, 65%, 70%, 75%, 80%, 85%, 90%, 95%, 96%, 97%, 98% or 99% sequence identity to SEQ ID NO: 3 and retaining said cyclic terpene synthase activity, in particular drimenyl diphosphate synthase activity;

b. BazzHAD2 comprising an amino acid sequence of SEQ ID NO: 6, or a mutant or natural variant thereof comprising an amino acid sequence having at least 40%, 45%, 50%, 55%, 60%, 65%, 70%, 75%, 80%, 85%, 90%, 95%, 96%, 97%, 98% or 99% sequence identity to SEQ ID NO: 6 and retaining said cyclic terpene synthase activity, in particular albicanyl diphosphate synthase activity;

c. BazzHAD3 comprising an amino acid sequence of SEQ ID NO: 9, or a mutant or natural variant thereof comprising an amino acid sequence having at least 40%, 45%, 50%, 55%, 60%, 65%, 70%, 75%, 80%, 85%, 90%, 95%, 96%, 97%, 98% or 99% sequence identity to SEQ ID NO: 9 and retaining said cyclic terpene synthase activity, in particular albicanyl diphosphate synthase activity;

d. BtHAD comprising an amino acid sequence of SEQ ID NO: 12, or a mutant or natural variant thereof comprising an amino acid sequence having at least 40%, 45%, 50%, 55%, 60%, 65%, 70%, 75%, 80%, 85%, 90%, 95%, 96%, 97%, 98% or 99% sequence identity to SEQ ID NO: 12 and retaining said cyclic terpene synthase activity, in particular drimenyl diphosphate synthase activity;

e. SmHAD1 comprising an amino acid sequence of SEQ ID NO: 19, or a mutant or natural variant thereof comprising an amino acid sequence having at least 40%, 45%, 50%, 55%, 60%, 65%, 70%, 75%, 80%, 85%, 90%, 95%, 96%, 97%, 98% or 99% sequence identity to SEQ ID NO: 19 and retaining said cyclic terpene synthase activity, in particular drimenyl diphosphate synthase activity and/or in particular albicanyl diphosphate synthase activity;

f. SmHAD2 comprising an amino acid sequence of SEQ ID NO: 26, or a mutant or natural variant thereof comprising an amino acid sequence having at least 40%, 45%, 50%, 55%, 60%, 65%, 70%, 75%, 80%, 85%, 90%, 95%, 96%, 97%, 98% or 99% sequence identity to SEQ ID NO: 26 and retaining said cyclic terpene synthase activity, in particular drimenyl diphosphate synthase activity and/or in particular albicanyl diphosphate synthase activity;

A particular subgroup of TPSs refers to TPSs listed above under a), b), c) and d), more particularly a), b) and c).

A more particular aspect of this embodiment relates to polypeptide variants or in particular non-natural mutants of the above novel polypeptides of the invention which comprise cyclic terpene synthase activity as identified above. These variants or non-natural mutants are derived from anyone of the particular amino acid sequences of SEQ ID NOs: 3, 6, 9, 12, 19, and 26. These variants are selected from polypeptides comprising an amino acid sequence having at least 70%, 75%, 80%, 85%, 90%, 95%, 96%, 97%, 98%, or 99% sequence identity to anyone of SEQ ID NO: 3, 6, 9, 12, 19, and 26, which contain at least one amino acid sequence difference, such as at least one amino acid sequence position which is modified by addition, substitution, insertion or deletion relative to the respective non-modified polypeptide of SEQ ID NOs: 3, 6, 9, 12, 19 or 26. Thus such variants have less than 100% sequence identity to the respective non-modified polypeptide. "At least one" in this context encompasses at least 1 to 20, 1 to 15, 1 to 10, and more particularly 1, 2, 3, 4 or 5 amino acid sequence positions independently of each other modified by amino acid residue addition, substitution, insertion or deletion.

particularly, a drimanyl diphosphate; and/or wherein the drimane sesquiterpene alcohol is drimenol and/or albicanol.

4. The polypeptide of embodiment 1, 2 or 3, comprising the ability to produce a) drimenyl diphosphate and/or albicanyl diphosphate from famesyl diphosphate (FPP) as substrate; or b) drimenyl diphosphate and/or albicanyl diphosphate from famesyl diphosphate (FPP) as substrate; and drimenol and/or albicanol, either directly from FPP as substrate or via the respective diphosphate precursor; or c) drimenol and/or albicanol from FPP as substrate, either directly from FPP as substrate or via the respective diphosphate precursor.

In the following Table 1 an overview of particular TPS of the invention, their particular sequence motifs including their relative position in the full amino acid sequence and their respective product profile (based on type of drimane alcohol) is shown.

| | SEQ ID NO: | Class II | QW | Other motifs | Products (drimane sesquiterpene and/or respective diphosphate) | |
|---|---|---|---|---|---|---|
| BazzHAD1 | NA SEQ ID NO: 1 wt | PDDLDSTS SEQ ID NO: 47 | QNVDGSW SEQ ID NO: 52 | LRSHIWFNYSMG (SEQ ID NO: 57) (aa 68 to 79) | Drimenol | |
| | NA SEQ ID NO: 2 E.coli | (aa 318 to 325) | (aa 489 to 495) | YFDPLRLRVDPVAATN (SEQ ID NO: 63) (aa 362 to 377) | | |
| | AA SEQ ID NO: 3 | | | GTLYYRTPEAFLY (SEQ ID NO: 70) (aa 410 to 422) | | |
| BazzHAD2 | NA SEQ ID NO: 4 wt | PDDLDTTS SEQ ID NO: 48 | QCDDGGW SEQ ID NO: 53 | LRSATWAAYECG (SEQ ID NO: 58) (aa 37 to 48) | Albicanol | Unknown compound 1 |
| | NA SEQ ID NO: 5 E.coli | (aa 269 to 276) | (aa 431 to 437) | YFDETRPRVDAVVNVN (SEQ ID NO: 64) (aa 309 to 324) | | |
| | AA SEQ ID NO: 6 | | | GTLFYYHAESFLY (SEQ ID NO: 71) (aa 357 to 369) | | |
| BazzHAD3 | NA SEQ ID NO: 7 wt | PNDLDTTS SEQ ID NO: 50 | QSSDGGW SEQ ID NO: 54 | LRTPTWGKYECD (SEQ ID NO: 59) (aa 45 to 56) | Albicanol | |
| | NA SEQ ID NO: 8 E.coli | (aa 277 to 284) | (aa 439 to 445) | YFDKTRPRVDPVVCVN (SEQ ID NO: 65) (aa 317 to 332) | | |
| | AA SEQ ID NO: 9 | | | GTLFYYHAESFLY (SEQ ID NO: 71) (aa 365 to 377) | | |
| BtHAD | NA SEQ ID NO: 10 wt | PNDLDTTS SEQ ID NO: 47 | QNVDGSW SEQ ID NO: 52 | LRSHIWFNYSMG (SEQ ID NO: 57) (aa 68 to 79) | Drimenol | |
| | NA SEQ ID NO: 11 E.coli | (aa 318 to 325) | (aa 488 to 494) | YFDPLRDLVDPVAATN (SEQ ID NO: 63) (aa 362 to 377) | | |
| | AA SEQ ID NO: 12 | | | GTLYYRTPEAFLY (SEQ ID NO: 70) (aa 410 to 422) | | |
| SmHAD1 | NA SEQ ID NO: 17 wt | PPDIDTMS SEQ ID NO: 49 | QNEDGSW SEQ ID NO: 55 | LQHSSFLAYSCG (SEQ ID NO: 60) (aa 28 to 39) | Drimenol | Albicanol |
| | NA SEQ ID NO: 18 E.coli | (aa 255 to 262) | (aa 430 to 436) | YLDVERPRVDPVVIAN (SEQ ID NO: 66) (aa 299 to 314) | | |
| | AA SEQ ID NO: 19 | | | GTRYYLSQEDFLF (SEQ ID NO: 72) (aa 349 to 361) | | |
| SmHAD2 | NA SEQ ID NO: 24 wt | PPDIDTMS SEQ ID NO: 49 | QNEDGSW SEQ ID NO: 55 | LQHSSFLAYSCG (SEQ ID NO: 60) (aa 28 to 39) | Drimenol | Albicanol |
| | NA SEQ ID NO: 25 E.coli | (aa 255 to 262) | (aa 430 to 436) | YLDLERPRVDPVVIAN (SEQ ID NO: 67) (aa 299 to 314) | | |
| | AA SEQ ID NO: 26 | | | GTRYYSQEDFLF (SEQ ID NO: 72) (aa 349 to 361) | | |

2. The polypeptide of embodiment 1, comprising the ability to produce a) a phosphate precursor of at least one drimane sesquiterpene alcohol; or b) the phosphate precursor of at least one drimane sesquiterpene alcohol and the corresponding at least one drimane sesquiterpene alcohol; or c) at least one drimane sesquiterpene alcohol.

3. The polypeptide of embodiment 2, wherein the phosphate precursor is a drimanyl monophosphate, or, more 5. The polypeptide of one of the preceding embodiments, which is isolated from a. plants of the genus *Bazzania*, in particular of the species *Bazzania trilobata*; or b. plants of the genus *Selaginella*, in particular of the species *Selaginella moellendorffii;* c. other lycophytes, liverworts or monilophytes that contain drimane sesquiterpenes, including but not limited to *Porella* sp., *Hymenophyton* sp., and *Marchantia* sp.; or from other plant species.

6. The polypeptides of anyone of embodiments 1 to 5 further comprising a. a modified class II synthase motif as set forth in SEQ ID NO: 46 $(Px_0Dx_1D(T/S)(T/M)S)$, wherein $x_0$ and $x_1$ can be any naturally occurring amino acid residue, and $x_1$ particularly represents I or L, in particular the motif of any one of SEQ ID NOs: 47, 48, 49 or 50, wherein said modified class II synthase motif corresponds to i. sequence positions 318 to 325 of SEQ ID NO: 3,
        ii. sequence positions 269 to 276 of SEQ ID NO: 6,
        iii. sequence positions 277 to 284 of SEQ ID NO: 9,
        iv. sequence positions 318 to 325 of SEQ ID NO: 12,
        v. sequence positions 255 to 262 of SEQ ID NO: 19, and
        vi. sequence positions 255 to 262 of SEQ ID NO: 26, respectively;

b. a QW motif as set forth in SEQ ID NO: 51 $(Qx_2x_3DGx_4W)$, wherein $x_2$, $x_3$ and $x_4$ can be any naturally occurring amino acid residue, and $x_4$ particularly represents G or S, in particular the motif of any one of SEQ ID NOs: 52, 53, 54, or 55, wherein said QW motif corresponds to i. sequence positions 489 to 495 of SEQ ID NO: 3,
        ii. sequence positions 431 to 437 of SEQ ID NO: 6,
        iii. sequence positions 439 to 445 of SEQ ID NO: 9,
        iv. sequence positions 488 to 494 of SEQ ID NO: 12,
        v. sequence positions 430 to 436 of SEQ ID NO: 19, and
        vi. sequence positions 430 to 436 of SEQ ID NO: 26, respectively; and c. optionally at least one, as for example 1, 2 or 3, further sequence motif selected from (1) the conserved sequence motif 1 set forth in SEQ ID NO: 56 $(Lx5x_6x_7x_8(W/F)x_9x_{10}Yx_{11}x_{12}G)$, wherein $x_5$ to $x_{12}$ can be any naturally occurring amino acid residue, and $x_5$ particularly represents R or Q, $x_8$ particularly represents S, I or T, $x_{11}$ particularly represents E or S and $x_{12}$ particularly represents C or M, in particular the motif of SEQ ID NOs: 57, 58, 59, 60 or 61, wherein said conserved sequence motif 1 corresponds to i. sequence positions 68 to 79 of SEQ ID NO: 3,
            ii. sequence positions 37 to 48 of SEQ ID NO: 6,
            iii. sequence positions 45 to 56 of SEQ ID NO: 9,
            iv. sequence positions 68 to 79 of SEQ ID NO: 12,
            v. sequence positions 28 to 39 of SEQ ID NO: 19, and
            vi. sequence positions 28 to 39 of SEQ ID NO: 26, respectively;

(2) the conserved sequence motif 2 set forth in SEQ ID NO: 62 $(Yx_{13}Dx_{14}x_{15}Rx_{16}RVD(P/A)V(V/A)x_{17}x_{18}N)$, wherein $x_{13}$ to $x_{18}$ can be any naturally occurring amino acid residue, and $x_{13}$ particularly represents F or L, and $x_{16}$ particularly represents P or L, in particular the motif of SEQ ID NOs: 63, 64, 65, 66, 67 or 68, wherein said conserved sequence motif 2 corresponds to i. sequence positions 362 to 377 of SEQ ID NO: 3,
            ii. sequence positions 309 to 324 of SEQ ID NO: 6,
            iii. sequence positions 317 to 332 of SEQ ID NO: 9,
            iv. sequence positions 362 to 377 of SEQ ID NO: 12,
            v. sequence positions 299 to 314 of SEQ ID NO: 19, and
            vi. sequence positions 299 to 314 of SEQ ID NO: 26, respectively; and (3) the conserved sequence motif 3 set forth in SEQ ID NO: 69 $(GTx_{19}(Y/F)Yx_{20}x_{21}x_{22}Ex_{23}FL(Y/F))$, wherein $x_{19}$ to $x_{23}$ can be any naturally occurring amino acid residue, and $x_{19}$ particularly represents L or R, in particular the motif of SEQ ID NOs: 70, 71 or 72, wherein said conserved sequence motif 3 corresponds to i. sequence positions 410 to 422 of SEQ ID NO: 3,
            ii. sequence positions 357 to 369 of SEQ ID NO: 6,
            iii. sequence positions 365 to 377 of SEQ ID NO: 9,
            iv. sequence positions 410 to 422 of SEQ ID NO: 12,
            v. sequence positions 349 to 361 of SEQ ID NO: 19, and
            vi. sequence positions 349 to 361 of SEQ ID NO: 26, respectively.

More particularly, a TPS of the present invention comprises a class II motif, a QW motif, and at least one of the conserved motifs 1, 2 and 3.

Even more particularly, a TPS of the present invention comprises a class II motif, a QW motif, and at least two of the conserved motifs 1, 2 and 3.

Still more particularly, a TPS of the present invention comprises a class II motif, a QW motif, and all three of the conserved motifs 1, 2 and 3.

Figure 21B:
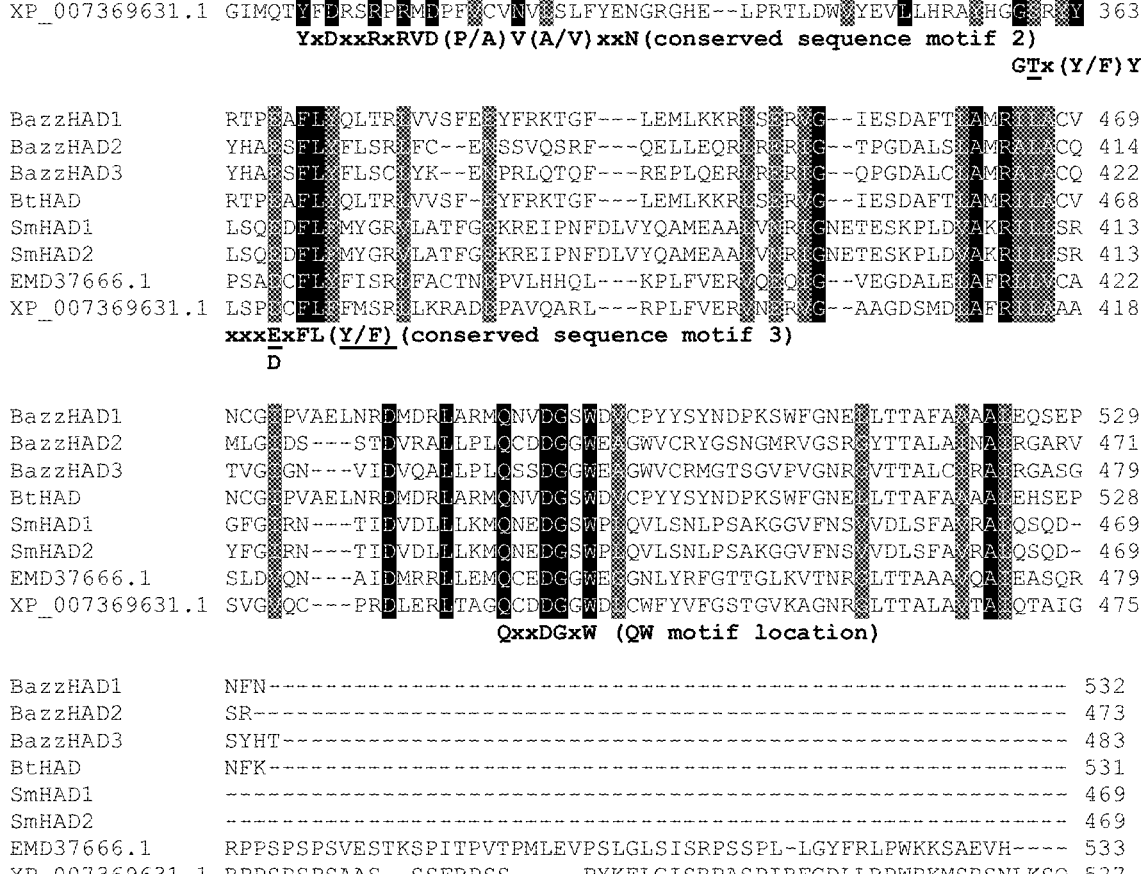
FIG. 21*b*. Amino acid sequences alignment of HAD-like TPSs: BazzHAD1 (SEQ ID NO: 3), BazzHAD2 (SEQ ID NO: 6), BazzHAD3 (SEQ ID NO: 9), BtHAD (SEQ ID NO: 12), SmHAD1 (SEQ ID NO: 19), SmHAD2 (SEQ ID NO: 26); EMD37666.1 (SEQ ID NO: 32) and XP_007369631.1 (SEQ ID NO: 36) as previously described in WO 2018/220113. The class I motif (DDxx(D/E); SEQ ID NO: 45) and class II motif (PxDxD(T/S)(T/M)S; SEQ ID NOs: 46) as well as three other conserved sequence motifs 1-3 (Lxxxx (W/F)xxYxxG; SEQ ID NO: 56, YxDxxRxRVD(P/A)V(V/A)xxN; SEQ ID NO: 62, GTx(Y/F)YxxxExFL(Y/F); SEQ ID NO: 69) are identified in the Figure.

The relative order of these sequence motifs of embodiment 6 within the respective amino acid sequences of each of the TPSs of the present invention is depicted below (see also FIGS. 21a-21b):

N-terminus—(conserved motif 1)—(class II motif)—(conserved motif 2)—(conserved motif 3)—(QW motif)—C-terminus The class I motif known from other TPS, which is missing in TPS of the invention would be located between Conserved Motif 1 and class II motif (see FIGS. 21a-21b).

7. The polypeptide of anyone of the preceding embodiments, which catalyzes the conversion of an acyclic farnesyl diphosphate (in particular of (2E,6E)-3,7,11-trimethyldodeca-2,6,10-triene-1-pyrophosphate; FPP) to an drimenyl phosphate derivative like a monophosphate and more particularly an drimenyl diphosphate, in particular with a selectivity of 50% ee or more, like 50 to 100% ee, or 60 to 90% ee or 70 to 80% ee.

8. The polypeptide of anyone of the preceding embodiments, which catalyses the conversion of an acyclic farnesyl diphosphate (in particular of (2E,6E)-3,7,11-trimethyldodeca-2,6,10-triene-1-pyrophosphate; FPP) to an albicanyl phosphate derivative like a monophosphate and more particularly an albicanyl diphosphate, in particular with a selectivity of 50% ee or more, like 50 to 100% ee, or 60 to 90% ee or 70 to 80% ee.

9. The isolated polypeptide of anyone of the preceding embodiments, which a. comprises an amino acid sequence selected from SEQ ID NOs: 3, 6, 9, 12, 19, and 26; or b. is encoded by a nucleic acid molecule comprising a coding nucleotide sequence selected from SEQ ID NOs: 1, 2, 4, 5, 7, 8, 10, 11, 17, 18, 24 and 25.

10. The isolated polypeptide of embodiment 9, which a. consists of an amino acid sequence selected from SEQ ID NOs: 3, 6, 9, 12, 19, and 26; or b. is encoded by a nucleic acid molecule consisting of a coding nucleotide sequence selected from SEQ ID NOs: 1, 2, 4, 5, 7, 8, 10, 11, 17, 18, 24 and 25.

11. An isolated nucleic acid molecule a. comprising a nucleotide sequence encoding the polypeptide of any one of the preceding embodiments; or b. comprising a nucleotide sequence selected from SEQ ID NOs: 1, 2, 4, 5, 7, 8, 10, 11, 17, 18, 24, and 25, or a nucleotide sequence having at least 40%, 45%, 50%, 55%, 60%, 65%, 70%, 75%, 80%, 85%, 90%, 95%, 96%, 97%, 98%, or 99% sequence identity to the nucleotide sequence of SEQ ID NOs: 1, 2, 4, 5, 7, 8, 17, 18, or 24, 25 and encoding a polypeptide of the HAD-like hydrolase superfamily, comprising terpene synthase activity, and in particular comprising the ability to produce a drimane sesquiterpene alcohol, and/or a phosphate precursor thereof, like a monophosphate and more particularly a diphosphate precursor thereof, in particular a drimenyl phosphate precursor like a monophosphate and more particularly an drimenyl diphosphate; and/oran albicanyl phosphate precursor like a monophosphate and more particularly an albicanyl diphosphate from farnesyl diphosphate (FPP) as substrate;

more particularly a product profile as described in Table 1, above; or c. comprising a nucleotide sequence comprising a sequence complementary to one of the sequences of b.; or d. comprising a nucleotide sequence hybridizing under stringent conditions to a nucleotide sequence of a., b. or c.

In one particular embodiment, the nucleic acid can be either present naturally in plants of the genus *Bazzania* or *Selaginella*, like the species *Bazzania trilobata* or *Selaginella moellendorffii*, or in other plant species, or be obtained by modifying SEQ ID NOs: 1, 2, 4, 5, 7, 8, 10, 11, 17, 18, 24, and 25 or the reverse complement thereof.

In another embodiment, the nucleic acid is isolated or is derived from plants of the genus *Bazzania* or *Selaginella*, like the species *Bazzania trilobata* or *Selaginella moellendorffili*

12. An expression construct comprising at least one nucleic acid molecule of embodiment 11, optionally in combination with at least one regulatory sequence.

13. A vector comprising at least one nucleic acid molecule of embodiment 11 or at least one expression construct of embodiment 12.

14. The vector of embodiment 13, wherein the vector is a prokaryotic, viral or eukaryotic vector.

15. The vector of embodiment 13 or 14, wherein the vector is an expression vector.

16. The vector of anyone of the embodiments 13 to 15, which is a plasmid vector.

17. A recombinant, non-natural non-human host cell or a recombinant non-human host organism, prepared by genetic engineering, comprising a. at least one isolated nucleic acid molecule of embodiment 11, optionally stably integrated into the genome; or b. at least one expression construct of embodiment 12, optionally stably integrated into the genome; or c. at least one vector of any one of embodiments 13 to 16.

A recombinant non-human host cell or a recombinant non-human host organism of this embodiment differs from natural non-human host cells or non-human host organisms in that foreign genetic material such as an isolated nucleic acid, an expression construct or a vector is artificially introduced into the host organism or host cell. A recombinant non-human host cell or a recombinant non-human host organism of this embodiment is a non-human host cell or non-human host organism (genetically) modified to comprise the desired foreign genetic material such as an isolated nucleic acid, an expression construct or a vector as described in the embodiments above. In particular, the recombinant non-human host cell or the recombinant non-human host organism of this embodiment is a cell or organism different from the cell or organism in which the desired genetic material is naturally present.

18. The host cell or host organism of embodiment 17, selected from a prokaryotic or eukaryotic organism, or a cell derived therefrom.

19. The host cell or host organism of embodiment 18, selected from bacterial, fungal and plant cells or plants.

20. The host cell or host organism of embodiment 19, wherein said fungal cells are yeast cells.

21. The host cell or host organism of embodiment 20, wherein said yeast cells are selected from the genus *Saccharomyces* or *Pichia*, in particular from the species *Saccharomyces cerevisiae* or *Pichia pastoris*.

22. The host cell or host organism of embodiment 18, wherein said bacterial cells are selected from the genus *Escherichia*, in particular from the species *E. coli*.

Some of these host cells or host organisms do not produce FPP naturally. To be suitable to carry out the method of an embodiment as described herein, organisms or cells that do not produce an acyclic terpene pyrophosphate precursor, e.g. FPP, naturally are genetically modified, in particular by transformation, transduction or conjugation, more particularly by transformation, to produce said precursor. The non-human host organism or non-human host cell can be, for example, modified (e.g., transformed) either before the modification with the nucleic acid described according to any of the above embodiments or simultaneously. Methods to modify (e.g., transform) organisms so that they produce an acyclic terpene pyrophosphate precursor, e.g. FPP, are already known in the art. For example, introducing enzyme activities of the mevalonate pathway (isoprenoid pathway) or MEP pathway is a suitable strategy to make the organism produce FPP (see also the examples section herein).

23. A method for producing at least one catalytically active polypeptide according to any one of embodiments 1 to 10 comprising:

a. culturing a non-human host cell or non-human host organism of embodiment 17 to express at least one polypeptide according to anyone of embodiments 1 to 10; and b. optionally isolating the polypeptide from the non-human host cell or organism cultured in step a.

24. The method of embodiment 23, further comprising, prior to step a. genetically modifying a non-human host cell or non-human host organism by inserting at least one nucleic acid according of embodiment 11, at least one expression construct of embodiment 12, or at least one vector of anyone of embodiments 13 to 16 into said non-human host cell or non-human host organism, in particular by transformation, transduction or conjugation, so that it expresses the polypeptide according to any one of embodiments 1 to 10.

25. A method for producing a drimane sesquiterpene alcohol, in particular drimenol and/or albicanol, comprising:

a. contacting farnesyl diphosphate (FPP) with a polypeptide as defined in anyone of embodiments 1 to 10, or with a polypeptide prepared according to embodiment 23 or 24, thereby obtaining at least one phosphate, in particular a diphosphate of drimane sesquiterpene alcohol, in particular a drimenyl and/or albicanyl phosphate, more particularly drimenyl diphosphate and/or albicanyl diphosphate;

b. chemically or enzymatically cleaving the phosphate moiety, in particular diphosphate moiety of said product obtained in step a.; and c. optionally isolating the drimane sesquiterpene alcohol, in particular drimenol and/or albicanol.

In a particular embodiment, the phosphate moiety is cleaved enzymatically, by applying a phosphatase enzyme, more particularly an acid or alkaline phosphatase. Alkaline phosphatases of different origin, like bacterial enzymes, are preferred. Suitable phosphatases are commercially available enzymes.

In one embodiment, the drimane sesquiterpene alcohol, in particular drimenol and/or albicanol, or the mixture comprising the drimane sesquiterpene alcohol is isolated.

In a particular embodiment, the above method further comprises as step d. processing of the drimane sesquiterpene alcohol, in particular drimenol and/or albicanol, formed in step b. or isolated in step c. to obtain a derivative thereof using chemical synthesis or biocatalytic synthesis (such as biochemical synthesis with expressed enzymes, or bioconversion with living cells that express enzymes) or a combination of both. Said drimane sesquiterpene alcohol derivative may in particular be selected from a hydrocarbon, alcohol, diol, triol, acetal, ketal, aldehyde, acid, ether, amide, ketone, lactone, epoxide, acetate, glycoside, and/or an ester. In one embodiment, the above method comprises contacting the drimane sesquiterpene alcohol with at least one enzyme to produce a drimane sesquiterpene alcohol derivative. In particular, the drimane sesquiterpene alcohol derivative can be obtained using a biochemical method by contacting the drimane sesquiterpene alcohol with an enzyme such as, but not limited to, an oxidoreductase, a monooxygenase, a dioxygenase, a transferase. The biochemical conversion can be performed in vitro using isolated enzymes, enzymes from lysed cells or in vivo using whole cells. In another embodiment, the above method comprises converting the drimane sesquiterpene alcohol to a drimane sesquiterpene alcohol derivative using chemical synthesis. In particular, the drimane sesquiterpene alcohol derivative can be obtained by a chemical method such as, but not limited to, oxidation, reduction, alkylation, acylation and/or rearrangement. In another embodiment, the above method comprises as step e. optionally isolating the derivative of step d.

26. The method of embodiment 25, wherein the drimane sesquiterpene alcohol comprises drimenol and/or albicanol, particularly as the main product.

27. The method of any one of embodiments 25 and 26, which comprises providing, in particular transforming, a non-human host cell or non-human host organism with at least one nucleic acid according to embodiment 11, at least one expression construct of embodiment 12, or at least one vector of anyone of the embodiments 13 to 16 so that it expresses a polypeptide according to any one of embodiments 1 to 10.

28. The method of any one of embodiments 25 to 27, wherein FPP is contacted with a non-human host cell or non-human host organism of any one of embodiments 17 to 22, with a cell lysate thereof, or a culture medium containing said non-human host cell or non-human host organism; and/or with the polypeptide as defined in anyone of the embodiments 1 to 10, expressed in or isolated from said non-human host cell or non-human host organism, cell lysate or culture medium.

29. The method of embodiment 28, wherein said drimane sesquiterpene alcohol is fermentatively produced by said non-human host organism or non-human host cell.

30. The method of embodiment 28, wherein said drimane sesquiterpene alcohol is produced by an enzymatic process, comprising the conversion of FPP with an isolated polypeptide of anyone of the embodiments 1 to 10, optionally in the presence of further adjuvants.

In a particular embodiment, in the method of any one of embodiments 25 to 30, the polypeptide comprises a. an amino acid sequence having at least 90% sequence identity to SEQ ID NO: 3 or SEQ ID NO: 12;

b. a class II synthase motif having the amino acid sequence PDDLDSTS (SEQ ID NO: 47); and c. a QW motif having the amino acid sequence QNVDGSW (SEQ ID NO: 52); and d. optionally at least one further sequence motif selected from the amino acid sequences i. Lxxxx(W/F)xxYxxG (SEQ ID NO: 56), wherein x can be any naturally occurring amino acid residue, and particularly the amino acid sequence LRSHIWFNYSMG (SEQ ID NO: 57);

ii. YxDxxRxRVD(P/A)V(V/A)xxN (SEQ ID NO: 62), wherein x can be any naturally occurring amino acid residue, and particularly the amino acid sequence YFDPLRLRVDPVAATN (SEQ ID NO: 63); and iii. GTx(Y/F)xYxxxExFL(Y/F) (SEQ ID NO: 69), wherein x can be any naturally occurring amino acid residue, and particularly the amino acid sequence GTLYYRTPEAFLY (SEQ ID NO: 70);

and the drimane sesquiterpene alcohol comprises drimenol.

In another particular embodiment, in the method of any one of embodiments 25 to 30, the polypeptide comprises a. an amino acid sequence having at least 90% sequence identity to SEQ ID NO: 6 or SEQ ID NO: 9;

b. a class II synthase motif having the amino acid sequence PxDxD(T/S)(T/M)S (SEQ ID NO 46), wherein x can be any naturally occurring amino acid residue, and particularly the amino acid sequence PDDLDTTS (SEQ ID NO: 48) or PNDLDTTS (SEQ ID NO: 50); and c. a QW motif comprising the amino acid sequence Qxix$_2$DGx$_3$W (SEQ ID NO: 51), wherein x$_1$ and x$_2$ can be any naturally occurring amino acid residue and x$_3$ is G, and particularly the amino acid sequence QCDDGGW (SEQ ID NO: 53) or QSSDGGW (SEQ ID NO: 54); and d. optionally at least one further sequence motif selected from the amino acid sequences i. LRxxTWxxYECG (SEQ ID NO: 61), wherein x can be any naturally occurring amino acid residue, and particularly the amino acid sequence LRSATWAAYECG (SEQ ID NO: 58) or LRTPTWGKYECG (SEQ ID NO: 59);

ii. Y(F/L)Dx(T/E)RPRVD(P/A)VVx(A/V)N(SEQ ID NO: 68), wherein x can be any naturally occurring amino acid residue, and particularly the amino acid sequence YFDETRPRVDAVVNVN (SEQ ID NO: 64) or YFDKTRPRVDPVVCVN (SEQ ID NO: 65); and iii. GTx(Y/F)YxxxExFL(Y/F) (SEQ ID NO: 69), wherein x can be any naturally occurring amino acid residue, and particularly the amino acid sequence GTLFYYHAESFLY (SEQ ID NO: 71);

and the drimane sesquiterpene alcohol comprises albicanol.

In another particular embodiment, in the method of any one of embodiments 25 to 30, the polypeptide comprises a. an amino acid sequence having at least 90% sequence identity to SEQ ID NO: 19 or SEQ ID NO: 26;

b. a class II synthase motif having the amino acid sequence PPDIDTMS (SEQ ID NO: 49); and c. a QW motif having the amino acid sequence QNEDGSW (SEQ ID NO: 55); and d. optionally at least one further sequence motif selected from the amino acid sequences i. Lxxxx(W/F)xxYxxG (SEQ ID NO: 56), wherein x can be any naturally occurring amino acid residue, and particularly the amino acid sequence LQHSS-FLAYSCG (SEQ ID NO: 60);

ii. Y(F/L)Dx(T/E)RPRVD(P/A)VVx(A/V)N(SEQ ID NO: 68), wherein x can be any naturally occurring amino acid residue, and particularly the amino acid sequence YLDVERPRVDPVVIAN (SEQ ID NO: 66) or YLDLERPRVDPVVIAN (SEQ ID NO: 67); and iii. GTx(Y/F)xYxxxExFLx (SEQ ID NO: 69), wherein x can be any naturally occurring amino acid residue, and particularly the amino acid sequence GTRYYLSQEDFLF (SEQ ID NO: 72);

and the drimane sesquiterpene alcohol comprises drimenol and albicanol.

More particularly, the TPS as applied comprises a class II motif, a QW motif, and at least one of the conserved motifs i., ii. and iii.

Even more particularly, a TPS as applied comprises a class II motif, a QW motif, and at least two of the conserved motifs i., ii. and iii.

Still more particularly, a TPS as applied comprises a class II motif, a QW motif, and all three of the conserved motifs i., ii. and iii.

31. The use of a polypeptide as defined in anyone of the embodiments 1 to 10 for preparing odorants, flavours or fragrance ingredients, in particular Ambrox (preferably via drimenol/drimenyl diphosphate).

32. The use of a drimane sesquiterpene alcohol as prepared according to anyone of the embodiments 25 to 30 for preparing odorants, flavours or fragrance ingredients, in particular Ambrox.

33. A method of producing Ambrox, which method comprises a. providing drimenol and/or albicanol by a method of anyone of the embodiments as recited in any one of embodiments 25 to 30, b. optionally isolating drimenol and/or albicanol as produced in step a.; and c. converting drimenol and/or albicanol in a manner know per se to Ambrox, for example as reported in Tetrahedron: Asymmetry 11 (2000) 1375-1388.

34. A composition comprising the substance prepared according to embodiment 32 or 33.

35. The composition according to embodiment 34 selected from the group consisting of body care compositions, home care compositions and fragrance compositions.

36. A method for producing a drimane sesquiterpene alcohol, in particular drimenol and/or albicanol, comprising:

a. culturing a non-human host organism or a non-human host cell capable of producing FPP and transformed to express a polypeptide of anyone of the embodiments 1 to 10; and b. optionally isolating the drimane sesquiterpene alcohol, in particular drimenol and/or albicanol.

In one embodiment, a non-human host organism or a non-human host cell which does not produce FPP naturally is genetically modified, in particular by transformation, transduction or conjugation, more particularly by transformation, to produce said precursor. The non-human host organism or non-human host cell may be, for example, modified (e.g., transformed) either before the modification with the nucleic acid described according to any of the above embodiments or simultaneously. Methods to modify (e.g., transform) organisms so that they produce an acyclic terpene pyrophosphate precursor, e.g. FPP, are already known in the art. For example, introducing enzyme activities of the mevalonate pathway (isoprenoid pathway) or MEP pathway is a suitable strategy to make the organism produce FPP (see also the examples section herein).

37. A method for preparing a mutant polypeptide of the Haloacid dehalogenase-like (HAD-like) hydrolase superfamily comprising terpene synthase activity, in particular comprising the ability to produce a drimane sesquiterpene alcohol, and/or a phosphate derivative thereof, like a monophosphate and more particularly a diphosphate derivative thereof; and in particular to produce a drimenyl phosphate derivative like a monophosphate and more particularly a drimenyl diphosphate, and/or an albicanyl phosphate derivative like a monophosphate and more particularly an albicanyl diphosphate, from farnesyl diphosphate (FPP) as substrate, which method comprises the steps of:

a. selecting a nucleic acid molecule according to embodiment 11;

b. modifying the selected nucleic acid molecule to obtain at least one mutant nucleic acid molecule;

c. genetically modifying non-human host cells or unicellular non-human host organisms with the mutant nucleic acid sequence to express a polypeptide encoded by the mutant nucleic acid sequence, in particular by horizontal gen transfer such as transformation, transduction or conjugation, more particularly by transforming said host cells or unicellular host organisms;

d. screening the expression product for at least one mutant comprising terpene synthase activity, in particular comprising the ability to produce a drimane sesquiterpene alcohol, and/or a phosphate precursor thereof, like a monophosphate and more particularly a diphosphate derivative thereof; and in particular to produce a drimenyl phosphate precursor like a monophosphate and more particularly a drimenyl diphosphate, and/or an albicanyl phosphate precursor like a monophosphate and more particularly an albicanyl diphosphate, from FPP as substrate; and, e. optionally, if the polypeptide has no desired mutant activity, repeat the process steps a. to d. until a polypeptide with a desired mutant activity is obtained; and, f. optionally, if a polypeptide having a desired mutant activity was identified in step d., isolating the corresponding mutant nucleic acid obtained in step c.

If not stated otherwise within the above degree ranges of "at least 40%, 45%, 50%, 55%, 60%, 65%, 70%, 75%, 80%, 85%, 90%, 95%, 96%, 97%, 98%, or 99% sequence identity", particular values are those of at least 60%, 65%, 70%, 75%, 80%, 85%, 90%, 95%, 96%, 97%, 98%, or 99% sequence identity and values of at least 80%, 85%, 90%, 95%, 96%, 97%, 98%, or 99% sequence identity are even more particular.

c. Polypeptides Applicable According to the Invention

In this context the following definitions apply: The generic term "polypeptide" or "peptide", which may be used interchangeably, refers to a natural or synthetic linear chain of consecutive, peptidically linked amino acid residues (amino acid sequence), comprising about 10 residues up to more than 1.000 residues. In some embodiments provided herein, a polypeptide comprises an amino acid sequence that is an enzyme, or a fragment, or a variant thereof. Short chain polypeptides with up to 30 residues are also designated as "oligopeptides".

The term "isolated polypeptide" refers to an amino acid sequence that is removed from its natural environment by any method or combination of methods known in the art and includes recombinant, biochemical and synthetic methods.

The term "protein" refers to a macromolecular structure consisting of one or more polypeptides. It includes oligopeptides, peptides, polypeptides and full length proteins whether naturally occurring or synthetic. The amino acid sequence of its polypeptide(s) represents the "primary structure" of the protein. The amino acid sequence also predetermines the "secondary structure" of the protein by the formation of special structural elements, such as alpha-helical and beta-sheet structures formed within a polypeptide chain. The arrangement of a plurality of such secondary structural elements defines the "tertiary structure" or spatial arrangement of the protein. If a protein comprises more than one polypeptide chains said chains are spatially arranged forming the "quaternary structure" of the protein. A correct spatial arrangement or "folding" of the protein is prerequisite of protein function. Denaturation or unfolding destroys protein function. If such destruction is reversible, protein function may be restored by refolding.

A typical protein function referred to herein is an "enzyme function", i.e. the protein acts as biocatalyst on a substrate, for example a chemical compound, and catalyzes the conversion of said substrate to a product. An enzyme may show a high or low degree of substrate and/or product specificity.

A "polypeptide" referred to herein as having a particular "activity" thus implicitly refers to a correctly folded protein showing the indicated activity, as for example a specific enzyme activity. Thus, unless otherwise indicated the term "polypeptide" also encompasses the terms "protein" and "enzyme".

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, i.e., N-terminal end, of the protein or polypeptide, or may be used to replace a native targeting polypeptide.

The present invention also relates to "functional equivalents" (also designated as "analogs" or "functional mutations") of the polypeptides specifically described herein.

For example, "functional equivalents" refer to polypeptides which, in a test used for determining enzymatic drimenyl and/or albicanyl diphosphate synthase activity, display at least a 1 to 10%, or at least 20%, or at least 50%, or at least 75%, or at least 90% higher or lower drimenyl and/or albicanyl diphosphate synthase activity, as that of the polypeptides specifically described herein.

"Functional equivalents", according to the invention, also cover particular mutants, which, in at least one sequence position of an amino acid sequences stated herein, have an amino acid that is different from that concretely stated one, but nevertheless possess one of the aforementioned biological activities, as for example enzyme activity. "Functional equivalents" thus comprise mutants obtainable by one or more, like 1 to 20, in particular 1 to 15 or 5 to 10 amino acid additions, substitutions, in particular conservative substitutions (i.e. the amino acid in question is replaced by an amino acid of the same charge, size, polarity and/or solubility), deletions and/or inversions, where the stated changes can occur in any sequence position, provided they lead to a mutant with the profile of properties according to the invention. Functional equivalence is in particular also provided if the activity patterns coincide qualitatively between the mutant and the unchanged polypeptide, i.e. if, for example, interaction with the same agonist or antagonist or substrate, however at a different rate, (i.e. expressed by a $EC_{50}$ or $IC_{50}$ value or any other parameter suitable in the present technical field) is observed. Examples of suitable (conservative) amino acid substitutions are shown in the following table:

| Original residue | Examples of substitution |
| --- | --- |
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described herein, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent polypeptides can be determined on the basis of the concrete parameters of the invention.

"Functional equivalents" also comprise "fragments", like individual domains or sequence motifs, of the polypeptides according to the invention, or N- and or C-terminally truncated forms, which may or may not display the desired biological function. Preferably such "fragments" retain the desired biological function at least qualitatively.

"Functional equivalents" are, moreover, fusion proteins which have one of the polypeptide sequences stated herein or functional equivalents derived therefrom and at least one further, functionally different, heterologous sequence in functional N-terminal or C-terminal association (i.e. without substantial mutual functional impairment of the fusion protein parts). Non-limiting examples of these heterologous sequences are, e.g., signal peptides, histidine anchors or enzymes.

"Functional equivalents" which are also comprised in accordance with the invention are homologs to the specifically disclosed polypeptides. These have at least 60%, preferably at least 75%, in particular at least 80 or 85%, such as, for example, 90, 91, 92, 93, 94, 95, 96, 97, 98 or 99%, homology (or identity) to one of the specifically disclosed amino acid sequences, calculated by the algorithm of Pearson and Lipman, Proc. Natl. Acad, Sci. (USA) 85(8), 1988, 2444-2448. A homology or identity, expressed as a percentage, of a homologous polypeptide according to the invention means in particular an identity, expressed as a percentage, of the amino acid residues based on the total length of one of the amino acid sequences described specifically herein.

The identity data, expressed as a percentage, may also be determined with the aid of BLAST alignments, algorithm blastp (protein-protein BLAST), or by applying the Clustal settings specified herein below.

In the case of a possible protein glycosylation, "functional equivalents" according to the invention comprise polypeptides as described herein in deglycosylated or glycosylated form as well as modified forms that can be obtained by altering the glycosylation pattern.

Functional equivalents or homologues of the polypeptides according to the invention can be produced by mutagenesis, e.g. by point mutation, lengthening or shortening of the protein or as described in more detail below.

Functional equivalents or homologs of the polypeptides according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art.

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues.

An embodiment provided herein provides orthologs and paralogs of polypeptides disclosed herein as well as methods for identifying and isolating such orthologs and paralogs. A definition of the terms "ortholog" and "paralog" is given below and applies to amino acid and nucleic acid sequences.

The polypeptides of the invention include all active forms, including active subsequences, e.g., catalytic domains or active sites, of an enzyme of the invention. In one aspect, the invention provides catalytic domains or active sites as set forth below. In one aspect, the invention provides a peptide or polypeptide comprising or consisting of an active site domain as predicted through use of a database such as Pfam (pfam.wustl.edu/hmmsearch.shtml) (which is a large collection of multiple sequence alignments and hidden Markov models covering many common protein families, The Pfam protein families database, A. Bateman, E. Birney, L. Cerruti, R. Durbin, L. Etwiller, S. R. Eddy, S. Griffiths-Jones, K. L. Howe, M. Marshall, and E. L. L. Sonnhammer, Nucleic Acids Research, 30(1):276-280, 2002) or equivalent, as for example InterPro and SMART databases (www.ebi.ac.uk/interpro/scan.html, smart.embl-heidelberg.de/).

The invention also encompasses a "polypeptide variant" having the desired activity, wherein the variant polypeptide is selected from an amino acid sequence having at least 40%, 45%, 50%, 55%, 60%, 65%, 70%, 75%, 80%, 85%, 90%, 91%, 92%, 93%, 94%, 95%, 96%, 97%, 98% or 99%, sequence identity to a specific, in particular natural, amino acid sequence as referred to by a specific SEQ ID NO and contains at least one, as for example 1 to 30 or 1 to 20, like 1, 2, 3, 4, 5, 6, 7, 8, 9 or 10 amino acid sequence differences, such as amino acid additions, substitutions, insertions or deletions relative to said (non-modified) SEQ ID NO.

d. Coding Nucleic Acid Sequences Applicable According to the Invention

In this context the following definitions apply:

The terms "nucleic acid sequence", "nucleic acid", "nucleic acid molecule" and "polynucleotide" are used interchangeably meaning a sequence of nucleotides. A nucleic acid sequence may be a single-stranded or double-stranded deoxyribonucleotide, or ribonucleotide, of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U).

The term "nucleotide sequence" should also be understood as comprising a polynucleotide molecule or an oligonucleotide molecule in the form of a separate fragment or as a component of a larger nucleic acid.

The term "naturally-occurring" as used herein as applied to a nucleic acid refers to a nucleic acid that is found in a cell or an organism in nature and which has not been intentionally modified by a human in the laboratory.

A "fragment" of a polynucleotide or nucleic acid sequence refers to a contiguous nucleotide that is particularly at least 15 bp, at least 30 bp, at least 40 bp, at least 50 bp and/or at least 60 bp in length of the polynucleotide of an embodiment herein. Particularly, the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

"Recombinant nucleic acid sequences" are nucleic acid sequences that result from the use of laboratory methods (for example, molecular cloning) to bring together genetic material from more than one source, creating or modifying a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002, Cold Spring Harbor Lab Press; and Sambrook et al., 1989, Cold Spring Harbor, NY, Cold Spring Harbor Laboratory Press.

The term "gene" means a DNA sequence comprising a region which is transcribed into a RNA molecule, e.g., an mRNA in a cell, operably linked to suitable regulatory regions, e.g., a promoter. A gene may thus comprise several operably linked sequences, such as a promoter, a 5'-leader sequence comprising, e.g., sequences involved in translation initiation, a coding region of cDNA or genomic DNA, introns, exons, and/or a 3'-non-translated sequence comprising, e.g., transcription termination sites.

A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region", or "3'end") refers to the nucleic acid sequence found downstream of the coding sequence of a gene, which comprises, for example, a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., the cytoplasm.

The term "primer" refers to a short nucleic acid sequence that is hybridized to a template nucleic acid sequence and is used for polymerization of a nucleic acid sequence complementary to the template.

The invention also relates to nucleic acid sequences that code for polypeptides as defined herein.

In particular, the invention also relates to nucleic acid sequences (single-stranded and double-stranded DNA and RNA sequences, e.g. cDNA, genomic DNA and mRNA), coding for one of the above polypeptides and their functional equivalents which can be obtained for example using artificial nucleotide analogs.

The present invention also relates to nucleic acids with a certain degree of "identity" to the sequences specifically disclosed herein. "Identity" between two nucleic acids means identity of the nucleotides, in each case over the entire length of the nucleic acid.

The "identity" between two nucleotide sequences (the same applies to peptide or amino acid sequences) is a function of the number of nucleotide residues (or amino acid residues) that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web. Particularly, the BLAST program (Tatiana et al, FEMS Microbiol Lett., 1999, 174: 247-250, 1999) set to the default parameters, available from the National Center for Biotechnology Information (NCBI) website at blast.ncbi.nlm.nih.gov/Blast.cgi, can be used to obtain an optimal alignment of protein or nucleic acid sequences and to calculate the percentage of sequence identity. In another example the identity may be calculated by means of the Vector NTI Suite 7.1 program of the company Informax (USA) employing the Clustal Method (Higgins D G, Sharp P M. (1989)) with the following settings:

Multiple Alignment Parameters:

| Gap opening penalty | 10 |
| Gap extension penalty | 10 |
| Gap separation penalty range | 8 |
| Gap separation penalty | off |
| % identity for alignment delay | 40 |
| Residue specific gaps | off |

-continued

| | | |
|---|---|---|
| Hydrophilic residue gap | off | |
| Transition weighing | 0 | |

Pairwise Alignment Parameter:

| | | |
|---|---|---|
| FAST algorithm | on | |
| K-tuple size | 1 | |
| Gap penalty | 3 | |
| Window size | 5 | |
| Number of best diagonals | 5 | |

Alternatively the identity may be determined according to Chenna, et al. (2003), the web page: www.ebi.ac.uk/Tools/clustalw/index.html # and the following settings

| | | |
|---|---|---|
| DNA Gap Open Penalty | 15.0 | |
| DNA Gap Extension Penalty | 6.66 | |
| DNA Matrix | Identity | |
| Protein Gap Open Penalty | 10.0 | |
| Protein Gap Extension Penalty | 0.2 | |
| Protein matrix | Gonnet | |
| Protein/DNA ENDGAP | −1 | |
| Protein/DNA GAPDIST | 4 | |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual over-lapping, complementary nucleic acid building blocks of the double helix. Chemical synthesis of oligonucleotides can, for example, be performed in a known way, by the phos-phoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The nucleic acid molecules according to the invention can in addition contain non-translated sequences from the 3' and/or 5' end of the coding genetic region.

The invention further relates to the nucleic acid molecules that are complementary to the concretely described nucleo-tide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (as defined herein elsewhere) on at least about 12, preferably at least about 25, for example about 40, 50 or 75 successive nucleotides of a sense strand of a nucleic acid sequence according to the invention or of a corresponding antisense strand.

"Homologous" sequences include orthologous or paralo-gous sequences. Methods of identifying orthologs or para-logs including phylogenetic methods, sequence similarity and hybridization methods are known in the art and are described herein.

"Paralogs" result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

"Orthologs", or "orthologous sequences", are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homolo-gous sequences is comparing of the transcript profiles in host cells or host organisms, such as plants or microorganisms, overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner by making the host cells, host organisms such as plants or microorganisms producing terpene synthase pro-teins.

The term "selectable marker" refers to any gene which upon expression may be used to select a cell or cells that include the selectable marker. Examples of selectable mark-ers are described below. The skilled artisan will know that different antibiotic, fungicide, auxotrophic or herbicide selectable markers are applicable to different target species.

The invention relates to both isolated nucleic acid mol-ecules, which code for polypeptides according to the inven-tion or biologically active segments thereof, and to nucleic acid fragments, which can be used for example as hybrid-ization probes or primers for identifying or amplifying coding nucleic acids according to the invention.

An "isolated nucleic acid" or "isolated nucleic acid sequence" relates to a nucleic acid or nucleic acid sequence that is in an environment different from that in which the nucleic acid or nucleic acid sequence naturally occurs and can include those that are substantially free from contami-nating endogenous material. An isolated nucleic acid mol-ecule is, thus, separated from other nucleic acid molecules that are present in the natural source of the nucleic acid and can moreover be substantially free from other cellular mate-rial or culture medium, if it is being produced by recombi-nant techniques, or can be free from chemical precursors or other chemicals, if it is being synthesized chemically.

A nucleic acid molecule according to the invention can be isolated by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, (1989)).

In addition, a nucleic acid molecule comprising one of the disclosed sequences, or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences according to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These "standard conditions" vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), (1985), Brown (ed) (1991).

"Hybridization" can in particular be carried out under stringent conditions. Such hybridization conditions are for example described in Sambrook (1989), or in Current Protocols in Molecular Biology, John Wiley & Sons, N.Y. (1989), 6.3.1-6.3.6.

As used herein, the term "hybridization" or "hybridizes under certain conditions" is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995, Current Protocols in Molecular Biology, John Wiley & Sons, sections 2, 4, and 6). Additionally, stringency conditions are described in Sambrook et al. (1989, Molecular Cloning: A Laboratory Manual, 2nd ed., Cold Spring Harbor Press, chapters 7, 9, and 11).

As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10⁶ cpm of 32P-labeled probe is used. Filters are incubated in hybridization mixture for 18-20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5-20×10⁶ cpm of 32P-labeled probe is used. Filters are incubated in hybridization mixture for 30 h at 50° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in the prehybridization mixture containing 100 µg/ml denatured salmon sperm DNA and 5-20×10⁶ cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes.

Other conditions of low, moderate, and high stringency well known in the art (e.g., as employed for cross-species hybridizations) may be used if the above conditions are inappropriate (e.g., as employed for cross-species hybridizations).

A detection kit for nucleic acid sequences encoding a polypeptide of the invention may include primers and/or probes specific for nucleic acid sequences encoding the polypeptide, and an associated protocol to use the primers and/or probes to detect nucleic acid sequences encoding the polypeptide in a sample. Such detection kits may be used to determine whether a plant, organism, microorganism or cell has been modified, i.e., transformed with a sequence encoding the polypeptide.

To test a function of variant DNA sequences according to an embodiment herein, the sequence of interest is operably linked to a selectable or screenable marker gene and expression of said reporter gene is tested in transient expression assays, for example, with microorganisms or with protoplasts or in stably transformed plants.

The invention also relates to derivatives of the concretely disclosed or derivable nucleic acid sequences.

Thus, further nucleic acid sequences according to the invention can be derived from the sequences specifically disclosed herein and can differ from it by one or more, like 1 to 20, in particular 1 to 15 or 5 to 10 additions, substitutions, insertions or deletions of one or several (like for example 1 to 10) nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism.

According to a particular embodiment of the invention variant nucleic acids may be prepared in order to adapt its nucleotide sequence to a specific expression system. For example, bacterial expression systems are known to more efficiently express polypeptides if amino acids are encoded by particular codons. Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the polypeptides described herein may be optimized for increased expression in the host cell. For example, nucleic acids of an embodiment herein may be synthesized using codons particular to a host for improved expression.

The invention also encompasses naturally occurring variants, e.g. splicing variants or allelic variants, of the sequences described therein.

Allelic variants may have at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

The invention also relates to sequences that can be obtained by conservative nucleotide substitutions (i.e. as a result thereof the amino acid in question is replaced by an amino acid of the same charge, size, polarity and/or solubility).

The invention also relates to the molecules derived from the concretely disclosed nucleic acids by sequence polymorphisms. Such genetic polymorphisms may exist in cells from different populations or within a population due to natural allelic variation. Allelic variants may also include functional equivalents. These natural variations usually produce a variance of 1 to 5% in the nucleotide sequence of a gene. Said polymorphisms may lead to changes in the amino acid sequence of the polypeptides disclosed herein. Allelic variants may also include functional equivalents.

Furthermore, derivatives are also to be understood to be homologs of the nucleic acid sequences according to the invention, for example animal, plant, fungal or bacterial homologs, shortened sequences, single-stranded DNA or RNA of the coding and noncoding DNA sequence. For example, homologs have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

e. Generation of Functional Polypeptide Mutants

Moreover, a person skilled in the art is familiar with methods for generating functional mutants, that is to say nucleotide sequences which code for a polypeptide with at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to anyone of amino acid related SEQ ID NOs as disclosed herein and/or encoded by a nucleic acid molecule comprising a nucleotide sequence having at least 70% sequence identity to anyone of the nucleotide related SEQ ID NOs as disclosed herein.

Depending on the technique used, a person skilled in the art can introduce entirely random or else more directed mutations into genes or else noncoding nucleic acid regions (which are for example important for regulating expression) and subsequently generate genetic libraries. The methods of molecular biology required for this purpose are known to the skilled worker and for example described in Sambrook and Russell, Molecular Cloning. 3$^{rd}$ Edition, Cold Spring Harbor Laboratory Press 2001.

Methods for modifying genes and thus for modifying the polypeptide encoded by them have been known to the skilled worker for a long time, such as, for example site-specific mutagenesis, where individual or several nucleotides of a gene are replaced in a directed fashion (Trower M K (Ed.) 1996; In vitro mutagenesis protocols. Humana Press, New Jersey), saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcarel R, Stunnenberg H G (1994) Nucleic Acids Res 22:541; Barik S (1995) Mol Biotechnol 3:1), error-prone polymerase chain reaction, where nucleotide sequences are mutated by error-prone DNA polymerases (Eckert K A, Kunkel T A (1990) Nucleic Acids Res 18:3739), the SeSaM method (sequence saturation method), in which preferred exchanges are prevented by the polymerase. Schenk et al., Biospektrum, Vol. 3, 2006, 277-279), the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an *E. coli* mutator strain. In: Trower M K (Ed.) In vitro mutagenesis protocols. Humana Press, New Jersey), or DNA shuffling, in which a pool of closely related genes is formed and digested and the fragments are used as templates for a polymerase chain reaction in which, by repeated strand separation and reassociation, full-length mosaic genes are ultimately generated (Stemmer W P C (1994) Nature 370:389; Stemmer W P C (1994) Proc Natl Acad Sci USA 91:10747).

Using so-called directed evolution (described, inter alia, in Reetz M T and Jaeger K-E (1999), Topics Curr Chem 200:31; Zhao H, Moore J C, Volkov A A, Arnold F H (1999), Methods for optimizing industrial polypeptides by directed evolution, In: Demain A L, Davies J E (Ed.) Manual of industrial microbiology and biotechnology, American Society for Microbiology), a skilled worker can produce functional mutants in a directed manner and on a large scale. To this end, in a first step, gene libraries of the respective polypeptides are first produced, for example using the methods given above. The gene libraries are expressed in a suitable way, for example by bacteria or by phage display systems.

The relevant genes of host organisms which express functional mutants with properties that largely correspond to the desired properties can be submitted to another mutation cycle. The steps of the mutation and selection or screening can be repeated iteratively until the present functional mutants have the desired properties to a sufficient extent. Using this iterative procedure, a limited number of mutations, for example 1, 2, 3, 4 or 5 mutations, can be performed in stages and assessed and selected for their influence on the activity in question. The selected mutant can then be submitted to a further mutation step in the same way. In this way, the number of individual mutants to be investigated can be reduced significantly.

The results according to the invention also provide important information relating to structure and sequence of the relevant polypeptides, which is required for generating, in a targeted fashion, further polypeptides with desired modified properties. In particular, it is possible to define so-called "hot spots", i.e. sequence segments that are potentially suitable for modifying a property by introducing targeted mutations.

Information can also be deduced regarding amino acid sequence positions, in the region of which mutations can be effected that should probably have little effect on the activity, and can be designated as potential "silent mutations".

f. Constructs for Expressing Polypeptides of the Invention

In this context the following definitions apply:

"Expression of a gene" encompasses "heterologous expression" and "overexpression" and involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one "regulatory sequence", which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

"Promoter" refers to a nucleic acid sequence that controls the expression of a coding sequence by providing a binding site for RNA polymerase and other factors required for proper transcription including, without limitation, transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequence is usually located downstream of the promoter with respect to the direction of the transcription starting at the transcription initiation site.

In this context, a "functional" or "operative" linkage is understood as meaning for example the sequential arrangement of one of the nucleic acids with a regulatory sequence. For example the sequence with promoter activity and of a nucleic acid sequence to be transcribed and optionally further regulatory elements, for example nucleic acid sequences which ensure the transcription of nucleic acids, and for example a terminator, are linked in such a way that each of the regulatory elements can perform its function upon transcription of the nucleic acid sequence. This does not necessarily require a direct linkage in the chemical sense. Genetic control sequences, for example enhancer sequences, can even exert their function on the target sequence from more remote positions or even from other DNA molecules. Preferred arrangements are those in which the nucleic acid sequence to be transcribed is positioned behind (i.e. at the 3'-end of) the promoter sequence so that the two sequences are joined together covalently. The distance between the promoter sequence and the nucleic acid sequence to be expressed recombinantly can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, CA (1990).

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences to be linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartments. Such nucleotide sequences particularly encode proteins conferring desirable phenotypic traits to the host cells or host organism altered (genetically modified) or transformed therewith. More particularly, the associated nucleotide sequence leads to the production of the product or products of interest as herein defined in the cell or organism, such as particularly albicanol and/or drimenol or a mixture comprising albicanol and/or drimenol or a mixture comprising albicanol and/or drimenol and one or more terpenes. Particularly, the nucleotide sequence encodes a polypeptide having an enzyme activity as herein defined, such as particularly a terpene synthase.

An "expression system" as used herein encompasses any combination of nucleic acid molecules required for the expression of one, or the co-expression of two or more polypeptides either in vivo of a given expression host, or in vitro. The respective coding sequences may either be located on a single nucleic acid molecule or vector, as for example a vector containing multiple cloning sites, or on a polycistronic nucleic acid, or may be distributed over two or more physically distinct vectors.

As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs, oligo dT primer) for amplifying (e.g., by polymerase chain reaction, PCR) naturally expressed (e.g., genomic DNA or mRNA) or recombinant (e.g., cDNA) nucleic acids of the invention in vivo, ex vivo or in vitro.

The nucleotide sequence as described herein above may be part of an "expression cassette". The terms "expression cassette" and "expression construct" are used synonymously. The (preferably recombinant) expression construct contains a nucleotide sequence which encodes a polypeptide according to the invention and which is under genetic control of regulatory nucleic acid sequences.

In a process applied according to the invention, the expression cassette may be part of an "expression vector", in particular of a recombinant expression vector.

An "expression unit" is understood as meaning, in accordance with the invention, a nucleic acid with expression activity which comprises a promoter as defined herein and, after functional linkage with a nucleic acid to be expressed or with a gene to be expressed, regulates the expression, i.e. the transcription and the translation of said nucleic acid or said gene. It is therefore in this connection also referred to as a "regulatory nucleic acid sequence". In addition to the promoter, other regulatory elements, for example enhancers, can also be present.

An "expression cassette" or "expression construct" is understood as meaning, in accordance with the invention, an expression unit which is functionally linked to the nucleic acid to be expressed or the gene to be expressed. In contrast to an expression unit, an expression cassette therefore comprises not only nucleic acid sequences which regulate transcription and translation, but also the nucleic acid sequences that are to be expressed as protein as a result of transcription and translation.

The terms "expression" or "overexpression" describe, in the context of the invention, the production or increase in intracellular activity of one or more polypeptides in a microorganism, which are encoded by the corresponding DNA. To this end, it is possible for example to introduce a gene into an organism, replace an existing gene with another gene, increase the copy number of the gene(s), use a strong promoter or use a gene which encodes for a corresponding polypeptide with a high activity; optionally, these measures can be combined.

Preferably such constructs according to the invention comprise a promoter 5'-upstream of the respective coding sequence and a terminator sequence 3'-downstream and optionally other usual regulatory elements, in each case in operative linkage with the coding sequence.

Nucleic acid constructs according to the invention comprise in particular a sequence coding for a polypeptide for example derived from the amino acid related SEQ ID NOs as described therein or the reverse complement thereof, or derivatives and homologs thereof and which have been linked operatively or functionally with one or more regulatory signals, advantageously for controlling, for example increasing, gene expression.

In addition to these regulatory sequences, the natural regulation of these sequences may still be present before the actual structural genes and optionally may have been genetically modified so that the natural regulation has been switched off and expression of the genes has been enhanced. The nucleic acid construct may, however, also be of simpler construction, i.e. no additional regulatory signals have been inserted before the coding sequence and the natural promoter, with its regulation, has not been removed. Instead, the natural regulatory sequence is mutated such that regulation no longer takes place and the gene expression is increased.

A preferred nucleic acid construct advantageously also comprises one or more of the already mentioned "enhancer" sequences in functional linkage with the promoter, which sequences make possible an enhanced expression of the nucleic acid sequence. Additional advantageous sequences may also be inserted at the 3'-end of the DNA sequences, such as further regulatory elements or terminators. One or more copies of the nucleic acids according to the invention may be present in a construct. In the construct, other markers, such as genes which complement auxotrophisms or antibiotic resistances, may also optionally be present so as to select for the construct.

Examples of suitable regulatory sequences are present in promoters such as cos, tac, trp, tet, trp-tet, lpp, lac, lpp-lac, lacIq, T7, T5, T3, gal, trc, ara, rhaP (rhaPBAD)SP6, lambda-PR or in the lambda-PL promoter, and these are advantageously employed in Gram-negative bacteria. Further advantageous regulatory sequences are present for example in the Gram-positive promoters amy and SP02, in the yeast or fungal promoters ADC1, MFalpha, AC, P-60, CYC1, GAPDH, TEF, rp28, ADH. Artificial promoters may also be used for regulation.

For expression in a host cell or host organism, the nucleic acid construct is inserted advantageously into a vector such as, for example, a plasmid or a phage, which makes possible optimal expression of the genes in the host. Vectors are also understood as meaning, in addition to plasmids and phages, all the other vectors which are known to the skilled worker, that is to say for example viruses such as SV40, CMV, baculovirus and adenovirus, transposons, IS elements, phasmids, cosmids and linear or circular DNA or artificial chromosomes. These vectors are capable of replicating autonomously in the host organism or else chromosomally. These vectors are a further development of the invention. Binary or co-integration vectors are also applicable.

Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-IIII13-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac+, pBIN19, pAK2004 or pDH51. The abovementioned plasmids are a small selection of the plasmids which are possible. Further plasmids are well known to the skilled worker and can be found for example in the book Cloning Vectors (Eds. Pouwels P. H. et al. Elsevier, Amsterdam-New York-Oxford, 1985, ISBN 0 444 904018).

In a further development of the vector, the vector which comprises the nucleic acid construct according to the invention or the nucleic acid according to the invention can advantageously also be introduced into the microorganisms in the form of a linear DNA and integrated into the host cell's or host organism's genome via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences to match the specific "codon usage" used in the organism. The "codon usage" can be determined readily by computer evaluations of other, known genes of the organism in question.

An expression cassette according to the invention is generated by fusing a suitable promoter to a suitable coding nucleotide sequence and a terminator or polyadenylation signal. Customary recombination and cloning techniques are used for this purpose, as are described, for example, in T. Maniatis, E. F. Fritsch and J. Sambrook, Molecular Cloning: A Laboratory Manual, Cold Spring Harbor Laboratory, Cold Spring Harbor, NY (1989) and in T. J. Silhavy, M. L. Berman and L. W. Enquist, Experiments with Gene Fusions, Cold Spring Harbor Laboratory, Cold Spring Harbor, NY (1984) and in Ausubel, F. M. et al., Current Protocols in Molecular Biology, Greene Publishing Assoc. and Wiley Interscience (1987).

For expression in a suitable host cell or host organism, the recombinant nucleic acid construct or gene construct is advantageously inserted into a host-specific vector which makes possible optimal expression of the genes in the host. Vectors are well known to the skilled worker and can be found for example in "cloning vectors" (Pouwels P. H. et al., Ed., Elsevier, Amsterdam-New York-Oxford, 1985).

An alternative embodiment of an embodiment herein provides a method to "alter (modify) gene expression" in a host cell. For instance, the polynucleotide of an embodiment herein may be enhanced or overexpressed or induced in certain contexts (e.g. upon exposure to certain temperatures or culture conditions) in a host cell or host organism.

Alteration of expression of a polynucleotide provided herein may also result in ectopic expression which is a different expression pattern in an altered and in a control or wild-type organism. Alteration of expression occurs from interactions of the polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity.

In one embodiment, provided herein is also an isolated, recombinant or synthetic polynucleotide encoding a polypeptide or variant polypeptide provided herein.

In one embodiment, several polypeptide encoding nucleic acid sequences are co-expressed in a single host, particularly under control of different promoters. In another embodiment, several polypeptide encoding nucleic acid sequences can be present on a single transformation vector or be co-transformed at the same time using separate vectors and selecting transformants comprising both chimeric genes. Similarly, one or more polypeptide encoding genes may be expressed in a single plant, cell, microorganism or organism together with other chimeric genes.

g. Hosts to be Applied for the Present Invention

Depending on the context, the term "host" can mean the wild-type host or a genetically modified (altered), "recombinant host" or both.

In principle, all prokaryotic or eukaryotic organisms may be considered as host or recombinant host organisms for the nucleic acids or the nucleic acid constructs according to the invention.

Using the vectors according to the invention, recombinant hosts can be produced, which are for example transformed with at least one vector according to the invention and can be used for producing the polypeptides according to the invention. Advantageously, the recombinant constructs according to the invention, described above, are introduced into a suitable host system and expressed. Preferably common cloning and transfection methods, known by a person skilled in the art, are used, for example co-precipitation, protoplast fusion, electroporation, retroviral transfection and the like, for expressing the stated nucleic acids in the respective expression system. Suitable systems are described for example in Current Protocols in Molecular Biology, F. Ausubel et al., Ed., Wiley Interscience, New York 1997, or Sambrook et al. Molecular Cloning: A Laboratory Manual. $2^{nd}$ edition, Cold Spring Harbor Laboratory, Cold Spring Harbor Laboratory Press, Cold Spring Harbor, NY, 1989.

Advantageously, microorganisms such as bacteria, fungi or yeasts are used as host organisms. Advantageously, Gram-positive or Gram-negative bacteria are used, preferably bacteria of the families Enterobacteriaceae, Pseudomonadaceae, Rhizobiaceae, Streptomycetaceae, Streptococcaceae or Nocardiaceae, especially preferably bacteria of the genera *Escherichia, Pseudomonas, Streptomyces, Lactococcus, Nocardia, Burkholderia, Salmonella, Agrobacterium, Clostridium* or *Rhodococcus*. The genus and species *Escherichia coli* is quite especially preferred. Furthermore, other advantageous bacteria are to be found in the group of alpha-Proteobacteria, beta-Proteobacteria or gamma-Proteobacteria. Advantageously also yeasts of families like *Saccharomyces* or *Pichia* are suitable hosts.

Alternatively, entire plants or plant cells may serve as natural or recombinant host. As non-limiting examples the following plants or cells derived therefrom may be mentioned: the genera *Nicotiana*, in particular *Nicotiana benthamiana* and *Nicotiana tabacum* (tobacco); as well as *Arabidopsis*, in particular *Arabidopsis thaliana*.

Depending on the host organism, the organisms used in the method according to the invention are grown or cultured in a manner known by a person skilled in the art. Culture can be batchwise, semi-batchwise or continuous. Nutrients can be present at the beginning of fermentation or can be supplied later, semi-continuously or continuously. This is also described in more detail below.

h. Recombinant Production of Polypeptides According to the Invention

The invention further relates to methods for recombinant production of polypeptides according to the invention or functional, biologically active fragments thereof, wherein a polypeptide-producing microorganism is cultured, optionally the expression of the polypeptides is induced by applying at least one inducer inducing gene expression and the expressed polypeptides are isolated from the culture. The polypeptides can also be produced in this way on an industrial scale, if desired.

The microorganisms produced according to the invention can be cultured continuously or discontinuously in the batch method or in the fed-batch method or repeated fed-batch method. A summary of known cultivation methods can be found in the textbook by Chmiel (Bioprozesstechnik 1. EinfUhrung in die Bioverfahrenstechnik [Bioprocess technology 1. Introduction to bioprocess technology] (Gustav Fischer Verlag, Stuttgart, 1991)) or in the textbook by Storhas (Bioreaktoren und periphere Einrichtungen [Bioreactors and peripheral equipment] (Vieweg Verlag, Braunschweig/Wiesbaden, 1994)).

The culture medium to be used must suitably meet the requirements of the respective strains. Descriptions of culture media for various microorganisms are given in the manual "Manual of Methods for General Bacteriology" of the American Society for Bacteriology (Washington D. C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It can also be advantageous to add mixtures of different carbon sources. Other possible carbon sources are oils and fats, for example soybean oil, sunflower oil, peanut oil and coconut oil, fatty acids, for example palmitic acid, stearic acid or linoleic acid, alcohols, for example glycerol, methanol or ethanol and organic acids, for example acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soya flour, soya protein, yeast extract, meat extract and others. The nitrogen sources can be used alone or as a mixture.

Inorganic salt compounds that can be present in the media comprise the chloride, phosphorus or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, as well as organic sulfur compounds, such as mercaptans and thiols, can be used as the sulfur source.

Phosphoric acid, potassium dihydrogen phosphate or dipotassium hydrogen phosphate or the corresponding sodium-containing salts can be used as the phosphorus source.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, which include for example biotin, riboflavin, thiamine, folic acid, nicotinic acid, pantothenate and pyridoxine. Growth factors and salts often originate from the components of complex media, such as yeast extract, molasses, corn-steep liquor and the like. Moreover, suitable precursors can be added to the culture medium. The exact composition of the compounds in the medium is strongly dependent on the respective experiment and is decided for each specific case individually. Information on media optimization can be found in the textbook "Applied Microbiol. Physiology, A Practical Approach" (Ed. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the medium are sterilized, either by heat (20 min at 1.5 bar and 121° C.) or by sterile filtration. The components can either be sterilized together, or separately if necessary. All components of the medium can be present at the start of culture or can be added either continuously or batchwise.

The culture temperature is normally between 15° C. and 45° C., preferably 25° C. to 40° C. and can be varied or kept constant during the experiment. The pH of the medium should be in the range from 5 to 8.5, preferably around 7.0. The pH for growing can be controlled during growing by adding basic compounds such as sodium hydroxide, potassium hydroxide, ammonia or ammonia water or acid compounds such as phosphoric acid or sulfuric acid. Antifoaming agents, for example fatty acid polyglycol esters, can be used for controlling foaming. To maintain the stability of plasmids, suitable selective substances, for example antibiotics, can be added to the medium. To maintain aerobic conditions, oxygen or oxygen-containing gas mixtures, for example ambient air, are fed into the culture. The temperature of the culture is normally in the range from 20° C. to 45° C. The culture is continued until a maximum of the desired product has formed. This target is normally reached within 10 hours to 160 hours.

The fermentation broth is then processed further. Depending on requirements, the biomass can be removed from the fermentation broth completely or partially by separation techniques, for example centrifugation, filtration, decanting or a combination of these methods or can be left in it completely.

If the polypeptides are not secreted in the culture medium, the cells can also be lysed and the product can be obtained from the lysate by known methods for isolation of proteins. The cells can optionally be disrupted with high-frequency ultrasound, high pressure, for example in a French press, by osmolysis, by the action of detergents, lytic enzymes or organic solvents, by means of homogenizers or by a combination of several of the aforementioned methods.

The polypeptides can be purified by known chromatographic techniques, such as molecular sieve chromatography (gel filtration), such as Q-sepharose chromatography, ion exchange chromatography and hydrophobic chromatography, and with other usual techniques such as ultrafiltration, crystallization, salting-out, dialysis and native gel electrophoresis. Suitable methods are described for example in Cooper, T. G., Biochemische Arbeitsmethoden [Biochemical processes], Verlag Walter de Gruyter, Berlin, New York or in Scopes, R., Protein Purification, Springer Verlag, New York, Heidelberg, Berlin.

For isolating the recombinant protein, it can be advantageous to use vector systems or oligonucleotides, which lengthen the cDNA by defined nucleotide sequences and therefore code for altered polypeptides or fusion proteins, which for example serve for easier purification. Suitable modifications of this type are for example so-called "tags" functioning as anchors, for example the modification known as hexa-histidine anchor or epitopes that can be recognized as antigens of antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be used as packing in a chromatography column, or can be used on a microtiter plate or on some other carrier.

At the same time these anchors can also be used for recognition of the proteins. For recognition of the proteins, it is moreover also possible to use usual markers, such as fluorescent dyes, enzyme markers, which form a detectable reaction product after reaction with a substrate, or radioactive markers, alone or in combination with the anchors for derivatization of the proteins.

i. Polypeptide Immobilization

The enzymes or polypeptides according to the invention can be used free or immobilized in the method described herein. An immobilized enzyme is an enzyme that is fixed to an inert carrier. Suitable carrier materials and the enzymes immobilized thereon are known from EP-A-1149849, EP-A-1 069 183 and DE-OS 100193773 and from the references cited therein. Reference is made in this respect to the disclosure of these documents in their entirety. Suitable carrier materials include for example clays, clay minerals, such as kaolinite, diatomaceous earth, perlite, silica, aluminum oxide, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For making the supported enzymes, the carrier materials are usually employed in a finely-divided, particulate form, porous forms being preferred. The particle size of the carrier material is usually not more than 5 mm, in particular not more than 2 mm (particle-size distribution curve). Similarly, when using dehydrogenase as whole-cell catalyst, a free or immobilized form can be selected. Carrier materials are e.g. Ca-alginate, and carrageenan. Enzymes as well as cells can also be crosslinked directly with glutaraldehyde (cross-linking to CLEAs). Corresponding and other immobilization techniques are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out methods according to the invention are also given for example in Rehm et al. (Ed.) Biotechnology, $2^{nd}$ Edn, Vol 3, Chapter 17, VCH, Weinheim.

j. Reaction Conditions for Biocatalytic Production Methods of the Invention

An "enzymatically catalyzed" or "biocatalytic" method means that said method is performed under the catalytic action of an enzyme, including enzyme mutants, as herein defined. Thus, the method can either be performed in the presence of said enzyme in isolated (purified, enriched) or crude form or in the presence of a cellular system, in particular, natural or recombinant microbial cells containing said enzyme in active form, and having the ability to catalyze the conversion reaction as disclosed herein. Hence, the reaction of the present invention may be performed under in vivo or in vitro conditions.

The at least one polypeptide/enzyme which is present during a method of the invention or an individual step of a multistep-method as defined herein above, can be present in living cells naturally or recombinantly producing the enzyme or enzymes, in harvested cells. i.e. under in vivo conditions (bioconversion), or, in dead cells, in permeabilized cells, in crude cell extracts, in purified extracts, or in essentially pure or completely pure form, i.e. under in vitro conditions (biochemical synthesis). The at least one enzyme may be present in solution or as an enzyme immobilized on a carrier. One or several enzymes may simultaneously be present in soluble and/or immobilized form.

The methods according to the invention can be performed in common reactors, which are known to those skilled in the art, and in different ranges of scale, e.g. from a laboratory scale (few millilitres to dozens of litres of reaction volume) to an industrial scale (several litres to thousands of cubic meters of reaction volume). If the polypeptide is used in a form encapsulated by non-living, optionally permeabilized cells, in the form of a more or less purified cell extract or in purified form, a chemical reactor can be used. The chemical reactor usually allows controlling the amount of the at least one enzyme, the amount of the at least one substrate, the pH, the temperature and the circulation of the reaction medium. When the at least one polypeptide/enzyme is present in living cells, the process will be a fermentation. In this case the biocatalytic production will take place in a bioreactor (fermenter), where parameters necessary for suitable living conditions for the living cells (e.g. culture medium with nutrients, temperature, aeration, presence or absence of oxygen or other gases, antibiotics, and the like) can be controlled. Those skilled in the art are familiar with chemical reactors or bioreactors, e.g. with procedures for up-scaling chemical or biotechnological methods from laboratory scale to industrial scale, or for optimizing process parameters, which are also extensively described in the literature (for biotechnological methods see e.g. Crueger und Crueger, Biotechnologie-Lehrbuch der angewandten Mikrobiologie, 2. Ed., R. Oldenbourg Verlag, Munchen, Wien, 1984).

Cells containing the at least one enzyme can be permeabilized by physical or mechanical means, such as ultrasound or radiofrequency pulses, French presses, or chemical means, such as hypotonic media, lytic enzymes and detergents present in the medium, or combination of such methods. Examples for detergents are digitonin, n-dodecylmaltoside, octylglycoside, Triton® X-100, Tween® 20, deoxycholate, CHAPS (3-[(3-Cholamidopropyl)dimethyl-ammonio]-1-propansulfonate), Nonidet® P40 (Ethylphenol-poly(ethyleneglycolether), and the like.

Instead of living cells biomass of non-living cells containing the required biocatalyst(s) may be applied of the biotransformation reactions of the invention as well.

If the at least one enzyme is immobilized, it is attached to an inert carrier as described above.

The conversion reaction can be carried out batch wise, semi-batch wise or continuously. Reactants (and optionally nutrients) can be supplied at the start of reaction or can be supplied subsequently, either semi-continuously or continuously.

The reaction of the invention, depending on the particular reaction type, may be performed in an aqueous, aqueous-organic or non-aqueous reaction medium.

An aqueous or aqueous-organic medium may contain a suitable buffer in order to adjust the pH to a value in the range of 5 to 11, like 6 to 10.

In an aqueous-organic medium an organic solvent miscible, partly miscible or immiscible with water may be applied. Non-limiting examples of suitable organic solvents are listed below. Further examples are mono- or polyhydric, aromatic or aliphatic alcohols, in particular polyhydric aliphatic alcohols like glycerol.

The non-aqueous medium may be substantially free of water, i.e. will contain less that about 1 wt.-% or 0.5 wt.-% of water.

Biocatalytic methods may also be performed in an organic non-aqueous medium. As suitable organic solvents there may be mentioned aliphatic hydrocarbons having for example 5 to 8 carbon atoms, like pentane, cyclopentane, hexane, cyclohexane, heptane, octane or cyclooctane; aromatic carbohydrates, like benzene, toluene, xylenes, chlorobenzene or dichlorobenzene, aliphatic acyclic and ethers, like diethylether, methyl-tert-butylether, ethyl-tert.-butyle-ther, dipropylether, diisopropylether, dibutylether; or mixtures thereof.

The concentration of the reactants/substrates may be adapted to the optimum reaction conditions, which may depend on the specific enzyme applied. For example, the initial substrate concentration may be in the 0.1 to 0.5 M, as for example 10 to 100 mM.

The reaction temperature may be adapted to the optimum reaction conditions which may depend on the specific enzyme applied. For example, the reaction may be performed at a temperature in a range of from 0 to 70° C., as for example 20 to 50 or 25 to 40° C. Examples for reaction temperatures are about 30° C., about 35° C., about 37° C., about 40° C., about 45° C., about 50° C., about 55° C. and about 60° C.

The process may proceed until equilibrium between the substrate and then product(s) is achieved, but may be stopped earlier. Usual process times are in the range from 1 minute to 25 hours, in particular 10 min to 6 hours, as for example in the range from 1 hour to 4 hours, in particular 1.5 hours to 3.5 hours. These parameters are non-limiting examples of suitable process conditions.

If the host is a transgenic plant, optimal growth conditions can be provided, such as optimal light, water and nutrient conditions, for example.

1. Product Isolation

The methodology of the present invention can further include a step of recovering an end or intermediate product, optionally in stereoisomerically or enantiomerically substantially pure form. The term "recovering" includes extracting, harvesting, isolating or purifying the compound from culture or reaction media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Identity and purity of the isolated product may be determined by known techniques, like High Performance Liquid Chromatography (HPLC), Gas Chromatography (GC), Spectroscopy (like IR, UV, NMR), Colouring methods, TLC, NIRS, enzymatic or microbial assays (see for example: Patek et al. (1994) Appl. Environ. Microbiol. 60:133-140; Malakhova et al. (1996) Biotekhnologiya 11 27-32; and Schmidt et al. (1998) Bioprocess Engineer. 19:67-70. Ullmann's Encyclopedia of Industrial Chemistry (1996) Bd. A27, VCH: Weinheim, p. 89-90, p. 521-540, p. 540-547, p. 559-566, 575-581 and p. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Bd. 17).

The cyclic terpene compound produced in any of the methods described herein can be converted to derivatives such as, but not limited to hydrocarbons, esters, amides, glycosides, ethers, epoxides, aldehydes, cycloaddition products, ketones, alcohols, diols, acetals or ketals. The terpene compound derivatives can be obtained by a chemical method such as, but not limited to oxidation, reduction, alkylation, acylation and/or rearrangement. Alternatively, the terpene compound derivatives can be obtained using a biochemical method by contacting the terpene compound with an enzyme such as, but not limited to an oxidoreductase, a monooxygenase, esterase, a dioxygenase, a transferase. The biochemical conversion can be performed in vitro using isolated enzymes, enzymes from lysed cells or in vivo using whole cells.

m. Fermentative Production of Drimenyl Diphosphate and/or Drimenol, and/or Albicanyl Diphosphate and/or Albicanol The invention also relates to methods for the fermentative production of drimenyl diphosphate and/or drimenol, and/or albicanyl diphosphate and/or albicanol.

The term "fermentative production" or "fermentation" refers to the ability of a microorganism (assisted by enzyme activity contained in or generated by said microorganism) to produce a chemical compound in cell culture utilizing at least one carbon source added to the incubation.

The term "fermentation broth" is understood to mean a liquid, particularly aqueous or aqueous/organic solution which is based on a fermentative process and has not been worked up or has been worked up, for example, as described herein.

A fermentation as used according to the present invention can, for example, be performed in stirred fermenters, bubble columns and loop reactors. A comprehensive overview of the possible method types including stirrer types and geometric designs can be found in "Chmiel: Bioprozesstechnik: EinfMhrung in die Bioverfahrenstechnik, Band 1 [Bioprocess technology 1. Introduction to bioprocess technology]". In the process of the invention, typical variants available are the following variants known to those skilled in the art or explained, for example, in "Chmiel, Hammes and Bailey: Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield ($Y_P/S$).

"Yield" and/or the "conversion rate" of a reaction according to the invention is determined over a defined period of, for example, 4, 6, 8, 10, 12, 16, 20, 24, 36 or 48 hours, in which the reaction takes place. In particular, the reaction is carried out under precisely defined conditions, for example at "standard conditions" as herein defined.

The different yield parameters ("Yield" or $Y_{P/S}$; "Specific Productivity Yield"; or Space-Time-Yield (STY)) are well known in the art and are determined as described in the literature.

"Yield" and "$Y_{P/S}$" (each expressed in mass of product produced/mass of material consumed) are herein used as synonyms.

The specific productivity-yield describes the amount of a product that is produced per h and L fermentation broth per g of biomass. The amount of wet cell weight stated as WCW describes the quantity of biologically active microorganism in a biochemical reaction. The value is given as g product per g WCW per h (i.e. g $g_{WCW}^{-1}$ h$^{-1}$). Alternatively, the quantity of biomass can also be expressed as the amount of dry cell weight stated as DCW. Furthermore, the biomass concentration can be more easily determined by measuring the optical density at 600 nm ($OD_{600}$) and by using an experimentally determined correlation factor for estimating the corresponding wet cell or dry cell weight, respectively.

The culture medium that is to be used according to the present invention must satisfy the requirements of the particular strains in an appropriate manner. Descriptions of culture media for various microorganisms are given in the handbook "Manual of Methods for General Bacteriology" of the American Society for Bacteriology (Washington D. C., USA, 1981).

These media that can be used according to the invention may comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as corn-steep liquor, soybean flour, soy-bean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, di-thionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, corn-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (1997) Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions. The temperature of the culture is normally from 20° C. to 45° C. Culture is continued until a maximum of the desired product has formed. This is normally achieved within 1 hour to 160 hours.

The methodology of the present invention can further include a step of recovering drimenyl diphosphate and/or drimenol, and/or albicanyl diphosphate and/or albicanol The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Before the intended isolation the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value.

In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The following examples are illustrative only and are not intended to limit the scope of the claims an embodiments described herein.

The numerous possible variations that will become immediately evident to a person skilled in the art after heaving considered the disclosure provided herein also fall within the scope of the invention.

Experimental Part

The invention will now be described in further detail by way of the following Examples.

Materials:

Unless otherwise stated, all chemical and biochemical materials and microorganisms or cells employed herein are commercially available products.

Unless otherwise specified, recombinant proteins are cloned and expressed by standard methods, such as, for example, as described by Sambrook, J., Fritsch, E. F. and Maniatis, T., Molecular Cloning: A Laboratory Manual, $2^{nd}$ Edition, Cold Spring Harbor Laboratory, Cold Spring Harbor Laboratory Press, Cold Spring Harbor, NY, 1989.

Methods:

GC/MS

GC/MS analysis was performed on a GC/MS 6890N/5975 (Agilent). Separation was achieved using a DB-IMS column (30 m×0.25 mm i.d.×0.25 μm film thickness, J & W Scientific, Agilent Technologies, Foster City, CA). The carrier gas was helium at a constant flow of 0.7 mL/min. Injection was in split (1:5) mode with the injector temperature set at 250° C. The oven temperature was programmed to increase first from 50° C. (5 min hold) to 300° C. incrementing at 5° C./min, and then to 340° C. incrementing at 50° C./min, where it was held for 3 min. Data were acquired by scan mode with m/z 29-450. Alkanes ($C_6$-$C_{30}$) were injected for calculation of retention index. Compounds were identified by matching mass spectra and retention index with that of in-house library.

Example 1

Discovery of HAD-Like TPSs

Fresh leaves of *Bazzania* species (Nagobase ID: PA-2018-0168 to PA-2018-0173, which contain drimane-type sesquiterpene alcohols including albicanol and drimenol) were sourced in Hunan, China. Total RNA was extracted from the fresh leaves using the RNeasy Plant Mini Kit (50) 74904 from QIAGEN and used for RNA sequencing. The RNA sequencing data were then assembled by CLC genomics workbench (7.6.1). The sequence of the fern HAD-like TPS, DfHAD, from prior art (PCT/EP2019/063824; herein SEQ ID NOs: 73 and 74) was used for searching the potential drimane-type sesquiterpene synthase in the protein sequence data of *Bazzania* species. Novel sequences were discovered from both assemblies of *Bazzania* transcriptomes by BLAST, resulting in HAD-like TPSs designated BazzHAD1 (SEQ ID NO: 3), BazzHAD2 (SEQ ID NO: 6) and BazzHAD3 (SEQ ID NO: 9); their corresponding nucleotide sequences are SEQ ID NO: 1, 4 and 7, respectively.

The RNAseq raw data of *Bazzania trilobata* (SRA ID: ERR364415) was downloaded from NCBI and assembled by CLC genomics workbench to deliver the transcriptome from which the BtHAD (SEQ ID NO: 12) was discovered by BLAST; its corresponding nucleotide sequence is SEQ ID NO: 10.

Homologous sequences of DfHAD in the NCBI database were thoroughly mined by using BLAST with threshold scores (E-value<10, Hit list size<500) until plant genes were observed, resulting in two similar sequences from *Selaginella moellendorffii* that were deposited with accession numbers EFJ10816.1 and EFJ26126.1 (GenBank ID) as hypothetical proteins, not relevant to the said HAD-like TPS. The proteins were respectively designated SmHAD1 (SEQ ID NO: 19) and SmHAD2 (SEQ ID NO: 26) in this study; their corresponding nucleotide sequences are SEQ ID NOs: 17 and 24, respectively.

To study their homology, an alignment was performed by Clustalw for SmHAD1, SmHAD2, BtHAD, BazzHAD1, BazzHAD2 and BazzHAD3 together with DfHAD (PCT/EP2019/063824) and several fungal HAD-like drimane sesquiterpene synthases including AstC (PCT/EP2019/063824). We found that the protein sequences of SmHAD1 and SmHAD2 have a very low degree of identity with all other known HAD-like TPSs (~14-20%) but show high homology between themselves (>96%), BtHAD and BazzHAD1 show a slightly higher homology to fern and fungal HAD-like TPSs (~22-30%) and 96% identity between themselves, whereas BazzHAD2 and BazzHAD3 show an intermediate homology to fern and fungal HAD-like TPSs (~22-43%) and 67% identity between themselves (Table 1).

TABLE 2

Pairwise comparisons of BazzHAD1, BazzHAD2, BazzHAD3, BtHAD, SmHAD1, SmHAD2 and known
HAD-like TPSs. The comparison shows identity of the aligned sequence between proteins.

|  | Seq | | | | | | |
|---|---|---|---|---|---|---|---|
|  | SCH73__24012 | XP__008034151.1 | CrVo07609-2 | XP__007369631.1 | EMD37666.1 | EMD37666-B | OCH93767.1 |
| SCH73__24012 | ID | | | | | | |
| XP__008034151.1 | 0.84 | ID | | | | | |
| CrVo07609-2 | 0.7 | 0.72 | ID | | | | |
| XP__007369631.1 | 0.73 | 0.76 | 0.84 | ID | | | |
| EMD37666.1 | 0.57 | 0.59 | 0.58 | 0.59 | ID | | |
| EMD37666-B | 0.57 | 0.6 | 0.59 | 0.6 | 0.99 | ID | |
| OCH93767.1 | 0.58 | 0.6 | 0.59 | 0.6 | 0.88 | 0.89 | ID |
| XP__009547469.1 | 0.5 | 0.5 | 0.5 | 0.51 | 0.53 | 0.53 | 0.53 |
| KLO09124.1 | 0.43 | 0.43 | 0.42 | 0.43 | 0.43 | 0.43 | 0.44 |
| ACg006372 | 0.41 | 0.42 | 0.39 | 0.41 | 0.4 | 0.4 | 0.41 |
| OJJ98394.1 | 0.42 | 0.42 | 0.42 | 0.43 | 0.41 | 0.42 | 0.41 |
| OJI95797.1 | 0.38 | 0.38 | 0.39 | 0.41 | 0.39 | 0.39 | 0.39 |
| XP__001217376.1 | 0.37 | 0.39 | 0.37 | 0.39 | 0.37 | 0.37 | 0.37 |
| BazzHAD2 | 0.4 | 0.38 | 0.38 | 0.39 | 0.39 | 0.39 | 0.39 |
| BazzHAD3 | 0.38 | 0.38 | 0.37 | 0.38 | 0.38 | 0.38 | 0.38 |
| KIA75676.1 | 0.39 | 0.38 | 0.37 | 0.38 | 0.39 | 0.39 | 0.4 |
| CEN60542.1 | 0.4 | 0.39 | 0.37 | 0.38 | 0.39 | 0.4 | 0.39 |
| XP__001820867.2 | 0.38 | 0.39 | 0.4 | 0.4 | 0.37 | 0.37 | 0.38 |
| GAO87501.1 | 0.38 | 0.39 | 0.4 | 0.41 | 0.39 | 0.4 | 0.4 |
| AstC | 0.36 | 0.37 | 0.33 | 0.33 | 0.34 | 0.35 | 0.35 |
| CCD33681.1 | 0.35 | 0.35 | 0.36 | 0.36 | 0.35 | 0.35 | 0.36 |
| BazzHAD1 | 0.25 | 0.24 | 0.24 | 0.24 | 0.23 | 0.23 | 0.24 |
| BtHAD | 0.24 | 0.24 | 0.24 | 0.24 | 0.22 | 0.22 | 0.23 |
| DfHAD-9(V274A) | 0.21 | 0.2 | 0.2 | 0.21 | 0.19 | 0.19 | 0.19 |
| DfHAD | 0.21 | 0.2 | 0.2 | 0.21 | 0.19 | 0.19 | 0.19 |
| DfHAD-8(K532R) | 0.21 | 0.2 | 0.2 | 0.22 | 0.19 | 0.19 | 0.19 |
| SmHAD1 | 0.16 | 0.17 | 0.17 | 0.16 | 0.15 | 0.15 | 0.16 |
| SmHAD2 | 0.16 | 0.17 | 0.16 | 0.17 | 0.15 | 0.15 | 0.16 |

|  | Seq | | | | | | |
|---|---|---|---|---|---|---|---|
|  | XP__009547469.1 | KLO09124.1 | ACg006372 | OJJ98394.1 | OJI95797.1 | XP__001217376.1 | BazzHAD2 |
| SCH73__24012 | | | | | | | |
| XP__008034151.1 | | | | | | | |
| CrVo07609-2 | | | | | | | |
| XP__007369631.1 | | | | | | | |
| EMD37666.1 | | | | | | | |
| EMD37666-B | | | | | | | |
| OCH93767.1 | | | | | | | |
| XP__009547469.1 | ID | | | | | | |
| KLO09124.1 | 0.44 | ID | | | | | |
| ACg006372 | 0.42 | 0.49 | ID | | | | |
| OJJ98394.1 | 0.39 | 0.37 | 0.37 | ID | | | |
| OJI95797.1 | 0.41 | 0.37 | 0.34 | 0.53 | ID | | |
| XP__001217376.1 | 0.37 | 0.34 | 0.33 | 0.52 | 0.51 | ID | |
| BazzHAD2 | 0.42 | 0.42 | 0.38 | 0.41 | 0.4 | 0.41 | ID |
| BazzHAD3 | 0.41 | 0.4 | 0.4 | 0.41 | 0.38 | 0.4 | 0.66 |
| KIA75676.1 | 0.41 | 0.34 | 0.34 | 0.4 | 0.38 | 0.38 | 0.38 |
| CEN60542.1 | 0.41 | 0.34 | 0.33 | 0.42 | 0.39 | 0.38 | 0.37 |
| XP__001820867.2 | 0.4 | 0.37 | 0.39 | 0.41 | 0.36 | 0.38 | 0.41 |
| GAO87501.1 | 0.4 | 0.39 | 0.41 | 0.41 | 0.38 | 0.39 | 0.42 |
| AstC | 0.37 | 0.35 | 0.34 | 0.35 | 0.33 | 0.33 | 0.37 |
| CCD33681.1 | 0.36 | 0.33 | 0.32 | 0.36 | 0.33 | 0.34 | 0.33 |
| BazzHAD1 | 0.24 | 0.25 | 0.25 | 0.26 | 0.25 | 0.26 | 0.26 |
| BtHAD | 0.23 | 0.25 | 0.24 | 0.25 | 0.24 | 0.26 | 0.26 |
| DfHAD-9(V274A) | 0.22 | 0.21 | 0.22 | 0.22 | 0.21 | 0.22 | 0.22 |
| DfHAD | 0.22 | 0.21 | 0.22 | 0.22 | 0.21 | 0.22 | 0.22 |
| DfHAD-8(K532R) | 0.22 | 0.21 | 0.22 | 0.22 | 0.21 | 0.23 | 0.22 |
| SmHAD1 | 0.14 | 0.15 | 0.16 | 0.16 | 0.17 | 0.2 | 0.17 |
| SmHAD2 | 0.14 | 0.15 | 0.16 | 0.16 | 0.17 | 0.2 | 0.17 |

|  | Seq | | | | | | |
|---|---|---|---|---|---|---|---|
|  | BazzHAD3 | KIA75676.1 | CEN60542.1 | XP__001820867.2 | GAO87501.1 | AstC | CCD33681.1 |
| SCH73__24012 | | | | | | | |
| XP__008034151.1 | | | | | | | |
| CrVo07609-2 | | | | | | | |
| XP__007369631.1 | | | | | | | |
| EMD37666.1 | | | | | | | |
| EMD37666-B | | | | | | | |
| OCH93767.1 | | | | | | | |

TABLE 2-continued

Pairwise comparisons of BazzHAD1, BazzHAD2, BazzHAD3, BtHAD, SmHAD1, SmHAD2 and known
HAD-like TPSs. The comparison shows identity of the aligned sequence between proteins.

| | | | | | | | |
|---|---|---|---|---|---|---|---|
| XP_009547469.1 | | | | | | | |
| KLO09124.1 | | | | | | | |
| ACg006372 | | | | | | | |
| OJJ98394.1 | | | | | | | |
| OJI95797.1 | | | | | | | |
| XP_001217376.1 | | | | | | | |
| BazzHAD2 | | | | | | | |
| BazzHAD3 | ID | | | | | | |
| KIA75676.1 | 0.37 | ID | | | | | |
| CEN60542.1 | 0.37 | 0.72 | ID | | | | |
| XP_001820867.2 | 0.4 | 0.39 | 0.4 | ID | | | |
| GAO87501.1 | 0.4 | 0.39 | 0.37 | 0.68 | ID | | |
| AstC | 0.38 | 0.35 | 0.35 | 0.38 | 0.36 | ID | |
| CCD33681.1 | 0.32 | 0.33 | 0.34 | 0.35 | 0.35 | 0.32 | ID |
| BazzHAD1 | 0.24 | 0.24 | 0.23 | 0.26 | 0.25 | 0.23 | 0.25 |
| BtHAD | 0.24 | 0.24 | 0.23 | 0.27 | 0.25 | 0.23 | 0.24 |
| DfHAD-9(V274A) | 0.22 | 0.19 | 0.2 | 0.21 | 0.22 | 0.21 | 0.2 |
| DfHAD | 0.22 | 0.19 | 0.2 | 0.21 | 0.22 | 0.21 | 0.2 |
| DfHAD-8(K532R) | 0.22 | 0.19 | 0.2 | 0.21 | 0.22 | 0.21 | 0.2 |
| SmHAD1 | 0.17 | 0.17 | 0.16 | 0.17 | 0.17 | 0.16 | 0.15 |
| SmHAD2 | 0.17 | 0.17 | 0.16 | 0.17 | 0.16 | 0.16 | 0.15 |

| | Seq | | | | | | |
|---|---|---|---|---|---|---|---|
| | BazzHAD1 | BtHAD | DfHAD-9(V274A) | DfHAD | DfHAD-8(K532R) | SmHAD1 | SmHAD2 |
| SCH73_24012 | | | | | | | |
| XP_008034151.1 | | | | | | | |
| CrVo07609-2 | | | | | | | |
| XP_007369631.1 | | | | | | | |
| EMD37666.1 | | | | | | | |
| EMD37666-B | | | | | | | |
| OCH93767.1 | | | | | | | |
| XP_009547469.1 | | | | | | | |
| KLO09124.1 | | | | | | | |
| ACg006372 | | | | | | | |
| OJJ98394.1 | | | | | | | |
| OJI95797.1 | | | | | | | |
| XP_001217376.1 | | | | | | | |
| BazzHAD2 | | | | | | | |
| BazzHAD3 | | | | | | | |
| KIA75676.1 | | | | | | | |
| CEN60542.1 | | | | | | | |
| XP_001820867.2 | | | | | | | |
| GAO87501.1 | | | | | | | |
| AstC | | | | | | | |
| CCD33681.1 | | | | | | | |
| BazzHAD1 | ID | | | | | | |
| BtHAD | 0.96 | ID | | | | | |
| DfHAD-9(V274A) | 0.29 | 0.29 | ID | | | | |
| DfHAD | 0.29 | 0.29 | 1 | ID | | | |
| DfHAD-8(K532R) | 0.29 | 0.29 | 1 | 1 | ID | | |
| SmHAD1 | 0.17 | 0.17 | 0.16 | 0.16 | 0.16 | ID | |
| SmHAD2 | 0.16 | 0.16 | 0.16 | 0.16 | 0.16 | 0.97 | ID |

Example 2

Functional Expression and Characterization of the Plant HAD-Like TPSs in an *E. coli* Expression System (In Vivo Biochemical Assay)

The coding sequences of BazzHAD1, BazzHAD2, BazzHAD3, BtHAD, SmHAD1 (EFJ10816.1) and SmHAD2 (EFJ26126.1) were optimized by Genscript following their genetic codon usage frequency table for *E. coli* (SEQ ID NOs: 2, 5, 8, 11, 18 and 25, respectively). They were then synthesized in vitro and subcloned into the pETDuet-1 plasmid (Novagen) for subsequent expression in *E. coli*, generating the plasmids pETDuet-BazzHAD1, pET-Duet-BazzHAD2, pETDuet-BazzHAD3, pETDuet-BtHAD, pETDuet-SmHAD1, and pETDuet-SmHAD2, respectively.

BL21(DE3) *E. coli* cells (Tiangen) were co-transformed with the plasmid pACYC/ScMVA, containing the genes encoding for a heterologous mevalonate (MVA) pathway, and each of the plasmids pETDuet-BazzHAD1, pETDuet-BazzHAD2, pETDuet-BazzHAD3, pETDuet-BtHAD, pET-Duet-SmHAD1, and pETDuet-SmHAD2, respectively. The pACYC/ScMVA plasmid for the expression of a farnesyl pyrophosphate (FPP) synthase gene and the genes for a complete MVA pathway were constructed. Briefly, the eight biosynthetic genes of the MVA pathway were divided into 2 synthetic operons referred to as the 'upper' and 'lower' MVA pathway. As an 'upper' MVA pathway, a synthetic operon was created consisting of an acetoacetyl-CoA thiolase from *E. coli* encoded by atoB, a HMG-CoA synthase and a truncated version of HMG-CoA reductase from *Saccharomyces cerevisiae* encoded by ERG13 and ERG19, respectively. This operon transforms the primary metabolite Acetyl-CoA into (R)-mevalonate. As a 'lower' mevalonate pathway, a second synthetic operon was created encoding a mevalonate kinase (ERG12, *S. cerevisiae*), a phosphomeva- lonate kinase (ERG8, *S. cerevisiae*), a phosphomevalonate decarboxylase (MVD1, *S. cerevisiae*), an isopentenyl diphosphate isomerase (idi, *E. coli*) and a FPP synthase (IspA, *E. coli*). Finally, a second FPP synthase from *S. cerevisiae* (ERG20) was introduced into the upper pathway operon to improve the conversion of the isoprenoid C5 units (IPP and DMAPP) into FPP. Each operon was subcloned into one of the multiple-cloning sites of a low-copy expres- sion plasmid under the control of a bacteriophage T7 pro- moter (pACYCDuet-1, Invitrogen) providing the plasmid pACYC/ScMVA. This plasmid thus contains the genes encoding all enzymes of the biosynthetic pathway leading from acetyl-coenzyme A to FPP.

The co-transformed cells were selected on LB-agar plates containing ampicillin (50 µg/mL) and chloramphenicol (34 µg/mL). Single colonies were used to inoculate 5 mL liquid LB medium supplemented with the same antibiotics. Cul- tures were incubated overnight at 37° C. while shaking at 200 rpm. The next day, 2 mL of TB medium supplemented with the above-mentioned antibiotics and glycerol (3% w/v final) were inoculated with 0.2 mL of the overnight culture. After 5 hours of incubation at 37° C. and shaking at 200 rpm, the culture was cooled down to 25° C. and shaken a further hour at 200 rpm. IPTG (0.1 mM final) was then added to each tube and the culture overlaid with 200 µL of decane. The cultures were incubated for a further 48 hours at 25° C. at 200 rpm and then extracted twice with 1 volume of ethyl acetate. 50 µL of isolongifolene at 2 mg/mL were added to the organic phase as internal standard before analysing the samples by GC/MS. The carrier gas was helium at a constant flow of 0.7 mL/min. Injection was in split (1:25) mode with the injector temperature set at 250° C. The oven temperature was programmed to increase first from 50° C. (5 min hold) to 300° C. incrementing at 5° C./min, and then to 340° C. incrementing at 50° C./min where it was held for 3 min. Identification of products was based on mass spectra and retention indices.

GC/MS analysis revealed that recombinant cells express- ing BazzHAD1 and BtHAD produced 37.3 mg/L and 26.0 mg/L drimenol, respectively; the expression of BazzHAD2 resulted in the production of 35.3 mg/L albicanol and 0.2 mg/L unknown sesquiterpene 1 (unknown SQT1); the expression of BazzHAD3 resulted in the production of 422.7 mg/L albicanol; whereas the expression of SmHAD1 resulted in the production of 0.5 mg/L albicanol and 6.2 mg/L drimenol; and the expression of SmHAD2 resulted in the production of 1.4 mg/L albicanol and 10.7 mg/L drime- nol, see FIGS. 1-16.

Example 3

Importance of the Class II Motif and QW Motif in Plant HAD-Like TPSs (Enzyme Mutants and Functional Proofs for the Motifs)

To confirm the importance of the class II terpene synthase motif (SEQ ID NO: 46), mutants of this motif were designed and generated for BtHAD, SmHAD1 and SmHAD2 (SEQ ID NOs: 13, 20 and 27, respectively). As BazzHAD1 is an ortholog of BtHAD (with 96% identity) from *Bazzania trilobata*, it can be represented by BtHAD and was thus not included in this study. In addition to the class II motif, the QW motif (SEQ ID NO: 51) was also mutated in BtHAD, SmHAD1 and SmHAD2 (SEQ ID NOs: 15, 22 and 29, respectively) in order to study its importance for the syn- thase activity. Since the known fungal HAD-like TPSs contain both class I and class II motifs (e.g., SEQ ID NOs:

56, 57 and 58 of WO 2018/220113), EMD37666.1 (SEQ ID NO: 31) and XP_007369631.1 (SEQ ID NO: 35) were selected and their class II motif mutated (SEQ ID NOs: 33 and 37, respectively) in order to investigate if the class I motif is sufficient for the synthase activity. In the mutants of the class II synthase motif in BtHAD (D320A/D322A), SmHAD1 (D257A/D259A), SmHAD2 (D257A/D259A), EMD37666.1 (D276A/S277A/D279A) and XP_007369631.1 (D272A/D273A/D275A), the polar Asp was substituted by Ala (SEQ ID NOs: 39 to 42). In the mutants of the QW motif in BtHAD (D491A), SmHAD1 (E432A/D433A) and SmHAD2 (E432A/D433A), the polar Glu and Asp were substituted by Ala (SEQ ID NOs: 43 and 44).

The sequences of BtHAD, SmHAD1, SmHAD2, XP_007369631.1, EMD37666.1 and their corresponding mutants for the class II synthase motif and—if present—for the QW motif were optimized by Genscript following their genetic codon usage frequency table for *E. coli* (BtHAD SEQ ID NOs: 11, 13, 15; SmHAD1 SEQ ID NOs: 18, 20, 22; SmHAD2 SEQ ID NOs: 25, 27, 29; EMD37666.1 SEQ ID NOs: 31, 33; and XP_007369631.1 SEQ ID NOs: 35, 37). The sequences were then synthesized in vitro by Gen- script and subcloned into the pETDuet-1 plasmid (Novagen) for subsequent expression in *E. coli*, generating the plasmids pETDuet-BtHAD, pETDuet-SmHAD1, pETDuet- SmHAD2, pETDuet-EMD37666.1, pETDuet- XP_007369631.1; pETDuet-BtHAD-ClassII mut, pETDuet- SmHAD1-ClassII mut, pETDuet-SmHAD2-ClassII mut, pETDuet-EMD37666.1-ClassII mut, pETDuet- XP_007369631.1-ClassII mut; and pETDuet-BtHAD-QW mut, pETDuet-SmHAD1-QW mut, and pETDuet- SmHAD2-QW mut, respectively.

BL21(DE3) *E. coli* cells (Tiangen) were co-transformed with the plasmid pACYC/ScMVA, containing the genes encoding for a heterologous mevalonate pathway, and each of the plasmids pETDuet-BtHAD, pETDuet-SmHAD1, pETDuet-SmHAD2, pETDuet-EMD37666.1, pETDuet- XP_007369631.1, pETDuet-BtHAD-ClassII mut, pETDuet- SmHAD1-ClassII mut, pETDuet-SmHAD2-ClassII mut, pETDuet-EMD37666.1-ClassII mut, pETDuet- XP_007369631.1-ClassII mut, pETDuet-BtHAD-QW mut, pETDuet-SmHAD1-QW mut, and pETDuet-SmHAD2-QW mut, respectively. The construction of the pACYC/ScMVA for the expression of an FPP synthase gene and the genes for a complete MVA pathway is described above (Example 2). This plasmid contains the genes encoding all enzymes of the biosynthetic pathway leading from acetyl-coenzyme A to FPP.

The co-transformed cells were selected on LB-agar plates containing ampicillin (50 µg/mL) and chloramphenicol (34 µg/mL). Single colonies were used to inoculate 5 mL liquid LB medium supplemented with the same antibiotics. Cul- tures were incubated overnight at 37° C. while shaking at 200 rpm. The next day, 2 mL of TB medium supplemented with the above-mentioned antibiotics and glycerol (3% w/v final) were inoculated with 0.2 mL of the overnight culture. After 5 hours of incubation at 37° C. and shaking at 200 rpm, the culture was cooled down to 25° C. and shaken a further hour at 200 rpm. IPTG (0.1 mM final) was then added to each tube, and the culture overlaid with 200 µL of decane. The cultures were incubated for a further 48 hours at 25° C. at 200 rpm and then extracted twice with 1 volume of ethyl acetate. 50 µL of isolongifolene at 2 mg/mL were added to the organic phase as internal standard before analysing the samples by GC/MS.

Figure 19:
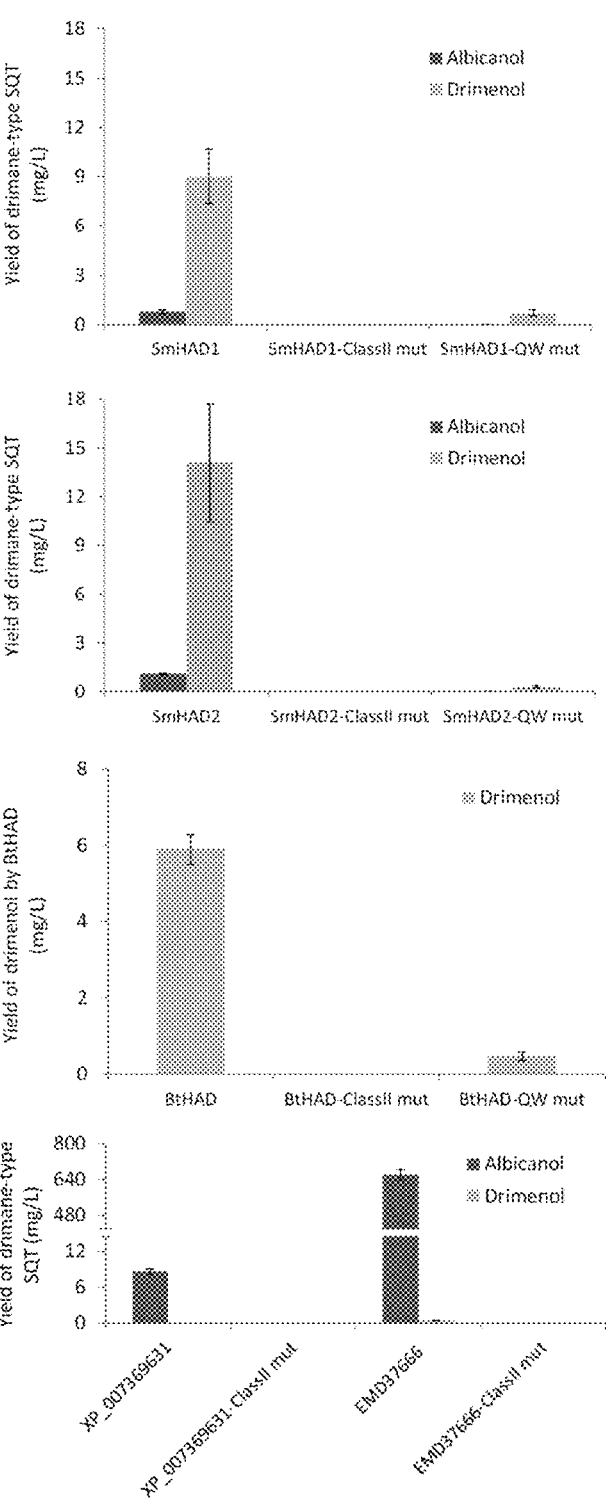
FIG. 19. Comparison of yields (Mean±SE, n=4~5) of drimane-type sesquiterpenes synthesized by SmHAD1, SmHAD2, BtHAD, XP_007369631.1 and EMD37666.1 and their mutants in an in vivo biochemical assay. The SmHAD1 and SmHAD2 mutants comprise the mutations D257A and D259A in the class II motif (SEQ ID NOs: 21, 28 and 40) and the mutations E432A and D433A in the QW motif (SEQ ID NOs: 23, 30 and 44); the BtHAD mutant comprises the mutations D320A and D322A in the class II motif (SEQ ID NOs: 14 and 39) and the mutation D491A in the QW motif (SEQ ID NOs: 16 and 43); the EMD37666.1 mutant comprises the mutations D276A, D277A, and D279A in the class II motif (SEQ ID NOs: 34 and 41); the XP_007369631.1 mutant comprises the mutations D272A, D273A and D275A in the class II motif (SEQ ID NOs: 38 and 42).

BtHAD, SmHAD1, SmHAD2, the fungal HAD-like TPSs and their mutants were analysed in an in vivo biochemical assay. In all the enzymes with a mutated class II motif, neither albicanol nor drimenol was detected. These results support the hypothesis of a protonation-initiated cyclisation of FPP, with the involvement of a class II motif, rather than a classic ionisation-initiated cyclisation mediated by a class I motif (FIG. 19). We also observed a 90% and higher loss of productivity of albicanol and drimenol by the mutants of QW motif, possibly associated with the enzyme integrity and thermostability.

Example 4

Characterisation of the Plant HAD-Like TPSs in an In Vitro System (Proof of the Presumably Albicanyl and Drimenyl Diphosphates).

An in vitro biochemical assay was performed to study the cyclisation mechanism of the newly identified plant HAD-like drimane sesquiterpene synthases.

BL21(DE3) *E. coli* cells (Tiangen) were transformed with the plasmids pETDuet-SmHAD1, pETDuet-SmHAD2 and pETDuet-BtHAD, respectively. The transformed cells were selected on LB-agar plates containing ampicillin (50 µg/mL). Single colonies were used to inoculate 25 mL liquid LB medium supplemented with the same antibiotics. The culture was incubated for 5 hours at 37° C. at 200 rpm, until an $OD_{600}$ of about 0.5 has been reached, was then cooled down to 20° C. and shaken a further 0.5 hour at 200 rpm. Then, IPTG (0.1 mM final) was added to each tube and the cultures were incubated for a further 18 hours at 20° C. at 200 rpm.

For the in vitro biochemical assay, 25 mL of *E. coli* culture expressing SmHAD1, SmHAD2, or BtHAD, respectively, were centrifuged and re-suspended in 5 mL 50 mM Tris-HCl pH 8.0 buffer (10 mM $MgCl_2$, 5 mM DTT), followed by sonication to yield the crude cell lysates. 29 µM FPP were added to 1 mL of each of the crude cell lysates for the reaction and incubated at 30° C., 50 rpm for 2 hours. The samples were then split into two halves and to one of them 20 µL of a bacterial alkaline phosphatase (BAP; Sangon- B004081-100) was added and the reaction pursued for an extra 1 hour at 25° C. (BAP can remove the potential diphosphate groups from drimenyl and/or albicanyl diphosphates to yield drimenol and/or albicanol). A control with no BAP (second half of the sample) was incubated under the same conditions. 10 µL of isolongifolene (internal standard) at 2 mg/mL was added into a 0.5 mL aliquot of the organic phase as internal standard. The reactions were then extracted with 0.25 mL ethyl acetate and analysed by GC/MS, the method as described above.

Figure 20:
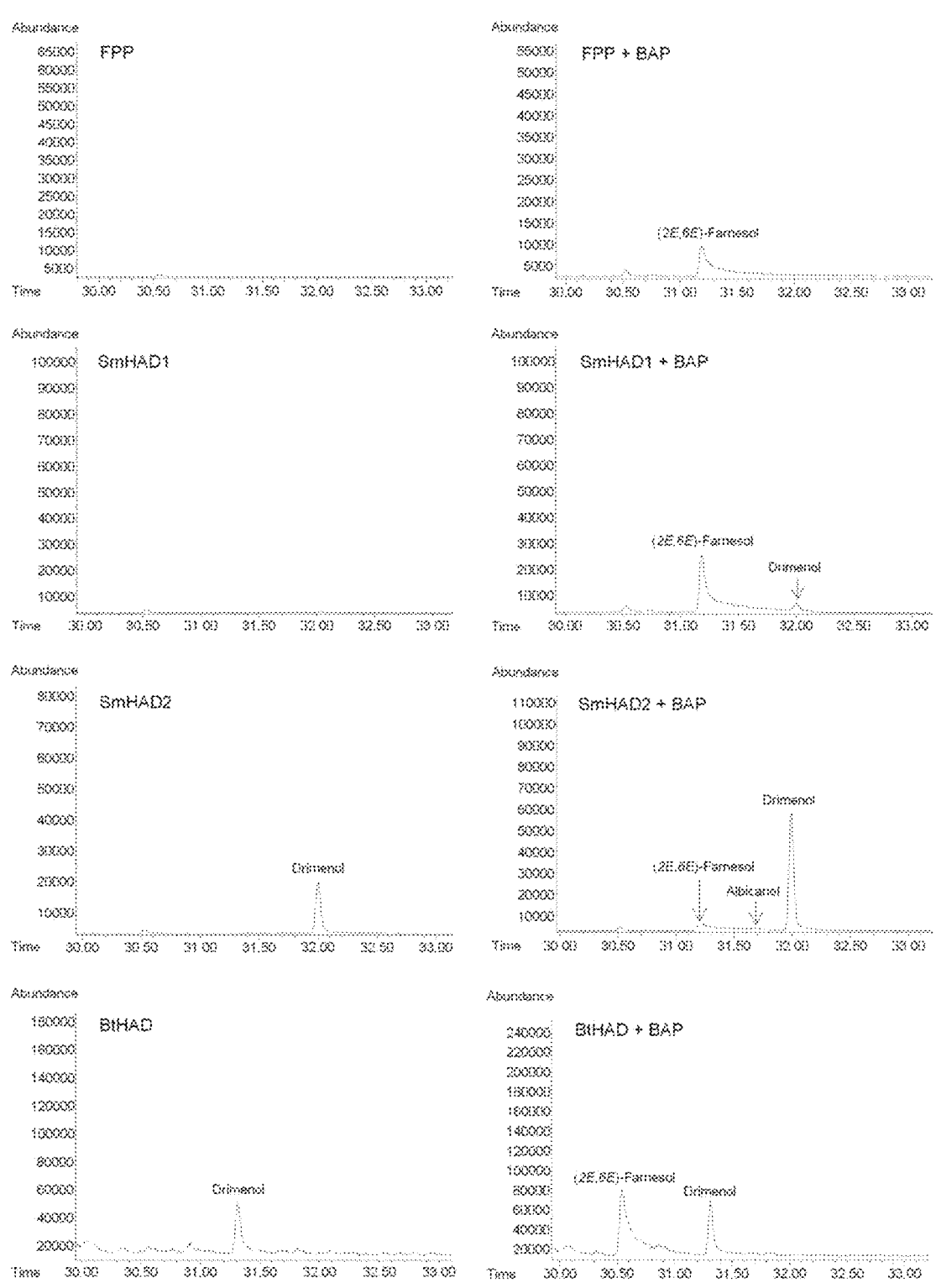
FIG. 20. GC/MS chromatograms of samples from the in vitro biochemical assay of SmHAD1, SmHAD2 and BtHAD in the absence or presence of BAP (Bacterial alkaline phosphatase). (2E,6E)-Farnesol results from the dephosphorylation of the precursor FPP, whereas albicanol and drimenol are presumably the products of the dephosphorylation of albicanyl and drimenyl diphosphates, respectively.

The addition of BAP to the reactions using SmHAD2 and BtHAD lysates resulted in a 3.5-fold and 1.8-fold increase in the amount of drimenol, respectively. The presence of drimenol in the reactions in lack of BAP treatment can be explained by the activity of *E. coli*'s native phosphatases. The reaction using SmHAD1 lysate did not produce an observable amount of drimenol, but the addition of BAP allowed its detection, albeit in a minute amount. Likewise, only a minute amount of albicanol could be detected in the reaction using SmHAD2 lysate and in the reaction where BAP was added (FIG. 20 and Table 3).

TABLE 3

| Productivity of SmHAD1 and SmHAD2 in in vitro biochemical assay | | |
|---|---|---|
| | Identification | Titre (mg/L) |
| SmHAD2 + BAP | Albicanol | 0.01 |
| | Drimenol | 3.32 |
| BtHAD | Drimenol | 0.32 |
| BtHAD + BAP | Drimenol | 0.59 |

These findings support the assumption of protonation-initiated cyclisation mechanism for the biosynthesis of drimenyl and albicanyl diphosphates.

All the publications mentioned in this application are incorporated by reference to disclose and describe the methods and/or materials in connection with which the publications are cited.

Listing of Sequences

TABLE 4

| Sequences described and used herein | | | |
|---|---|---|---|
| SEQ ID NO | Description | Source | Type |
| 1 | BazzHAD1_wt_nucleic acid sequence | *Bazzania sp.* | NA |
| 2 | BazzHAD1_*E. coli* optimized | *Bazzania sp.* | NA |
| 3 | BazzHAD1_amino acid sequence | *Bazzania sp.* | AA |
| 4 | BazzHAD2_wt_nucleic acid sequence | *Bazzania sp.* | NA |
| 5 | BazzHAD2_*E. coli* optimized | *Bazzania sp.* | NA |
| 6 | BazzHAD2_amino acid sequence | *Bazzania sp.* | AA |
| 7 | BazzHAD3_wt_nucleic acid sequence | *Bazzania sp.* | NA |
| 8 | BazzHAD3_*E. coli* optimized | *Bazzania sp.* | NA |
| 9 | BazzHAD3_amino acid sequence | *Bazzania sp.* | AA |
| 10 | BtHAD_wt_nucleic acid sequence | *Bazzania trilobata* | NA |
| 11 | BtHAD_*E. coli* optimized | *Bazzania trilobata* | NA |
| 12 | BtHAD_amino acid sequence | *Bazzania trilobata* | AA |

TABLE 4-continued

Sequences described and used herein

| SEQ ID NO | Description | Source | Type |
|---|---|---|---|
| 13 | BtHAD mutant of class II motif_*E. coli* optimized | Artificial | NA |
| 14 | BtHAD mutant of class II motif | Artificial | AA |
| 15 | BtHAD mutant of QW motif_*E. coli* optimized | Artificial | NA |
| 16 | BtHAD mutant of QW motif | Artificial | AA |
| 17 | SmHAD1_wt_nucleic acid sequence | *Selaginella moellendorffii* | NA |
| 18 | SmHAD1_*E. coli* optimized | *Selaginella moellendorffii* | NA |
| 19 | SmHAD1_amino acid sequence | *Selaginella moellendorffii* | AA |
| 20 | SmHAD1 mutant of class II motif_*E. coli* optimized | Artificial | NA |
| 21 | SmHAD1 mutant of class II motif | Artificial | AA |
| 22 | SmHAD1 mutant of QW motif_*E. coli* optimized | Artificial | NA |
| 23 | SmHAD1 mutant of QW motif | Artificial | AA |
| 24 | SmHAD2_wt_nucleic acid sequence | *Selaginella moellendorffii* | NA |
| 25 | SmHAD2_*E. coli* optimized | *Selaginella moellendorffii* | NA |
| 26 | SmHAD2_amino acid sequence | *Selaginella moellendorffii* | AA |
| 27 | SmHAD2 mutant of class II motif_*E. coli* optimized | Artificial | NA |
| 28 | SmHAD2 mutant of class II motif | Artificial | AA |
| 29 | SmHAD2 mutant of QW motif_*E. coli* optimized | Artificial | NA |
| 30 | SmHAD2 mutant of QW motif | Artificial | AA |
| 31 | EMD37666.1_*E. coli* optimized | *Gelatoporia subvermispora* | NA |
| 32 | EMD37666.1_amino acid sequence | *Gelatoporia subvermispora* | AA |
| 33 | EMD37666.1 mutant of class II motif_*E.coli* optimized | Artificial | NA |
| 34 | EMD37666.1 mutant of class II motif | Artificial | AA |
| 35 | XP 007369631.1_*E. coli* optimized | *Dichomitus squalens* | NA |
| 36 | XP_007369631.1 amino acid sequence | *Dichomitus squalens* | AA |
| 37 | XP_007369631.1 mutant of class II motif_*E.coli* optimized | Artificial | NA |
| 38 | XP_007369631.1 mutant of class II motif | Artificial | AA |
| 39 | class II synthase motif_mutated_BtHAD | Artificial | AA |
| 40 | class II synthase motif_mutated_SmHAD1 + 2 | Artificial | AA |
| 41 | class II synthase motif_mutated_EMD37666.1 | Artificial | AA |
| 42 | class II synthase motif_mutated_XP_007369631.1 | Artificial | AA |
| 43 | QW motif_mutated BtHAD | Artificial | AA |
| 44 | QW motif_mutated SmHAD1 + 2 | Artificial | AA |

TABLE 4-continued

Sequences described and used herein

| SEQ ID NO | Description | Source | Type |
|---|---|---|---|
| 45 | class I synthase motif Dxx(D/E) | Artificial | AA |
| 46 | class II synthase motif PxDxD(T/S)(T/M)S | Artificial | AA |
| 47 | class II synthase motif PDDLDSTS | Artificial | AA |
| 48 | class II synthase motif PDDLDTTS | Artificial | AA |
| 49 | class II synthase motif PPDIDTMS | Artificial | AA |
| 50 | class II synthase motif PNDIDTTS | Artificial | AA |
| 51 | QW motif QxxDGxW | Artificial | AA |
| 52 | QW motif QNVDGSW | Artificial | AA |
| 53 | QW motif QCDDGGW | Artificial | AA |
| 54 | QW motif QSSDGGW | Artificial | AA |
| 55 | QW motif QNEDGSW | Artificial | AA |
| 56 | conserved motif 1 Lxxxx(W/F)xxYxxG | Artificial | AA |
| 57 | conserved motif 1 LRSHIWFNYSMG | Artificial | AA |
| 58 | conserved motif 1 LRSATWAAYECG | Artificial | AA |
| 59 | conserved motif 1 LRTPTWGKYECG | Artificial | AA |
| 60 | conserved motif 1 LQHSSFLAYSCG | Artificial | AA |
| 61 | conserved motif 1 LRxxTWxxYECG | Artificial | AA |
| 62 | conserved motif 2 YxDxxRxRVD(P/A)V(V/A)xxN | Artificial | AA |
| 63 | conserved motif 2 YFDPLRLRVDPVAATN | Artificial | AA |
| 64 | conserved motif 2 YFDETRPRVDAVVNVN | Artificial | AA |
| 65 | conserved motif 2 YFDKTRPRVDPVVCVN | Artificial | AA |
| 66 | conserved motif 2 YLDVERPRVDPVVIAN | Artificial | AA |
| 67 | conserved motif 2 YLDLERPRVDPVVIAN | Artificial | AA |
| 68 | conserved motif 2 Y(F/L)Dx(T/E)RPRVD(P/A)VVx(A/V)N | Artificial | AA |
| 69 | conserved motif 3 GTx(Y/F)YxxxExFL(Y/F) | Artificial | AA |
| 70 | conserved motif 3 GTLYYRTPEAFLY | Artificial | AA |
| 71 | conserved motif 3 GTLFYYHAESFLY | Artificial | AA |
| 72 | conserved motif 3 GTRYYLSQEDFLF | Artificial | AA |
| 73 | DfHAD_wt_nucleic acid sequence | Dryopteris fragrans | NA |
| 74 | DfHAD_amino acid sequence | Dryopteris fragrans | AA |
| 75 | class II synthase motif DxDxxS | Artificial | AA |
| 76 | QW motif QxxxxxW | Artificial | AA |

SEQ ID NO: 1

*Bazzania* sp._BazzHAD1_wt_nucleic acid sequence
ATGGCTCCTCCTTTCGGATTTATTGGTGGGAATGCAACGAGTGTGACGACTTCCCCAGATGTCCTCGACTACA
ACTATGACGGTGGCCCTCCTACTGGCCAATACAAGAGTTTGATTTTAGACATTGGTGGAGTGTTGCTTCAGCC
CAACCTTGACAGGAGCTATGGCACGATTGTACCACCTGTGCAATTCAACGTATGTTGCGCTCGCACATCTGG
TTCAATTACTCAATGGGAAAGATGTCTGCGGAGGAAGTGTTTCGGCAGCTCTCCGTGAAGTCTGGCTACCCGG
CAGAAGATATCCGGAGTTTTGGTCGCAAAGCGAGAGAGTCTCTTGTCCCCATCACACAAATAACGGATCTTCT
GTTCAAACTCAGCAAGGAATCGAAGGTCAGACTGTTCTGTATGACCAATTGCCCTGCAGAAGACTTCGAATAC
CTCTCACAGGCATATCCCAAGCTTTTCGGCTTGTTCGAGAGGATTTTTACGTCGGCATCCACCGGTATGCGCA
AGCCAAACAGGAATTTCTTCCGACATGTACTCCAGGAGACGGGAATCAGAGCGTCGGAGACTATTTTCGTAGA
CGACCTGGTACCGAACATTATGGCCGCCGAGGCGCTGGACTTCACGGCGATTCACGTTTCTCCAGAGTCGCCC
GCCGAGACCGTGAGGTTGCTGATGTTCCATCTCCGTAAGCCAGAAGAGCGGCTGGCGGCGGCGCGCGACTATC
TCCTGCGCAACCGTGGAGTGGACAAAGCTCTCTCTCTCACATCTGATGGAGTCCAGGTCCAGGTTTATTTCGA
CCACTTCGTGGTCGCCGAAGTGCTCAACGACGAGCGATTCTTGCCAATCACTGCAGCTCCGGAGTCCGGGACT
ATGAACTTTTTCCCGAAGGAGGAACGCAAAGCGACTCGAGATATAACGACCAATGCAGTCACACACGTGGACC
TTCCCGATGATCTTGACTCCACCTCTGTCGCCTTATCGGTCCTTTACAAATTCTCCAAAGTGGGGATGGAGAC
GGTTCAAAGGGTCCTGGATATGATGGAGAAACGTGTGGATGATGACGGCATTTTTCAAACGTACTTCGATCCT
TTGCGGCTGCGTGTTGACCCGGTGGCCGCTACTAACACCGTCTACCTCTTCCATCTAGGAGGTCGTCCCGGAC
CTACTCAGCAGACGGAACAATTCCTCTCCAAGTTACTGGAAAAGAGATCTTATCTCCGCGGCACACTCTACTA
CCGGACCCCCGAGGCATTTCTCTATCAACTCACCAGATTGGTGGTATCATTTGAGGAGTATTTCAGAAAGACA
GGCTTCCTGGAAATGCTCAAGAAAAGGCTGAGTGAGCGAGTGGGCATAGAGAGCGATGCATTCACGTTGGCGA
TGAGGATTCTAGCGTGTGTGAATTGTGGAATCCCTGTTGCTGAGCTGAACAGAGATATGGACAGACTAGCACG
GATGCAAAATGTGGATGGTTCATGGGACGTCTGCCCTTACTACAGCTACAATGATCCCAAGAGTTGGTTTGGG
AACGAGCTTCTTACCACAGCTTTTGCTGCTGCCGCTCTTGAGCAGTCTGAGCCCAACTTTAACTGA

SEQ ID NO: 2

*Bazzania* sp._BazzHAD1_*E. coli* optimized
ATGGCTCCGCCGTTCGGCTTTATCGGTGGCAACGCGACCAGCGTTACCACCAGCCCGGATGTGCTGGACTACA
ACTATGATGGTGGCCCGCCGACCGGCCAGTACAAAAGCCTGATCCTGGATATTGGTGGCGTTCTGCTGCAACC
GAACCTGGACCGTAGCTATGGCACCATCGTTCCGCCGGTGCAGTTCAAGCGTATGCTGCGTAGCCACATTTGG
TTTAACTACAGCATGGGTAAAATGAGCGCGGAGGAAGTTTTCCGTCAACTGAGCGTGAAGAGCGGTTATCCGG
CGGAGGATATCCGTAGCTTTGGCCGTAAAGCGCGTGAAGCCTGGTTCCGATCACCCAGATTACCGACCTGCT
GTTCAAGCTGAGCAAAGAGAGCAAAGTGCGTCTGTTCTGCATGACCAACTGCCCGGCGGAGGACTTTGAATAC
CTGAGCCAAGCGTATCCGAAACTGTTCGGTCTGTTTGAACGTATTTTTACCAGCGCGAGCACCGGCATGCGTA
AGCCGAACCGTAACTTCTTTCGTCACGTGCTGCAGGAGACCGGCATCCGTAGCGAGCGAAACCATTTTCGTTGA
CGATCTGGTGCCGAACATCATGGCGGCGGAGGCGCTGGATTTTACCGCGATTCACGTTAGCCCGGAGAGCCCG
GCGGAAACCGTGCGTCTGCTGATGTTCCACCTGCGTAAACCGGAGGAACGTCTGGCGGCGGCGCGTGACTACC
TGCTGCGTAACCGTGGTGTTGATAAAGCGCTGAGCCTGACCAGCGATGGTGTGCGTGTTCAGGTGTATTTCGA
TCACTTTGTGGTTGCGGAAGTGCTGAACGACGAACGTTTTCTGCCGATCACCGCGGCGCCGGAAAGCGGCACC
ATGAACTTCTTTCCGAAAGAGGAACGCAAGGCGACCCGTGATATTACCACCAACGCGGTTACCCACGTGGATC
TGCCGGACGATCTGGACAGCACCAGCGTTGCGCTGAGCGTGCTGTACAAATTCAGCAAGGTTGGTATGGAGAC
CGTTCAGCGTGTGCTGGACATGATGGAAAAGCGTGTGGACGATGACGGCATCTTCCAAACCTACTTTGATCCG
CTGCGTCTGCGTGTTGACCCGGTGGCGGCGACCAACACCGTTTACCTGTTTCATCTGGGTGGCCGTCCGGGTC
CGACCCAGCAAACCGAGCAGTTTCTGAGCAAACTGCTGGAAAAGCGTAGCTATCTGCGTGGCCACCCTGTACTA
TCGTACCCCGGAGGCGTTCCTGTACCAACTGACCCGTCTGGTGGTTAGCTTCGAGGAATATTTTCGTAAAACC
GGTTTCCTGGAAATGCTGAAGAAACGTCTGAGCGAGCGTGTGGGCATTGAAAGCGATGCGTTTACCCTGGCGA
TGCGTATCCTGGCGTGCGTTAACTGCGGTATTCCGGTGGCGGAGCTGAACCGTGATATGGACCGTCTGGCGCG
TATGCAGAACGTTGATGGTAGCTGGGACGTGTGCCCGTACTATAGCTACAACGACCCGAAGAGCTGGTTCGGC
AACGAACTGCTGACCACCGCGTTTGCGGCGGCGGCGCTGGAGCAAAGCGAACCGAACTTCAACTAA

SEQ ID NO: 3

*Bazzania* sp._BazzHAD1_amino acid sequence
MAPPFGFIGGNATSVTTSPDVLDYNYDGGPPTGQYKSLILDIGGVLLQPNLDRSYGTIVPPVQFKRM**LRSHIW
FNYSMG**KMSAEEVFRQLSVKSGYPAEDIRSFGRKARESLVPITQITDLLFKLSKESKVRLFCMTNCPAEDFEY
LSQAYPKLFGLFERIFTSASTGMRKPNRNFFRHVLQETGIRASETIVDLVPNIMAAEALDFTAIHVSPESP
AETVRLLMFHLRKPEERLAAARDYLLRNRGVDKALSLTSDGVRVQVYFDHFVVAEVLNDERFLPITAAPESGT
MNFFPKEERKATRDITTNAVTHVDLPDDLDSTSVALSVLYKFSKVGMETVQRVLDMMEKRVDDDGIFQT**YFDP
LRLRVDPVAATNTVYLFHLGGRPGPTQQTEQFLSKLLEKRSYLRGTLYYRTPEAFLY**QLTRLVVSFEEYFRKT
GFLEMLKKRLSERVGIESDAFTLAMRILACVNCGIPVAELNRDMDRLARMQNVDGSWDVCPYYSYNDPKSWFG
NELLTTAFAAAALEQSEPNFN

SEQ ID NO: 4

*Bazzania* sp._BazzHAD2_wt nucleic acid sequence
ATGGAAAGACCTCATTTCGACACTCTGATCATGGACCTGGGAGGTGTTCTTGTCGACTTCTCTCTTCAAACAT
CCACATCCACTTCTGTGAAATCTCTCAAGTTTGTATTACGTTCCGCCACCTGGGCAGCTTACGAGTGCGGCCA
TATGTCAGAATCGGATTGCTATGCTGCAGTGGCTAAAGATCTTGGAAGCTCTGCAAACGCATCTCAAGTTGGT
GAAGCCATCTCAGAAGTTCGAAAGTCACTGCAGGTCAATGAAGATTTGATAGGGGTGATTCGGGAGCTCAAAG
CCCAGAACGGCCTTCGAGTTTACGTAATGTCCAACATACCACAACCAGACTTCGATGCCGTCAAAGCTAAGTC
AGCGAGCTGGGGAGTATTCGATGCATGTATCCCTCGTATGCGGTGGGCACCCATAAGCCCGATCTTGCTTTC
TATCGACACGTACTCGAAGAGACAAACACAGACCCTCTCAAAGCGATCTTTGTCGACGACAGCTTACAAAATG
TCATTGCAGCCAGATCTTTTGGATTGACAGGAATTATCTACAATGATACTGTCAATGCTGCTCGAACGCTGCG
AAATCTCCTTGGTGATCCTATCTTGAGGAGGTGAGCAGTACCTTTCGTCCCACGCTGGACAATTGCTGTCTATC
TCAGACACAGGAACCCCCTTCCCAGATAACTTTTCACAGCTTTTAATTTTGGATGCTACCGGAAACCGTGATC
TTGTTGTTCTTGAAAACCCTCAGCGAACATGGAACTACTTCATCGGAAAGCCTGTGTTGACGTCTGAAACATT
CCCTGATGATCTAGATACGACATCTATCGCCCTCATGGCATTGAATGTAGACCTAGAGGTGGCCAATTCTGTG
ATGGATGAGATGCTGGAGTTTAGAAACAGTGATGGATTGTTTCTGACGTACTTTGACGAAACAAGGCCGCGGG
TAGATGCTGTTGTCAATGTTAATGTTCTTCGTCTCTTCCATCGATGAACGGGAGAGAGAGCCCAGCAACC
GCTGGAGTGGATTACCAACGTCCTTACCCACCGAGCGTATGTTGATGGCACACTATTTTACTACCATGCTGAG
AGCTTCTTATATTTCCTTTCGCGACTGTTCTGTGAGAACTCCAGCGTCCAATCACGATTTCAAGAGCTTCTTG
AACAACGCCTGCGGGAACGAATTGGAACCCCGGGCGACGCACTGAGTCTAGCCATGCGTGCATTAGCATGCCA
GATGCTGGGAATCGATAGTTCTACCGACGTTCGCGCTCTTCTGCCCTTGCAATGCGACGACGGCGGTTGGGAA -continued GCTGGCTGGGTGTGCAGATACGGTTCAAATGGTATGCGCGTTGGAAGCCGGGGATACACTACGGCTTTGGCTA
TAAATGCTATCAGAGGGGCAAGAGTCTCGAGGTGA

SEQ ID NO: 5

*Bazzania* sp._BazzHAD2_*E. coli* optimized
ATGGAACGTCCGCACTTCGACACCCTGATCATGGATCTGGGTGGCGTGCTGGTTGACTTTAGCCTGCAGACCA
GCACCAGCACCAGCGTTAAGAGCCTGAAATTTGTGCTGCGTAGCGCGACCTGGGCGGCGTACGAATGCGGTCA
CATGAGCGAGAGCGACTGCTATGCGGCGGTTGCGAAGGATCTGGGTAGCAGCGCGAACGCGAGCCAAGTGGGT
GAAGCGATCAGCGAGGTTCGTAAGAGCCTGCAAGTGAACGAGATCTGATCGGTGTTATTCGTGAGCTGAAAG
CGCAGAACGGCCTGCGTGTGTACGTTATGAGCAACATTCCGCAACCGGACTTCGATGCGGTTAAGGCGAAAAG
CGCGAGCTGGGGTGTGTTTGATGGCATGTACCCGAGCTATGCGGTTGGCACCCACAAGCCGGACCTGGCCGTTT
TATCGTCACGTGCTGGAGGAAACCAACACCGATCCGCTGAAAGCGATCTTCGTTGACGATAGCCTGCAAAACG
TGATTGCGGCGCGTAGCTTTGGTCTGACCGGCATCATTTACAACGACACCGTGAACGCGGCGCGTACCCTGCG
TAACCTGCTGGGTGATCCGATCCTGCGTGGCGAACAGTATCTGAGCAGCCACGCGGGTCAACTGCTGAGCATT
AGCGACACCGGCACCCCGTTCCCGGATAACTTTAGCCAGCTGCTGATTCTGGACGCGACCGGTAACCGTGATC
TGGTGGTTCTGGAAAACCCGCAACGTACCTGGAACTACTTCATCGGCAAACCGGTTCTGACCAGCGAGACCTT
TCCGGACGATCTGGACACCACCAGCATTGCGCTGATGGCGCTGAACGTGGACCTGGAAGTTGCGAACAGCGTG
ATGGATGAAATGCTGGAGTTCCGTAACAGCGACGGTCTGTTCCTGACCTACTTTGACGAGACCCGTCCGCGTG
TGGATGCGGTGGTTAACGTGAACGTTCTGCGTCTGTTTCACCGTCACGAGCGTGAACGTGAGGCGCAGCAACC
GCTGGAGTGGATTACCAACGTTCTGACCCACCGTGCGTACGTGGACGGCACCCTGTTCTACTATCACGCGGAA
AGCTTCCTGTATTTTCTGAGCCGTCTGTTCTGCGAGAACAGCAGCGTTCAGAGCCGTTTTCAAGAACTGCTGG
AGCAGCGTCTGCGTGAACGTATTGGCACCCCGGGTGATGCGCTGAGCCTGGCGATGCGTGCGCTGGCGTGCCA
GATGCTGGGTATTGACAGCAGCACCGATGTGCGTGCGCTGCTGCCGCTGCAATGCGATGATGGTGGCTGGGAG
GCGGGTTGGGTTTGCCGTTACGGTAGCAACGGCATGCGTGTGGGTAGCCGTGGCTATACCACCGCGCTGGCGA
TCAACGCGATTCGTGGTGCGCGTGTTAGCCGTTAA

SEQ ID NO: 6

*Bazzania* sp._BazzHAD2_amino acid sequence
MERPHFDTLIMDLGGVLVDFSLQTSTSTSVKSLKFVLRSATWAAYECGHMSESDCYAAVAKDLGSSANASQVG
EAISEVRKSLQVNEDLIGVIRELKAQNGLRVYVMSNIPQPDFDAVKAKSASWGVFDGMYPSYAVGTHKPDLAF
YRHVLEETNTDPLKAIFVDDSLQNVIAARSFGLTGIIYNDTVNAARTLRNLLGDPILRGEQYLSSHAGQLLSI
SDTGTPFPDNFSQLLILDATGNRDLVVLENPQRTWNYFIGKPVLTSETFPDDLDTTSIALMALNVDLEVANSV
MDEMLEFRNSDGLFLTYFDETRPRVDAVVNVNVLRLFHRHEREREAQQPLEWITNVLTHRAYVDGTLFYYHAE
SFLYFLSRLFCENSSVQSRFQELLEQRLRERIGTPGDALSLAMRALACQMLGIDSSTDVRALLPLQCDDGGWE
AGWVCRYGSNGMRVGSRGYTTALAINAIRGARVSR

SEQ ID NO: 7

*Bazzania* sp_BazzHAD3_wt_nucleic acid sequence
ATGCCTGCTTTAAGCTCGCATATGGAGCCACCTAATTTTGACACCCTGATCCTGGACCTGGGAGATGTCCTTG
TGGGAGGCTCTCTTCAAGGCTCTTACGCCTTGGCCATGAAGAGAATTCTGAAACTCTCATTACGTACCCCGAC
GTGGGGAAAATACGAGTGCGGCCAATTATCAGAATTAGATTGCTATGACGCTGTGGCTGAAGATCTTGGGAAC
TCCACAAGCTCCGCTCAAGTGGGTGAGGTCGTCTCAGAAGCTCGAAAGTCATTGCAGGTCAATGAAGACCTGA
TAAAGGTGCTTCAGGAGCTAAAGGCTGAGAACAATCTCCGGGTTTATGTCATGTCCAATATACCCAAGCCGGA
TTTGGCTGTTGTGAAGGCCAAGTCAGTGAACTGGGGAGTCATCGATGGCTGGTATCCCTCTTATGCTGTGGGC
TTCCACAAGCCGGATCTCGCTTTCTACCGGCATGTACTTGAAGAGACAAACACCGATCCTCTTAAGGCCATCT
TCGTTGATGACAAGGTTCAGAATGTCATTGTTGCCAGATCCTTTGGAATGACAGGCATTGTCTTCAAGGACAC
TAAGAGCACTACCAAGGAGCTGAAGAATCTCCTTGGTGACCCCGTCAAGAGAGGGGACACTTCCTCTCAGCT
CATGCCAAACAATTGGAGTCTGTCTGTGGGGATGGCACCCACTTTCCTTGACAACTTCGCCCAGCTGCTGATTC
TTCATGATACTGGAAACAGCGATCTTGTGGCTCGTCAGCACCATGGCAGAACCTGGAACTACTTCATTGGCAA
GCCGATGGGGACGACAGACACATTCCCCAACGACCTAGATACCACCTCCATCGCTCTGCTGACTCTGAATGTA
GACTCAGAAGTAGCGAGGTCTGTGTTAGATGAGATGCTGCTGTACACCAGCAGTGATGGGCTGGTAGAGGTGT
ATTTTGACAAAACTAGACCTCGGGTGGATCCCGTTGTCTGTGTCAACGTGCTACGTCTCTTCTCTAAATATGG
GAGGGAGCTCCAGCTTCAGAAGACTCTGGACTGGGTAACTGAGGTCCTTGTTCACCGAGCTTACATTGACGGC
ACACTCTTCTACTACCACGCTGAGAGCTTCTTGTACTTCCTTTCGTGTCTCTACAAAGAGAACCCCCGGCTGC
AGACTCAATTTCGGGAGCCTCTACAAGAACGCCTGCGGGAGGAGATTGGGCAGCCCGGGGATGCACTTTGTCT
GGCTATGCGTGCAATCGCATGCCAGACTGTGGGGATTGGGAATGTTATTGATGCGCAAGCTCTTCTGCCATTG
CAATCTAGTGATGGTGGTTGGGAGGCTGGCTGGGTCTGCAGAATGGGCACGTCTGGTGTTCCTGTTGGAAACC
GAGGAGTCACAACGGCACTTTGTATTAGAGCTATTCGAGGCGCATCAGGGAGCTACCACACTTGA

SEQ ID NO: 8

*Bazzania* sp._BazzHAD3_*E. coli* optimized
ATGCCGGCGCTGAGCAGCCACATGGAACCGCCGAACTTCGACACCCTGATTCTGGACCTGGGTGATGTGCTGG
TTGGTGGCAGCCTGCAGGGTAGCTACGCGCTGGCGATGAAGCGTATCCTGAAACTGAGCCTGCGTACCCCGAC
CTGGGGCAAGTACGAATGCGGCCAGCTGAGCGAGCTGGACTGCTATGATGCGGTTGCGGAAGACCTGGGTAAC
AGCACCAGCAGCGCGCAAGTGGGCGAGGTGGTTAGCGAAGCGCGTAAAAGCCTGCAGGTTAACGAGGATCTGA
TCAAGGTGCTGCAAGAGCTGAAAGCGGAAAACAACCTGCGTGTGTACGTTATGAGCAACATTCCGAAGCCGGA
CCTGGCCGGTGGTTAAGGCGAAAAGCGTGAACTGGGGTGTTATCGATGGCTGGTATCCGAGCTATGCGGTTGGT
TTCCACAAACCGGACCTGGCGTTTTATCGTCACGTGCTGGAAGAAACCAACACCGATCCGCTGAAGGCGATCT
TCGTGGACGATAAAGTTCAGAACGTGATTGTTGCGCGTAGCTTCGGTATGACCGGCATCGTTTTTAAGGACAC
CAAAAGCACCACCAAGGAACTGAAAAACCTGCTGGGTGATCCGGTTAAGCGTGGCGAACACTTTCTGAGCGCG
CACGCGAAACAACTGGAGAGCGTGTGCGGTGACGGCACCACCTTCCTGGATAACTTTGCGCAGCTGCTGATTC
TGCACGACACCGGTAACAGCGATCTGGTGGCGCGTCAACACCAGCAGTGATGGGCTGGTAGAGGTGT
GCCGATGGGCACCACCGATACCTTTCCGAACGACCTGGATACCACCAGCATCGCGCTGCTGACCCTGAACGTG
GACAGCGAAGTTGCGCGTAGCGTGCTGGATGAGATGCTGCTGTACACCAGCAGCGACGGTCTGGTTGAGGTGT
ATTTCGACAAACCCGTCCGCGTGTTGATCCGGTGGTTTGCGTGAACGTTCTGCGTCTGTTTAGCAAGTACGG
TCGTGAACTGCAGCTGCAAAAAACCCTGGATTGGGTGACCGAGGTGCTGGTTCACCGTGCGTATATCGACGGC
ACCCTGTTCTACTATCACGCGGAAAGCTTCCTGTACTTTCTGAGCTGCCTGTATAAGGAGAACCCGCGTCTGC
AGACCCAATTTCGTGAGCCGCTGCAGGAACGTCTGCGTGAGCGTATTGGTCAGCCGGGTGATGCGCTGTGCCT
GGCGATGCGTGCGATCGCGTGCCAGACCGTTGGTATCGGCAACGTGATTGATGTTCAAGCGCTGCTGCCGCTG
CAGAGCAGCGATGGTGGCTGGGAGGCGGGTTGGGTTTGCCGTATGGGCACCAGCGGTGTGCCGGTTGGTAACC
GTGGCGTGACCACCGCGCTGTGCATCCGTGCGATTCGTGGTGCGGAGCGGCAGCTATCACACCTAA -continued SEQ ID NO: 9
*Bazzania* sp._BazzHAD3_amino acid sequence
MPALSSHMEPPNFDTLILDLGDVLVGGSLQGSYALAMKRILKLSLRTPTWGKYECGQLSELDCYDAVAEDLGN
STSSAQVGEVVSEARKSLQVNEDLIKVLQELKAENNLRVYVMSNIPKPDLAVVKAKSVNWGVIDGWYPSYAVG
FHKPDLAFYRHVLEETNTDPLKAIFVDDKVQNVIVARSFGMTGIVFKDTKSTTKELKNLLGDPVKRGEHFLSA
HAKQLESVCGDGTTFLDNFAQLLILHDTGNSDLVARQHHGRTWNYFIGKPMGTTDTFPNDLDTTSIALLTLNV
DSEVARSVLDEMLLYTSSDGLVEVYFDKTRPRVDPVVCVNVLRLFSKYGRELQLQKTLDWVTEVLVHRAYID**G
TLFYYHAESFLY**FLSCLYKENPRLQTQFREPLQERLRERIGQPGDALCLAMRAIACQTVGIGNVIDVQALLPL
QSSDGGWEAGWVCRMGTSGVPVGNRGVTTALCIRAIRGASGSYHT SEQ ID NO: 10
*Bazzania trilobata*_BtHAD_wt_nucleic acid sequence
ATGGCTCCTCCTTTCGGATATATTGGTGGGAATGAATCGAGTGTGACGACGTCCCCAGACGTCCTCGACTACA
GCTATGATGGTGGCCCTCCTACTGGCCAATACAAGAGTATGATTTTAGACATTGGCGGAGTGTTGCTTCAGCC
CAACCTTGACAGGAGCTATGGCACGATTGTACCACCTGTGCAATTCAAACGTATGTTGCGCTCGCACATCTGG
TTCAATTACTCAATGGGAAAGGTGTCTGCGGAGGAAGTGTTTCGGCAGCTCTCCGTGAAGTCTGGCTACCCGG
CAGAAGATATCCGGAGTTTTGCTCGAAAAGCGAGAGAGTCTCTTGTGCCCATCACACAAATAACGGATCTTCT
GGTCAAACTCAGCAAGGAATCGAAGATCAGACTGTTCTGTATGACCAATTGCCCTGCCGAAGACTTCGCATAC
CTCTCACAGGCATATCCCAACCTTTTCGGATTGTTCGAGAGGATTTTTACGTCGGCGTCCACCGGTATGCGCA
AGCCAAACAGGAATTTCTTCCGACATGTACTCCAGGAGACGGGAATCAGTGCGACGGAGACTATTTTCGTAGA
CGACCTGGTACCGAACATCATGGCCGCCGAGGCGCTGGACTTCACGGCAATTCACGTTTCTCCAGAGTCGCCC
GCCGAGACCGTGAGGTTGCTGATGTTCCATCTCCGTAAGCCAGAAGAGCGGCTGGCGGCGGCGCGCGACTATC
TCCTGCGCAACCGTGGAGTGGACAAAGCTCTCTCTCTCACATCTGACGGAGTCCGAGTCCAGGTTTATTTCGA
CCACTTCGTGGTCGCCGAAGTGCTCAACGACGAGCGATTCTTGCCAATCACTGCAGCTCCGAAGTCCGGGACT
ATGAACTTTTTCCCGAAGGAGGAACGCAACGCGACTCGAGATATGACGACCAATGCAGTCACACACGTGGACC
TTCCCGATGATCTTGACTCCACCTCTGTCGCCTTATCGGTCCTTTACAAATTCTCCAAAGTGGCGATGGAGAC
GGTTCAGAGGGTCCTGGATATGATGGAGAAACGTGTGGACGATGACGGCATTTTTCAAACGTACTTCGATCCT
TTGCGGCTGCGTGTTGACCCGGTGGCCGCTACTAACACCGTCTACCTCTTCCATTTAGGAGGTCGTCCCGGAC
CTACTCAGCAGACGGAACAATTCCTCTCCAAGTTACTGGAAAAGAGATCTTACGTCCGCGGCCACACTCTACTA
CAGGACCCCCGAGGCATTTCTCTATCAACTCACCAGATTGGTGGTATCATTTGAGTATTTCAGAAAGACAGGC
TTCCTGGAAATGCTCAAGAAAAGGCTGAGTGAGCGAGTGGGCATCGAGAGCGATGCATTCACGTTGGCGATGA
GGATTCTAGCGTGTGTGAATTGTGGAATCCCTGTTGCTGAGCTGAACAGAGATATGGACAGACTAGCACGGAT
GCAAAATGTGGATGGTTCATGGGACGTCTGCCCTTACTACAGCTACAATGATCCCAAGAGTTGGTTTGGCAAC
GAGCTTCTTACCACAGCGTTTGCTGCTGCCGCTCTTGAGCATTCTGAGCCCAACTTTAAGTGA SEQ ID NO: 11
*Bazzania trilobata*_BtHAD_*E. coli* optimized
ATGGCTCCGCCGTTCGGTTACATTGGTGGCAACGAGAGCAGCGTTACCACCAGCCCGGATGTGCTGGACTACA
GCTATGATGGTGGCCCGCCGACCGGCCAGTACAAAAGCATGATCCTGGATATTGGTGGCGTTCTGCTGCAACC
GAACCTGGACCGTAGCTATGGCACCATCGTTCCGCCGGTGCAGTTCAAGCGTATGCTGCGTAGCCACATTTGG
TTTAACTACAGCATGGGTAAAGTTAGCGCGGAGGAAGTGTTCCGTCAACTGAGCGTGAAGAGCGGCTATCCGG
CGGAGGATATCCGTAGCTTTGCGCGTAAAGCGCGTGAAAGCCTGGTTCCGATCACCCAGATTACCGACCTGCT
GGTGAAGCTGAGCAAAGAGAGCAAGATTCGTCTGTTCTGCATGACCAACTGCCCGGCGGAAGACTTTGCGTAC
CTGAGCCAAGCGTATCCGAACCTGTTCGGTCTGTTTGAGCGTATCTTCACCAGCGCGAGCACCGGCATGCGTA
AGCCGAACCGTAACTTCTTTCGTCACGTTCTGCAGGAGACCGGCATCAGCGCGACCGAAACCATTTTCGTTGA
CGATCTGGTGCCGAACATCATGGCGGCGGAAGCGCTGGATTTTACCGCGATTCACGTTAGCCCGGAGAGCCCG
GCGGAAACCGTGCGTCTGCTGATGTTTCACCTGCGTAAACCGGAGGAACGTCTGGCGGCGGCGCGTGACTACC
TGCTGCGTAACCGTGGTGTTGATAAAGCGCTGAGCCTGACCAGCGATGGTGTGCGTGTTCAAGTGTATTTCGA
TCACTTTGTGGTTGCGGAAGTGCTGAACGACGAACGTTTCCTGCCGATTACCGCGGCGCCGAAAAGCGGCACC
ATGAACTTCTTTCCGAAAGAGGAGCGTAACGCGACCGTGATATGACCAACAACGCGGTTACCCACGTGGATC
TGCCGGACGATCTGGACAGCACCAGCGTTGCGCTGAGCGTGCTGTATCAAATTTAGCAAGGTTGCGATGGAGAC
CGTTCAGCGTGTGCTGGACATGATGGAAAAACGTGTGGACGATGACGGCATCTTCCAAACCTACTTTGATCCG
CTGCGTCTGCGTGTTGACCCGGTGGCGGCGACCAACACCGTTTACCTGTTCCATCTGGGTGGCCGTCCGGGTC
CGACCCAGCAAACCGAGCAGTTTCTGAGCAAACTGCTGGAAAAGCGTAGCTATGTGCGTGGCACCCTGTACTA
TCGTACCCCGGAAGCGTTCCTGTACCAACTGACCCGTCTGGTGGTTAGCTTCGAGTATTTTCGTAAGACCGGT
TTTCTGGAAATGCTGAAGAAACGTCTGAGCGAGCGTGTGGGCATCGAAAGCGATGCGTTCACCCTGGCGATGC
GTATCCTGGCGTGCGTTAACTGCGGTATTCCGGTGGCGGAGCTGAACCGTGATATGGACCGTCTGGCGCGTAT
GCAGAACGTTGATGGTAGCTGGGACGTGTGCCCGTACTATAGCTACAACGACCCGAAAAGCTGGTTCGGCAAC
GAACTGCTGACCACCGCGTTTGCGGCGGCGGCGCTGGAGCACAGCGAACCGAACTTCAAGTAA SEQ ID NO: 12
*Bazzania trilobata*_BtHAD_amino acid sequence
MAPPFGYIGGNESSVTTSPDVLDYSYDGGPPTGQYKSMILDIGGVLLQPNLDRSYGTIVPPVQFKRM**LRSHIW
FNYSMG**KVSAEEVFRQLSVKSGYPAEDIRSFARKARESLVPITQITDLLVKLSKESKIRLFCMTNCPAEDFAY
LSQAYPNLFGLFERIFTSASTGMRKPNRNFFRHVLQETGISATETIFVDDLVPNIMAAEALDFTAIHVSPESP
AETVRLLMFHLRKPEERLAAARDYLLRNRGVDKALSLTSDGVRVQVYFDHFVVAEVLNDERFLPITAAPKSGT
MNFFPKEERNATRDMTTNAVTHVDLPDDLDSTSVALSVLYKFSKVAMETVQRVLDMMEKRVDDDGIFQT**YFDP
LRLRVDPVAATNTVYLFHLGGRPGPTQQTEQFLSKLLEKRSYVRGTLYYRTPEAFLY**QLTRLVVSFEYFRKTG
FLEMLKKRLSERVGIESDAFTLAMRILACVNCGIPVAELNRDMDRLARMQNVDGSWDVCPYYSYNDPKSWFGN
ELLTTAFAAAALEHSEPNFK SEQ ID NO: 13
Artificial_BtHAD mutant of class II motif_*E.coli* optimized
ATGGCTCCGCCGTTCGGTTACATTGGTGGCAACGAGAGCAGCGTTACCACCAGCCCGGATGTGCTGGACTACA
GCTATGATGGTGGCCCGCCGACCGGCCAGTACAAAAGCATGATCCTGGATATTGGTGGCGTTCTGCTGCAACC
GAACCTGGACCGTAGCTATGGCACCATCGTTCCGCCGGTGCAGTTCAAGCGTATGCTGCGTAGCCACATTTGG
TTTAACTACAGCATGGGTAAAGTTAGCGCGGAGGAAGTGTTCCGTCAACTGAGCGTGAAGAGCGGCTATCCGG
CGGAGGATATCCGTAGCTTTGCGCGTAAAGCGCGTGAAAGCCTGGTTCCGATCACCCAGATTACCGACCTGCT
GGTGAAGCTGAGCAAAGAGAGCAAGATTCGTCTGTTCTGCATGACCAACTGCCCGGCGGAAGACTTTGCGTAC
CTGAGCCAAGCGTATCCGAACCTGTTCGGTCTGTTTGAGCGTATCTTCACCAGCGCGAGCACCGGCATGCGTA -continued

```
AGCCGAACCGTAACTTCTTTCGTCACGTTCTGCAGGAGACCGGCATCAGCGCGACCGAAACCATTTTCGTTGA
CGATCTGGTGCCGAACATCATGGCGGCGGAAGCGCTGGATTTTACCGCGATTCACGTTAGCCCGGAGAGCCCG
GCGGAAACCGTGCGTCTGCTGATGTTTCACCTGCGTAAACCGGAGGAACGTCTGGCGGCGGCGCGTGACTACC
TGCTGCGTAACCGTGGTGTTGATAAAGCGCTGAGCCTGACCAGCGATGGTGTGCGTGTTCAAGTGTATTTCGA
TCACTTTGTGGTTGCGGAAGTGCTGAACGACGAACGTTTCCTGCCGATTACCGCGGCGCCGAAAAGCGGCACC
ATGAACTTCTTTCCGAAAGAGGAGCGTAACGCGACCCGTGATATGACCACCAACGCGGTTACCCACGTGGATC
TGCCGGACGCGCTGGCGAGCACCAGCGTTGCGCTGAGCGTGCTGTACAAATTTAGCAAGGTTGCGATGGAGAC
CGTTCAGCGTGTGCTGGACATGATGGAAAAACGTGTGGACGATGACGGCATCTTCCAAACCTACTTTGATCCG
CTGCGTCTGCGTGTTGACCCGGTGGCGGCGACCAACACCGTTTACCTGTTCCATCTGGGTGGCCGTCCGGGTC
CGACCCAGCAAACCGAGCAGTTTCTGAGCAAACTGCTGGAAAAGCGTAGCTATGTGCGTGGCACCCTGTACTA
TCGTACCCCGGAAGCGTTCCTGTACCAACTGACCCGTCTGGTGGTTAGCTTCGAGTATTTTCGTAAGACCGGT
TTTCTGGAAATGCTGAAGAAACGTCTGAGCGAGCGTGTGGGCATCGAAAGCGATGCGTTCACCCTGGCGATGC
GTATCCTGGCGTGCGTTAACTGCGGTATTCCGGTGGCGGAGCTGAACCGTGATATGGACCGTCTGGCGCGTAT
GCAGAACGTTGATGGTAGCTGGGACGTGTGCCCGTACTATAGCTACAACGACCCGAAAAGCTGGTTCGGCAAC
GAACTGCTGACCACCGCGTTTGCGGCGGCGGCGCTGGAGCACAGCGAACCGAACTTCAAGTAA
```

```
                                                                 SEQ ID NO: 14
Artificial_BtHAD mutant of class II motif
MAPPFGYIGGNESSVTTSPDVLDYSYDGGPPTGQYKSMILDIGGVLLQPNLDRSYGTIVPPVQFKRMLRSHIW
FNYSMGKVSAEEVFRQLSVKSGYPAEDIRSFARKARESLVPITQITDLLVKLSKESKIRLFCMTNCPAEDFAY
LSQAYPNLFGLFERIFTSASTGMRKPNRNFFRHVLQETGISATETIFVDDLVPNIMAAEALDFTAIHVSPESP
AETVRLLMFHLRKPEERLAAARDYLLRNGVDKALSLTSDGVRVQVYFDHFVVAEVLNDERFLPITAAPKSGT
MNFFPKEERNATRDMTTNAVTHVDLPDALASTSVALSVLYKFSKVAMETVQRVLDMMEKRVDDDGIFQTYFDP
LRLRVDPVAATNTVYLFHLGGRPGPTQQTEQFLSKLLEKRSYVRGTLYYRTPEAFLYQLTRLVVSFEYFRKTG
FLEMLKKRLSERVGIESDAFTLAMRILACVNCGIPVAELNRDMDRLARMQNVDGSWDVCPYYSYNDPKSWFGN
ELLTTAFAAAALEHSEPNFK
```

```
                                                                 SEQ ID NO: 15
Artificial_BtHAD mutant of QW motif_E. coli optimized
ATGGCTCCGCCGTTCGGTTACATTGGTGGCAACGAGAGCAGCGTTACCACCAGCCCGGATGTGCTGGACTACA
GCTATGATGGTGGCCCGCCGACCGGCCAGTACAAAAGCATGATCCTGGATATTGGTGGCGTTCTGCTGCAACC
GAACCTGGACCGTAGCTATGGCACCATCGTTCCGCCGGTGCAGTTCAAGCGTATGCTGCGTAGCCACATTTGG
TTTAACTACAGCATGGGTAAAGTTAGCGCGGAGGAAGTGTTCCGTCAACTGAGCGTGAAGAGCGGCTATCCGG
CGGAGGATATCCGTAGCTTTGCGCGTAAAGCGCGTGAAAGCCTGGTTCCGATCACCCAGATTACCGACCTGCT
GGTGAAGCTGAGCAAAGAGAGCAAGATTCGTCTGTTCTGCATGACCAACTGCCCGGCGGAAGACTTTGCGTAC
CTGAGCCAAGCGTATCCGAACCTGTTCGGTCTGTTTGAGCGTATCTTCACCAGCGCGAGCACCGGCATGCGTA
AGCCGAACCGTAACTTCTTTCGTCACGTTCTGCAGGAGACCGGCATCAGCGCGACCGAAACCATTTTCGTTGA
CGATCTGGTGCCGAACATCATGGCGGCGGAAGCGCTGGATTTTACCGCGATTCACGTTAGCCCGGAGAGCCCG
GCGGAAACCGTGCGTCTGCTGATGTTTCACCTGCGTAAACCGGAGGAACGTCTGGCGGCGGCGCGTGACTACC
TGCTGCGTAACCGTGGTGTTGATAAAGCGCTGAGCCTGACCAGCGATGGTGTGCGTGTTCAAGTGTATTTCGA
TCACTTTGTGGTTGCGGAAGTGCTGAACGACGAACGTTTCCTGCCGATTACCGCGGCGCCGAAAAGCGGCACC
ATGAACTTCTTTCCGAAAGAGGAGCGTAACGCGACCCGTGATATGACCACCAACGCGGTTACCCACGTGGATC
TGCCGGACGCGCTGGCGAGCACCAGCGTTGCGCTGAGCGTGCTGTACAAATTTAGCAAGGTTGCGATGGAGAC
CGTTCAGCGTGTGCTGGACATGATGGAAAAACGTGTGGACGATGACGGCATCTTCCAAACCTACTTTGATCCG
CTGCGTCTGCGTGTTGACCCGGTGGCGGCGACCAACACCGTTTACCTGTTCCATCTGGGTGGCCGTCCGGGTC
CGACCCAGCAAACCGAGCAGTTTCTGAGCAAACTGCTGGAAAAGCGTAGCTATGTGCGTGGCACCCTGTACTA
TCGTACCCCGGAAGCGTTCCTGTACCAACTGACCCGTCTGGTGGTTAGCTTCGAGTATTTTCGTAAGACCGGT
TTTCTGGAAATGCTGAAGAAACGTCTGAGCGAGCGTGTGGGCATCGAAAGCGATGCGTTCACCCTGGCGATGC
GTATCCTGGCGTGCGTTAACTGCGGTATTCCGGTGGCGGAGCTGAACCGTGATATGGACCGTCTGGCGCGTAT
GCAGAACGTTGCGGGTAGCTGGGACGTGTGCCCGTACTATAGCTACAACGACCCGAAAAGCTGGTTCGGCAAC
GAACTGCTGACCACCGCGTTTGCGGCGGCGGCGCTGGAGCACAGCGAACCGAACTTCAAGTAA
```

```
                                                                 SEQ ID NO: 16
Artificial_BtHAD mutant of QW motif
MAPPFGYIGGNESSVTTSPDVLDYSYDGGPPTGQYKSMILDIGGVLLQPNLDRSYGTIVPPVQFKRMLRSHIW
FNYSMGKVSAEEVFRQLSVKSGYPAEDIRSFARKARESLVPITQITDLLVKLSKESKIRLFCMTNCPAEDFAY
LSQAYPNLFGLFERIFTSASTGMRKPNRNFFRHVLQETGISATETIFVDDLVPNIMAAEALDFTAIHVSPESP
AETVRLLMFHLRKPEERLAAARDYLLRNGVDKALSLTSDGVRVQVYFDHFVVAEVLNDERFLPITAAPKSGT
MNFFPKEERNATRDMTTNAVTHVDLPDDLDSTSVALSVLYKFSKVAMETVQRVLDMMEKRVDDDGIFQTYFDP
LRLRVDPVAATNTVYLFHLGGRPGPTQQTEQFLSKLLEKRSYVRGTLYYRTPEAFLYQLTRLVVSFEYFRKTG
FLEMLKKRLSERVGIESDAFTLAMRILACVNCGIPVAELNRDMDRLARMQNVAGSWDVCPYYSYNDPKSWFGN
ELLTTAFAAAALEHSEPNFK
```

```
                                                                 SEQ ID NO: 17
Selaginella moellendorffii_SmHAD1_wt_nucleic acid sequence
ATGATAATCATTAGCTTTGCTTGCTTGCTCAAGTTTGGATGTGGAGACAATGGCCCCCGGGGAGATCTCCTCC
GCAGGGCTCTCCAGCACTCCTCCTTCTTGGCCTATTCTTGCGGGGAGCTCGATCGCACTGCCGCAATCTCGAC
AATCTCGCGCAAATTCAAGCTCACGGACCCAGCTCTCGTGGATTCCATGCTGCTCGAGGCCGCTTCCAGCTGC
GAGGTGGACAAGGAGCTACTGTCACTGCTCCAGTCAACGAGGCAGCAGCTCCTGGGATGGATTGATATTCCTC
CACAAGAGTGGGAGCGAGTTTACAGCCTCTTCCCGGTGTCGCTCTGGAAGAACTTCGCTACAATCTCCCGCGA
TCTAGATTCCCTCCTTGGAGATATCAGGTCCCATGCTGTGATTGTCGATAAAAGCGTGGAGATGGCCGCGCTA
CATGCCTTCGAGAGCTTGCTCGCTCTCCCGTATGCCTCGCCCAACAAGAAGCTTGCCAGGACTTCTTGAAGC
GTCGGTTCCTGCTGCCTCGAGCTGTGAAGCTGGGGATGGATCGAGTCAAGGAGGAGGTGAGATCCAAGCAGCT
CAAATCACTCTACCTGCTTGACAATGGCCGGCACGAGCTCGTCTCCGAGATCTTCTTTCCCTGCGTGGCGGCC
TGGTGCCTTCCGGAGATCATTCCTCTCGGCTGGATGAAATATCTCCAGGTACTGATCAAGCGCGGCCATCCCT
TCGGTTACTTCGGTGCCGACGTCTCGCGCTATCCGCCGGACATCGACACCATGTCGACTTGTGTCTCCACACT
TTTTGATCTTAGTCTCGTCACCTCCGCGCAAGCTATGCACTTTCTGGAGATTTGTCTCGAGAACGTCAACGAT
CAAAACCAGCTTCTCACGTACCTGGACGTGGAGCGGCCTCGAGTGGATCCGGTCGTCATAGCCAACGTTGTCT
ATCTCGCCTATGCGCTCTCCATGGAAGATCACCCGGTTGTCCGCCACAACGAGAATCTGATCCAGAGATATCT
GTTAAGCGGCGGATTCGTATACGGGACTCGCTATTACCTCAGCCAGGAGGACTTCTTGTTCATGTATGGCCGG
GTCCTCGCGACGTTTGGAGAGAAGAGGGGAGATTCCCAACTTTGATCTCGTGTATCAAGCGATGGAGGCGGCTC
```

-continued

```
TCGTCAACCGGATCGGGAACGAGACCGAGTCGAAGCCACTGGACGTTGCCAAAAGGATTCTGCTCAGCAGGGG
TTTTGGAATCCGGAACACGATAGATGTAGACTTGCTCCTCAAGATGCAGAACGAGGATGGTTCCTGGCCTTTG
CAAGTGCTCAGCAATCTTCCATCTGCTAAAGGTGGTGTCTTCAATTCGGTGGTGGACTTGAGCTTTGCGGTGA
GAGCACTGCAAAGTCAAGATTGA
```

SEQ ID NO: 18

*Selaginella moellendorffii*_SmHAD1_*E. coli* optimized
```
ATGATCATTATCAGCTTCGCGTGCCTGCTGAAGTTTGGTTGCGGTGACAACGGTCCGCGTGGCGATCTGCTGC
GTCGTGCGCTGCAGCACAGCAGCTTCCTGGCGTATAGCTGCGGCGAGCTGGACCGTACCGCGGCGATTAGCAC
CATCAGCCGTAAGTTTAAACTGACCGACCCGGCGCTGGTTGATAGCATGCTGCTGGAAGCGGCGAGCAGCTGC
GAGGTGGACAAAGAACTGCTGAGCCTGCTGCAGAGCACCCGTCAGCAACTGCTGGGTTGGATTGATATCCCGC
CGCAAGAGTGGGAACGTGTGTACAGCCTGTTCCCGGTTAGCCTGTGGAAGAACTTTGCGACCATTAGCCGTGA
CCTGGATAGCCTGCTGGGCGACATTCGTAGCCACGCGGTGATCGTTGATAAAAGCGTTGAGATGGCGGCGCTG
CACGCGTTCGAAAGCCTGCTGGCGCTGCCGTATGCGAGCCCGAACAAGAAAGCGTGCCAGGACTTCCTGAAGC
GTCGTTTTCTGCTGCCGCGTGCGGTGAAGCTGGGTATGGATCGTGTGAAAGAGGAAGTTCGTAGCAAGCAACT
GAAAAGCCTGTACCTGCTGGACAACGGCCGTCACGAGCTGGTTAGCGAAATTTTCTTTCCGTGCGTTGCGGCG
TGGTGCCTGCCGGAGATTATCCCGCTGGGTTGGATGAAGTATCTGCAGGTTCTGATTAAACGTGGCCACCCGT
TCGGTTACTTTGGTGCGGATGTGAGCCGTTATCCGCCGGACATCGATACCATGAGCACCTGCGTGAGCACCCT
GTTCGATCTGAGCCTGGTTACCAGCGCGCAAGCGATGCACTTTCTGGAGATCTGCCTGGAAAACGTTAACGAC
CAGAACCAACTGCTGACCTACCTGGACGTGGAACGTCCGCGTGTTGATCCGGTGGTTATTGCGAACGTGGTTT
ACCTGGCGTATGCGCTGAGCATGGAGGATCACCCGGTGGTTCGTCACAACGAAAACCTGATCCAGCGTTACCT
GCTGAGCGGTGGCTTCGTTTATGGCACCCGTTACTATCTGAGCCAAGAGGACTTCCTGTTTATGTACGGTCGT
GTGCTGGCGACCTTCGGCGAGAAACGTGAAATCCCGAACTTTGATCTGGTGTATCAGGCGATGGAAGCGGCGC
TGGTTAACCGTATTGGTAACGAGACCGAAAGCAAGCCGCTGGACGTTGCGAAACGTATCCTGCTGAGCCGTGG
TTTTGGCATTCGTAACACCATCGACGTGGATCTGCTGCTGAAGATGCAGAACGAGGATGGCAGCTGGCCGCTG
CAAGTGCTGAGCAACCTGCCGAGCGCGAAAGGTGGCGTTTTCAACAGCGTGGTTGACCTGAGCTTTGCGGTGC
GTGCGCTGCAGAGCCAAGATTAA
```

SEQ ID NO: 19

*Selaginella moellendorffii*_SmHAD1_amino acid sequence
```
MIIISFACLLKFGCGDNGPRGDLLRRALQHSSFLAYSCGELDRTAAISTISRKFKLTDPALVDSMLLEAASSC
EVDKELLSLLQSTRQQLLGWIDIPPPQEWERVYSLFPVSLWKNFATISRDLDSLLGDIRSHAVIVDKSVEMAAL
HAFESLLALPYASPNKKACQDFLKRRFLLPRAVKLGMDRVKEEVRSKQLKSLYLLDNGRHELVSEIFFPCVAA
WCLPEIIPLGWMKYLQVLIKRGHPFGYFGADVSRYPPDIDTMSTCVSTLFDLSLVTSAQAMHFLEICLENVND
QNQLLTYLDVERPRVDPVVIANVVYLAYALSMEDHPVVRHNENLIQRYLLSGGFVYGTRYYLSQEDFLFMYGR
VLATFGEKREIPNFDLVYQAMEAALVNRIGNETESKPLDVAKRILLSRGFGIRNTIDVDLLLKMQNEDGSWPL
QVLSNLPSAKGGVFNSVVDLSFAVRALQSQD
```

SEQ ID NO: 20

Artificial_SmHAD1 mutant of class II motif_*E. coli* optimized
```
ATGATCATTATCAGCTTCGCGTGCCTGCTGAAGTTTGGTTGCGGTGACAACGGTCCGCGTGGCGATCTGCTGC
GTCGTGCGCTGCAGCACAGCAGCTTCCTGGCGTATAGCTGCGGCGAGCTGGACCGTACCGCGGCGATTAGCAC
CATCAGCCGTAAGTTTAAACTGACCGACCCGGCGCTGGTTGATAGCATGCTGCTGGAAGCGGCGAGCAGCTGC
GAGGTGGACAAAGAACTGCTGAGCCTGCTGCAGAGCACCCGTCAGCAACTGCTGGGTTGGATTGATATCCCGC
CGCAAGAGTGGGAACGTGTGTACAGCCTGTTCCCGGTTAGCCTGTGGAAGAACTTTGCGACCATTAGCCGTGA
CCTGGATAGCCTGCTGGGCGACATTCGTAGCCACGCGGTGATCGTTGATAAAAGCGTTGAGATGGCGGCGCTG
CACGCGTTCGAAAGCCTGCTGGCGCTGCCGTATGCGAGCCCGAACAAGAAAGCGTGCCAGGACTTCCTGAAGC
GTCGTTTTCTGCTGCCGCGTGCGGTGAAGCTGGGTATGGATCGTGTGAAAGAGGAAGTTCGTAGCAAGCAACT
GAAAAGCCTGTACCTGCTGGACAACGGCCGTCACGAGCTGGTTAGCGAAATTTTCTTTCCGTGCGTTGCGGCG
TGGTGCCTGCCGGAGATTATCCCGCTGGGTTGGATGAAGTATCTGCAGGTTCTGATTAAACGTGGCCACCCGT
TCGGTTACTTTGGTGCGGATGTGAGCCGTTATCCGCCGGACATCGATACCATGAGCACCTGCGTGAGCACCCT
GTTCGATCTGAGCCTGGTTACCAGCGCGCAAGCGATGCACTTTCTGGAGATCTGCCTGGAAAACGTTAACGAC
CAGAACCAACTGCTGACCTACCTGGACGTGGAACGTCCGCGTGTTGATCCGGTGGTTATTGCGAACGTGGTTT
ACCTGGCGTATGCGCTGAGCATGGAGGATCACCCGGTGGTTCGTCACAACGAAAACCTGATCCAGCGTTACCT
GCTGAGCGGTGGCTTCGTTTATGGCACCCGTTACTATCTGAGCCAAGAGGACTTCCTGTTTATGTACGGTCGT
GTGCTGGCGACCTTCGGCGAGAAACGTGAAATCCCGAACTTTGATCTGGTGTATCAGGCGATGGAAGCGGCGC
TGGTTAACCGTATTGGTAACGAGACCGAAAGCAAGCCGCTGGACGTTGCGAAACGTATCCTGCTGAGCCGTGG
TTTTGGCATTCGTAACACCATCGACGTGGATCTGCTGCTGAAGATGCAGAACGAGGATGGCAGCTGGCCGCTG
CAAGTGCTGAGCAACCTGCCGAGCGCGAAAGGTGGCGTTTTCAACAGCGTGGTTGACCTGAGCTTTGCGGTGC
GTGCGCTGCAGAGCCAAGATTAA
```

SEQ ID NO: 21

Artificial_SmHAD1 mutant of class II motif
```
MIIISFACLLKFGCGDNGPRGDLLRRALQHSSFLAYSCGELDRTAAISTISRKFKLTDPALVDSMLLEAASSC
EVDKELLSLLQSTRQQLLGWIDIPPPQEWERVYSLFPVSLWKNFATISRDLDSLLGDIRSHAVIVDKSVEMAAL
HAFESLLALPYASPNKKACQDFLKRRFLLPRAVKLGMDRVKEEVRSKQLKSLYLLDNGRHELVSEIFFPCVAA
WCLPEIIPLGWMKYLQVLIKRGHPFGYFGADVSRYPPAIATMSTCVSTLFDLSLVTSAQAMHFLEICLENVND
QNQLLTYLDVERPRVDPVVIANVVYLAYALSMEDHPVVRHNENLIQRYLLSGGFVYGTRYYLSQEDFLFMYGR
VLATFGEKREIPNFDLVYQAMEAALVNRIGNETESKPLDVAKRILLSRGFGIRNTIDVDLLLKMQNEDGSWPL
QVLSNLPSAKGGVFNSVVDLSFAVRALQSQD
```

SEQ ID NO: 22

Artificial_SmHAD1 mutant of QW motif_*E. coli* optimized
```
ATGATCATTATCAGCTTCGCGTGCCTGCTGAAGTTTGGTTGCGGTGACAACGGTCCGCGTGGCGATCTGCTGC
GTCGTGCGCTGCAGCACAGCAGCTTCCTGGCGTATAGCTGCGGCGAGCTGGACCGTACCGCGGCGATTAGCAC
CATCAGCCGTAAGTTTAAACTGACCGACCCGGCGCTGGTTGATAGCATGCTGCTGGAAGCGGCGAGCAGCTGC
GAGGTGGACAAAGAACTGCTGAGCCTGCTGCAGAGCACCCGTCAGCAACTGCTGGGTTGGATTGATATCCCGC
CGCAAGAGTGGGAACGTGTGTACAGCCTGTTCCCGGTTAGCCTGTGGAAGAACTTTGCGACCATTAGCCGTGA
CCTGGATAGCCTGCTGGGCGACATTCGTAGCCACGCGGTGATCGTTGATAAAAGCGTTGAGATGGCGGCGCTG
CACGCGTTCGAAAGCCTGCTGGCGCTGCCGTATGCGAGCCCGAACAAGAAAGCGTGCCAGGACTTCCTGAAGC
GTCGTTTTCTGCTGCCGCGTGCGGTGAAGCTGGGTATGGATCGTGTGAAAGAGGAAGTTCGTAGCAAGCAACT
```

-continued
GAAAAGCCTGTACCTGCTGGACAACGGCCGTCACGAGCTGGTTAGCGAAATTTTCTTTCCGTGCGTTGCGGCG
TGGTGCCTGCCGGAGATTATCCCGCTGGGTTGGATGAAGTATCTGCAGGTTCTGATTAAACGTGGCCACCCGT
TCGGTTACTTTGGTGCGGATGTGAGCCGTTATCCGCCGGACATCGATACCATGAGCACCTGCGTGAGCACCCT
GTTCGATCTGAGCCTGGTTACCAGCGCGCAAGCGATGCACTTTCTGGAGATCTGCCTGGAAAACGTTAACGAC
CAGAACCAACTGCTGACCTACCTGGACGTGGAACGTCCGCGTGTTGATCCGGTGGTTATTGCGAACGTGGTTT
ACCTGGCGTATGCGCTGAGCATGGAGGATCACCCGGTGGTTCGTCACAACGAAAACCTGATCCAGCGTTACCT
GCTGAGCGGTGGCTTCGTTTATGGCACCCGTTACTATCTGAGCCAAGAGGACTTCCTGTTTATGTACGGTCGT
GTGCTGGCGACCTTCGGCGAGAAACGTGAAATCCCGAACTTTGATCTGGTGTATCAGGCGATGGAAGCGGCGC
TGGTTAACCGTATTGGTAACGAGACCGAAAGCAAGCCGCTGGACGTTGCGAAACGTATCCTGCTGAGCCGTGG
TTTTGGCATTCGTAACACCATCGACGTGGATCTGCTGCTGAAGATGCAGAACGCGGCGGGCAGCTGGCCGCTG
CAAGTGCTGAGCAACCTGCCGAGCGCGAAAGGTGGCGTTTTCAACAGCGTGGTTGACCTGAGCTTTGCGGTGC
GTGCGCTGCAGAGCCAAGATTAA

SEQ ID NO: 23

Artificial_SmHAD1 mutant of QW motif
MIIISFACLLKFGCGDNGPRGDLLRRALQHSSFLAYSCGELDRTAAISTISRKFKLTDPALVDSMLLEAASSC
EVDKELLSLLQSTRQQLLGWIDIPPQEWERVYSLFPVSLWKNFATISRDLDSLLGDIRSHAVIVDKSVEMAAL
HAFESLLALPYASPNKKACQDFLKRRFLLPRAVKLGMDRVKEEVRSKQLKSLYLLDNGRHELVSEIFFPCVAA
WCLPEIIPLGWMKYLQVLIKRGHPFGYFGADVSRYPPDIDTMSTCVSTLFDLSLVTSAQAMHFLEICLENVND
QNQLLTYLDVERPRVDPVVIANVVYLAYALSMEDHPVVRHNENLIQRYLLSGGFVYGTRYYLSQEDFLFMYGR
VLATFGEKREIPNFDLVYQAMEAALVNRIGNETESKPLDVAKRILLSRGFGIRNTIDVDLLLKMQNAAGSWPL
QVLSNLPSAKGGVFNSVVDLSFAVRALQSQD

SEQ ID NO: 24

*Selaginella moellendorffii*_SmHAD2_wt_nucleic acid sequence
ATGATAATCATTAGTTTTGCTTGCTTGCTTAAGTTCGGATGTGGAGACAGTGGCCCCCGGGGAGATCTCCTCC
GCAGGGCTCTCCAGCACTCCTCCTTCTTGGCCTATTCTTGCGGGGAGCTCGATCGCGCTGCCGCAATCTCGAC
AATCTCGCGCAAATTCAAGCTCAAGGAGCCAGCTCTCCTGGATTCCATGCTGCTCGAGGCCGCTTCCAGCTGC
GAGGTGGACGAGGAGCTACTGTCACTGCTCCAGTCAACGAGGCAGCAGCTCCTGGGATGGATTGATATTCCTC
CACAAGAGTGGGAGCGAGTTTACAACCTCTTCCCGTGGTCGCTCTGGAAGAACTTCGCTACAATCTCCCGCGA
TCTAGATTCCCTCCTTGGAGATATCAGGTTCCATGCTGTGATTGTCGATAAAAGCGTGGAGATGGCCGCGCTA
CATGCCTTCGAGAGCTTGCTCGCTCTCCCGTATGCCTCGCCCAACAAGAAAGCTTGCCAGGACTTCTTGAAGC
GTCGGTTCCTGCTGCCTCGAGCTGTGAAGCTGGGGATGGATCGAGTCAAGGAGGAGGTGAGATCCAAGCAGCT
CAAATCACTCTACCTGCTTGACAACGGCCGGCAGGAGCTCGTCTCCGAGATCTTCTTTCCCTGCGTGGCGGCC
TGGTGCCTTCCTGAGATCATTCCTCTCGGCTGGATGGAATCTCTCCAGGTACTGATCGAGCGCGGCCATCCCT
TCGGTTACTTCGGTGCCGACGTCTCGCGCTATCCGCCGGACATCGACACCATGTCGACTTGTGTCTCCACACT
TTTTGATCTTAGCCTCGTCACCTCCGCGCAAGCTATGCACTTTCTGGAGATTTGTCTCGAGAACGTCAACGAT
CAAAACCAGCTTCTCACGTACCTGGACTTGGAGCGGCCTCGAGTGGATCCGGTCGTCATAGCCAACGTTGTCT
ATTTCGCCTATGCGCTCTCCATGGAAGATCACCCGGTTGTCCGCCACAACGAGAATCTGATCCAGAGATATCT
GTTAAGCGGCGGATTCGTATACGGGACTCGCTATTACCTCAGCCAGGAGGACTTCTTGTTCATGTATGGCCGG
GTCCTCGCGACGTTTGGAGAGAAGAGGGAGATTCCCAACTTTGATCTCGTGTATCAAGCGATGGAGGCGGCTC
TCGTCAACCGGATCGGGAACGAGACCGAGTCGAAGCCACTGGACGTTGCCAAAAGGATTCTGCTCAGCAGGTA
CTTTGGAATCCGGAACACGATAGATGTGGACTTGCTCCTCAAGATGCAGAACGAGGATGGTTCCTGGCCCTTG
CAAGTGCTCAGCAATCTTCCATCTGCTAAAGGTGGTGTCTTCAATTCGGTGGTGGACTTGAGCTTTGCGGTGA
GAGCACTGCAAAGTCAAGATTGA

SEQ ID NO: 25

*Selaginella moellendorffii*_SmHAD2_*E. coli* optimized
ATGATCATTATCAGCTTCGCGTGCCTGCTGAAATTTGGTTGCGGTGATAGCGGTCCGCGTGGCGATCTGCTGC
GTCGTGCGCTGCAGCACAGCAGCTTCCTGGCGTATAGCTGCGGCGAGCTGGACCGTGCGGCGGCGATTAGCAC
CATCAGCCGTAAGTTTAAACTGAAGGAACCGGCGCTGCTGGACAGCATGCTGCTGGAGGCGGCGAGCAGCTGC
GAAGTTGATGAGGAACTGCTGAGCCTGCTGCAGAGCACCCGTCAGCAACTGCTGGGTTGGATTGATATCCCGC
CGCAAGAGTGGGAACGTGTGTATAACCTGTTCCCGTGGAGCCTGTGGAAAAACTTTGCGACCATTAGCCGTGA
CCTGGATAGCCTGCTGGGCGACATTCGTTTCCACGCGGTGATCGTTGATAAGAGCGTTGAGATGGCGGCGCTG
CACGCGTTTGAAAGCCTGCTGGCGCTGCCGTACGCGAGCCCGAACAAGAAAGCGTGCCAAGACTTCCTGAAGC
GTCGTTTTCTGCTGCCGCGTGCGGTGAAACTGGGTATGGATCGTGTGAAGGAAGAGGTGCGCAGCAAACAGCT
GAAGAGCCTGTATCTGCTGGACAACGGCCGTCAAGAGCTGGTTAGCGAAATTTTCTTTCCGTGCGTTGCGGCG
TGGTGCCTGCCGGAGATTATCCCGCTGGGTTGGATGGAGAGCCTGCAGGTTCTGATTGAACGTGGCCACCCGT
TCGGTTACTTTGGTGCGGATGTGAGCCGTTATCCGCCGGACATCGATACCATGAGCACCTGCGTGAGCACCCT
GTTCGATCTGAGCCTGGTTACCAGCGCGCAAGCGATGCACTTTCTGGAGATCTGCCTGGAAAACGTTAACGAC
CAGAACCAACTGCTGACCTACCTGGACCTGGAACGTCCGCGTGTGGATCCGGTGGTTATTGCGAACGTGGTTT
ACTTCGCGTATGCGCTGAGCATGGAGGATCACCCGGTGGTTCGTCACAACGAAAACCTGATCCAGCGTTACCT
GCTGAGCGGTGGCTTTGTTTATGGCACCCGTTACTATCTGAGCCAAGAGGACTTCCTGTTTATGTACGGTCGT
GTGCTGGCGACCTTCGGCGAGAAACGTGAAATCCCGAACTTTGATCTGGTGTATCAGGCGATGGAAGCGGCGC
TGGTTAACCGTATTGGCAACGAGACCGAAAGCAAACCGCTGGACGTTGCGAAGCGTATCCTGCTGAGCCGTTA
CTTCGGTATTCGTAACACCATCGACGTGGATCTGCTGCTGAAAATGCAGAACGAGGATGGCAGCTGGCCGCTG
CAAGTGCTGAGCAACCTGCCGAGCGCGAAGGGTGGCGTTTTCAACAGCGTGGTTGACCTGAGCTTTGCGGTGC
GTGCGCTGCAGAGCCAAGATTAA

SEQ ID NO: 26

*Selaginella moellendorffii*_SmHAD2_amino acid sequence
MIIISFACLLKFGCGDSGPRGDLLRRALQHSSFLAYSCGELDRAAAISTISRKFKLKEPALLDSMLLEAASSC
EVDEELLSLLQSTRQQLLGWIDIPPQEWERVYNLFPWSLWKNFATISRDLDSLLGDIRFHAVIVDKSVEMAAL
HAFESLLALPYASPNKKACQDFLKRRELLPRAVKLGMDRVKEEVRSKQLKSLYLLDNGRQELVSEIFFPCVAA
WCLPEIIPLGWMESLQVLIERGHPFGYFGADVSRYPPDIDTMSTCVSTLFDLSLVTSAQAMHFLEICLENVND
QNQLLTYLDLERPRVDPVVIANVVYFAYALSMEDHPVVRHNENLIQRYLLSGGFVYGTRYYLSQEDFLFMYGR
VLATFGEKREIPNFDLVYQAMEAALVNRIGNETESKPLDVAKRILLSRYFGIRNTIDVDLLLKMQNEDGSWPL
QVLSNLPSAKGGVFNSVVDLSFAVRALQSQD -continued

```
                                                          SEQ ID NO: 27
Artificial_SmHAD2 mutant of class II motif_E. coli optimized
ATGATCATTATCAGCTTCGCGTGCCTGCTGAAATTTGGTTGCGGTGATAGCGGTCCGCGTGGCGATCTGCTGC
GTCGTGCGCTGCAGCACAGCAGCTTCCTGGCGTATAGCTGCGGCGAGCTGGACCGTGCGGCGGCGATTAGCAC
CATCAGCCGTAAGTTTAAACTGAAGGAACCGGCGCTGCTGGACAGCATGCTGCTGGAGGCGGCGAGCAGCTGC
GAAGTTGATGAGGAACTGCTGAGCCTGCTGCAGAGCACCCGTCAGCAACTGCTGGGTTGGATTGATATCCCGC
CGCAAGAGTGGGAACGTGTGTATAACCTGTTCCCGTGGAGCCTGTGGAAAAACTTTGCGACCATTAGCCGTGA
CCTGGATAGCCTGCTGGGCGACATTCGTTTCCACGCGGTGATCGTTGATAAGAGCGTTGAGATGGCGGCGCTG
CACGCGTTTGAAAGCCTGCTGGCGCTGCCGTACGCGAGCCCGAACAAGAAAGCGTGCCAAGACTTCCTGAAGC
GTCGTTTTCTGCTGCCGCGTGCGGTGAAACTGGGTATGGATCGTGTGAAGGAAGAGGTGCGCAGCAAACAGCT
GAAGAGCCTGTATCTGCTGGACAACGGCCGTCAAGAGCTGGTTAGCGAAATTTTCTTTCCGTGCGTTGCGGCG
TGGTGCCTGCCGGAGATTATCCCGCTGGGTTGGATGGAGAGCCTGCAGGTTCTGATTGAACGTGGCCACCCGT
TCGGTTACTTTGGTGCGGATGTGAGCCGTTATCCGCCGGCGATCGCGACCATGAGCACCTGCGTGAGCACCCT
GTTCGATCTGAGCCTGGTTACCAGCGCGCAAGCGATGCACTTTCTGGAGATCTGCCTGGAAAACGTTAACGAC
CAGAACCAACTGCTGACCTACCTGGACCTGGAACGTCCGCGTGTGGATCCGGTGGTTATTGCGAACGTGGTTT
ACTTCGCGTATGCGCTGAGCATGGAGGATCACCCGGTGGTTCGTCACAACGAAAACCTGATCCAGCGTTACCT
GCTGAGCGGTGGCTTTGTTTATGGCACCCGTTACTATCTGAGCCAAGAGGACTTCCTGTTTATGTACGGTCGT
GTGCTGGCGACCTTCGGCGAGAAACGTGAAATCCCGAACTTTGATCTGGTGTATCAGGCGATGGAAGCGGCGC
TGGTTAACCGTATTGGCAACGAGACCGAAAGCAAACCGCTGGACGTTGCGAAGCGTATCCTGCTGAGCCGTTA
CTTCGGTATTCGTAACACCATCGACGTGGATCTGCTGCTGAAAATGCAGAACGAGGATGGCAGCTGGCCGCTG
CAAGTGCTGAGCAACCTGCCGAGCGCGAAGGGTGGCGTTTTCAACAGCGTGGTTGACCTGAGCTTTGCGGTGC
GTGCGCTGCAGAGCCAAGATTAA
```

```
                                                          SEQ ID NO: 28
Artificial_SmHAD2 mutant of class II motif
MIIISFACLLKFGCGDSGPRGDLLRRALQHSSFLAYSCGELDRAAAISTISRKFKLKEPALLDSMLLEAASSC
EVDEELLSLLQSTRQQLLGWIDIPPQEWERVYNLFPWSLWKNFATISRDLDSLLGDIRFHAVIVDKSVEMAAL
HAFESLLALPYASPNKKACQDFLKRRFLLPRAVKLGMDRVKEEVRSKQLKSLYLLDNGRQELVSEIFFPCVAA
WCLPEIIPLGWMESLQVLIERGHPFGYFGADVSRYPPAIATMSTCVSTLFDLSLVTSAQAMHFLEICLENVND
QNQLLTYLDLERPRVDPVVIANVVYFAYALSMEDHPVVRHNENLIQRYLLSGGFVYGTRYYLSQEDFLFMYGR
VLATFGEKREIPNFDLVYQAMEAALVNRIGNETESKPLDVAKRILLSRYFGIRNTIDVDLLLKMQNEDGSWPL
QVLSNLPSAKGGVFNSVVDLSFAVRALQSQD
```

```
                                                          SEQ ID NO: 29
Artificial_SmHAD2 mutant of QW motif_E. coli optimized
ATGATCATTATCAGCTTCGCGTGCCTGCTGAAATTTGGTTGCGGTGATAGCGGTCCGCGTGGCGATCTGCTGC
GTCGTGCGCTGCAGCACAGCAGCTTCCTGGCGTATAGCTGCGGCGAGCTGGACCGTGCGGCGGCGATTAGCAC
CATCAGCCGTAAGTTTAAACTGAAGGAACCGGCGCTGCTGGACAGCATGCTGCTGGAGGCGGCGAGCAGCTGC
GAAGTTGATGAGGAACTGCTGAGCCTGCTGCAGAGCACCCGTCAGCAACTGCTGGGTTGGATTGATATCCCGC
CGCAAGAGTGGGAACGTGTGTATAACCTGTTCCCGTGGAGCCTGTGGAAAAACTTTGCGACCATTAGCCGTGA
CCTGGATAGCCTGCTGGGCGACATTCGTTTCCACGCGGTGATCGTTGATAAGAGCGTTGAGATGGCGGCGCTG
CACGCGTTTGAAAGCCTGCTGGCGCTGCCGTACGCGAGCCCGAACAAGAAAGCGTGCCAAGACTTCCTGAAGC
GTCGTTTTCTGCTGCCGCGTGCGGTGAAACTGGGTATGGATCGTGTGAAGGAAGAGGTGCGCAGCAAACAGCT
GAAGAGCCTGTATCTGCTGGACAACGGCCGTCAAGAGCTGGTTAGCGAAATTTTCTTTCCGTGCGTTGCGGCG
TGGTGCCTGCCGGAGATTATCCCGCTGGGTTGGATGGAGAGCCTGCAGGTTCTGATTGAACGTGGCCACCCGT
TCGGTTACTTTGGTGCGGATGTGAGCCGTTATCCGCCGGCGATCGCGACCATGAGCACCTGCGTGAGCACCCT
GTTCGATCTGAGCCTGGTTACCAGCGCGCAAGCGATGCACTTTCTGGAGATCTGCCTGGAAAACGTTAACGAC
CAGAACCAACTGCTGACCTACCTGGACCTGGAACGTCCGCGTGTGGATCCGGTGGTTATTGCGAACGTGGTTT
ACTTCGCGTATGCGCTGAGCATGGAGGATCACCCGGTGGTTCGTCACAACGAAAACCTGATCCAGCGTTACCT
GCTGAGCGGTGGCTTTGTTTATGGCACCCGTTACTATCTGAGCCAAGAGGACTTCCTGTTTATGTACGGTCGT
GTGCTGGCGACCTTCGGCGAGAAACGTGAAATCCCGAACTTTGATCTGGTGTATCAGGCGATGGAAGCGGCGC
TGGTTAACCGTATTGGCAACGAGACCGAAAGCAAACCGCTGGACGTTGCGAAGCGTATCCTGCTGAGCCGTTA
CTTCGGTATTCGTAACACCATCGACGTGGATCTGCTGCTGAAAATGCAGAACGCGGCGGGCAGCTGGCCGCTG
CAAGTGCTGAGCAACCTGCCGAGCGCGAAGGGTGGCGTTTTCAACAGCGTGGTTGACCTGAGCTTTGCGGTGC
GTGCGCTGCAGAGCCAAGATTAA
```

```
                                                          SEQ ID NO: 30
Artificial_SmHAD2 mutant of QW motif
MIIISFACLLKFGCGDSGPRGDLLRRALQHSSFLAYSCGELDRAAAISTISRKFKLKEPALLDSMLLEAASSC
EVDEELLSLLQSTRQQLLGWIDIPPQEWERVYNLFPWSLWKNFATISRDLDSLLGDIRFHAVIVDKSVEMAAL
HAFESLLALPYASPNKKACQDFLKRRFLLPRAVKLGMDRVKEEVRSKQLKSLYLLDNGRQELVSEIFFPCVAA
WCLPEIIPLGWMESLQVLIERGHPFGYFGADVSRYPPDIDTMSTCVSTLFDLSLVTSAQAMHFLEICLENVND
QNQLLTYLDLERPRVDPVVIANVVYFAYALSMEDHPVVRHNENLIQRYLLSGGFVYGTRYYLSQEDFLFMYGR
VLATFGEKREIPNFDLVYQAMEAALVNRIGNETESKPLDVAKRILLSRYFGIRNTIDVDLLLKMQNAAGSWPL
QVLSNLPSAKGGVFNSVVDLSFAVRALQSQD
```

```
                                                          SEQ ID NO: 31
Gelatoporia subvermispora_EMD37666.1_E. coli optimized
ATGTCTGCGGCGGCTCAATACACGACTTTGATTCTGGATCTGGGTGATGTTCTGTTCACTTGGTCCCCGAAAA
CCAAGACCAGCATCCCTCCGCGTACCCTGAAAGAAATCCTGAATAGCGCTACCTGGTATGAGTACGAGCGTGG
TCGCATTTCCCAAGACGAGTGTTACGAACGTGTGGGCACCGAGTTCGGCATTGCGCCGAGCGAGATTGACAAC
GCGTTCAAACAAGCGCGCGATTCGATGGAAAGCAATGATGAACTGATCGCACTGGTCCGTGAGCTGAAAACGC
AGCTGGACGGTGAGCTGCTGGTTTTCGCACTGTCCAATATTAGCCTGCCGGATTACGAATACGTCTTGACCAA
ACCGGCGGACTGGAGCATCTTTGACAAAGTGTTCCCTAGCGCCTTGGTGGGCGAGCGTAAGCCGCATCTGGGC
GTTTATAAACACGTTATTGCGGAAACGGGCATTGATCCGCGCGACGGTTTTCGTTGGACGACAAGATTGACA
ATGTGTTAAGCGCACGCAGCGTCGGTATGCATGGTATCGTGTTTGAGAAACAAGAAGATGTCATCGTGCACT
GCGTAACATCTTTGGTGATCCGGTCCGTCGTGGTCGTGAGTATCGCGTAGAAACGAATGCGTCTGGAGTCC
GTGACCGACCACGGCGTGGCGTTTGGTGAGAACTTTACCCAGTTGCTGATTCTGGAATTGACGAACGACCCGA
GCCTGGTCACCCTGCCTGATCGTCCGCGTACCTGGAACTTTTTTCGCGGCAATGGTGGCCGCCCGAGCAAGCC
GCTGTTCAGCGAAGCGTTCCCGGATGATCTGGATACCACGAGCCTGGCGCTGACCGTGCTGCAGCGCGACCCG
```

-continued

```
GGTGTTATCAGCAGCGTTATGGACGAAATGCTGAATTACCGTGACCCGGACGGTATCATGCAGACTTATTTCG
ATGACGGTCGCCAACGCTTGGACCCATTTGTGAACGTCAATGTTCTGACCTTTTTCTATACGAACGGCCGTGG
TCACGAACTGGACCAGTGTCTGACGTGGGTGCGTGAAGTCCTCTTGTATCGTGCGTACCTTGGTGGCTCACGC
TACTACCCATCGGCGGATTGCTTCCTGTACTTCATCTCTCGTCTGTTTGCGTGTACCAATGACCCGGTGCTGC
ACCATCAGCTGAAGCCACTGTTTGTTGAGCGTGTCCAAGAGCAAATTGGTGTCGAGGGTGATGCACTGGAACT
GGCTTTTCGTCTGCTGGTCTGCGCCAGCCTGGATGTCCAGAATGCCATCGACATGCGCCGTCTGCTGGAAATG
CAGTGCGAAGATGGCGGTTGGGAGGGTGGTAACCTCTACCGCTTCGGCACCACGGGCCTGAAAGTTACCAACC
GCGGTCTGACGACCGCAGCCGCCGTTCAAGCGATCGAAGCGAGCCAACGCCGTCCGCCGAGCCCGAGCCCGTC
TGTAGAGAGCACGAAAAGCCCGATTACCCCGGTGACCCCGATGCTGGAAGTTCCAAGCCTGGGCTTATCTATC
AGCCGTCCGTCCAGCCCGCTGCTGGGTTATTTCCGTTTGCCGTGGAAGAAAAGCGCAGAAGTGCACTAA

SEQ ID NO: 32
Gelatoporia subvermispora_EMD37666.1_amino acid sequence
MSAAAQYTTLILDLGDVLFTWSPKTKTSIPPRTLKEILNSATWYEYERGRISQDECYERVGTEFGIAPSEIDN
AFKQARDSMESNDELIALVRELKTQLDGELLVFALSNISLPDYEYVLTKPADWSIFDKVFPSALVGERKPHLG
VYKHVIAETGIDPRTTVFVDDKIDNVLSARSVGMHGIVFEKQEDVMRALRNIFGDPVRRGREYLRRNAMRLES
VTDHGVAFGENFTQLLILELTNDPSLVTLPDRPRTWNFFRGNGGRPSKPLFSEAFPDDLDTTSLALTVLQRDP
GVISSVMDEMLNYRDPDGIMQTYFDDGRQRLDPFVNVNVLTFFYTNGRGHELDQCLTWVREVLLYRAYLGGSR
YYPSADCFLYFISRLFACTNDPVLHHQLKPLFVERVQEQIGVEGDALELAFRLLVCASLDVQNAIDMRRLLEM
QCEDGGWEGGNLYRFGTTGLKVTNRGLTTAAAVQAIEASQRRPPSPSPSVESTKSPITPVTPMLEVPSLGLSI
SRPSSPLLGYFRLPWKKSAEVH SEQ ID NO: 33
Artificial_EMD37666.1_mutant of class II motif_E.coli optimized
ATGAGCGCGGCGGCGCAGTACACCACCCTGATCCTGGACCTGGGTGATGTGCTGTTCACCTGGAGCCCGAAGA
CCAAAACCAGCATCCCGCCGCGTACCCTGAAGGAAATTCTGAACAGCGCGACCTGGTACGAGTATGAACGTGG
CCGTATCAGCCAAGACGAGTGCTATGAACGTGTTGGCACCGAGTTCGGCATCGCGCCGAGCGAAATTGATAAC
GCGTTTAAGCAGGCGCGTGACAGCATGGAGAGCAACGATGAACTGATTGCGCTGGTGCGTGAGCTGAAAACCC
AACTGGACGGTGAACTGCTGGTTTTCGCGCTGAGCAACATCAGCCTGCCGGATTACGAGTATGTGCTGACCAA
GCCGGCGGACTGGAGCATTTTCGATAAAGTTTTTCCGAGCGCGCTGGTTGGTGAACGCAAGCCGCACCTGGGC
GTTTACAAACACGTGATCGCGGAAACCGGTATTGACCCGCGTACCACCGTGTTTGTTGACGATAAGATCGATA
ACGTTCTGAGCGCGCGTAGCGTGGGTATGCACGGCATTGTTTTCGAGAAACAGGAAGACGTGATGCGTGCGCT
GCGTAACATCTTTGGTGATCCGGTTCGTCGTGGCCGTGAGTATCTGCGTCGTAACGCGATGCGTCTGGAAAGC
GTTACCGACCACGGTGTGGCCGTTCGGCGAGAACTTTACCCAACTGCTGATTCTGGAACTGACCAACGATCCGA
GCCTGGTGACCCTGCCGGATCGTCCGCGTACCTGGAACTTCTTTCGTGGTAACGGTGGCCGTCCGAGCAAGCC
GCTGTTCAGCGAAGCGTTTCCGGCGGCGCTGGCGACCACCAGCCTGGCGCTGACCGTTCTGCAGCGTGACCCG
GGCGTTATCAGCAGCGTGATGGATGAGATGCTGAACTACCGTGACCCGGATGGTATTATGCAGACCTATTTCG
ACGATGGCCGTCAACGTCTGGACCCGTTTGTGAACGTTAACGTGCTGACCTTCTTTTACACCAACGGTCGTGG
CCACGAGCTGGATCAGTGCCTGACCTGGGTTCGTGAAGTGCTGCTGTACCGTGCGTATCTGGGTGGCAGCCGT
TACTATCCGAGCGCGGACTGCTTCCTGTATTTTATCAGCCGTCTGTTCGCGTGCACCAACGATCCGGTGCTGC
ACCACCAACTGAAACCGCTGTTTGTTGAGCGTGTGCAGGAACAAATCGGTGTTGAGGGCGACGCGCTGGAACT
GGCGTTCCGTCTGCTGGTGTGCGCGAGCCTGGACGTTCAGAACGCGATTGATATGCGTCGTCTGCTGGAGATG
CAATGCGAAGATGGTGGCTGGGAAGGTGGCAACCTGTACCGTTTTGGCACCACCGGCCTGAAGGTGACCAACC
GTGGTCTGACCACCGCGGCGGCGGTTCAGGCGATTGAGGCGAGCCAACGTCGTCCGCCGAGCCCGAGCCCGAG
CGTGGAAAGCACCAAAAGCCCGATCACCCCGGTGACCCCGATGCTGGAAGTGCCGAGCCTGGGTCTGAGCATT
AGCCGTCCGAGCAGCCCGCTGCTGGGTTACTTCCGTCTGCCGTGGAAGAAAAGCGCGGAAGTGCACTAA SEQ ID NO: 34
Artificial_EMD37666.1_mutant of class II motif
MSAAAQYTTLILDLGDVLFTWSPKTKTSIPPRTLKEILNSATWYEYERGRISQDECYERVGTEFGIAPSEIDN
AFKQARDSMESNDELIALVRELKTQLDGELLVFALSNISLPDYEYVLTKPADWSIFDKVFPSALVGERKPHLG
VYKHVIAETGIDPRTTVFVDDKIDNVLSARSVGMHGIVFEKQEDVMRALRNIFGDPVRRGREYLRRNAMRLES
VTDHGVAFGENFTQLLILELTNDPSLVTLPDRPRTWNFFRGNGGRPSKPLFSEAFPAALATTSLALTVLQRDP
GVISSVMDEMLNYRDPDGIMQTYFDDGRQRLDPFVNVNVLTFFYINGRGHELDQCLTWVREVLLYRAYLGGSR
YYPSADCFLYFISRLFACTNDPVLHHQLKPLFVERVQEQIGVEGDALELAFRLLVCASLDVQNAIDMRRLLEM
QCEDGGWEGGNLYRFGTTGLKVTNRGLTTAAAVQAIEASQRRPPSPSPSVESTKSPITPVTPMLEVPSLGLSI
SRPSSPLLGYFRLPWKKSAEVH SEQ ID NO: 35
Dichomitus squalens_XP_007369631.1_E. coli optimized
ATGGCGAGCATCCACCGTCGTTACACCACCCTGATTCTGGACCTGGGTGATGTTCTGTTTCGTTGGAGCCCGA
AGACCGAGACCGCGATCCCGCCGCAGCAACTGAAAGACATTCTGAGCAGCGCGACCTGGTTCGAGTACGAACG
TGGCCGTCTGAGCCAGGAAGCGTGCTATGAACGTTGCGCGGAGGAATTTAAGATCGAGGCGAGCGTTATTGCG
GAAGCGTTCAAACAAGCGCGTGGTAGCCTGCGTCCGAACGAGGAATTTATCGCGCTGATTCGTGACCTGCGTC
GTGAGATGCACGGCGATCTGACCGTGCTGGCGCTGAGCAACATCAGCCTGCCGGACTACGAATATATTATGAG
CCTGAGCAGCGACTGGACCACCGTTTTCGATCGTGTGTTTCCGAGCGCGCTGGTTGGTGAGCGTAAGCCGCAC
CTGGGCTGCTATCGTAAAGTGATCAGCGAGATGAACCTGGAACCGCAGACCACCGTGTTCGTTGACGATAAGC
TGGATAACGTTGCGAGCGCGCGTAGCGTGGGTATGCATGGTATTGTTTTCGACAACCAGGCGAACGTGTTTCG
TCAACTGCGTAACATCTTCGGTGATCCGATTCGTCGTGGCCAAGAGTACCTGCGTGGTCACGCGGGCAAACTG
GAAAGCAGCACCGACAACGGTCTGATCTTCGAGGAAAACTTTACCCAGCTGATCATTTATGAGCTGACCCAAG
ATCGTACCCTGATTAGCCTGAGCGAATGCCCGCGTACCTGGAACTTCTTTCGTGGCGAGCGCTGTTCAGCGA
AACCTTCCCGGACGACGTTGACACCACCAGCGTTGCGCTGACCGTGCTGCAGCGCGACCCGGTGCGCTGGTTAAC
AGCGTGCTGGATGAGATGCTGGAATACGTGGACGCGGATGGTATCATGCAAACCTATTTTGACCGTAGCCGTC
CGCGTATGGATCCGTTTGTGTGCGTTAACGTGCTGAGCCTGTTCTACGAGAACGGTCGTGGCCACGAACTGCC
GCGTACCCTGGACTGGGTTTACGAGGTGCTGCTGCACCGTGCGTATCACGGTGGCAGCCGTTACTATCTGAGC
CCGGATTGCTTCCTGTTCTTTATGAGCCGTCTGCTGAAACGTGCGGATGATCCGGCGGTTCAGGCGCGTCTGC
GTCCGCTGTTTGTTGAGCGTGTGAACAACGTGTTGGTGCGGCGGGTGACAGCATGGATCTGGCGTTCCGTAT
CCTGGCGGCGGCGAGCGTTGGTGTGCAGTGCCCGCGTGACCTGGAACGTCTGACCGCGGGTCAATGCGATGAT
```

-continued

```
GGTGGCTGGGATCTGTGCTGGTTCTACGTTTTTGGTAGCACCGGCGTGAAAGCGGGTAACCGTGGCCTGACCA
CCGCGCTGGCGGTGACCGCGATTCAAACCGCGATTGGTCGTCCGCCGAGCCCGAGCCCGAGCGCGGCGAGCAG
CAGCTTTCGTCCGAGCAGCCCGTATAAATTCCTGGGTATCAGCCGTCCGGCGAGCCCGATTCGTTTTGGTGAC
CTGCTGCGTCCGTGGCGTAAGATGAGCCGTAGCAACCTGAAAAGCCAATAA
```

SEQ ID NO: 36

*Dichomitus squalens*_XP_007369631.1_amino acid sequence
```
MASIHRRYTTLILDLGDVLFRWSPKTETAIPPQQLKDILSSVTWFEYERGRLSQEACYERCAEEFKIEASVIA
EAFKQARGSLRPNEEFIALIRDLRREMHGDLTVLALSNISLPDYEYIMSLSSDWTTVFDRVFPSALVGERKPH
LGCYRKVISEMNLEPQTTVFVDDKLDNVASARSLGMHGIVFDNQANVFRQLRNIFGDPIRRGQEYLRGHAGKL
ESSTDNGLIFEENFTQLIIYELTQDRTLISLSECPRTWNFFRGEPLFSETFPDDVDTTSVALTVLQPDRALVN
SVLDEMLEYVDADGIMQTYFDRSRPRMDPFVCVNVLSLFYENGRGHELPRTLDWVYEVLLHRAYHGGSRYYLS
PDCFLFFMSRLLKRADDPAVQARLRPLFVERVNERVGAAGDSMDLAFRILAAASVGVQCPRDLERLTAGQCDD
GGWDLCWFYVFGSTGVKAGNRGLTTALAVTAIQTAIGRPPSPSPSAASSSFRPSSPYKFLGISRPASPIRFGD
LLRPWRKMSRSNLKSQ
```

SEQ ID NO: 37

Artificial_XP_007369631.1_mutant of class II motif E.coli optimized
```
ATGGCGAGCATCCACCGTCGTTACACCACCCTGATTCTGGACCTGGGTGATGTTCTGTTTCGTTGGAGCCCGA
AGACCGAGACCGCGATCCCGCCGCAGCAACTGAAAGACATTCTGAGCAGCGTGACCTGGTTCGAGTACGAACG
TGGCCGTCTGAGCCAGGAAGCGTGCTATGAACGTTGCGCGGAGGAATTTAAGATCGAGGCGAGCGTTATTGCG
GAAGCGTTCAAACAAGCGCGTGGTAGCCTGCGTCCGAACGAGGAATTTATCGCGCTGATTCGTGACCTGCGTC
GTGAGATGCACGGCGATCTGACCGTGCTGGCGCTGAGCAACATCAGCCTGCCGGACTACGAATATATTATGAG
CCTGAGCAGCGACTGGACCACCGTTTTCGATCGTGTGTTTCCGAGCGCGCTGGTTGGTGAGCGTAAGCCGCAC
CTGGGCTGCTATCGTAAAGTGATCAGCGAGATGAACCTGGAACCGCAGACCACCGTGTTCGTTGACGATAAGC
TGGATAACGTTGCGAGCGCGCGTAGCCTGGGTATGCATGGTATTGTTTTCGACAACCAGGCGAACGTGTTTCG
TCAACTGCGTAACATCTTCGGTGATCCGATTCGTCGTGGCCAAGAGTACCTGCGTGGTCACGCGGGCAAACTG
GAAAGCAGCACCGACAACGGTCTGATCTTCGAGGAAAACTTTACCCAGCTGATCATTTATGAGCTGACCCAAG
ATCGTACCCTGATTAGCCTGAGCGAATGCCCGCGTACCTGGAACTTCTTTCGTGGCGAGCCGCTGTTCAGCGA
AACCTTCCCGGCGGCGGTTGCGACCACCAGCGTTGCGCTGACCGTGCTGCAGCCGGACCGTGCGCTGGTTAAC
AGCGTGCTGGATGAGATGCTGGAATACGTGGACGCGGATGGTATCATGCAAACCTATTTTGACCGTAGCCGTC
CGCGTATGGATCCGTTTGTGTGCGTTAACGTGCTGAGCCTGTTCTACGAGAACGGTCGTGGCCACGAACTGCC
GCGTACCCTGGACTGGGTTTACGAGGTGCTGCTGCACCGTGCGTACCACGGTGGCAGCCGTTACTATCTGAGC
CCGGATTGCTTCCTGTTCTTTATGAGCCGTCTGCTGAAACGTGCGGATGATCCGGCGGTTCAGGCGCGTCTGC
GTCCGCTGTTTGTTGAGCGTGTGAACGAACGTGTTGGTGCGGCGGGTGACAGCATGGATCTGGCGTTCCGTAT
CCTGGCGGCGGCGAGCGTTGGTGTGCAGTGCCCGCGTGACCTGGAACGTCTGACCGCGGGTCAATGCGATGAT
GGTGGCTGGGATCTGTGCTGGTTCTACGTTTTTGGTAGCACCGGCGTGAAAGCGGGTAACCGTGGCCTGACCA
CCGCGCTGGCGGTGACCGCGATTCAAACCGCGATTGGTCGTCCGCCGAGCCCGAGCCCGAGCGCGGCGAGCAG
CAGCTTTCGTCCGAGCAGCCCGTATAAATTCCTGGGTATCAGCCGTCCGGCGAGCCCGATTCGTTTTGGTGAC
CTGCTGCGTCCGTGGCGTAAGATGAGCCGTAGCAACCTGAAAAGCCAATAA
```

SEQ ID NO: 38

Artificial_XP_007369631.1_mutant of class II motif
```
MASIHRRYTTLILDLGDVLFRWSPKTETAIPPQQLKDILSSVTWFEYERGRLSQEACYERCAEEFKIEASVIA
EAFKQARGSLRPNEEFIALIRDLRREMHGDLTVLALSNISLPDYEYIMSLSSDWTTVFDRVFPSALVGERKPH
LGCYRKVISEMNLEPQTTVFVDDKLDNVASARSLGMHGIVFDNQANVFRQLRNIFGDPIRRGQEYLRGHAGKL
ESSTDNGLIFEENFTQLIIYELTQDRTLISLSECPRTWNFFRGEPLFSETFPAAVATTSVALTVLQPDRALVN
SVLDEMLEYVDADGIMQTYFDRSRPRMDPFVCVNVLSLFYENGRGHELPRTLDWVYEVLLHRAYHGGSRYYLS
PDCFLFFMSRLLKRADDPAVQARLRPLFVERVNERVGAAGDSMDLAFRILAAASVGVQCPRDLERLTAGQCDD
GGWDLCWFYVFGSTGVKAGNRGLTTALAVTAIQTAIGRPPSPSPSAASSSFRPSSPYKFLGISRPASPIRFGD
LLRPWRKMSRSNLKSQ
```

SEQ ID NO: 39

Artificial_class II synthase motif_mutated_BtHAD
```
PDALASTS
```

SEQ ID NO: 40

Artificial_class II synthase motif_mutated_SmHAD1 + 2
```
PPAIATMS
```

SEQ ID NO: 41

Artificial_class II synthase motif_mutated_EMD37666
```
PDAALATTS
```

SEQ ID NO: 42

Artificial_class II synthase motif_mutated_XP_007369631
```
PDAAVATTS
```

SEQ ID NO: 43

Artificial_QW motif_mutated_BtHAD
```
QNVAGSW
```

SEQ ID NO: 44

Artificial_QW motif_mutated_SmHAD1+2
```
QNAAGSW
```

SEQ ID NO: 45

Artificial_class I synthase motif DDxx(D/E)
```
DDxx(D/E)
```

-continued

```
                                                   SEQ ID NO: 46
Artificial_class II synthase motif PxDxD T/S)(T/M)S
PxDxD(T/S)(T/M)S SEQ ID NO: 47
Artificial_class II synthase motif PDDLDSTS
PDDLDSTS SEQ ID NO: 48
Artificial_class II synthase motif PDDLDTTS
PDDLDTTS SEQ ID NO: 49
Artificial_class II synthase motif PPDIDTMS
PPDIDTMS SEQ ID NO: 50
Artificial_class II synthase motif PNDIDTMS
PNDIDTTS SEQ ID NO: 51
Artificial_QW motif
QxxDGxW SEQ ID NO: 52
Artificial_QW motif QNVDGSW
QNVDGSW SEQ ID NO: 53
Artificial_QW motif QCDDGGW
QCDDGGW SEQ ID NO: 54
Artificial_QW motif QSSDGGW
QSSDGGW SEQ ID NO: 55
Artificial_QW motif QNEDGSW
QNEDGSW SEQ ID NO: 56
Artificial_conserved motif 1 Lxxxx(W/F)xxYxxG
Lxxxx(W/F)xxYxxG SEQ ID NO: 57
Artificial_conserved motif 1 LRSHIWFNYSMG
LRSHIWFNYSMG SEQ ID NO: 58
Artificial_conserved motif 1 LRSATWAAYECG
LRSATWAAYECG SEQ ID NO: 59
Artificial_conserved motif 1 LRTPTWGKYECG
LRTPTWGKYECG SEQ ID NO: 60
Artificial_conserved motif 1 LQHSSFLAYSCG
LQHSSFLAYSCG SEQ ID NO: 61
Artificial_conserved motif 1 LRxxTWxxYECG
LRxxTWxxYECG SEQ ID NO: 62
Artificial_conserved motif 2 YxDxxRxRVD(P/A)V(V/A)xxN
YxDxxRxRVDxVxxxN SEQ ID NO: 63
Artificial_conserved motif 2 YFDPLRLRVDPVAATN
YFDPLRLRVDPVAATN SEQ ID NO: 64
Artificial_conserved motif 2 YFDETRPRVDAVVNVN
YFDETRPRVDAVVNVN SEQ ID NO: 65
Artificial_conserved motif 2 YFDKTRPRVDPVVCVN
YFDKTRPRVDPVVCVN
```

-continued

```
                                                    SEQ ID NO: 66
Artificial_conserved motif 2 YLDVERPRVDPVVIAN
YLDVERPRVDPVVIAN SEQ ID NO: 67
Artificial_conserved motif 2 YLDLERPRVDPVVIAN
YLDLERPRVDPVVIAN SEQ ID NO: 68
Artificial_conserved motif 2 Y(F/L)Dx(T/E)RPRVD(P/A)VVx(A/V)N
YxDxxRPRVDxVVxxN SEQ ID NO: 69
Artificial_conserved motif 3 GTx(Y/F)YxxxExFL(Y/F)
GTxxYxxxExFLx SEQ ID NO: 70
Artificial_conserved motif 3 GTLYYRTPEAFLY
GTLYYRTPEAFLY SEQ ID NO: 71
Artificial_conserved motif 3 GTLFYYHAESFLY
GTLFYYHAESFLY SEQ ID NO: 72
Artificial_conserved motif 3 GTRYYLSQEDFLF
GTRYYLSQEDFLF SEQ ID NO: 73
Dryopteris fragrans_DfHAD_wt_nucleic acid sequence
ATGGAGTTCTCTGCCTCTGCTCCTCCTCCTAGGCTAGCCAGTGTCATAATATTGGAGCCTCTCGGCTTCCTCC
TCACACCACACTACTCCTCTCAGCTTCCCAAAAAGCTGCTCCGTCGCCTGTTGTGCACTAGAATCTGGCACAG
GTATCAGCGAGGCCGCCTTCGCCTGCGTGACGCTGCTATGCTGCTCGCCCAGCTCCCATTCCTAGCTGTGTCT
GATCACCCCTGGGCTCTGGACAATCTCGCAAGCCTGCTCCGCCCCACAGCTGTGCGTGCGGTGCCATGGATGC
TGCTGCTGCTCGACTTCCTACGAGACGAGCTCCATCTGAAGGTAGTCTGCGCGACCAACTCCTCCCCAGAAGA
GCTGCAAGAGCTGCGCCACCAGTTTCCGGCCCTCTTTGCCAAGGTCGATGCCACCGTTTCTTCAGGCGAGGAG
GGCGTGGGCAAGCCGTCCGTGCGCTTCCTGCAGGCTGCGTTGGACAAAGCCGGTGTCCACGCGCAGCAAACCT
TGTATCTTGACTCTTTTGACAGCTTGGAGACCATCATGGCTGCACGCTCTCTTGGCATGCATGCACTATCTGT
AGAGCCATGCCACATTGATGAGCTCACCGCCAGGGCCTCTTCCGGCCAGCTAAGAGATGCACAGCTTATAAGG
CGTATTGTGTGCGCCATGCACGGGCCAGCAGTATCTGCAGTTGTGTCGGGCAGTATCACATCGTCCGGCCCAC
AGACAGCAAAGATCGAGGAATTGCCAACAGCTGCTGATAGTCATCTCCGCAGCGCAGCTCTCACTTCTGCTCA
GCAGTTTTTCCTCAAAGTTATTGCTCCACATCGTCCTGAGAAGCCATTCGTCCAGCTTCCATCTCTCCACCTCG
GAGGGCATCCGAATATACGACACCTTTGCACAGTTTGTCATAGCCGACCTGCTCGACGACACCCGCTTCCTAC
CCATGCAATCTCCTCCTCCCAATGGGCTCATCACCTTTGTTAACCCAAGCGCGTACCTTGCTGATGATATAAA
GAATGGCAACAGCCATATTGTCCCGGGTGTGCAATTTTACGCATCCGATGCGTGCACTCTCATCGACATCCCA
CATGACCTAGACACCACCTCCGTTGGCTTGTCAGTACTGCACAAGTTTGGAAAGGTGGACAAGGACACACTCA
ACAAAGTGCTAGACAGAATGCTCGAGCAAGTGAGTGAAGACGACGGCATTCTGCAGGTGTATTTTGATGTGGA
GCGTCCGCGCATCGATCCAGTTGTGGTGGCAAACACGGTGTTTCTGTTCCACTTGGGAAAGAGAGGGCATGAG
GTGGCGAGGAGTGAGAAGTTTGTGGAGAGTGTGCTGCTGCAGAGGGCATACGAAGAAGGGACGTTGTATTACA
ACCTGGGGGAAGCATTTTTGGTGAGTGTGGCGAGGCTGGTGCACGAGTTTAAGGAGCACTTTACAAGGAGCGG
CATGAGGAGGGCACTGGAGGAGAGGCTAAGAGAGCGGGCAAGGGCGGGCATGCAAGAGAGGGATGATGCGCTG
GCGCTAGCCATGCGCCATTCGTGCATGCGCTTTGTGTGGCCTGGCCGGAGAGGGCCTCACAAAAGCAGCAGAGC
AGGAGCTTTTGCGCCTGCAGTGCAAGTCCAAGGGCTGTTGGGGGTGCCACCCTTTCTATCGCAATGGCAGTAA
TGTGCTCAGCTGGATCGGCAGTGAGGCCCTTACCACTGCTTACGCTATTGCTGCGCTACAGCCCATTGATATT
TAA SEQ ID NO: 74
Dryopteris fragrans_DfHAD_amino acid sequence
MEFSASAPPPRLASVIILEPLGFLLTPHYSSQLPKKLLRRLLCTRIWHRYQRGRLRLRDAAMLLAQLPFLAVS
DHPWALDNLASLLRPTAVRAVPWMLLLLDFLRDELHLKVVCATNSSPEELQELRHQPPALFAKVDATVSSGEE
GVGKPSVRFLQAALDKAGVHAQQTLYLDSFDSLETIMAARSLGMHALSVEPCHIDELTARASSGQLRDAQLIR
RIVCAMHGPAVSAVVSGSITSSGPQTAKIEELPTAADSHLRSAALTSAQQFFLKVIAPHRPEKPFVQLPSLTS
EGIRIYDTFAQPVIADLLDDTRFLPMQSPPPNGLITFVNPSAYLADDIKNGNSHIVPGVQFYASDACTLIDIP
HDLDTTSVGLSVLHKFGKVDKDTLNKVLDRMLEQVSEDDGILQVYFDVERPRIDPVVVANTVFLFHLGKRGHE
VARSEKFVESVLLQRAYEEGTLYYNLGEAFLVSVARLVHEFKEHFTRSGMRRALEERLRERARAGMQERDDAL
ALAMRIRACALCGLAGEGLTKAAEQELLRLQCKSKGCWGCHPFYRNGSNVLSWIGSEALTTAYAIAALQPIDI SEQ ID NO: 75
Artificial Sequence_class II synthase motif
DxDxxS SEQ ID NO: 76
Artificial Sequence_QW motif
QxxxxxW
```

The invention claimed is:

1. A method for producing a drimane sesquiterpene, comprising:

a. contacting farnesyl diphosphate (FPP) with an isolated polypeptide of the haloacid dehalogenase-like (HAD-like) hydrolase superfamily comprising cyclic terpene synthase activity having an, amino acid sequence with at least 70% sequence identity to SEQ ID NO: 3, 6, 9, 12, 19, or 26 and wherein the amino acid sequence does not include a class I motif as set forth in SEQ ID NO: 45 (DDxx(D/E), thereby obtaining at least one diphosphate of drimane sesquiterpene;

b. chemically or enzymatically cleaving the diphosphate moiety of said at least one diphosphate of drimane sesquiterpene obtained in step a.; and c. optionally isolating the drimane sesquiterpene.

2. The method of claim 1, wherein the enzymatic step b. is performed by applying the same polypeptide as used in step a. which polypeptide further comprises phosphatase activity, or by applying a polypeptide different therefrom and having phosphatase activity.

3. The method of claim 1, wherein the drimane sesquiterpene produced is drimenol and/or albicanol.

4. The method of claim 3 further comprising converting 5 the drimenol and/or albicanol to (−)-(3aR,5aS,9aS,9bR)-3a, 6,6,9a-tetramethyldodecahydronaphto[2,1-b]furan.

* * * * *

SEQUENCE LISTING

<160> NUMBER OF SEQ ID NOS: 76

<210> SEQ ID NO 1
<211> LENGTH: 1599
<212> TYPE: DNA
<213> ORGANISM: Bazzania sp.
<220> FEATURE:
<221> NAME/KEY: misc_feature
<223> OTHER INFORMATION: BazzHAD1_wt_nucleic acid sequence

<400> SEQUENCE: 1

```
atggctcctc ctttcggatt tattggtggg aatgcaacga gtgtgacgac ttccccagat      60
gtcctcgact acaactatga cggtggccct cctactggcc aatacaagag tttgatttta     120
gacattggtg gagtgttgct tcagcccaac cttgacagga gctatggcac gattgtacca     180
cctgtgcaat tcaaacgtat gttgcgctcg cacatctggt tcaattactc aatgggaaag     240
atgtctgcgg aggaagtgtt tcggcagctc tccgtgaagt ctggctaccc ggcagaagat     300
atccggagtt ttggtcgcaa agcgagagag tctcttgtcc ccatcacaca ataacggat      360 cttctgttca aactcagcaa ggaatcgaag gtcagactgt tctgtatgac caattgccct     420
gcagaagact tcgaatacct ctcacaggca tatcccaagc ttttcggctt gttcgagagg     480 attttttacgt cggcatccac cggtatgcgc aagccaaaca ggaatttctt ccgacatgta     540
ctccaggaga cgggaatcag agcgtcggag actattttcg tagacgacct ggtaccgaac     600
attatggccg ccgaggcgct ggacttcacg gcgattcacg tttctccaga gtcgcccgcc     660
gagaccgtga ggttgctgat gttccatctc cgtaagccag aagagcggct ggcggcggcg     720
cgcgactatc tcctgcgcaa ccgtggagtg gacaaagctc tctctctcac atctgatgga     780
gtccgagtcc aggtttattt cgaccacttc gtggtcgccg aagtgctcaa cgacgagcga     840
ttcttgccaa tcactgcagc tccggagtcc gggactatga acttttttccc gaaggaggaa     900 cgcaaagcga ctcgagatat aacgaccaat gcagtcacac acgtggacct tcccgatgat     960
cttgactcca cctctgtcgc cttatcggtc ctttacaaat tctccaaagt ggggatggag    1020
acggttcaaa gggtcctgga tatgatggag aaacgtgtgg atgatgacgg catttttcaa    1080
acgtacttcg atcctttgcg gctgcgtgtt gacccggtgg ccgctactaa caccgtctac    1140
ctcttccatc taggaggtcg tcccggacct actcagcaga cggaacaatt cctctccaag    1200
ttactggaaa agagatctta tctccgcggc acactctact accggacccc cgaggcattt    1260
ctctatcaac tcaccagatt ggtggtatca tttgaggagt atttcagaaa gacaggcttc    1320
ctggaaatgc tcaagaaaag gctgagtgag cgagtgggca tagagagcga tgcattcacg    1380
ttggcgatga ggattctagc gtgtgtgaat tgtggaatcc ctgttgctga gctgaacaga    1440
gatatggaca gactagcacg gatgcaaaat gtggatggtt catgggacgt ctgcccttac    1500
tacagctaca atgatcccaa gagttggttt gggaacgagc ttcttaccac agcttttgct    1560
gctgccgctc ttgagcagtc tgagcccaac tttaactga                           1599
```

<210> SEQ ID NO 2
<211> LENGTH: 1599
<212> TYPE: DNA
<213> ORGANISM: Bazzania sp.
<220> FEATURE:
<221> NAME/KEY: misc_feature
<223> OTHER INFORMATION: BazzHAD1_E. coli optimized

<400> SEQUENCE: 2

```
atggctccgc cgttcggctt tatcggtggc aacgcgacca gcgttaccac cagcccggat      60
```

```
gtgctggact acaactatga tggtggcccg ccgaccggcc agtacaaaag cctgatcctg     120
gatattggtg gcgttctgct gcaaccgaac ctggaccgta gctatggcac catcgttccg     180
ccggtgcagt tcaagcgtat gctgcgtagc cacatttggt ttaactacag catgggtaaa     240
atgagcgcgg aggaagtttt ccgtcaactg agcgtgaaga gcggttatcc ggcggaggat     300
atccgtagct ttggccgtaa agcgcgtgaa agcctggttc cgatcaccca gattaccgac     360
ctgctgttca agctgagcaa agagagcaaa gtgcgtctgt tctgcatgac caactgcccg     420
gcggaggact ttgaatacct gagccaagcg tatccgaaac tgttcggtct gtttgaacgt     480
atttttacca gcgcgagcac cggcatgcgt aagccgaacc gtaacttctt tcgtcacgtg     540
ctgcaggaga ccggcatccg tgcgagcgaa accattttcg ttgacgatct ggtgccgaac     600
atcatggcgg cggaggcgct ggattttacc gcgattcacg ttagcccgga gagcccggcg     660
gaaaccgtgc gtctgctgat gttccacctg cgtaaaccgg aggaacgtct ggcggcggcg     720
cgtgactacc tgctgcgtaa ccgtggtgtt gataaagcgc tgagcctgac cagcgatggt     780
gtgcgtgttc aggtgtattt cgatcacttt gtggttgcgg aagtgctgaa cgacgaacgt     840
tttctgccga tcaccgcggc gccggaaagc ggcaccatga acttctttcc gaaagaggaa     900
cgcaaggcga cccgtgatat taccaccaac gcggttaccc acgtggatct gccggacgat     960
ctggacagca ccagcgttgc gctgagcgtg ctgtacaaat tcagcaaggt tggtatggag    1020
accgttcagc gtgtgctgga catgatggaa aagcgtgtgg acgatgacgg catcttccaa    1080
acctactttg atccgctgcg tctgcgtgtt gacccggtgg cggcgaccaa caccgtttac    1140
ctgttccatc tgggtggccg tccgggtccg acccagcaaa ccgagcagtt tctgagcaaa    1200
ctgctggaaa agcgtagcta tctgcgtggc accctgtact atcgtacccc ggaggcgttc    1260
ctgtaccaac tgaccccgtct ggtggttagc ttcgaggaat attttcgtaa aaccggtttc    1320
ctggaaatgc tgaagaaacg tctgagcgag cgtgtgggca ttgaaagcga tgcgtttacc    1380
ctggcgatgc gtatcctggc gtgcgttaac tgcggtattc cggtggcgga gctgaaccgt    1440
gatatggacc gtctggcgcg tatgcagaac gttgatggta ctgggacgt gtgcccgtac    1500 tatagctaca cgacccgaa gagctggttc ggcaacgaac tgctgaccac cgcgtttgcg    1560
gcggcggcgc tggagcaaag cgaaccgaac ttcaactaa                          1599
```

```
<210> SEQ ID NO 3
<211> LENGTH: 532
<212> TYPE: PRT
<213> ORGANISM: Bazzania sp.
<220> FEATURE:
<221> NAME/KEY: MISC_FEATURE
<223> OTHER INFORMATION: BazzHAD1_amino acid sequence

<400> SEQUENCE: 3

Met Ala Pro Pro Phe Gly Phe Ile Gly Gly Asn Ala Thr Ser Val Thr
1               5                   10                  15

Thr Ser Pro Asp Val Leu Asp Tyr Asn Tyr Asp Gly Gly Pro Pro Thr
            20                  25                  30

Gly Gln Tyr Lys Ser Leu Ile Leu Asp Ile Gly Gly Val Leu Leu Gln
        35                  40                  45

Pro Asn Leu Asp Arg Ser Tyr Gly Thr Ile Val Pro Pro Val Gln Phe
    50                  55                  60

Lys Arg Met Leu Arg Ser His Ile Trp Phe Asn Tyr Ser Met Gly Lys
65                  70                  75                  80
```

-continued

```
Met Ser Ala Glu Glu Val Phe Arg Gln Leu Ser Val Lys Ser Gly Tyr
                85                  90                  95

Pro Ala Glu Asp Ile Arg Ser Phe Gly Arg Lys Ala Arg Glu Ser Leu
            100                 105                 110

Val Pro Ile Thr Gln Ile Thr Asp Leu Leu Phe Lys Leu Ser Lys Glu
            115                 120                 125

Ser Lys Val Arg Leu Phe Cys Met Thr Asn Cys Pro Ala Glu Asp Phe
    130                 135                 140

Glu Tyr Leu Ser Gln Ala Tyr Pro Lys Leu Phe Gly Leu Phe Glu Arg
145                 150                 155                 160

Ile Phe Thr Ser Ala Ser Thr Gly Met Arg Lys Pro Asn Arg Asn Phe
                165                 170                 175

Phe Arg His Val Leu Gln Glu Thr Gly Ile Arg Ala Ser Glu Thr Ile
            180                 185                 190

Phe Val Asp Asp Leu Val Pro Asn Ile Met Ala Ala Glu Ala Leu Asp
            195                 200                 205

Phe Thr Ala Ile His Val Ser Pro Glu Ser Pro Ala Glu Thr Val Arg
    210                 215                 220

Leu Leu Met Phe His Leu Arg Lys Pro Glu Glu Arg Leu Ala Ala Ala
225                 230                 235                 240

Arg Asp Tyr Leu Leu Arg Asn Arg Gly Val Asp Lys Ala Leu Ser Leu
                245                 250                 255

Thr Ser Asp Gly Val Arg Val Gln Val Tyr Phe Asp His Phe Val Val
            260                 265                 270

Ala Glu Val Leu Asn Asp Glu Arg Phe Leu Pro Ile Thr Ala Ala Pro
            275                 280                 285

Glu Ser Gly Thr Met Asn Phe Phe Pro Lys Glu Glu Arg Lys Ala Thr
    290                 295                 300

Arg Asp Ile Thr Thr Asn Ala Val Thr His Val Asp Leu Pro Asp Asp
305                 310                 315                 320

Leu Asp Ser Thr Ser Val Ala Leu Ser Val Leu Tyr Lys Phe Ser Lys
                325                 330                 335

Val Gly Met Glu Thr Val Gln Arg Val Leu Asp Met Met Glu Lys Arg
            340                 345                 350

Val Asp Asp Asp Gly Ile Phe Gln Thr Tyr Phe Asp Pro Leu Arg Leu
            355                 360                 365

Arg Val Asp Pro Val Ala Ala Thr Asn Thr Val Tyr Leu Phe His Leu
    370                 375                 380

Gly Gly Arg Pro Gly Pro Thr Gln Gln Thr Glu Gln Phe Leu Ser Lys
385                 390                 395                 400

Leu Leu Glu Lys Arg Ser Tyr Leu Arg Gly Thr Leu Tyr Tyr Arg Thr
                405                 410                 415

Pro Glu Ala Phe Leu Tyr Gln Leu Thr Arg Leu Val Val Ser Phe Glu
            420                 425                 430

Glu Tyr Phe Arg Lys Thr Gly Phe Leu Glu Met Leu Lys Lys Arg Leu
            435                 440                 445

Ser Glu Arg Val Gly Ile Glu Ser Asp Ala Phe Thr Leu Ala Met Arg
    450                 455                 460

Ile Leu Ala Cys Val Asn Cys Gly Ile Pro Val Ala Glu Leu Asn Arg
465                 470                 475                 480

Asp Met Asp Arg Leu Ala Arg Met Gln Asn Val Asp Gly Ser Trp Asp
                485                 490                 495

Val Cys Pro Tyr Tyr Ser Tyr Asn Asp Pro Lys Ser Trp Phe Gly Asn
```

-continued

```
               500              505             510
Glu Leu Leu Thr Thr Ala Phe Ala Ala Ala Ala Leu Glu Gln Ser Glu
        515              520             525

Pro Asn Phe Asn
     530

<210> SEQ ID NO 4
<211> LENGTH: 1422
<212> TYPE: DNA
<213> ORGANISM: Bazzania sp.
<220> FEATURE:
<221> NAME/KEY: misc_feature
<223> OTHER INFORMATION: BazzHAD2_wt_nucleic acid sequence

<400> SEQUENCE: 4
atggaaagac ctcatttcga cactctgatc atggacctgg gaggtgttct tgtcgacttc      60
tctcttcaaa catccacatc cacttctgtg aaatctctca agtttgtatt acgttccgcc     120
acctgggcag cttacgagtg cggccatatg tcagaatcgg attgctatgc tgcagtggct     180
aaagatcttg gaagctctgc aaacgcatct caagttggtg aagccatctc agaagttcga     240
aagtcactgc aggtcaatga agatttgata ggggtgattc gggagctcaa agcccagaac     300
ggccttcgag tttacgtaat gtccaacata ccacaaccag acttcgatgc cgtcaaagct     360
aagtcagcga gctggggagt attcgatggc atgtatccct cgtatgcggt gggcacccat     420
aagcccgatc ttgctttcta tcgacacgta ctcgaagaga caaacacaga ccctctcaaa     480
gcgatctttg tcgacgacag cttacaaaat gtcattgcag ccagatcttt tggattgaca     540
ggaattatct acaatgatac tgtcaatgct gctcgaacgc tgcgaaatct ccttggtgat     600
cctatcttga gaggtgagca gtacctttcg tcccacgctg acaattgct gtctatctca      660 gacacaggaa cccccttccc agataacttt tcacagcttt taattttgga tgctaccgga     720
aaccgtgatc ttgttgttct tgaaaaccct cagcgaacat ggaactactt catcggaaag     780
cctgtgttga cgtctgaaac attccctgat gatctagata cgacatctat cgccctcatg     840
gcattgaatg tagacctaga ggtggccaat tctgtgatgg atgagatgct ggagtttaga     900
aacagtgatg gattgtttct gacgtacttt gacgaaacaa ggccgcgggt agatgctgtt     960
gtcaatgtta atgttcttcg tctcttccat cgacatgaac gggagagaga ggcccagcaa    1020
ccgctggagt ggattaccaa cgtccttacc caccgagcgt atgttgatgg cacactattt    1080
tactaccatg ctgagagctt cttatatttc ctttcgcgac tgttctgtga gaactccagc    1140
gtccaatcac gatttcaaga gcttcttgaa caacgcctgc gggaacgaat ggaaccccg     1200 ggcgacgcac tgagtctagc catgcgtgca ttagcatgcc agatgctggg aatcgatagt    1260
tctaccgacg ttcgcgctct tctgcccttg caatgcgacg acggcggttg ggaagctggc    1320
tgggtgtgca gatacggttc aaatggtatg cgcgttggaa gccggggata cactacggct    1380
ttggctataa atgctatcag aggggcaaga gtctcgaggt ga                       1422

<210> SEQ ID NO 5
<211> LENGTH: 1422
<212> TYPE: DNA
<213> ORGANISM: Bazzania sp.
<220> FEATURE:
<221> NAME/KEY: misc_feature
<223> OTHER INFORMATION: BazzHAD2_E. coli optimized

<400> SEQUENCE: 5
atggaacgtc cgcacttcga caccctgatc atggatctgg gtggcgtgct ggttgacttt       60
```

-continued

```
agcctgcaga ccagcaccag caccagcgtt aagagcctga aatttgtgct gcgtagcgcg          120
acctgggcgg cgtacgaatg cggtcacatg agcgagagcg actgctatgc ggcggttgcg          180
aaggatctgg gtagcagcgc gaacgcgagc caagtgggtg aagcgatcag cgaggttcgt          240
aagagcctgc aagtgaacga agatctgatc ggtgttattc gtgagctgaa agcgcagaac          300
ggcctgcgtg tgtacgttat gagcaacatt ccgcaaccgg acttcgatgc ggttaaggcg          360
aaaagcgcga gctggggtgt gtttgatggc atgtacccga gctatgcggt tggcacccac          420
aagccggacc tggcgtttta tcgtcacgtg ctggaggaaa ccaacaccga tccgctgaaa          480
gcgatcttcg ttgacgatag cctgcaaaac gtgattgcgg cgcgtagctt tggtctgacc          540
ggcatcattt acaacgacac cgtgaacgcg gcgcgtaccc tgcgtaacct gctgggtgat          600
ccgatcctgc gtggcgaaca gtatctgagc agccacgcgg gtcaactgct gagcattagc          660
gacaccggca ccccgttccc ggataacttt agccagctgc tgattctgga cgcgaccggt          720
aaccgtgatc tggtggttct ggaaaacccg caacgtacct ggaactactt catcggcaaa          780
ccggttctga ccagcgagac ctttccggac gatctggaca ccaccagcat tgcgctgatg          840
gcgctgaacg tggacctgga agttgcgaac agcgtgatgg atgaaatgct ggagttccgt          900
aacagcgacg tgtctgttcct gacctacttt gacgagaccc gtccgcgtgt ggatgcggtg          960
gttaacgtga acgttctgcg tctgtttcac cgtcacgagc gtgaacgtga ggcgcagcaa         1020
ccgctggagt ggattaccaa cgttctgacc caccgtgcgt acgtggacgg cacctgttc          1080 tactatcacg cggaaagctt cctgtatttt ctgagccgtc tgttctgcga aacagcagc         1140 gttcagagcc gttttcaaga actgctggag cagcgtctgc gtgaacgtat tggcacccg          1200 ggtgatcgc tgagcctggc gatgcgtgcg ctggcgtgcc agatgctggg tattgacagc         1260
agcaccgatg tgcgtgcgct gctgccgctg caatgcgatg atggtggctg ggaggcgggt         1320
tgggtttgcc gttacggtag caacggcatg cgtgtgggta ccgtggcta taccaccgcg         1380 ctggcgatca acgcgattcg tggtgcgcgt gttagccgtt aa                            1422
```

```
<210> SEQ ID NO 6
<211> LENGTH: 473
<212> TYPE: PRT
<213> ORGANISM: Bazzania sp.
<220> FEATURE:
<221> NAME/KEY: MISC_FEATURE
<223> OTHER INFORMATION: BazzHAD2_amino acid sequence

<400> SEQUENCE: 6

Met Glu Arg Pro His Phe Asp Thr Leu Ile Met Asp Leu Gly Gly Val
1               5                   10                  15

Leu Val Asp Phe Ser Leu Gln Thr Ser Thr Ser Thr Ser Val Lys Ser
                20                  25                  30

Leu Lys Phe Val Leu Arg Ser Ala Thr Trp Ala Ala Tyr Glu Cys Gly
            35                  40                  45

His Met Ser Glu Ser Asp Cys Tyr Ala Ala Val Ala Lys Asp Leu Gly
        50                  55                  60

Ser Ser Ala Asn Ala Ser Gln Val Gly Glu Ala Ile Ser Glu Val Arg
65                  70                  75                  80

Lys Ser Leu Gln Val Asn Glu Asp Leu Ile Gly Val Ile Arg Glu Leu
                85                  90                  95

Lys Ala Gln Asn Gly Leu Arg Val Tyr Val Met Ser Asn Ile Pro Gln
            100                 105                 110
```

```
Pro Asp Phe Asp Ala Val Lys Ala Lys Ser Ala Ser Trp Gly Val Phe
        115                 120                 125

Asp Gly Met Tyr Pro Ser Tyr Ala Val Gly Thr His Lys Pro Asp Leu
        130                 135                 140

Ala Phe Tyr Arg His Val Leu Glu Glu Thr Asn Thr Asp Pro Leu Lys
145                 150                 155                 160

Ala Ile Phe Val Asp Asp Ser Leu Gln Asn Val Ile Ala Ala Arg Ser
                165                 170                 175

Phe Gly Leu Thr Gly Ile Ile Tyr Asn Asp Thr Val Asn Ala Ala Arg
        180                 185                 190

Thr Leu Arg Asn Leu Leu Gly Asp Pro Ile Leu Arg Gly Glu Gln Tyr
        195                 200                 205

Leu Ser Ser His Ala Gly Gln Leu Leu Ser Ile Ser Asp Thr Gly Thr
210                 215                 220

Pro Phe Pro Asp Asn Phe Ser Gln Leu Leu Ile Leu Asp Ala Thr Gly
225                 230                 235                 240

Asn Arg Asp Leu Val Val Leu Glu Asn Pro Gln Arg Thr Trp Asn Tyr
                245                 250                 255

Phe Ile Gly Lys Pro Val Leu Thr Ser Glu Thr Phe Pro Asp Asp Leu
                260                 265                 270

Asp Thr Thr Ser Ile Ala Leu Met Ala Leu Asn Val Asp Leu Glu Val
        275                 280                 285

Ala Asn Ser Val Met Asp Glu Met Leu Glu Phe Arg Asn Ser Asp Gly
        290                 295                 300

Leu Phe Leu Thr Tyr Phe Asp Glu Thr Arg Pro Arg Val Asp Ala Val
305                 310                 315                 320

Val Asn Val Asn Val Leu Arg Leu Phe His Arg His Glu Arg Glu Arg
                325                 330                 335

Glu Ala Gln Gln Pro Leu Glu Trp Ile Thr Asn Val Leu Thr His Arg
        340                 345                 350

Ala Tyr Val Asp Gly Thr Leu Phe Tyr Tyr His Ala Glu Ser Phe Leu
        355                 360                 365

Tyr Phe Leu Ser Arg Leu Phe Cys Glu Asn Ser Ser Val Gln Ser Arg
370                 375                 380

Phe Gln Glu Leu Leu Glu Gln Arg Leu Arg Glu Arg Ile Gly Thr Pro
385                 390                 395                 400

Gly Asp Ala Leu Ser Leu Ala Met Arg Ala Leu Ala Cys Gln Met Leu
                405                 410                 415

Gly Ile Asp Ser Ser Thr Asp Val Arg Ala Leu Leu Pro Leu Gln Cys
                420                 425                 430

Asp Asp Gly Gly Trp Glu Ala Gly Trp Val Cys Arg Tyr Gly Ser Asn
        435                 440                 445

Gly Met Arg Val Gly Ser Arg Gly Tyr Thr Thr Ala Leu Ala Ile Asn
        450                 455                 460

Ala Ile Arg Gly Ala Arg Val Ser Arg
465                 470
```

<210> SEQ ID NO 7
<211> LENGTH: 1452
<212> TYPE: DNA
<213> ORGANISM: Bazzania sp.
<220> FEATURE:
<221> NAME/KEY: misc_feature
<223> OTHER INFORMATION: BazzHAD3_wt_nucleic acid sequence

<400> SEQUENCE: 7

```
atgcctgctt taagctcgca tatggagcca cctaattttg acaccctgat cctggacctg      60
ggagatgtcc ttgtgggagg ctctcttcaa ggctcttacg ccttggccat gaagagaatt     120
ctgaaactct cattacgtac cccgacgtgg ggaaaatacg agtgcggcca attatcagaa     180
ttagattgct atgacgctgt ggctgaagat cttgggaact ccacaagctc cgctcaagtg     240
ggtgaggtcg tctcagaagc tcgaaagtca ttgcaggtca atgaagacct gataaaggtg     300
cttcaggagc taaaggctga gaacaatctc cgggtttatg tcatgtccaa tatacccaag     360
ccggatttgg ctgttgtgaa ggccaagtca gtgaactggg gagtcatcga tggctggtat     420
ccctcttatg ctgtgggctt ccacaagccg gatctcgctt tctaccggca tgtacttgaa     480
gagacaaaca ccgatcctct taaggccatc ttcgttgatg acaaggttca gaatgtcatt     540
gttgccagat cctttggaat gacaggcatt gtcttcaagg acactaagag cactaccaag     600
gagctgaaga atctccttgg tgaccccgtc aagagagggg agcacttcct ctcagctcat     660
gccaaacaat tggagtctgt ctgtggggat ggcaccactt tccttgacaa cttcgcccag     720
ctgctgattc ttcatgatac tggaaacagc gatcttgtgg ctcgtcagca ccatggcaga     780
acctggaact acttcattgg caagccgatg gggacgacag acacattccc caacgaccta     840
gataccacct ccatcgctct gctgactctg aatgtagact cagaagtagc gaggtctgtg     900
ttagatgaga tgctgctgta caccagcagt gatgggctgg tagaggtgta ttttgacaaa     960
actagacctc gggtggatcc cgttgtctgt gtcaacgtgc tacgtctctt ctctaaatat    1020
gggagggagc tccagcttca gaagactctg gactgggtaa ctgaggtcct tgttcaccga    1080
gcttacattg acggcacact cttctactac cacgctgaga gcttcttgta cttcctttcg    1140
tgtctctaca agagaaccc ccggctgcag actcaatttc gggagcctct acaagaacgc     1200
ctgcgggaga ggattgggca gcccggggat gcactttgtc tggctatgcg tgcaatcgca    1260
tgccagactg tggggattgg gaatgttatt gatgtgcaag ctcttctgcc attgcaatct    1320
agtgatggtg gttgggaggc tggctgggtc tgcagaatgg gcacgtctgg tgttcctgtt    1380
ggaaaccgag gagtcacaac ggcactttgt attagagcta ttcgaggcgc atcagggagc    1440
taccacactt ga                                                        1452
```

<210> SEQ ID NO 8
<211> LENGTH: 1452
<212> TYPE: DNA
<213> ORGANISM: Bazzania sp.
<220> FEATURE:
<221> NAME/KEY: misc_feature
<223> OTHER INFORMATION: BazzHAD3_E. coli optimized

<400> SEQUENCE: 8

```
atgccggcgc tgagcagcca catggaaccg ccgaacttcg acaccctgat tctggacctg      60
ggtgatgtgc tggttggtgg cagcctgcag ggtagctacg cgctggcgat gaagcgtatc     120
ctgaaactga gcctgcgtac cccgacctgg ggcaagtacg aatgcggcca gctgagcgag     180
ctggactgct atgatgcggt tgcggaagac ctgggtaaca gcaccagcag cgcgcaagtg     240
ggcgaggtgg ttagcgaagc gcgtaaaagc ctgcaggtta cgaggatctg atcaaggtg     300 ctgcaagagc tgaaagcgga aaacaacctg cgtgtgtacg ttatgagcaa cattccgaag     360
ccggacctgg cggtggttaa ggcgaaaagc gtgaactggg gtgttatcga tggctggtat     420
ccgagctatg cggttggttt ccacaaaccg gacctggcgt tttatcgtca cgtgctggag     480
gaaaccaaca ccgatccgct gaaggcgatc ttcgtggacg ataaagttca gaacgtgatt     540
```

-continued

```
gttgcgcgta gcttcggtat gaccggcatc gtttttaagg acaccaaaag caccaccaag    600
gaactgaaaa acctgctggg tgatccggtt aagcgtggcg aacactttct gagcgcgcac    660
gcgaaacaac tggagagcgt gtgcggtgac ggcaccacct tcctggataa ctttgcgcag    720
ctgctgattc tgcacgacac cggtaacagc gatctggtgg cgcgtcaaca ccacggccgt    780
acctggaact acttcattgg caagccgatg ggcaccaccg atacctttcc gaacgacctg    840
gataccacca gcatcgcgct gctgaccctg aacgtggaca gcgaagttgc gcgtagcgtg    900
ctggatgaga tgctgctgta caccagcagc gacggtctgg ttgaggtgta tttcgacaaa    960
acccgtccgc gtgttgatcc ggtggtttgc gtgaacgttc tgcgtctgtt tagcaagtac    1020
ggtcgtgaac tgcagctgca aaaaaccctg gattgggtga ccgaggtgct ggttcaccgt    1080
gcgtatatcg acggcaccct gttctactat cacgcggaaa gcttcctgta ctttctgagc    1140
tgcctgtata aggagaaccc gcgtctgcag acccaatttc gtgagccgct gcaggaacgt    1200
ctgcgtgagc gtattggtca gccgggtgat gcgctgtgcc tggcgatgcg tgcgatcgcg    1260
tgccagaccg ttggtatcgg caacgtgatt gatgttcaag cgctgctgcc gctgcagagc    1320
agcgatggtg gctgggaggc gggttggggtt tgccgtatgg gcaccagcgg tgtgccggtt    1380
ggtaaccgtg gcgtgaccac cgcgctgtgc atccgtgcga ttcgtggtgc gagcggcagc    1440
tatcacacct aa    1452
```

```
<210> SEQ ID NO 9
<211> LENGTH: 483
<212> TYPE: PRT
<213> ORGANISM: Bazzania sp.
<220> FEATURE:
<221> NAME/KEY: MISC_FEATURE
<223> OTHER INFORMATION: BazzHAD3_amino acid sequence

<400> SEQUENCE: 9

Met Pro Ala Leu Ser Ser His Met Glu Pro Pro Asn Phe Asp Thr Leu
1               5                   10                  15

Ile Leu Asp Leu Gly Asp Val Leu Val Gly Gly Ser Leu Gln Gly Ser
            20                  25                  30

Tyr Ala Leu Ala Met Lys Arg Ile Leu Lys Leu Ser Leu Arg Thr Pro
        35                  40                  45

Thr Trp Gly Lys Tyr Glu Cys Gly Gln Leu Ser Glu Leu Asp Cys Tyr
    50                  55                  60

Asp Ala Val Ala Glu Asp Leu Gly Asn Ser Thr Ser Ser Ala Gln Val
65                  70                  75                  80

Gly Glu Val Val Ser Glu Ala Arg Lys Ser Leu Gln Val Asn Glu Asp
                85                  90                  95

Leu Ile Lys Val Leu Gln Glu Leu Lys Ala Glu Asn Asn Leu Arg Val
            100                 105                 110

Tyr Val Met Ser Asn Ile Pro Lys Pro Asp Leu Ala Val Val Lys Ala
        115                 120                 125

Lys Ser Val Asn Trp Gly Val Ile Asp Gly Trp Tyr Pro Ser Tyr Ala
    130                 135                 140

Val Gly Phe His Lys Pro Asp Leu Ala Phe Tyr Arg His Val Leu Glu
145                 150                 155                 160

Glu Thr Asn Thr Asp Pro Leu Lys Ala Ile Phe Val Asp Asp Lys Val
                165                 170                 175

Gln Asn Val Ile Val Ala Arg Ser Phe Gly Met Thr Gly Ile Val Phe
            180                 185                 190
```

```
Lys Asp Thr Lys Ser Thr Thr Lys Glu Leu Lys Asn Leu Leu Gly Asp
        195                 200                 205

Pro Val Lys Arg Gly Glu His Phe Leu Ser Ala His Ala Lys Gln Leu
    210                 215                 220

Glu Ser Val Cys Gly Asp Gly Thr Thr Phe Leu Asp Asn Phe Ala Gln
225                 230                 235                 240

Leu Leu Ile Leu His Asp Thr Gly Asn Ser Asp Leu Val Ala Arg Gln
                245                 250                 255

His His Gly Arg Thr Trp Asn Tyr Phe Ile Gly Lys Pro Met Gly Thr
                260                 265                 270

Thr Asp Thr Phe Pro Asn Asp Leu Asp Thr Thr Ser Ile Ala Leu Leu
            275                 280                 285

Thr Leu Asn Val Asp Ser Glu Val Ala Arg Ser Val Leu Asp Glu Met
    290                 295                 300

Leu Leu Tyr Thr Ser Ser Asp Gly Leu Val Glu Val Tyr Phe Asp Lys
305                 310                 315                 320

Thr Arg Pro Arg Val Asp Pro Val Val Cys Val Asn Val Leu Arg Leu
                325                 330                 335

Phe Ser Lys Tyr Gly Arg Glu Leu Gln Leu Gln Lys Thr Leu Asp Trp
                340                 345                 350

Val Thr Glu Val Leu Val His Arg Ala Tyr Ile Asp Gly Thr Leu Phe
            355                 360                 365

Tyr Tyr His Ala Glu Ser Phe Leu Tyr Phe Leu Ser Cys Leu Tyr Lys
    370                 375                 380

Glu Asn Pro Arg Leu Gln Thr Gln Phe Arg Glu Pro Leu Gln Glu Arg
385                 390                 395                 400

Leu Arg Glu Arg Ile Gly Gln Pro Gly Asp Ala Leu Cys Leu Ala Met
                405                 410                 415

Arg Ala Ile Ala Cys Gln Thr Val Gly Ile Gly Asn Val Ile Asp Val
            420                 425                 430

Gln Ala Leu Leu Pro Leu Gln Ser Ser Asp Gly Gly Trp Glu Ala Gly
        435                 440                 445

Trp Val Cys Arg Met Gly Thr Ser Gly Val Pro Val Gly Asn Arg Gly
    450                 455                 460

Val Thr Thr Ala Leu Cys Ile Arg Ala Ile Arg Gly Ala Ser Gly Ser
465                 470                 475                 480

Tyr His Thr
```

```
<210> SEQ ID NO 10
<211> LENGTH: 1596
<212> TYPE: DNA
<213> ORGANISM: Bazzania trilobata
<220> FEATURE:
<221> NAME/KEY: misc_feature
<223> OTHER INFORMATION: BtHAD_wt_nucleic acid sequence

<400> SEQUENCE: 10
atggctcctc ctttcggata tattggtggg aatgaatcga gtgtgacgac gtccccagac      60
gtcctcgact acagctatga tggtggccct cctactggcc aatacaagag tatgattta     120 gacattggcg gagtgttgct tcagcccaac cttgacagga gctatggcac gattgtacca     180
cctgtgcaat tcaaacgtat gttgcgctcg cacatctggt tcaattactc aatgggaaag     240
gtgtctgcgg aggaagtgtt tcggcagctc tccgtgaagt ctggctaccc ggcagaagat     300
atccggagtt ttgctcgaaa agcgagagag tctcttgtgc ccatcacaca aataacggat     360
```

-continued

```
cttctggtca aactcagcaa ggaatcgaag atcagactgt tctgtatgac caattgccct      420
gccgaagact tcgcatacct ctcacaggca tatcccaacc ttttcggatt gttcgagagg      480
atttttacgt cggcgtccac cggtatgcgc aagccaaaca ggaatttctt ccgacatgta      540
ctccaggaga cgggaatcag tgcgacggag actattttcg tagacgacct ggtaccgaac      600
atcatggccg ccgaggcgct ggacttcacg gcaattcacg tttctccaga gtcgcccgcc      660
gagaccgtga ggttgctgat gttccatctc cgtaagccag aagagcggct ggcggcggcg      720
cgcgactatc tcctgcgcaa ccgtggagtg gacaaagctc tctctctcac atctgacgga      780
gtccgagtcc aggtttattt cgaccacttc gtggtcgccg aagtgctcaa cgacgagcga      840
ttcttgccaa tcactgcagc tccgaagtcc gggactatga actttttccc gaaggaggaa      900
cgcaacgcga ctcgagatat gacgaccaat gcagtcacac acgtggacct tcccgatgat      960
cttgactcca cctctgtcgc cttatcggtc ctttacaaat tctccaaagt ggcgatggag     1020
acggttcaga gggtcctgga tatgatggag aaacgtgtgg acgatgacgg cattttttcaa     1080 acgtacttcg atcctttgcg gctgcgtgtt gacccggtgg ccgctactaa caccgtctac     1140
ctcttccatt taggaggtcg tcccggacct actcagcaga cggaacaatt cctctccaag     1200
ttactggaaa agagatctta cgtccgcggc acactctact acaggacccc cgaggcattt     1260
ctctatcaac tcaccagatt ggtggtatca tttgagtatt tcagaaagac aggcttcctg     1320
gaaatgctca agaaaaggct gagtgagcga gtgggcatcg agagcgatgc attcacgttg     1380
gcgatgagga ttctagcgtg tgtgaattgt ggaatccctg ttgctgagct gaacagagat     1440
atggacagac tagcacggat gcaaaatgtg gatggttcat gggacgtctg cccttactac     1500
agctacaatg atcccaagag ttggtttggc aacgagcttc ttaccacagc gtttgctgct     1560
gccgctcttg agcattctga gcccaacttt aagtga                              1596
```

```
<210> SEQ ID NO 11
<211> LENGTH: 1596
<212> TYPE: DNA
<213> ORGANISM: Bazzania trilobata
<220> FEATURE:
<221> NAME/KEY: misc_feature
<223> OTHER INFORMATION: BtHAD_E. coli optimized

<400> SEQUENCE: 11
```

```
atggctccgc cgttcggtta cattggtggc aacgagagca gcgttaccac cagcccggat       60
gtgctggact acagctatga tggtggcccg ccgaccggcc agtacaaaag catgatcctg      120
gatattggtg gcgttctgct gcaaccgaac ctggaccgta gctatggcac catcgttccg      180
ccggtgcagt tcaagcgtat gctgcgtagc cacatttggt ttaactacag catgggtaaa      240
gttagcgcgg aggaagtgtt ccgtcaactg agcgtgaaga gcggctatcc ggcggaggat      300
atccgtagct ttgcgcgtaa agcgcgtgaa agcctggttc cgatcaccca gattaccgac      360
ctgctggtga agctgagcaa agagagcaag attcgtctgt tctgcatgac caactgcccg      420
gcggaagact ttgcgtacct gagccaagcg tatccgaacc tgttcggtct gtttgagcgt      480
atcttcacca gcgcgagcac cggcatgcgt aagccgaacc gtaacttctt tcgtcacgtt      540
ctgcaggaga ccggcatcag cgcgaccgaa accatttttcg ttgacgatct ggtgccgaac      600
atcatggcgg cggaagcgct ggattttacc gcgattcacg ttagcccgga gagcccggcg      660
gaaaccgtgc gtctgctgat gtttcacctg cgtaaaccgg aggaacgtct ggcggcggcg      720
cgtgactacc tgctgcgtaa ccgtggtgtt gataaagcgc tgagcctgac cagcgatggt      780
```

-continued

```
gtgcgtgttc aagtgtattt cgatcacttt gtggttgcgg aagtgctgaa cgacgaacgt    840
ttcctgccga ttaccgcggc gccgaaaagc ggcaccatga acttctttcc gaaagaggag    900
cgtaacgcga cccgtgatat gaccaccaac gcggttaccc acgtggatct gccggacgat    960
ctggacagca ccagcgttgc gctgagcgtg ctgtacaaat ttagcaaggt tgcgatggag    1020
accgttcagc gtgtgctgga catgatggaa aaacgtgtgg acgatgacgg catcttccaa    1080
acctactttg atccgctgcg tctgcgtgtt gacccggtgg cggcgaccaa caccgtttac    1140
ctgttccatc tgggtggccg tccgggtccg acccagcaaa ccgagcagtt tctgagcaaa    1200
ctgctggaaa agcgtagcta tgtgcgtggc accctgtact atcgtacccc ggaagcgttc    1260
ctgtaccaac tgacccgtct ggtggttagc ttcgagtatt ttcgtaagac cggttttctg    1320
gaaatgctga agaaacgtct gagcgagcgt gtgggcatcg aaagcgatgc gttcaccctg    1380
gcgatgcgta tcctggcgtg cgttaactgc ggtattccgg tggcggagct gaaccgtgat    1440
atggaccgtc tggcgcgtat gcagaacgtt gatggtagct gggacgtgtg cccgtactat    1500
agctacaacg acccgaaaag ctggttcggc aacgaactgc tgaccaccgc gtttgcggcg    1560
gcggcgctgg agcacagcga accgaacttc aagtaa                                1596
```

```
<210> SEQ ID NO 12
<211> LENGTH: 531
<212> TYPE: PRT
<213> ORGANISM: Bazzania trilobata
<220> FEATURE:
<221> NAME/KEY: MISC_FEATURE
<223> OTHER INFORMATION: BtHAD_amino acid sequence

<400> SEQUENCE: 12

Met Ala Pro Pro Phe Gly Tyr Ile Gly Gly Asn Glu Ser Ser Val Thr
1               5                   10                  15

Thr Ser Pro Asp Val Leu Asp Tyr Ser Tyr Asp Gly Gly Pro Pro Thr
            20                  25                  30

Gly Gln Tyr Lys Ser Met Ile Leu Asp Ile Gly Gly Val Leu Leu Gln
        35                  40                  45

Pro Asn Leu Asp Arg Ser Tyr Gly Thr Ile Val Pro Pro Val Gln Phe
    50                  55                  60

Lys Arg Met Leu Arg Ser His Ile Trp Phe Asn Tyr Ser Met Gly Lys
65                  70                  75                  80

Val Ser Ala Glu Glu Val Phe Arg Gln Leu Ser Val Lys Ser Gly Tyr
                85                  90                  95

Pro Ala Glu Asp Ile Arg Ser Phe Ala Arg Lys Ala Arg Glu Ser Leu
            100                 105                 110

Val Pro Ile Thr Gln Ile Thr Asp Leu Leu Val Lys Leu Ser Lys Glu
        115                 120                 125

Ser Lys Ile Arg Leu Phe Cys Met Thr Asn Cys Pro Ala Glu Asp Phe
    130                 135                 140

Ala Tyr Leu Ser Gln Ala Tyr Pro Asn Leu Phe Gly Leu Phe Glu Arg
145                 150                 155                 160

Ile Phe Thr Ser Ala Ser Thr Gly Met Arg Lys Pro Asn Arg Asn Phe
                165                 170                 175

Phe Arg His Val Leu Gln Glu Thr Gly Ile Ser Ala Thr Glu Thr Ile
            180                 185                 190

Phe Val Asp Asp Leu Val Pro Asn Ile Met Ala Ala Glu Ala Leu Asp
        195                 200                 205
```

```
Phe Thr Ala Ile His Val Ser Pro Glu Ser Pro Ala Glu Thr Val Arg
    210             215             220
```

```
Leu Leu Met Phe His Leu Arg Lys Pro Glu Glu Arg Leu Ala Ala Ala
225             230             235             240
```

```
Arg Asp Tyr Leu Leu Arg Asn Arg Gly Val Asp Lys Ala Leu Ser Leu
            245             250             255
```

```
Thr Ser Asp Gly Val Arg Val Gln Val Tyr Phe Asp His Phe Val Val
            260             265             270
```

```
Ala Glu Val Leu Asn Asp Glu Arg Phe Leu Pro Ile Thr Ala Ala Pro
            275             280             285
```

```
Lys Ser Gly Thr Met Asn Phe Phe Pro Lys Glu Glu Arg Asn Ala Thr
    290             295             300
```

```
Arg Asp Met Thr Thr Asn Ala Val Thr His Val Asp Leu Pro Asp Asp
305             310             315             320
```

```
Leu Asp Ser Thr Ser Val Ala Leu Ser Val Leu Tyr Lys Phe Ser Lys
            325             330             335
```

```
Val Ala Met Glu Thr Val Gln Arg Val Leu Asp Met Met Glu Lys Arg
            340             345             350
```

```
Val Asp Asp Asp Gly Ile Phe Gln Thr Tyr Phe Asp Pro Leu Arg Leu
            355             360             365
```

```
Arg Val Asp Pro Val Ala Ala Thr Asn Thr Val Tyr Leu Phe His Leu
    370             375             380
```

```
Gly Gly Arg Pro Gly Pro Thr Gln Gln Thr Glu Gln Phe Leu Ser Lys
385             390             395             400
```

```
Leu Leu Glu Lys Arg Ser Tyr Val Arg Gly Thr Leu Tyr Tyr Arg Thr
            405             410             415
```

```
Pro Glu Ala Phe Leu Tyr Gln Leu Thr Arg Leu Val Val Ser Phe Glu
            420             425             430
```

```
Tyr Phe Arg Lys Thr Gly Phe Leu Glu Met Leu Lys Lys Arg Leu Ser
            435             440             445
```

```
Glu Arg Val Gly Ile Glu Ser Asp Ala Phe Thr Leu Ala Met Arg Ile
    450             455             460
```

```
Leu Ala Cys Val Asn Cys Gly Ile Pro Val Ala Glu Leu Asn Arg Asp
465             470             475             480
```

```
Met Asp Arg Leu Ala Arg Met Gln Asn Val Asp Gly Ser Trp Asp Val
            485             490             495
```

```
Cys Pro Tyr Tyr Ser Tyr Asn Asp Pro Lys Ser Trp Phe Gly Asn Glu
            500             505             510
```

```
Leu Leu Thr Thr Ala Phe Ala Ala Ala Ala Leu Glu His Ser Glu Pro
            515             520             525
```

```
Asn Phe Lys
    530
```

```
<210> SEQ ID NO 13
<211> LENGTH: 1596
<212> TYPE: DNA
<213> ORGANISM: Artificial Sequence
<220> FEATURE:
<223> OTHER INFORMATION: BtHAD mutant of class II motif_E. coli
      optimized
```

```
<400> SEQUENCE: 13
```

```
atggctccgc cgttcggtta cattggtggc aacgagagca gcgttaccac cagcccggat      60
gtgctggact acagctatga tggtggcccg ccgaccggcc agtacaaaag catgatcctg     120
gatattggtg gcgttctgct gcaaccgaac ctggaccgta gctatggcac catcgttccg     180
```

```
ccggtgcagt tcaagcgtat gctgcgtagc cacatttggt ttaactacag catgggtaaa      240
gttagcgcgg aggaagtgtt ccgtcaactg agcgtgaaga gcggctatcc ggcggaggat      300
atccgtagct ttgcgcgtaa agcgcgtgaa agcctggttc cgatcaccca gattaccgac      360
ctgctggtga agctgagcaa agagagcaag attcgtctgt tctgcatgac caactgcccg      420
gcggaagact ttgcgtacct gagccaagcg tatccgaacc tgttcggtct gtttgagcgt      480
atcttcacca gcgcgagcac cggcatgcgt aagccgaacc gtaacttctt tcgtcacgtt      540
ctgcaggaga ccggcatcag cgcgaccgaa accattttcg ttgacgatct ggtgccgaac      600
atcatggcgg cggaagcgct ggattttacc gcgattcacg ttagcccgga gagcccggcg      660
gaaaccgtgc gtctgctgat gtttcacctg cgtaaaccgg aggaacgtct ggcggcggcg      720
cgtgactacc tgctgcgtaa ccgtggtgtt gataaagcgc tgagcctgac cagcgatggt      780
gtgcgtgttc aagtgtattt cgatcacttt gtggttgcgg aagtgctgaa cgacgaacgt      840
ttcctgccga ttaccgcggc gccgaaaagc ggcaccatga acttctttcc gaaagaggag      900
cgtaacgcga cccgtgatat gaccaccaac gcggttaccc acgtggatct gccggacgcg      960
ctggcgagca ccagcgttgc gctgagcgtg ctgtacaaat ttagcaaggt tgcgatggag     1020
accgttcagc gtgtgctgga catgatggaa aaacgtgtgg acgatgacgg catcttccaa     1080
acctactttg atccgctgcg tctgcgtgtt gacccggtgg cggcgaccaa caccgtttac     1140
ctgttccatc tgggtggccg tccgggtccg acccagcaaa ccgagcagtt tctgagcaaa     1200
ctgctggaaa agcgtagcta tgtgcgtggc accctgtact atcgtacccc ggaagcgttc     1260
ctgtaccaac tgacccgtct ggtggttagc ttcgagtatt ttcgtaagac cggttttctg     1320
gaaatgctga agaacgtct gagcgagcgt gtgggcatcg aaagcgatgc gttcaccctg     1380
gcgatgcgta tcctggcgtg cgttaactgc ggtattccgg tggcggagct gaaccgtgat     1440
atggaccgtc tggcgcgtat gcagaacgtt gatggtagct gggacgtgtg cccgtactat     1500
agctacaacg acccgaaaag ctggttcggc aacgaactgc tgaccaccgc gtttgcggcg     1560
gcggcgctgg agcacagcga accgaacttc aagtaa                               1596
```

<210> SEQ ID NO 14
<211> LENGTH: 531
<212> TYPE: PRT
<213> ORGANISM: Artificial Sequence
<220> FEATURE:
<223> OTHER INFORMATION: BtHAD mutant of class II motif

<400> SEQUENCE: 14

```
Met Ala Pro Pro Phe Gly Tyr Ile Gly Gly Asn Glu Ser Ser Val Thr
1               5                   10                  15

Thr Ser Pro Asp Val Leu Asp Tyr Ser Tyr Asp Gly Gly Pro Pro Thr
            20                  25                  30

Gly Gln Tyr Lys Ser Met Ile Leu Asp Ile Gly Gly Val Leu Leu Gln
        35                  40                  45

Pro Asn Leu Asp Arg Ser Tyr Gly Thr Ile Val Pro Pro Val Gln Phe
    50                  55                  60

Lys Arg Met Leu Arg Ser His Ile Trp Phe Asn Tyr Ser Met Gly Lys
65                  70                  75                  80

Val Ser Ala Glu Glu Val Phe Arg Gln Leu Ser Val Lys Ser Gly Tyr
                85                  90                  95

Pro Ala Glu Asp Ile Arg Ser Phe Ala Arg Lys Ala Arg Glu Ser Leu
            100                 105                 110
```

-continued

```
Val Pro Ile Thr Gln Ile Thr Asp Leu Leu Val Lys Leu Ser Lys Glu
        115                 120                 125

Ser Lys Ile Arg Leu Phe Cys Met Thr Asn Cys Pro Ala Glu Asp Phe
        130                 135                 140

Ala Tyr Leu Ser Gln Ala Tyr Pro Asn Leu Phe Gly Leu Phe Glu Arg
145                 150                 155                 160

Ile Phe Thr Ser Ala Ser Thr Gly Met Arg Lys Pro Asn Arg Asn Phe
                165                 170                 175

Phe Arg His Val Leu Gln Glu Thr Gly Ile Ser Ala Thr Glu Thr Ile
                180                 185                 190

Phe Val Asp Asp Leu Val Pro Asn Ile Met Ala Ala Glu Ala Leu Asp
        195                 200                 205

Phe Thr Ala Ile His Val Ser Pro Glu Ser Pro Ala Glu Thr Val Arg
        210                 215                 220

Leu Leu Met Phe His Leu Arg Lys Pro Glu Glu Arg Leu Ala Ala Ala
225                 230                 235                 240

Arg Asp Tyr Leu Leu Arg Asn Arg Gly Val Asp Lys Ala Leu Ser Leu
                245                 250                 255

Thr Ser Asp Gly Val Arg Val Gln Val Tyr Phe Asp His Phe Val Val
                260                 265                 270

Ala Glu Val Leu Asn Asp Glu Arg Phe Leu Pro Ile Thr Ala Ala Pro
        275                 280                 285

Lys Ser Gly Thr Met Asn Phe Phe Pro Lys Glu Glu Arg Asn Ala Thr
        290                 295                 300

Arg Asp Met Thr Thr Asn Ala Val Thr His Val Asp Leu Pro Asp Ala
305                 310                 315                 320

Leu Ala Ser Thr Ser Val Ala Leu Ser Val Leu Tyr Lys Phe Ser Lys
                325                 330                 335

Val Ala Met Glu Thr Val Gln Arg Val Leu Asp Met Met Glu Lys Arg
                340                 345                 350

Val Asp Asp Asp Gly Ile Phe Gln Thr Tyr Phe Asp Pro Leu Arg Leu
        355                 360                 365

Arg Val Asp Pro Val Ala Ala Thr Asn Thr Val Tyr Leu Phe His Leu
        370                 375                 380

Gly Gly Arg Pro Gly Pro Thr Gln Gln Thr Glu Gln Phe Leu Ser Lys
385                 390                 395                 400

Leu Leu Glu Lys Arg Ser Tyr Val Arg Gly Thr Leu Tyr Tyr Arg Thr
                405                 410                 415

Pro Glu Ala Phe Leu Tyr Gln Leu Thr Arg Leu Val Val Ser Phe Glu
                420                 425                 430

Tyr Phe Arg Lys Thr Gly Phe Leu Glu Met Leu Lys Lys Arg Leu Ser
                435                 440                 445

Glu Arg Val Gly Ile Glu Ser Asp Ala Phe Thr Leu Ala Met Arg Ile
        450                 455                 460

Leu Ala Cys Val Asn Cys Gly Ile Pro Val Ala Glu Leu Asn Arg Asp
465                 470                 475                 480

Met Asp Arg Leu Ala Arg Met Gln Asn Val Asp Gly Ser Trp Asp Val
                485                 490                 495

Cys Pro Tyr Tyr Ser Tyr Asn Asp Pro Lys Ser Trp Phe Gly Asn Glu
                500                 505                 510

Leu Leu Thr Thr Ala Phe Ala Ala Ala Ala Leu Glu His Ser Glu Pro
        515                 520                 525
```

Asn Phe Lys
    530

<210> SEQ ID NO 15
<211> LENGTH: 1596
<212> TYPE: DNA
<213> ORGANISM: Artificial Sequence
<220> FEATURE:
<223> OTHER INFORMATION: BtHAD mutant of QW motif_E. coli optimized

<400> SEQUENCE: 15
atggctccgc cgttcggtta cattggtggc aacgagagca gcgttaccac cagcccggat        60
gtgctggact acagctatga tggtggcccg ccgaccggcc agtacaaaag catgatcctg       120
gatattggtg gcgttctgct gcaaccgaac ctggaccgta gctatggcac catcgttccg       180
ccggtgcagt tcaagcgtat gctgcgtagc cacatttggt ttaactacag catgggtaaa       240
gttagcgcgg aggaagtgtt ccgtcaactg agcgtgaaga gcggctatcc ggcggaggat       300
atccgtagct ttgcgcgtaa agcgcgtgaa agcctggttc gatcacccca gattaccgac       360
ctgctggtga agctgagcaa agagagcaag attcgtctgt tctgcatgac caactgcccg       420
gcggaagact ttgcgtacct gagccaagcg tatccgaacc tgttcggtct gtttgagcgt       480
atcttcacca gcgcgagcac cggcatgcgt aagccgaacc gtaacttctt tcgtcacgtt       540
ctgcaggaga ccggcatcag cgcgaccgaa accattttcg ttgacgatct ggtgccgaac       600
atcatggcgg cggaagcgct ggattttacc gcgattcacg ttagcccgga gagcccggcg       660
gaaaccgtgc gtctgctgat gtttcacctg cgtaaaccgg aggaacgtct ggcggcggcg       720
cgtgactacc tgctgcgtaa ccgtggtgtt gataaagcgc tgagcctgac cagcgatggt       780
gtgcgtgttc aagtgtattt cgatcacttt gtggttgcgg aagtgctgaa cgacgaacgt       840
ttcctgccga ttaccgcggc gccgaaaagc ggcaccatga acttctttcc gaaagaggag       900
cgtaacgcga cccgtgatat gaccaccaac gcggttaccc acgtggatct gccggacgat       960
ctggacagca ccagcgttgc gctgagcgtg ctgtacaaat ttagcaaggt tgcgatggag      1020
accgttcagc gtgtgctgga catgatggaa aaacgtgtgg acgatgacgg catcttccaa      1080
acctactttg atccgctgcg tctgcgtgtt gacccggtgg cggcgaccaa caccgtttac      1140
ctgttccatc tgggtggccc g tccgggtccg acccagcaaa ccgagcagtt tctgagcaaa      1200
ctgctggaaa gcgtagcta tgtgcgtggc accctgtact atcgtacccc ggaagcgttc      1260
ctgtaccaac tgacccgtct ggtggttagc ttcgagtatt ttcgtaagac cggttttctg      1320
gaaatgctga gaaacgtct gagcgagcgt gtgggcatcg aaagcgatgc gttcaccctg      1380
gcgatgcgta tcctggcgtg cgttaactgc ggtattccgg tggcggagct gaaccgtgat      1440
atggaccgtc tggcgcgtat gcagaacgtt gcgggtagct gggacgtgtg cccgtactat      1500
agctacaacg acccgaaaag ctggttcggc aacgaactgc tgaccaccgc gtttgcggcg      1560
gcggcgctgg agcacagcga accgaacttc aagtaa                              1596

<210> SEQ ID NO 16
<211> LENGTH: 531
<212> TYPE: PRT
<213> ORGANISM: Artificial Sequence
<220> FEATURE:
<223> OTHER INFORMATION: BtHAD mutant of QW motif

<400> SEQUENCE: 16

Met Ala Pro Pro Phe Gly Tyr Ile Gly Gly Asn Glu Ser Ser Val Thr
1               5                   10                  15

-continued

```
Thr Ser Pro Asp Val Leu Asp Tyr Ser Tyr Asp Gly Gly Pro Pro Thr
        20                  25                  30

Gly Gln Tyr Lys Ser Met Ile Leu Asp Ile Gly Gly Val Leu Leu Gln
        35                  40                  45

Pro Asn Leu Asp Arg Ser Tyr Gly Thr Ile Val Pro Pro Val Gln Phe
        50                  55                  60

Lys Arg Met Leu Arg Ser His Ile Trp Phe Asn Tyr Ser Met Gly Lys
65                  70                  75                  80

Val Ser Ala Glu Glu Val Phe Arg Gln Leu Ser Val Lys Ser Gly Tyr
                85                  90                  95

Pro Ala Glu Asp Ile Arg Ser Phe Ala Arg Lys Ala Arg Glu Ser Leu
                100                 105                 110

Val Pro Ile Thr Gln Ile Thr Asp Leu Leu Val Lys Leu Ser Lys Glu
                115                 120                 125

Ser Lys Ile Arg Leu Phe Cys Met Thr Asn Cys Pro Ala Glu Asp Phe
        130                 135                 140

Ala Tyr Leu Ser Gln Ala Tyr Pro Asn Leu Phe Gly Leu Phe Glu Arg
145                 150                 155                 160

Ile Phe Thr Ser Ala Ser Thr Gly Met Arg Lys Pro Asn Arg Asn Phe
                165                 170                 175

Phe Arg His Val Leu Gln Glu Thr Gly Ile Ser Ala Thr Glu Thr Ile
                180                 185                 190

Phe Val Asp Asp Leu Val Pro Asn Ile Met Ala Ala Glu Ala Leu Asp
        195                 200                 205

Phe Thr Ala Ile His Val Ser Pro Glu Ser Pro Ala Glu Thr Val Arg
        210                 215                 220

Leu Leu Met Phe His Leu Arg Lys Pro Glu Glu Arg Leu Ala Ala Ala
225                 230                 235                 240

Arg Asp Tyr Leu Leu Arg Asn Arg Gly Val Asp Lys Ala Leu Ser Leu
                245                 250                 255

Thr Ser Asp Gly Val Arg Val Gln Val Tyr Phe Asp His Phe Val Val
                260                 265                 270

Ala Glu Val Leu Asn Asp Glu Arg Phe Leu Pro Ile Thr Ala Ala Pro
        275                 280                 285

Lys Ser Gly Thr Met Asn Phe Phe Pro Lys Glu Glu Arg Asn Ala Thr
        290                 295                 300

Arg Asp Met Thr Thr Asn Ala Val Thr His Val Asp Leu Pro Asp Asp
305                 310                 315                 320

Leu Asp Ser Thr Ser Val Ala Leu Ser Val Leu Tyr Lys Phe Ser Lys
                325                 330                 335

Val Ala Met Glu Thr Val Gln Arg Val Leu Asp Met Met Glu Lys Arg
                340                 345                 350

Val Asp Asp Asp Gly Ile Phe Gln Thr Tyr Phe Asp Pro Leu Arg Leu
        355                 360                 365

Arg Val Asp Pro Val Ala Ala Thr Asn Thr Val Tyr Leu Phe His Leu
        370                 375                 380

Gly Gly Arg Pro Gly Pro Thr Gln Gln Thr Glu Gln Phe Leu Ser Lys
385                 390                 395                 400

Leu Leu Glu Lys Arg Ser Tyr Val Arg Gly Thr Leu Tyr Tyr Arg Thr
                405                 410                 415

Pro Glu Ala Phe Leu Tyr Gln Leu Thr Arg Leu Val Val Ser Phe Glu
        420                 425                 430
```

```
Tyr Phe Arg Lys Thr Gly Phe Leu Glu Met Leu Lys Lys Arg Leu Ser
        435             440             445
```

```
Glu Arg Val Gly Ile Glu Ser Asp Ala Phe Thr Leu Ala Met Arg Ile
        450             455             460
```

```
Leu Ala Cys Val Asn Cys Gly Ile Pro Val Ala Glu Leu Asn Arg Asp
465             470             475             480
```

```
Met Asp Arg Leu Ala Arg Met Gln Asn Val Ala Gly Ser Trp Asp Val
            485             490             495
```

```
Cys Pro Tyr Tyr Ser Tyr Asn Asp Pro Lys Ser Trp Phe Gly Asn Glu
            500             505             510
```

```
Leu Leu Thr Thr Ala Phe Ala Ala Ala Ala Leu Glu His Ser Glu Pro
            515             520             525
```

```
Asn Phe Lys
        530
```

```
<210> SEQ ID NO 17
<211> LENGTH: 1410
<212> TYPE: DNA
<213> ORGANISM: Selaginella moellendorffii
<220> FEATURE:
<221> NAME/KEY: misc_feature
<223> OTHER INFORMATION: SmHAD1_wt_nucleic acid sequence
```

```
<400> SEQUENCE: 17
```

```
atgataatca ttagctttgc ttgcttgctc aagtttggat gtggagacaa tggccccgg      60 ggagatctcc tccgcagggc tctccagcac tcctccttct tggcctattc ttgcggggag     120
ctcgatcgca ctgccgcaat ctcgacaatc tcgcgcaaat tcaagctcac ggacccagct     180
ctcgtggatt ccatgctgct cgaggccgct tccagctgcg aggtggacaa ggagctactg     240
tcactgctcc agtcaacgag gcagcagctc ctgggatgga ttgatattcc tccacaagag     300
tgggagcgag tttacagcct cttcccggtg tcgctctgga agaacttcgc tacaatctcc     360
cgcgatctag attccctcct tggagatatc aggtcccatg ctgtgattgt cgataaaagc     420
gtggagatgg ccgcgctaca tgccttcgag agcttgctcg ctctcccgta tgcctcgccc     480
aacaagaaag cttgccagga cttcttgaag cgtcggttcc tgctgcctcg agctgtgaag     540
ctggggatgg atcgagtcaa ggaggaggtg agatccaagc agctcaaatc actctacctg     600
cttgacaatg ccggcacga gctcgtctcc gagatcttct ttccctgcgt ggcggcctgg     660
tgccttccgg agatcattcc tctcggctgg atgaaatatc tccaggtact gatcaagcgc     720
ggccatccct tcggttactt cggtgccgac gtctcgcgct atccgccgga catcgacacc     780
atgtcgactt gtgtctccac acttttgat cttagtctcg tcacctccgc gcaagctatg     840
cactttctgg agatttgtct cgagaacgtc aacgatcaaa accagcttct cacgtacctg     900
gacgtggagc ggcctcgagt ggatccggtc gtcatagcca acgttgtcta tctcgcctat     960
gcgctctcca tggaagatca cccggttgtc cgccacaacg agaatctgat ccagagatat    1020
ctgttaagcg gcggattcgt tacgggact cgctattacc tcagccagga ggacttcttg    1080
ttcatgtatg gccgggtcct cgcgacgttt ggagagaaga gggagattcc caactttgat    1140
ctcgtgtatc aagcgatgga ggcggctctc gtcaaccgga tcgggaacga gaccgagtcg    1200
aagccactgg acgttgccaa aaggattctg ctcagcaggg ttttggaat ccggaacacg    1260 atagatgtag acttgctcct caagatgcag aacgaggatg gttcctggcc tttgcaagtg    1320
ctcagcaatc ttccatctgc taaaggtggt gtcttcaatt cggtggtgga cttgagcttt    1380
gcggtgagag cactgcaaag tcaagattga                                     1410
```

-continued

<210> SEQ ID NO 18
<211> LENGTH: 1410
<212> TYPE: DNA
<213> ORGANISM: Selaginella moellendorffii
<220> FEATURE:
<221> NAME/KEY: misc_feature
<223> OTHER INFORMATION: SmHAD1_E. coli optimized

<400> SEQUENCE: 18
atgatcatta tcagcttcgc gtgcctgctg aagtttggtt gcggtgacaa cggtccgcgt        60
ggcgatctgc tgcgtcgtgc gctgcagcac agcagcttcc tggcgtatag ctgcggcgag       120
ctggaccgta ccgcggcgat tagcaccatc agccgtaagt ttaaactgac cgacccggcg       180
ctggttgata gcatgctgct ggaagcggcg agcagctgcg aggtggacaa agaactgctg       240
agcctgctgc agagcacccg tcagcaactg ctgggttgga ttgatatccc gccgcaagag       300
tgggaacgtg tgtacagcct gttcccggtt agcctgtgga agaactttgc gaccattagc       360
cgtgacctgg atagcctgct gggcgacatt cgtagccacg cggtgatcgt tgataaaagc       420
gttgagatgg cggcgctgca cgcgttcgaa agcctgctgg cgctgccgta tgcgagcccg       480
aacaagaaag cgtgccagga cttcctgaag cgtcgttttc tgctgccgcg tgcggtgaag       540
ctgggtatgg atcgtgtgaa agaggaagtt cgtagcaagc aactgaaaag cctgtacctg       600
ctggacaacg ccgtcacga gctggttagc gaaattttct ttccgtgcgt tgcggcgtgg       660
tgcctgccgg agattatccc gctgggttgg atgaagtatc tgcaggttct gattaaacgt       720
ggccacccgt tcggttactt tggtgcggat gtgagccgtt atccgccgga catcgatacc       780
atgagcacct gcgtgagcac cctgttcgat ctgagcctgg ttaccagcgc gcaagcgatg       840
cactttctgg atatctgcct ggaaaacgtt aacgaccaga accaactgct gacctacctg       900
gacgtggaac gtccgcgtgt tgatccggtg gttattgcga cgtggtttta cctggcgtat       960
gcgctgagca tggaggatca cccggtggtt cgtcacaacg aaaacctgat ccagcgttac      1020
ctgctgagcg gtggcttcgt ttatggcacc cgttactatc tgagccaaga ggacttcctg      1080
tttatgtacg gtcgtgtgct ggcgaccttc ggcgagaaac gtgaaatccc gaactttgat      1140
ctggtgtatc aggcgatgga agcggcgctg gttaaccgta ttggtaacga gaccgaaagc      1200
aagccgctgg acgttgcgaa acgtatcctg ctgagccgtg ttttggcat tcgtaacacc      1260 atcgacgtgg atctgctgct gaagatgcag aacgaggatg gcagctggcc gctgcaagtg      1320
ctgagcaacc tgccgagcgc gaaaggtggc gttttcaaca gcgtggttga cctgagcttt      1380
gcggtgcgtg cgctgcagag ccaagattaa                                       1410

<210> SEQ ID NO 19
<211> LENGTH: 469
<212> TYPE: PRT
<213> ORGANISM: Selaginella moellendorffii
<220> FEATURE:
<221> NAME/KEY: MISC_FEATURE
<223> OTHER INFORMATION: SmHAD1_amino acid sequence

<400> SEQUENCE: 19

Met Ile Ile Ile Ser Phe Ala Cys Leu Leu Lys Phe Gly Cys Gly Asp
1               5                   10                  15

Asn Gly Pro Arg Gly Asp Leu Leu Arg Arg Ala Leu Gln His Ser Ser
            20                  25                  30

Phe Leu Ala Tyr Ser Cys Gly Glu Leu Asp Arg Thr Ala Ala Ile Ser
        35                  40                  45

```
Thr Ile Ser Arg Lys Phe Lys Leu Thr Asp Pro Ala Leu Val Asp Ser
    50              55              60

Met Leu Leu Glu Ala Ala Ser Ser Cys Glu Val Asp Lys Glu Leu Leu
65              70              75              80

Ser Leu Leu Gln Ser Thr Arg Gln Gln Leu Leu Gly Trp Ile Asp Ile
            85              90              95

Pro Pro Gln Glu Trp Glu Arg Val Tyr Ser Leu Phe Pro Val Ser Leu
        100             105             110

Trp Lys Asn Phe Ala Thr Ile Ser Arg Asp Leu Asp Ser Leu Leu Gly
        115             120             125

Asp Ile Arg Ser His Ala Val Ile Val Asp Lys Ser Val Glu Met Ala
    130             135             140

Ala Leu His Ala Phe Glu Ser Leu Leu Ala Leu Pro Tyr Ala Ser Pro
145             150             155             160

Asn Lys Lys Ala Cys Gln Asp Phe Leu Lys Arg Arg Phe Leu Leu Pro
            165             170             175

Arg Ala Val Lys Leu Gly Met Asp Arg Val Lys Glu Glu Val Arg Ser
            180             185             190

Lys Gln Leu Lys Ser Leu Tyr Leu Leu Asp Asn Gly Arg His Glu Leu
            195             200             205

Val Ser Glu Ile Phe Phe Pro Cys Val Ala Ala Trp Cys Leu Pro Glu
    210             215             220

Ile Ile Pro Leu Gly Trp Met Lys Tyr Leu Gln Val Leu Ile Lys Arg
225             230             235             240

Gly His Pro Phe Gly Tyr Phe Gly Ala Asp Val Ser Arg Tyr Pro Pro
            245             250             255

Asp Ile Asp Thr Met Ser Thr Cys Val Ser Thr Leu Phe Asp Leu Ser
            260             265             270

Leu Val Thr Ser Ala Gln Ala Met His Phe Leu Glu Ile Cys Leu Glu
            275             280             285

Asn Val Asn Asp Gln Asn Gln Leu Leu Thr Tyr Leu Asp Val Glu Arg
    290             295             300

Pro Arg Val Asp Pro Val Val Ile Ala Asn Val Val Tyr Leu Ala Tyr
305             310             315             320

Ala Leu Ser Met Glu Asp His Pro Val Val Arg His Asn Glu Asn Leu
            325             330             335

Ile Gln Arg Tyr Leu Leu Ser Gly Gly Phe Val Tyr Gly Thr Arg Tyr
            340             345             350

Tyr Leu Ser Gln Glu Asp Phe Leu Phe Met Tyr Gly Arg Val Leu Ala
            355             360             365

Thr Phe Gly Glu Lys Arg Glu Ile Pro Asn Phe Asp Leu Val Tyr Gln
    370             375             380

Ala Met Glu Ala Ala Leu Val Asn Arg Ile Gly Asn Glu Thr Glu Ser
385             390             395             400

Lys Pro Leu Asp Val Ala Lys Arg Ile Leu Leu Ser Arg Gly Phe Gly
            405             410             415

Ile Arg Asn Thr Ile Asp Val Asp Leu Leu Leu Lys Met Gln Asn Glu
            420             425             430

Asp Gly Ser Trp Pro Leu Gln Val Leu Ser Asn Leu Pro Ser Ala Lys
            435             440             445

Gly Gly Val Phe Asn Ser Val Val Asp Leu Ser Phe Ala Val Arg Ala
    450             455             460
```

Leu Gln Ser Gln Asp
465

<210> SEQ ID NO 20
<211> LENGTH: 1410
<212> TYPE: DNA
<213> ORGANISM: Artificial Sequence
<220> FEATURE:
<223> OTHER INFORMATION: SmHAD1 mutant of class II motif_E. coli
     optimized

<400> SEQUENCE: 20
atgatcatta tcagcttcgc gtgcctgctg aagtttggtt gcggtgacaa cggtccgcgt     60
ggcgatctgc tgcgtcgtgc gctgcagcac agcagcttcc tggcgtatag ctgcggcgag    120
ctggaccgta ccgcggcgat tagcaccatc agccgtaagt ttaaactgac cgacccggcg    180
ctggttgata gcatgctgct ggaagcggcg agcagctgcg aggtggacaa agaactgctg    240
agcctgctgc agagcacccg tcagcaactg ctgggttgga ttgatatccc gccgcaagag    300
tgggaacgtg tgtacagcct gttcccggtt agcctgtgga agaactttgc gaccattagc    360
cgtgacctgg atagcctgct gggcgacatt cgtagccacg cggtgatcgt tgataaaagc    420
gttgagatgg cggcgctgca cgcgttcgaa agcctgctgg cgctgccgta tgcgagcccg    480
aacaagaaag cgtgccagga cttcctgaag cgtcgttttc tgctgccgcg tgcggtgaag    540
ctgggtatgg atcgtgtgaa agaggaagtt cgtagcaagc aactgaaaag cctgtacctg    600
ctggacaacg ccgtcacga gctggttagc gaaatttTct ttccgtgcgt tgcggcgtgg    660
tgcctgccgg agattatccc gctgggttgg atgaagtatc tgcaggttct gattaaacgt    720
ggccacccgt tcggttactt tggtgcggat gtgagccgtt atccgccggc gatcgcgacc    780
atgagcacct gcgtgagcac cctgttcgat ctgagcctgg ttaccagcgc gcaagcgatg    840
cactttctgg agatctgcct ggaaaacgtt aacgaccaga accaactgct gacctacctg    900
gacgtggaac gtccgcgtgt tgatccggtg gttattgcga cgtggttta cctggcgtat    960 gcgctgagca tggaggatca cccggtggtt cgtcacaacg aaaacctgat ccagcgttac   1020
ctgctgagcg gtggcttcgt ttatggcacc cgttactatc tgagccaaga ggacttcctg   1080
tttatgtacg gtcgtgtgct ggcgaccttc ggcgagaaac gtgaaatccc gaactttgat   1140
ctggtgtatc aggcgatgga agcggcgctg gttaaccgta ttggtaacga gaccgaaagc   1200
aagccgctgg acgttgcgaa acgtatcctg ctgagccgtg gttttggcat tcgtaacacc   1260
atcgacgtgg atctgctgct gaagatgcag aacgaggatg gcagctggcc gctgcaagtg   1320
ctgagcaacc tgccgagcgc gaaaggtggc gtttTcaaca gcgtggttga cctgagcTTt   1380
gcggtgcgtg cgctgcagag ccaagattaa   1410

<210> SEQ ID NO 21
<211> LENGTH: 469
<212> TYPE: PRT
<213> ORGANISM: Artificial Sequence
<220> FEATURE:
<223> OTHER INFORMATION: SmHAD1 mutant of class II motif

<400> SEQUENCE: 21

Met Ile Ile Ile Ser Phe Ala Cys Leu Leu Lys Phe Gly Cys Gly Asp
1            5                 10                 15

Asn Gly Pro Arg Gly Asp Leu Leu Arg Arg Ala Leu Gln His Ser Ser
           20                 25                 30

Phe Leu Ala Tyr Ser Cys Gly Glu Leu Asp Arg Thr Ala Ala Ile Ser

-continued

```
                35                   40                   45

Thr Ile Ser Arg Lys Phe Lys Leu Thr Asp Pro Ala Leu Val Asp Ser
    50                   55                   60

Met Leu Leu Glu Ala Ala Ser Ser Cys Glu Val Asp Lys Glu Leu Leu
65                   70                   75                   80

Ser Leu Leu Gln Ser Thr Arg Gln Gln Leu Leu Gly Trp Ile Asp Ile
                85                   90                   95

Pro Pro Gln Glu Trp Glu Arg Val Tyr Ser Leu Phe Pro Val Ser Leu
                100                  105                  110

Trp Lys Asn Phe Ala Thr Ile Ser Arg Asp Leu Asp Ser Leu Leu Gly
                115                  120                  125

Asp Ile Arg Ser His Ala Val Ile Val Asp Lys Ser Val Glu Met Ala
    130                  135                  140

Ala Leu His Ala Phe Glu Ser Leu Leu Ala Leu Pro Tyr Ala Ser Pro
145                  150                  155                  160

Asn Lys Lys Ala Cys Gln Asp Phe Leu Lys Arg Arg Phe Leu Leu Pro
                165                  170                  175

Arg Ala Val Lys Leu Gly Met Asp Arg Val Lys Glu Glu Val Arg Ser
                180                  185                  190

Lys Gln Leu Lys Ser Leu Tyr Leu Leu Asp Asn Gly Arg His Glu Leu
                195                  200                  205

Val Ser Glu Ile Phe Phe Pro Cys Val Ala Ala Trp Cys Leu Pro Glu
    210                  215                  220

Ile Ile Pro Leu Gly Trp Met Lys Tyr Leu Gln Val Leu Ile Lys Arg
225                  230                  235                  240

Gly His Pro Phe Gly Tyr Phe Gly Ala Asp Val Ser Arg Tyr Pro Pro
                245                  250                  255

Ala Ile Ala Thr Met Ser Thr Cys Val Ser Thr Leu Phe Asp Leu Ser
                260                  265                  270

Leu Val Thr Ser Ala Gln Ala Met His Phe Leu Glu Ile Cys Leu Glu
                275                  280                  285

Asn Val Asn Asp Gln Asn Gln Leu Leu Thr Tyr Leu Asp Val Glu Arg
    290                  295                  300

Pro Arg Val Asp Pro Val Val Ile Ala Asn Val Val Tyr Leu Ala Tyr
305                  310                  315                  320

Ala Leu Ser Met Glu Asp His Pro Val Val Arg His Asn Glu Asn Leu
                325                  330                  335

Ile Gln Arg Tyr Leu Leu Ser Gly Gly Phe Val Tyr Gly Thr Arg Tyr
                340                  345                  350

Tyr Leu Ser Gln Glu Asp Phe Leu Phe Met Tyr Gly Arg Val Leu Ala
                355                  360                  365

Thr Phe Gly Glu Lys Arg Glu Ile Pro Asn Phe Asp Leu Val Tyr Gln
    370                  375                  380

Ala Met Glu Ala Ala Leu Val Asn Arg Ile Gly Asn Glu Thr Glu Ser
385                  390                  395                  400

Lys Pro Leu Asp Val Ala Lys Arg Ile Leu Leu Ser Arg Gly Phe Gly
                405                  410                  415

Ile Arg Asn Thr Ile Asp Val Asp Leu Leu Leu Lys Met Gln Asn Glu
                420                  425                  430

Asp Gly Ser Trp Pro Leu Gln Val Leu Ser Asn Leu Pro Ser Ala Lys
                435                  440                  445

Gly Gly Val Phe Asn Ser Val Val Asp Leu Ser Phe Ala Val Arg Ala
    450                  455                  460
```

-continued

Leu Gln Ser Gln Asp
465

<210> SEQ ID NO 22
<211> LENGTH: 1410
<212> TYPE: DNA
<213> ORGANISM: Artificial Sequence
<220> FEATURE:
<223> OTHER INFORMATION: SmHAD1 mutant of QW motif_E. coli optimized

<400> SEQUENCE: 22
atgatcatta tcagcttcgc gtgcctgctg aagtttggtt gcggtgacaa cggtccgcgt      60
ggcgatctgc tgcgtcgtgc gctgcagcac agcagcttcc tggcgtatag ctgcggcgag     120
ctggaccgta ccgcggcgat tagcaccatc agccgtaagt ttaaactgac cgacccggcg     180
ctggttgata gcatgctgct ggaagcggcg agcagctgcg aggtggacaa agaactgctg     240
agcctgctgc agagcacccg tcagcaactg ctgggttgga ttgatatccc gccgcaagag     300
tgggaacgtg tgtacagcct gttcccggtt agcctgtgga agaactttgc gaccattagc     360
cgtgacctgg atagcctgct gggcgacatt cgtagccacg cggtgatcgt tgataaaagc     420
gttgagatgg cggcgctgca cgcgttcgaa agcctgctgg cgctgccgta tgcgagcccg     480
aacaagaaag cgtgccagga cttcctgaag cgtcgttttc tgctgccgcg tgcggtgaag     540
ctgggtatgg atcgtgtgaa agaggaagtt cgtagcaagc aactgaaaag cctgtacctg     600
ctggacaacg ccgtcacga gctggttagc gaaattttct ttccgtgcgt tgcggcgtgg     660
tgcctgccgg agattatccc gctgggttgg atgaagtatc tgcaggttct gattaaacgt     720
ggccacccgt tcggttactt tggtgcggat gtgagccgtt atccgccgga catcgatacc     780
atgagcacct gcgtgagcac cctgttcgat ctgagcctgg ttaccagcgc gcaagcgatg     840
cactttctgg agatctgcct ggaaaacgtt aacgaccaga accaactgct gacctacctg     900
gacgtggaac gtccgcgtgt tgatccggtg gttattgcga acgtggttta cctggcgtat     960
gcgctgagca tggaggatca cccggtggtt cgtcacaacg aaaacctgat ccagcgttac    1020
ctgctgagcg gtggcttcgt ttatggcacc cgttactatc tgagccaaga ggacttcctg    1080
tttatgtacg gtcgtgtgct ggcgaccttc ggcgagaaac gtgaaatccc gaactttgat    1140
ctggtgtatc aggcgatgga agcggcgctg gttaaccgta ttggtaacga gaccgaaagc    1200
aagccgctgg acgttgcgaa acgtatcctg ctgagccgtg gttttggcat tcgtaacacc    1260
atcgacgtgg atctgctgct gaagatgcag aacgcggcgg gcagctggcc gctgcaagtg    1320
ctgagcaacc tgccgagcgc gaaaggtggc gtttttcaaca gcgtggttga cctgagcttt    1380
gcggtgcgtg cgctgcagag ccaagattaa                                     1410

<210> SEQ ID NO 23
<211> LENGTH: 469
<212> TYPE: PRT
<213> ORGANISM: Artificial Sequence
<220> FEATURE:
<223> OTHER INFORMATION: SmHAD1 mutant of QW motif

<400> SEQUENCE: 23

Met Ile Ile Ile Ser Phe Ala Cys Leu Leu Lys Phe Gly Cys Gly Asp
1               5                   10                  15

Asn Gly Pro Arg Gly Asp Leu Leu Arg Arg Ala Leu Gln His Ser Ser
            20                  25                  30

Phe Leu Ala Tyr Ser Cys Gly Glu Leu Asp Arg Thr Ala Ala Ile Ser

-continued

```
                35                      40                      45
Thr Ile Ser Arg Lys Phe Lys Leu Thr Asp Pro Ala Leu Val Asp Ser
    50                      55                      60
Met Leu Leu Glu Ala Ala Ser Ser Cys Glu Val Asp Lys Glu Leu Leu
65                      70                      75                      80
Ser Leu Leu Gln Ser Thr Arg Gln Gln Leu Gly Trp Ile Asp Ile
                85                      90                      95
Pro Pro Gln Glu Trp Glu Arg Val Tyr Ser Leu Phe Pro Val Ser Leu
                100                     105                     110
Trp Lys Asn Phe Ala Thr Ile Ser Arg Asp Leu Asp Ser Leu Leu Gly
                115                     120                     125
Asp Ile Arg Ser His Ala Val Ile Val Asp Lys Ser Val Glu Met Ala
    130                     135                     140
Ala Leu His Ala Phe Glu Ser Leu Leu Ala Leu Pro Tyr Ala Ser Pro
145                     150                     155                     160
Asn Lys Lys Ala Cys Gln Asp Phe Leu Lys Arg Arg Phe Leu Leu Pro
                165                     170                     175
Arg Ala Val Lys Leu Gly Met Asp Arg Val Lys Glu Glu Val Arg Ser
                180                     185                     190
Lys Gln Leu Lys Ser Leu Tyr Leu Leu Asp Asn Gly Arg His Glu Leu
                195                     200                     205
Val Ser Glu Ile Phe Phe Pro Cys Val Ala Ala Trp Cys Leu Pro Glu
    210                     215                     220
Ile Ile Pro Leu Gly Trp Met Lys Tyr Leu Gln Val Leu Ile Lys Arg
225                     230                     235                     240
Gly His Pro Phe Gly Tyr Phe Gly Ala Asp Val Ser Arg Tyr Pro Pro
                245                     250                     255
Asp Ile Asp Thr Met Ser Thr Cys Val Ser Thr Leu Phe Asp Leu Ser
                260                     265                     270
Leu Val Thr Ser Ala Gln Ala Met His Phe Leu Glu Ile Cys Leu Glu
                275                     280                     285
Asn Val Asn Asp Gln Asn Gln Leu Leu Thr Tyr Leu Asp Val Glu Arg
    290                     295                     300
Pro Arg Val Asp Pro Val Val Ile Ala Asn Val Val Tyr Leu Ala Tyr
305                     310                     315                     320
Ala Leu Ser Met Glu Asp His Pro Val Val Arg His Asn Glu Asn Leu
                325                     330                     335
Ile Gln Arg Tyr Leu Leu Ser Gly Gly Phe Val Tyr Gly Thr Arg Tyr
                340                     345                     350
Tyr Leu Ser Gln Glu Asp Phe Leu Phe Met Tyr Gly Arg Val Leu Ala
                355                     360                     365
Thr Phe Gly Glu Lys Arg Glu Ile Pro Asn Phe Asp Leu Val Tyr Gln
    370                     375                     380
Ala Met Glu Ala Ala Leu Val Asn Arg Ile Gly Asn Glu Thr Glu Ser
385                     390                     395                     400
Lys Pro Leu Asp Val Ala Lys Arg Ile Leu Leu Ser Arg Gly Phe Gly
                405                     410                     415
Ile Arg Asn Thr Ile Asp Val Asp Leu Leu Leu Lys Met Gln Asn Ala
                420                     425                     430
Ala Gly Ser Trp Pro Leu Gln Val Leu Ser Asn Leu Pro Ser Ala Lys
                435                     440                     445
Gly Gly Val Phe Asn Ser Val Val Asp Leu Ser Phe Ala Val Arg Ala
    450                     455                     460
```

Leu Gln Ser Gln Asp
465

<210> SEQ ID NO 24
<211> LENGTH: 1410
<212> TYPE: DNA
<213> ORGANISM: Selaginella moellendorffii
<220> FEATURE:
<221> NAME/KEY: misc_feature
<223> OTHER INFORMATION: SmHAD2_wt_nucleic acid sequence

<400> SEQUENCE: 24
atgataatca ttagttttgc ttgcttgctt aagttcggat gtggagacag tggcccccgg        60
ggagatctcc tccgcagggc tctccagcac tcctccttct tggcctattc ttgcggggag       120
ctcgatcgcg ctgccgcaat ctcgacaatc tcgcgcaaat tcaagctcaa ggagccagct       180
ctcctggatt ccatgctgct cgaggccgct tccagctgcg aggtggacga ggagctactg       240
tcactgctcc agtcaacgag gcagcagctc ctgggatgga ttgatattcc tccacaagag       300
tgggagcgag tttacaacct cttcccgtgg tcgctctgga agaacttcgc tacaatctcc       360
cgcgatctag attccctcct tggagatatc aggttccatg ctgtgattgt cgataaaagc       420
gtggagatgg ccgcgctaca tgccttcgag agcttgctcg ctctcccgta tgcctcgccc       480
aacaagaaag cttgccagga cttcttgaag cgtcggttcc tgctgcctcg agctgtgaag       540
ctggggatgg atcgagtcaa ggaggaggtg agatccaagc agctcaaatc actctacctg       600
cttgacaacg gccggcagga gctcgtctcc gagatcttct ttccctgcgt ggcggcctgg       660
tgccttcctg agatcattcc tctcggctgg atggaatctc tccaggtact gatcgagcgc       720
ggccatccct tcggttactt cggtgccgac gtctcgcgct atccgccgga catcgacacc       780
atgtcgactt gtgtctccac acttttttgat cttagcctcg tcacctccgc gcaagctatg       840
cactttctgg agatttgtct cgagaacgtc aacgatcaaa accagcttct cacgtacctg       900
gacttggagc ggcctcgagt ggatccggtc gtcatagcca acgttgtcta tttcgcctat       960
gcgctctcca tggaagatca cccggttgtc cgccacaacg agaatctgat ccagagatat      1020
ctgttaagcg gcggattcgt atacgggact cgctattacc tcagccagga ggacttcttg      1080
ttcatgtatg gccgggtcct cgcgacgttt ggagagaaga gggagattcc aactttgat       1140 ctcgtgtatc aagcgatgga ggcggctctc gtcaaccgga tcgggaacga gaccgagtcg      1200
aagccactgg acgttgccaa aaggattctg ctcagcaggt actttggaat ccggaacacg      1260
atagatgtgg acttgctcct caagatgcag aacgaggatg gttcctggcc cttgcaagtg      1320
ctcagcaatc ttccatctgc taaaggtggt gtcttcaatt cggtggtgga cttgagcttt      1380
gcggtgagag cactgcaaag tcaagattga                                        1410

<210> SEQ ID NO 25
<211> LENGTH: 1410
<212> TYPE: DNA
<213> ORGANISM: Selaginella moellendorffii
<220> FEATURE:
<221> NAME/KEY: misc_feature
<223> OTHER INFORMATION: SmHAD2_E. coli optimized

<400> SEQUENCE: 25
atgatcatta tcagcttcgc gtgcctgctg aaatttggtt gcggtgatag cggtccgcgt        60
ggcgatctgc tgcgtcgtgc gctgcagcac agcagcttcc tggcgtatag ctgcggcgag       120
ctggaccgtg cggcggcgat tagcaccatc agccgtaagt ttaaactgaa ggaaccggcg       180

```
ctgctggaca gcatgctgct ggaggcggcg agcagctgcg aagttgatga ggaactgctg      240
agcctgctgc agagcacccg tcagcaactg ctgggttgga ttgatatccc gccgcaagag      300
tgggaacgtg tgtataacct gttcccgtgg agcctgtgga aaactttgc gaccattagc       360 cgtgacctgg atagcctgct gggcgacatt cgtttccacg cggtgatcgt tgataagagc      420
gttgagatgg cggcgctgca cgcgtttgaa agcctgctgg cgctgccgta cgcgagcccg      480
aacaagaaag cgtgccaaga cttcctgaag cgtcgttttc tgctgccgcg tgcggtgaaa      540
ctgggtatgg atcgtgtgaa ggaagaggtg cgcagcaaac agctgaagag cctgtatctg      600
ctggacaacg ccgtcaaga gctggttagc gaaattttct ttccgtgcgt tgcggcgtgg       660
tgcctgccgg agattatccc gctgggttgg atggagagcc tgcaggttct gattgaacgt      720
ggccacccgt tcggttactt tggtgcggat gtgagccgtt atccgccgga catcgatacc      780
atgagcacct gcgtgagcac cctgttcgat ctgagcctgg ttaccagcgc gcaagcgatg      840
cactttctgg agatctgcct ggaaaacgtt aacgaccaga accaactgct gacctacctg      900
gacctggaac gtccgcgtgt ggatccggtg gttattgcga acgtggttta cttcgcgtat      960
gcgctgagca tggaggatca cccggtggtt cgtcacaacg aaaacctgat ccagcgttac     1020
ctgctgagcg gtggctttgt ttatggcacc cgttactatc tgagccaaga ggacttcctg     1080
tttatgtacg gtcgtgtgct ggcgaccttc ggcgagaaac gtgaaatccc gaactttgat     1140
ctggtgtatc aggcgatgga agcggcgctg gttaaccgta ttggcaacga gaccgaaagc     1200
aaaccgctgg acgttgcgaa gcgtatcctg ctgagccgtt acttcggtat tcgtaacacc     1260
atcgacgtgg atctgctgct gaaaatgcag aacgaggatg gcagctggcc gctgcaagtg     1320
ctgagcaacc tgccgagcgc gaagggtggc gttttcaaca gcgtggttga cctgagcttt     1380
gcggtgcgtg cgctgcagag ccaagattaa                                      1410
```

```
<210> SEQ ID NO 26
<211> LENGTH: 469
<212> TYPE: PRT
<213> ORGANISM: Selaginella moellendorffii
<220> FEATURE:
<221> NAME/KEY: MISC_FEATURE
<223> OTHER INFORMATION: SmHAD2_amino acid sequence

<400> SEQUENCE: 26

Met Ile Ile Ile Ser Phe Ala Cys Leu Leu Lys Phe Gly Cys Gly Asp
1               5                   10                  15

Ser Gly Pro Arg Gly Asp Leu Leu Arg Arg Ala Leu Gln His Ser Ser
            20                  25                  30

Phe Leu Ala Tyr Ser Cys Gly Glu Leu Asp Arg Ala Ala Ala Ile Ser
        35                  40                  45

Thr Ile Ser Arg Lys Phe Lys Leu Lys Glu Pro Ala Leu Leu Asp Ser
    50                  55                  60

Met Leu Leu Glu Ala Ala Ser Ser Cys Glu Val Asp Glu Glu Leu Leu
65                  70                  75                  80

Ser Leu Leu Gln Ser Thr Arg Gln Gln Leu Leu Gly Trp Ile Asp Ile
                85                  90                  95

Pro Pro Gln Glu Trp Glu Arg Val Tyr Asn Leu Phe Pro Trp Ser Leu
            100                 105                 110

Trp Lys Asn Phe Ala Thr Ile Ser Arg Asp Leu Asp Ser Leu Leu Gly
        115                 120                 125

Asp Ile Arg Phe His Ala Val Ile Val Asp Lys Ser Val Glu Met Ala
```

-continued

```
        130              135              140

Ala Leu His Ala Phe Glu Ser Leu Leu Ala Leu Pro Tyr Ala Ser Pro
145                 150              155              160

Asn Lys Lys Ala Cys Gln Asp Phe Leu Lys Arg Arg Phe Leu Leu Pro
                165              170              175

Arg Ala Val Lys Leu Gly Met Asp Arg Val Lys Glu Glu Val Arg Ser
                180              185              190

Lys Gln Leu Lys Ser Leu Tyr Leu Leu Asp Asn Gly Arg Gln Glu Leu
            195              200              205

Val Ser Glu Ile Phe Phe Pro Cys Val Ala Ala Trp Cys Leu Pro Glu
    210              215              220

Ile Ile Pro Leu Gly Trp Met Glu Ser Leu Gln Val Leu Ile Glu Arg
225              230              235              240

Gly His Pro Phe Gly Tyr Phe Gly Ala Asp Val Ser Arg Tyr Pro Pro
                245              250              255

Asp Ile Asp Thr Met Ser Thr Cys Val Ser Thr Leu Phe Asp Leu Ser
                260              265              270

Leu Val Thr Ser Ala Gln Ala Met His Phe Leu Glu Ile Cys Leu Glu
            275              280              285

Asn Val Asn Asp Gln Asn Gln Leu Leu Thr Tyr Leu Asp Leu Glu Arg
    290              295              300

Pro Arg Val Asp Pro Val Val Ile Ala Asn Val Val Tyr Phe Ala Tyr
305              310              315              320

Ala Leu Ser Met Glu Asp His Pro Val Val Arg His Asn Glu Asn Leu
                325              330              335

Ile Gln Arg Tyr Leu Leu Ser Gly Gly Phe Val Tyr Gly Thr Arg Tyr
                340              345              350

Tyr Leu Ser Gln Glu Asp Phe Leu Phe Met Tyr Gly Arg Val Leu Ala
            355              360              365

Thr Phe Gly Glu Lys Arg Glu Ile Pro Asn Phe Asp Leu Val Tyr Gln
    370              375              380

Ala Met Glu Ala Ala Leu Val Asn Arg Ile Gly Asn Glu Thr Glu Ser
385              390              395              400

Lys Pro Leu Asp Val Ala Lys Arg Ile Leu Leu Ser Arg Tyr Phe Gly
                405              410              415

Ile Arg Asn Thr Ile Asp Val Asp Leu Leu Leu Lys Met Gln Asn Glu
                420              425              430

Asp Gly Ser Trp Pro Leu Gln Val Leu Ser Asn Leu Pro Ser Ala Lys
            435              440              445

Gly Gly Val Phe Asn Ser Val Val Asp Leu Ser Phe Ala Val Arg Ala
    450              455              460

Leu Gln Ser Gln Asp
465
```

```
<210> SEQ ID NO 27
<211> LENGTH: 1410
<212> TYPE: DNA
<213> ORGANISM: Artificial Sequence
<220> FEATURE:
<223> OTHER INFORMATION: SmHAD2 mutant of class II motif_E. coli
      optimized

<400> SEQUENCE: 27
atgatcatta tcagcttcgc gtgcctgctg aaatttggtt gcggtgatag cggtccgcgt      60
ggcgatctgc tgcgtcgtgc gctgcagcac agcagcttcc tggcgtatag ctgcggcgag     120
```

```
ctggaccgtg cggcggcgat tagcaccatc agccgtaagt ttaaactgaa ggaaccggcg    180
ctgctggaca gcatgctgct ggaggcggcg agcagctgcg aagttgatga ggaactgctg    240
agcctgctgc agagcacccg tcagcaactg ctgggttgga ttgatatccc gccgcaagag    300
tgggaacgtg tgtataacct gttcccgtgg agcctgtgga aaaactttgc gaccattagc    360
cgtgacctgg atagcctgct gggcgacatt cgtttccacg cggtgatcgt tgataagagc    420
gttgagatgg cggcgctgca cgcgtttgaa agcctgctgg cgctgccgta cgcgagcccg    480
aacaagaaag cgtgccaaga cttcctgaag cgtcgttttc tgctgccgcg tgcggtgaaa    540
ctgggtatga tcgtgtgaa ggaagaggtg cgcagcaaac agctgaagag cctgtatctg    600
ctggacaacg ccgtcaaga gctggttagc gaaatttct ttccgtgcgt tgcggcgtgg    660
tgcctgccgg agattatccc gctgggttgg atggagagcc tgcaggttct gattgaacgt    720
ggccacccgt tcggttactt tggtgcggat gtgagccgtt atccgccggc gatcgcgacc    780
atgagcacct gcgtgagcac cctgttcgat ctgagcctgg ttaccagcgc gcaagcgatg    840
cactttctgg agatctgcct ggaaaacgtt aacgaccaga accaactgct gacctacctg    900
gacctggaac gtccgcgtgt ggatccggtg gttattgcga acgtggttta cttcgcgtat    960
gcgctgagca tggaggatca cccggtggtt cgtcacaacg aaaacctgat ccagcgttac    1020
ctgctgagcg gtggctttgt ttatggcacc cgttactatc tgagccaaga ggacttcctg    1080
tttatgtacg gtcgtgtgct ggcgaccttc ggcgagaaac gtgaaatccc gaactttgat    1140
ctggtgtatc aggcgatgga agcggcgctg gttaaccgta ttggcaacga gaccgaaagc    1200
aaaccgctgg acgttgcgaa gcgtatcctg ctgagccgtt acttcggtat tcgtaacacc    1260
atcgacgtgg atctgctgct gaaaatgcag aacgaggatg gcagctggcc gctgcaagtg    1320
ctgagcaacc tgccgagcgc gaagggtggc gtttttcaaca gcgtggttga cctgagcttt    1380
gcggtgcgtg cgctgcagag ccaagattaa                                      1410
```

<210> SEQ ID NO 28
<211> LENGTH: 469
<212> TYPE: PRT
<213> ORGANISM: Artificial Sequence
<220> FEATURE:
<223> OTHER INFORMATION: SmHAD2 mutant of class II motif

<400> SEQUENCE: 28

```
Met Ile Ile Ile Ser Phe Ala Cys Leu Leu Lys Phe Gly Cys Gly Asp
1               5                   10                  15

Ser Gly Pro Arg Gly Asp Leu Leu Arg Arg Ala Leu Gln His Ser Ser
            20                  25                  30

Phe Leu Ala Tyr Ser Cys Gly Glu Leu Asp Arg Ala Ala Ala Ile Ser
        35                  40                  45

Thr Ile Ser Arg Lys Phe Lys Leu Lys Glu Pro Ala Leu Leu Asp Ser
    50                  55                  60

Met Leu Leu Glu Ala Ala Ser Ser Cys Glu Val Asp Glu Glu Leu Leu
65                  70                  75                  80

Ser Leu Leu Gln Ser Thr Arg Gln Gln Leu Leu Gly Trp Ile Asp Ile
                85                  90                  95

Pro Pro Gln Glu Trp Glu Arg Val Tyr Asn Leu Phe Pro Trp Ser Leu
            100                 105                 110

Trp Lys Asn Phe Ala Thr Ile Ser Arg Asp Leu Asp Ser Leu Leu Gly
        115                 120                 125
```

-continued

```
Asp Ile Arg Phe His Ala Val Ile Val Asp Lys Ser Val Glu Met Ala
    130                 135                 140

Ala Leu His Ala Phe Glu Ser Leu Leu Ala Leu Pro Tyr Ala Ser Pro
145                 150                 155                 160

Asn Lys Lys Ala Cys Gln Asp Phe Leu Lys Arg Arg Phe Leu Leu Pro
                165                 170                 175

Arg Ala Val Lys Leu Gly Met Asp Arg Val Lys Glu Glu Val Arg Ser
                180                 185                 190

Lys Gln Leu Lys Ser Leu Tyr Leu Leu Asp Asn Gly Arg Gln Glu Leu
                195                 200                 205

Val Ser Glu Ile Phe Phe Pro Cys Val Ala Ala Trp Cys Leu Pro Glu
    210                 215                 220

Ile Ile Pro Leu Gly Trp Met Glu Ser Leu Gln Val Leu Ile Glu Arg
225                 230                 235                 240

Gly His Pro Phe Gly Tyr Phe Gly Ala Asp Val Ser Arg Tyr Pro Pro
                245                 250                 255

Ala Ile Ala Thr Met Ser Thr Cys Val Ser Thr Leu Phe Asp Leu Ser
                260                 265                 270

Leu Val Thr Ser Ala Gln Ala Met His Phe Leu Glu Ile Cys Leu Glu
                275                 280                 285

Asn Val Asn Asp Gln Asn Gln Leu Leu Thr Tyr Leu Asp Leu Glu Arg
    290                 295                 300

Pro Arg Val Asp Pro Val Val Ile Ala Asn Val Val Tyr Phe Ala Tyr
305                 310                 315                 320

Ala Leu Ser Met Glu Asp His Pro Val Val Arg His Asn Glu Asn Leu
                325                 330                 335

Ile Gln Arg Tyr Leu Leu Ser Gly Gly Phe Val Tyr Gly Thr Arg Tyr
                340                 345                 350

Tyr Leu Ser Gln Glu Asp Phe Leu Phe Met Tyr Gly Arg Val Leu Ala
                355                 360                 365

Thr Phe Gly Glu Lys Arg Glu Ile Pro Asn Phe Asp Leu Val Tyr Gln
    370                 375                 380

Ala Met Glu Ala Ala Leu Val Asn Arg Ile Gly Asn Glu Thr Glu Ser
385                 390                 395                 400

Lys Pro Leu Asp Val Ala Lys Arg Ile Leu Leu Ser Arg Tyr Phe Gly
                405                 410                 415

Ile Arg Asn Thr Ile Asp Val Asp Leu Leu Leu Lys Met Gln Asn Glu
                420                 425                 430

Asp Gly Ser Trp Pro Leu Gln Val Leu Ser Asn Leu Pro Ser Ala Lys
                435                 440                 445

Gly Gly Val Phe Asn Ser Val Val Asp Leu Ser Phe Ala Val Arg Ala
    450                 455                 460

Leu Gln Ser Gln Asp
465
```

```
<210> SEQ ID NO 29
<211> LENGTH: 1410
<212> TYPE: DNA
<213> ORGANISM: Artificial Sequence
<220> FEATURE:
<223> OTHER INFORMATION: SmHAD2 mutant of QW motif_E. coli optimized

<400> SEQUENCE: 29
atgatcatta tcagcttcgc gtgcctgctg aaatttggtt gcggtgatag cggtccgcgt      60
ggcgatctgc tgcgtcgtgc gctgcagcac agcagcttcc tggcgtatag ctgcggcgag     120
```

-continued

```
ctggaccgtg cggcggcgat tagcaccatc agccgtaagt ttaaactgaa ggaaccggcg      180
ctgctggaca gcatgctgct ggaggcggcg agcagctgcg aagttgatga ggaactgctg      240
agcctgctgc agagcacccg tcagcaactg ctgggttgga ttgatatccc gccgcaagag      300
tgggaacgtg tgtataacct gttcccgtgg agcctgtgga aaaactttgc gaccattagc      360
cgtgacctgg atagcctgct gggcgacatt cgtttccacg cggtgatcgt tgataagagc      420
gttgagatgg cggcgctgca cgcgtttgaa agcctgctgg cgctgccgta cgcgagcccg      480
aacaagaaag cgtgccaaga cttcctgaag cgtcgttttc tgctgccgcg tgcggtgaaa      540
ctgggtatgg atcgtgtgaa ggaagaggtg cgcagcaaac agctgaagag cctgtatctg      600
ctggacaacg ccgtcaaga gctggttagc gaaattttct ttccgtgcgt tgcggcgtgg      660
tgcctgccgg agattatccc gctgggttgg atggagagcc tgcaggttct gattgaacgt      720
ggccacccgt tcggttactt tggtgcggat gtgagccgtt atccgccgga catcgatacc      780
atgagcacct gcgtgagcac cctgttcgat ctgagcctgg ttaccagcgc gcaagcgatg      840
cactttctgg agatctgcct ggaaaacgtt aacgaccaga accaactgct gacctacctg      900
gacctggaac gtccgcgtgt ggatccggtg gttattgcga acgtggttta cttcgcgtat      960
gcgctgagca tggaggatca cccggtggtt cgtcacaacg aaaacctgat ccagcgttac     1020
ctgctgagcg gtggctttgt ttatggcacc cgttactatc tgagccaaga ggacttcctg     1080
tttatgtacg gtcgtgtgct ggcgaccttc ggcgagaaac gtgaaatccc gaactttgat     1140
ctggtgtatc aggcgatgga agcggcgctg gttaaccgta ttggcaacga gaccgaaagc     1200
aaaccgctgg acgttgcgaa gcgtatcctg ctgagccgtt acttcggtat tcgtaacacc     1260
atcgacgtgg atctgctgct gaaaatgcag aacgcggcgg gcagctggcc gctgcaagtg     1320
ctgagcaacc tgccgagcgc gaagggtggc gttttcaaca gcgtggttga cctgagcttt     1380
gcggtgcgtg cgctgcagag ccaagattaa                                      1410
```

<210> SEQ ID NO 30
<211> LENGTH: 469
<212> TYPE: PRT
<213> ORGANISM: Artificial Sequence
<220> FEATURE:
<223> OTHER INFORMATION: SmHAD2 mutant of QW motif

<400> SEQUENCE: 30

```
Met Ile Ile Ile Ser Phe Ala Cys Leu Leu Lys Phe Gly Cys Gly Asp
1               5                   10                  15

Ser Gly Pro Arg Gly Asp Leu Leu Arg Arg Ala Leu Gln His Ser Ser
            20                  25                  30

Phe Leu Ala Tyr Ser Cys Gly Glu Leu Asp Arg Ala Ala Ala Ile Ser
        35                  40                  45

Thr Ile Ser Arg Lys Phe Lys Leu Lys Glu Pro Ala Leu Leu Asp Ser
    50                  55                  60

Met Leu Leu Glu Ala Ala Ser Ser Cys Glu Val Asp Glu Glu Leu Leu
65                  70                  75                  80

Ser Leu Leu Gln Ser Thr Arg Gln Gln Leu Leu Gly Trp Ile Asp Ile
                85                  90                  95

Pro Pro Gln Glu Trp Glu Arg Val Tyr Asn Leu Phe Pro Trp Ser Leu
            100                 105                 110

Trp Lys Asn Phe Ala Thr Ile Ser Arg Asp Leu Asp Ser Leu Leu Gly
        115                 120                 125
```

```
Asp Ile Arg Phe His Ala Val Ile Val Asp Lys Ser Val Glu Met Ala
    130             135             140

Ala Leu His Ala Phe Glu Ser Leu Leu Ala Leu Pro Tyr Ala Ser Pro
145             150             155             160

Asn Lys Lys Ala Cys Gln Asp Phe Leu Lys Arg Arg Phe Leu Leu Pro
            165             170             175

Arg Ala Val Lys Leu Gly Met Asp Arg Val Lys Glu Glu Val Arg Ser
            180             185             190

Lys Gln Leu Lys Ser Leu Tyr Leu Leu Asp Asn Gly Arg Gln Glu Leu
        195             200             205

Val Ser Glu Ile Phe Phe Pro Cys Val Ala Ala Trp Cys Leu Pro Glu
    210             215             220

Ile Ile Pro Leu Gly Trp Met Glu Ser Leu Gln Val Leu Ile Glu Arg
225             230             235             240

Gly His Pro Phe Gly Tyr Phe Gly Ala Asp Val Ser Arg Tyr Pro Pro
            245             250             255

Asp Ile Asp Thr Met Ser Thr Cys Val Ser Thr Leu Phe Asp Leu Ser
            260             265             270

Leu Val Thr Ser Ala Gln Ala Met His Phe Leu Glu Ile Cys Leu Glu
        275             280             285

Asn Val Asn Asp Gln Asn Gln Leu Leu Thr Tyr Leu Asp Leu Glu Arg
    290             295             300

Pro Arg Val Asp Pro Val Val Ile Ala Asn Val Val Tyr Phe Ala Tyr
305             310             315             320

Ala Leu Ser Met Glu Asp His Pro Val Val Arg His Asn Glu Asn Leu
            325             330             335

Ile Gln Arg Tyr Leu Leu Ser Gly Gly Phe Val Tyr Gly Thr Arg Tyr
            340             345             350

Tyr Leu Ser Gln Glu Asp Phe Leu Phe Met Tyr Gly Arg Val Leu Ala
        355             360             365

Thr Phe Gly Glu Lys Arg Glu Ile Pro Asn Phe Asp Leu Val Tyr Gln
    370             375             380

Ala Met Glu Ala Ala Leu Val Asn Arg Ile Gly Asn Glu Thr Glu Ser
385             390             395             400

Lys Pro Leu Asp Val Ala Lys Arg Ile Leu Leu Ser Arg Tyr Phe Gly
            405             410             415

Ile Arg Asn Thr Ile Asp Val Asp Leu Leu Leu Lys Met Gln Asn Ala
            420             425             430

Ala Gly Ser Trp Pro Leu Gln Val Leu Ser Asn Leu Pro Ser Ala Lys
        435             440             445

Gly Gly Val Phe Asn Ser Val Val Asp Leu Ser Phe Ala Val Arg Ala
    450             455             460

Leu Gln Ser Gln Asp
465
```

<210> SEQ ID NO 31
<211> LENGTH: 1602
<212> TYPE: DNA
<213> ORGANISM: Gelatoporia subvermispora
<220> FEATURE:
<221> NAME/KEY: misc_feature
<223> OTHER INFORMATION: EMD37666.1_E. coli optimized

<400> SEQUENCE: 31
atgtctgcgg cggctcaata cacgactttg attctggatc tgggtgatgt tctgttcact          60

-continued

```
tggtccccga aaaccaagac cagcatccct ccgcgtaccc tgaaagaaat cctgaatagc      120
gctacctggt atgagtacga gcgtggtcgc atttcccaag acgagtgtta cgaacgtgtg      180
ggcaccgagt tcggcattgc gccgagcgag attgacaacg cgttcaaaca agcgcgcgat      240
tcgatggaaa gcaatgatga actgatcgca ctggtccgtg agctgaaaac gcagctggac      300
ggtgagctgc tggttttcgc actgtccaat attagcctgc cggattacga atacgtcttg      360
accaaaccgg cggactggag catctttgac aaagtgttcc ctagcgcctt ggtgggcgag      420
cgtaagccgc atctgggcgt ttataaacac gttattgcgg aaacgggcat tgatccgcgc      480
acgacggttt tcgtggacga caagattgac aatgtgttaa gcgcacgcag cgtcggtatg      540
catggtatcg tgtttgagaa acaagaagat gtcatgcgtg cactgcgtaa catctttggt      600
gatccggtcc gtcgtggtcg tgagtatctg cgtagaaacg caatgcgtct ggagtccgtg      660
accgaccacg gcgtggcgtt tggtgagaac tttacccagt tgctgattct ggaattgacg      720
aacgacccga gcctggtcac cctgcctgat cgtccgcgta cctggaactt ttttcgcggc      780
aatggtggcc gcccgagcaa gccgctgttc agcgaagcgt ccccggatga tctggatacc      840
acgagcctgg cgctgaccgt gctgcagcgc gacccgggtg ttatcagcag cgttatggac      900
gaaatgctga attaccgtga cccggacggt atcatgcaga cttatttcga tgacggtcgc      960
caacgcttgg acccatttgt gaacgtcaat gttctgacct ttttctatac gaacggccgt     1020
ggtcacgaac tggaccagtg tctgacgtgg gtgcgtgaag tcctcttgta tcgtgcgtac     1080
cttggtggct cacgctacta cccatcggcg gattgcttcc tgtacttcat ctctcgtctg     1140
tttgcgtgta ccaatgaccc ggtgctgcac catcagctga gccactgtt tgttgagcgt      1200 gtccaagagc aaaattggtgt cgagggtgat gcactggaac tggcttttcg tctgctggtc     1260
tgcgccagcc tggatgtcca gaatgccatc gacatgcgcc gtctgctgga aatgcagtgc     1320
gaagatggcg gttgggaggg tggtaacctc taccgcttcg gcaccacggg cctgaaagtt     1380
accaaccgcg gtctgacgac cgcagccgcc gttcaagcga tcgaagcgag ccaacgccgt     1440
ccgccgagcc cgagcccgtc tgtagagagc acgaaaagcc cgattacccc ggtgaccccg     1500
atgctggaag ttccaagcct gggcttatct atcagccgtc cgtccagccc gctgctgggt     1560
tatttccgtt tgccgtggaa gaaaagcgca gaagtgcact aa                        1602
```

<210> SEQ ID NO 32
<211> LENGTH: 533
<212> TYPE: PRT
<213> ORGANISM: Gelatoporia subvermispora
<220> FEATURE:
<221> NAME/KEY: MISC_FEATURE
<223> OTHER INFORMATION: EMD37666.1_amino acid sequence

<400> SEQUENCE: 32

```
Met Ser Ala Ala Ala Gln Tyr Thr Thr Leu Ile Leu Asp Leu Gly Asp
1               5                   10                  15

Val Leu Phe Thr Trp Ser Pro Lys Thr Lys Thr Ser Ile Pro Pro Arg
            20                  25                  30

Thr Leu Lys Glu Ile Leu Asn Ser Ala Thr Trp Tyr Glu Tyr Glu Arg
        35                  40                  45

Gly Arg Ile Ser Gln Asp Glu Cys Tyr Glu Arg Val Gly Thr Glu Phe
    50                  55                  60

Gly Ile Ala Pro Ser Glu Ile Asp Asn Ala Phe Lys Gln Ala Arg Asp
65                  70                  75                  80

Ser Met Glu Ser Asn Asp Glu Leu Ile Ala Leu Val Arg Glu Leu Lys
```

-continued

```
                85                  90                  95

Thr Gln Leu Asp Gly Glu Leu Leu Val Phe Ala Leu Ser Asn Ile Ser
            100                 105                 110

Leu Pro Asp Tyr Glu Tyr Val Leu Thr Lys Pro Ala Asp Trp Ser Ile
            115                 120                 125

Phe Asp Lys Val Phe Pro Ser Ala Leu Val Gly Glu Arg Lys Pro His
            130                 135                 140

Leu Gly Val Tyr Lys His Val Ile Ala Glu Thr Gly Ile Asp Pro Arg
145                 150                 155                 160

Thr Thr Val Phe Val Asp Asp Lys Ile Asp Asn Val Leu Ser Ala Arg
                165                 170                 175

Ser Val Gly Met His Gly Ile Val Phe Glu Lys Gln Glu Asp Val Met
                180                 185                 190

Arg Ala Leu Arg Asn Ile Phe Gly Asp Pro Val Arg Arg Gly Arg Glu
                195                 200                 205

Tyr Leu Arg Arg Asn Ala Met Arg Leu Glu Ser Val Thr Asp His Gly
            210                 215                 220

Val Ala Phe Gly Glu Asn Phe Thr Gln Leu Leu Ile Leu Glu Leu Thr
225                 230                 235                 240

Asn Asp Pro Ser Leu Val Thr Leu Pro Asp Arg Pro Arg Thr Trp Asn
                245                 250                 255

Phe Phe Arg Gly Asn Gly Gly Arg Pro Ser Lys Pro Leu Phe Ser Glu
                260                 265                 270

Ala Phe Pro Asp Asp Leu Asp Thr Thr Ser Leu Ala Leu Thr Val Leu
            275                 280                 285

Gln Arg Asp Pro Gly Val Ile Ser Ser Val Met Asp Glu Met Leu Asn
            290                 295                 300

Tyr Arg Asp Pro Asp Gly Ile Met Gln Thr Tyr Phe Asp Asp Gly Arg
305                 310                 315                 320

Gln Arg Leu Asp Pro Phe Val Asn Val Asn Val Leu Thr Phe Phe Tyr
                325                 330                 335

Thr Asn Gly Arg Gly His Glu Leu Asp Gln Cys Leu Thr Trp Val Arg
            340                 345                 350

Glu Val Leu Leu Tyr Arg Ala Tyr Leu Gly Gly Ser Arg Tyr Tyr Pro
            355                 360                 365

Ser Ala Asp Cys Phe Leu Tyr Phe Ile Ser Arg Leu Phe Ala Cys Thr
            370                 375                 380

Asn Asp Pro Val Leu His His Gln Leu Lys Pro Leu Phe Val Glu Arg
385                 390                 395                 400

Val Gln Glu Gln Ile Gly Val Glu Gly Asp Ala Leu Glu Leu Ala Phe
                405                 410                 415

Arg Leu Leu Val Cys Ala Ser Leu Asp Val Gln Asn Ala Ile Asp Met
            420                 425                 430

Arg Arg Leu Leu Glu Met Gln Cys Glu Asp Gly Gly Trp Glu Gly Gly
            435                 440                 445

Asn Leu Tyr Arg Phe Gly Thr Thr Gly Leu Lys Val Thr Asn Arg Gly
            450                 455                 460

Leu Thr Thr Ala Ala Ala Val Gln Ala Ile Glu Ala Ser Gln Arg Arg
465                 470                 475                 480

Pro Pro Ser Pro Ser Pro Ser Val Glu Ser Thr Lys Ser Pro Ile Thr
                485                 490                 495

Pro Val Thr Pro Met Leu Glu Val Pro Ser Leu Gly Leu Ser Ile Ser
            500                 505                 510
```

-continued

Arg Pro Ser Ser Pro Leu Leu Gly Tyr Phe Arg Leu Pro Trp Lys Lys
      515                 520                 525

Ser Ala Glu Val His
    530

<210> SEQ ID NO 33
<211> LENGTH: 1602
<212> TYPE: DNA
<213> ORGANISM: Artificial Sequence
<220> FEATURE:
<223> OTHER INFORMATION: EMD37666.1_mutant of class II motif_E.coli
      optimized

<400> SEQUENCE: 33
atgagcgcgg cggcgcagta caccaccctg atcctggacc tgggtgatgt gctgttcacc      60
tggagcccga agaccaaaac cagcatcccg ccgcgtaccc tgaaggaaat tctgaacagc     120
gcgacctggt acgagtatga acgtggccgt atcagccaag acgagtgcta tgaacgtgtt     180
ggcaccgagt tcggcatcgc gccgagcgaa attgataacg cgtttaagca ggcgcgtgac     240
agcatggaga gcaacgatga actgattgcg ctggtgcgtg agctgaaaac ccaactggac     300
ggtgaactgc tggttttcgc gctgagcaac atcagcctgc cggattacga gtatgtgctg     360
accaagccgg cggactggag cattttcgat aaagtttttc cgagcgcgct ggttggtgaa     420
cgcaagccgc acctgggcgt ttacaaacac gtgatcgcgg aaaccggtat tgacccgcgt     480
accaccgtgt ttgttgacga taagatcgat aacgttctga gcgcgcgtag cgtgggtatg     540
cacggcattg ttttcgagaa acaggaagac gtgatgcgtg cgctgcgtaa catctttggt     600
gatccggttc gtcgtggccg tgagtatctg cgtcgtaacg cgatgcgtct ggaaagcgtt     660
accgaccacg gtgtggcgtt cggcgagaac tttacccaac tgctgattct ggaactgacc     720
aacgatccga gcctggtgac cctgccggat cgtccgcgta cctggaactt ctttcgtggt     780
aacggtggcc gtccgagcaa gccgctgttc agcgaagcgt ttccggcggc gctggcgacc     840
accagcctgg cgctgaccgt tctgcagcgt gacccgggcg ttatcagcag cgtgatggat     900
gagatgctga actaccgtga cccggatggt attatgcaga cctatttcga cgatggccgt     960
caacgtctgg acccgtttgt gaacgttaac gtgctgacct tcttttacac caacggtcgt    1020
ggccacgagc tggatcagtg cctgacctgg gttcgtgaag tgctgctgta ccgtgcgtat    1080
ctgggtggca gccgttacta tccgagcgcg gactgcttcc tgtattttat cagccgtctg    1140
ttcgcgtgca ccaacgatcc ggtgctgcac caccaactga aaccgctgtt tgttgagcgt    1200
gtgcaggaac aaatcggtgt tgagggcgac gcgctggaac tggcgttccg tctgctggtg    1260
tgcgcgagcc tggacgttca gaacgcgatt gatatgcgtc gtctgctgga gatgcaatgc    1320
gaagatggtg gctgggaagg tggcaacctg taccgttttg gcaccaccgg cctgaaggtg    1380
accaaccgtg gtctgaccac cgcggcggcg gttcaggcga ttgaggcgag ccaacgtcgt    1440
ccgccgagcc cgagcccgag cgtggaaagc accaaaagcc cgatcacccc ggtgaccccg    1500
atgctggaag tgccgagcct gggtctgagc attagccgtc cgagcagccc gctgctgggt    1560
tacttccgtc tgccgtggaa gaaaagcgcg gaagtgcact aa                       1602

<210> SEQ ID NO 34
<211> LENGTH: 533
<212> TYPE: PRT
<213> ORGANISM: Artificial Sequence
<220> FEATURE:
<223> OTHER INFORMATION: EMD37666.1_mutant of class II motif -continued

<400> SEQUENCE: 34

Met Ser Ala Ala Ala Gln Tyr Thr Thr Leu Ile Leu Asp Leu Gly Asp
1                 5                   10                  15

Val Leu Phe Thr Trp Ser Pro Lys Thr Lys Thr Ser Ile Pro Pro Arg
            20                  25                  30

Thr Leu Lys Glu Ile Leu Asn Ser Ala Thr Trp Tyr Glu Tyr Glu Arg
        35                  40                  45

Gly Arg Ile Ser Gln Asp Glu Cys Tyr Glu Arg Val Gly Thr Glu Phe
    50                  55                  60

Gly Ile Ala Pro Ser Glu Ile Asp Asn Ala Phe Lys Gln Ala Arg Asp
65                  70                  75                  80

Ser Met Glu Ser Asn Asp Glu Leu Ile Ala Leu Val Arg Glu Leu Lys
                85                  90                  95

Thr Gln Leu Asp Gly Glu Leu Leu Val Phe Ala Leu Ser Asn Ile Ser
            100                 105                 110

Leu Pro Asp Tyr Glu Tyr Val Leu Thr Lys Pro Ala Asp Trp Ser Ile
            115                 120                 125

Phe Asp Lys Val Phe Pro Ser Ala Leu Val Gly Glu Arg Lys Pro His
    130                 135                 140

Leu Gly Val Tyr Lys His Val Ile Ala Glu Thr Gly Ile Asp Pro Arg
145                 150                 155                 160

Thr Thr Val Phe Val Asp Asp Lys Ile Asp Asn Val Leu Ser Ala Arg
                165                 170                 175

Ser Val Gly Met His Gly Ile Val Phe Glu Lys Gln Glu Asp Val Met
                180                 185                 190

Arg Ala Leu Arg Asn Ile Phe Gly Asp Pro Val Arg Arg Gly Arg Glu
            195                 200                 205

Tyr Leu Arg Arg Asn Ala Met Arg Leu Glu Ser Val Thr Asp His Gly
    210                 215                 220

Val Ala Phe Gly Glu Asn Phe Thr Gln Leu Leu Ile Leu Glu Leu Thr
225                 230                 235                 240

Asn Asp Pro Ser Leu Val Thr Leu Pro Asp Arg Pro Arg Thr Trp Asn
                245                 250                 255

Phe Phe Arg Gly Asn Gly Gly Arg Pro Ser Lys Pro Leu Phe Ser Glu
            260                 265                 270

Ala Phe Pro Ala Ala Leu Ala Thr Thr Ser Leu Ala Leu Thr Val Leu
            275                 280                 285

Gln Arg Asp Pro Gly Val Ile Ser Ser Val Met Asp Glu Met Leu Asn
    290                 295                 300

Tyr Arg Asp Pro Asp Gly Ile Met Gln Thr Tyr Phe Asp Asp Gly Arg
305                 310                 315                 320

Gln Arg Leu Asp Pro Phe Val Asn Val Asn Val Leu Thr Phe Phe Tyr
            325                 330                 335

Thr Asn Gly Arg Gly His Glu Leu Asp Gln Cys Leu Thr Trp Val Arg
            340                 345                 350

Glu Val Leu Leu Tyr Arg Ala Tyr Leu Gly Gly Ser Arg Tyr Tyr Pro
            355                 360                 365

Ser Ala Asp Cys Phe Leu Tyr Phe Ile Ser Arg Leu Phe Ala Cys Thr
    370                 375                 380

Asn Asp Pro Val Leu His His Gln Leu Lys Pro Leu Phe Val Glu Arg
385                 390                 395                 400

Val Gln Glu Gln Ile Gly Val Glu Gly Asp Ala Leu Glu Leu Ala Phe

-continued

```
                    405              410              415
Arg Leu Leu Val Cys Ala Ser Leu Asp Val Gln Asn Ala Ile Asp Met
            420              425              430

Arg Arg Leu Leu Glu Met Gln Cys Glu Asp Gly Gly Trp Glu Gly Gly
        435              440              445

Asn Leu Tyr Arg Phe Gly Thr Thr Gly Leu Lys Val Thr Asn Arg Gly
    450              455              460

Leu Thr Thr Ala Ala Ala Val Gln Ala Ile Glu Ala Ser Gln Arg Arg
465              470              475              480

Pro Pro Ser Pro Ser Pro Ser Val Glu Ser Thr Lys Ser Pro Ile Thr
            485              490              495

Pro Val Thr Pro Met Leu Glu Val Pro Ser Leu Gly Leu Ser Ile Ser
            500              505              510

Arg Pro Ser Ser Pro Leu Leu Gly Tyr Phe Arg Leu Pro Trp Lys Lys
            515              520              525

Ser Ala Glu Val His
    530
```

```
<210> SEQ ID NO 35
<211> LENGTH: 1584
<212> TYPE: DNA
<213> ORGANISM: Dichomitus squalens
<220> FEATURE:
<221> NAME/KEY: misc_feature
<223> OTHER INFORMATION: XP_007369631.1_E. coli optimized

<400> SEQUENCE: 35
atggcgagca tccaccgtcg ttacaccacc ctgattctgg acctgggtga tgttctgttt      60
cgttggagcc cgaagaccga gaccgcgatc ccgccgcagc aactgaaaga cattctgagc     120
agcgtgacct ggttcgagta cgaacgtggc cgtctgagcc aggaagcgtg ctatgaacgt     180
tgcgcggagg aatttaagat cgaggcgagc gttattgcgg aagcgttcaa acaagcgcgt     240
ggtagcctgc gtccgaacga ggaatttatc gcgctgattc gtgacctgcg tcgtgagatg     300
cacggcgatc tgaccgtgct ggcgctgagc aacatcagcc tgccggacta cgaatatatt     360
atgagcctga gcagcgactg gaccaccgtt ttcgatcgtg tgtttccgag cgcgctggtt     420
ggtgagcgta gccgcacct gggctgctat cgtaaagtga tcagcgagat gaacctggaa     480
ccgcagacca ccgtgttcgt tgacgataag ctggataacg ttgcgagcgc gcgtagcctg     540
ggtatgcatg gtattgtttt cgacaaccag gcgaacgtgt ttcgtcaact gcgtaacatc     600
ttcggtgatc gattcgtcg tggccaagag tacctgcgtg tcacgcgggg caaactggaa     660
agcagcaccg acaacggtct gatcttcgag gaaaacttta cccagctgat catttatgag     720
ctgacccaag atcgtaccct gattagcctg agcgaatgcc cgcgtacctg gaacttcttt     780
cgtggcgagc cgctgttcag cgaaaccttc ccggacgacg ttgacaccac cagcgttgcg     840
ctgaccgtgc tgcagccgga ccgtgcgctg gttaacagcg tgctggatga gatgctggaa     900
tacgtggacg cggatggtat catgcaaacc tattttgacc gtagccgtcc gcgtatggat     960
ccgtttgtgt gcgttaacgt gctgagcctg ttctacgaga cggtcgtgg ccacgaactg     1020 ccgcgtaccc tggactgggt ttacgaggtg ctgctgcacc gtgcgtatca cggtggcagc     1080
cgttactatc tgagcccgga ttgcttcctg ttctttatga ccgtctgct gaaacgtgcg     1140 gatgatccgg cggttcaggc gcgtctgcgt ccgctgtttg ttgagcgtgt gaacgaacgt     1200
gttggtgcgg cgggtgacag catggatctg gcgttccgta tcctggcggc ggcgagcgtt     1260
```

```
ggtgtgcagt gcccgcgtga cctggaacgt ctgaccgcgg gtcaatgcga tgatggtggc    1320
tgggatctgt gctggttcta cgtttttggt agcaccggcg tgaaagcggg taaccgtggc    1380
ctgaccaccg cgctggcggt gaccgcgatt caaaccgcga ttggtcgtcc gccgagcccg    1440
agcccgagcg cggcgagcag cagctttcgt ccgagcagcc cgtataaatt cctgggtatc    1500
agccgtccgg cgagcccgat tcgttttggt gacctgctgc gtccgtggcg taagatgagc    1560
cgtagcaacc tgaaaagcca ataa                                           1584
```

<210> SEQ ID NO 36
<211> LENGTH: 527
<212> TYPE: PRT
<213> ORGANISM: Dichomitus squalens
<220> FEATURE:
<221> NAME/KEY: MISC_FEATURE
<223> OTHER INFORMATION: XP_007369631.1_amino acid sequence

<400> SEQUENCE: 36

```
Met Ala Ser Ile His Arg Arg Tyr Thr Thr Leu Ile Leu Asp Leu Gly
1               5                   10                  15

Asp Val Leu Phe Arg Trp Ser Pro Lys Thr Glu Thr Ala Ile Pro Pro
            20                  25                  30

Gln Gln Leu Lys Asp Ile Leu Ser Ser Val Thr Trp Phe Glu Tyr Glu
        35                  40                  45

Arg Gly Arg Leu Ser Gln Glu Ala Cys Tyr Glu Arg Cys Ala Glu Glu
    50                  55                  60

Phe Lys Ile Glu Ala Ser Val Ile Ala Glu Ala Phe Lys Gln Ala Arg
65                  70                  75                  80

Gly Ser Leu Arg Pro Asn Glu Glu Phe Ile Ala Leu Ile Arg Asp Leu
                85                  90                  95

Arg Arg Glu Met His Gly Asp Leu Thr Val Leu Ala Leu Ser Asn Ile
            100                 105                 110

Ser Leu Pro Asp Tyr Glu Tyr Ile Met Ser Leu Ser Ser Asp Trp Thr
        115                 120                 125

Thr Val Phe Asp Arg Val Phe Pro Ser Ala Leu Val Gly Glu Arg Lys
    130                 135                 140

Pro His Leu Gly Cys Tyr Arg Lys Val Ile Ser Glu Met Asn Leu Glu
145                 150                 155                 160

Pro Gln Thr Thr Val Phe Val Asp Asp Lys Leu Asp Asn Val Ala Ser
                165                 170                 175

Ala Arg Ser Leu Gly Met His Gly Ile Val Phe Asp Asn Gln Ala Asn
            180                 185                 190

Val Phe Arg Gln Leu Arg Asn Ile Phe Gly Asp Pro Ile Arg Arg Gly
        195                 200                 205

Gln Glu Tyr Leu Arg Gly His Ala Gly Lys Leu Glu Ser Ser Thr Asp
    210                 215                 220

Asn Gly Leu Ile Phe Glu Glu Asn Phe Thr Gln Leu Ile Ile Tyr Glu
225                 230                 235                 240

Leu Thr Gln Asp Arg Thr Leu Ile Ser Leu Ser Glu Cys Pro Arg Thr
                245                 250                 255

Trp Asn Phe Phe Arg Gly Glu Pro Leu Phe Ser Glu Thr Phe Pro Asp
            260                 265                 270

Asp Val Asp Thr Thr Ser Val Ala Leu Thr Val Leu Gln Pro Asp Arg
        275                 280                 285

Ala Leu Val Asn Ser Val Leu Asp Glu Met Leu Glu Tyr Val Asp Ala
    290                 295                 300
```

```
Asp Gly Ile Met Gln Thr Tyr Phe Asp Arg Ser Arg Pro Arg Met Asp
305                 310                 315                 320

Pro Phe Val Cys Val Asn Val Leu Ser Leu Phe Tyr Glu Asn Gly Arg
                325                 330                 335

Gly His Glu Leu Pro Arg Thr Leu Asp Trp Val Tyr Glu Val Leu Leu
            340                 345                 350

His Arg Ala Tyr His Gly Gly Ser Arg Tyr Tyr Leu Ser Pro Asp Cys
            355                 360                 365

Phe Leu Phe Phe Met Ser Arg Leu Leu Lys Arg Ala Asp Asp Pro Ala
        370                 375                 380

Val Gln Ala Arg Leu Arg Pro Leu Phe Val Glu Arg Val Asn Glu Arg
385                 390                 395                 400

Val Gly Ala Ala Gly Asp Ser Met Asp Leu Ala Phe Arg Ile Leu Ala
                405                 410                 415

Ala Ala Ser Val Gly Val Gln Cys Pro Arg Asp Leu Glu Arg Leu Thr
                420                 425                 430

Ala Gly Gln Cys Asp Asp Gly Gly Trp Asp Leu Cys Trp Phe Tyr Val
            435                 440                 445

Phe Gly Ser Thr Gly Val Lys Ala Gly Asn Arg Gly Leu Thr Thr Ala
        450                 455                 460

Leu Ala Val Thr Ala Ile Gln Thr Ala Ile Gly Arg Pro Pro Ser Pro
465                 470                 475                 480

Ser Pro Ser Ala Ala Ser Ser Ser Phe Arg Pro Ser Ser Pro Tyr Lys
                485                 490                 495

Phe Leu Gly Ile Ser Arg Pro Ala Ser Pro Ile Arg Phe Gly Asp Leu
            500                 505                 510

Leu Arg Pro Trp Arg Lys Met Ser Arg Ser Asn Leu Lys Ser Gln
            515                 520                 525

<210> SEQ ID NO 37
<211> LENGTH: 1584
<212> TYPE: DNA
<213> ORGANISM: Artificial Sequence
<220> FEATURE:
<223> OTHER INFORMATION: XP_007369631.1_mutant of class II motif_ E.coli
      optimized

<400> SEQUENCE: 37
atggcgagca tccaccgtcg ttacaccacc ctgattctgg acctgggtga tgttctgttt      60
cgttggagcc cgaagaccga gaccgcgatc ccgccgcagc aactgaaaga cattctgagc     120
agcgtgacct ggttcgagta cgaacgtggc cgtctgagcc aggaagcgtg ctatgaacgt     180
tgcgcggagg aatttaagat cgaggcgagc gttattgcgg aagcgttcaa acaagcgcgt     240
ggtagcctgc gtccgaacga ggaatttatc gcgctgattc gtgacctgcg tcgtgagatg     300
cacggcgatc tgaccgtgct ggcgctgagc aacatcagcc tgccggacta cgaatatatt     360
atgagcctga gcagcgactg gaccaccgtt ttcgatcgtg tgtttccgag cgcgctggtt     420
ggtgagcgta agccgcacct gggctgctat cgtaaagtga tcagcgagat gaacctggaa     480
ccgcagacca ccgtgttcgt tgacgataag ctggataacg ttgcgagcgc gcgtagcctg     540
ggtatgcatg gtattgtttt cgacaaccag gcgaacgtgt ttcgtcaact gcgtaacatc     600
ttcggtgatc cgattcgtcg tggccaagag tacctgcgtg tcacgcgggg caaactggaa     660
agcagcaccg acaacggtct gatcttcgag gaaaacttta cccagctgat catttatgag     720
ctgacccaag atcgtaccct gattagcctg agcgaatgcc cgcgtacctg gaacttcttt     780
```

-continued

```
cgtggcgagc cgctgttcag cgaaaccttc ccggcggcgg ttgcgaccac cagcgttgcg    840
ctgaccgtgc tgcagccgga ccgtgcgctg gttaacagcg tgctggatga gatgctggaa    900
tacgtggacg cggatggtat catgcaaacc tattttgacc gtagccgtcc gcgtatggat    960
ccgtttgtgt gcgttaacgt gctgagcctg ttctacgaga cggtcgtgg ccacgaactg   1020 ccgcgtaccc tggactgggt ttacgaggtg ctgctgcacc gtgcgtatca cggtggcagc   1080
cgttactatc tgagcccgga ttgcttcctg ttctttatga gccgtctgct gaaacgtgcg   1140
gatgatccgg cggttcaggc gcgtctgcgt ccgctgtttg ttgagcgtgt gaacgaacgt   1200
gttggtgcgg cgggtgacag catggatctg gcgttccgta tcctggcggc ggcgagcgtt   1260
ggtgtgcagt gcccgcgtga cctggaacgt ctgaccgcgg tcaatgcga tgatggtggc   1320 tgggatctgt gctggttcta cgttttttggt agcaccggcg tgaaagcggg taaccgtggc   1380
ctgaccaccg cgctggcggt gaccgcgatt caaaccgcga ttggtcgtcc gccgagcccg   1440
agcccgagcg cggcgagcag cagctttcgt ccgagcagcc cgtataaatt cctgggtatc   1500
agccgtccgg cgagcccgat tcgtttttggt gacctgctgc gtccgtggcg taagatgagc   1560
cgtagcaacc tgaaaagcca ataa                                         1584
```

```
<210> SEQ ID NO 38
<211> LENGTH: 527
<212> TYPE: PRT
<213> ORGANISM: Artificial Sequence
<220> FEATURE:
<223> OTHER INFORMATION: XP_007369631.1_mutant of class II motif

<400> SEQUENCE: 38

Met Ala Ser Ile His Arg Arg Tyr Thr Thr Leu Ile Leu Asp Leu Gly
1               5                   10                  15

Asp Val Leu Phe Arg Trp Ser Pro Lys Thr Glu Thr Ala Ile Pro Pro
            20                  25                  30

Gln Gln Leu Lys Asp Ile Leu Ser Ser Val Thr Trp Phe Glu Tyr Glu
        35                  40                  45

Arg Gly Arg Leu Ser Gln Glu Ala Cys Tyr Glu Arg Cys Ala Glu Glu
    50                  55                  60

Phe Lys Ile Glu Ala Ser Val Ile Ala Glu Ala Phe Lys Gln Ala Arg
65                  70                  75                  80

Gly Ser Leu Arg Pro Asn Glu Glu Phe Ile Ala Leu Ile Arg Asp Leu
                85                  90                  95

Arg Arg Glu Met His Gly Asp Leu Thr Val Leu Ala Leu Ser Asn Ile
            100                 105                 110

Ser Leu Pro Asp Tyr Glu Tyr Ile Met Ser Leu Ser Ser Asp Trp Thr
        115                 120                 125

Thr Val Phe Asp Arg Val Phe Pro Ser Ala Leu Val Gly Glu Arg Lys
        130                 135                 140

Pro His Leu Gly Cys Tyr Arg Lys Val Ile Ser Glu Met Asn Leu Glu
145                 150                 155                 160

Pro Gln Thr Thr Val Phe Val Asp Asp Lys Leu Asp Asn Val Ala Ser
                165                 170                 175

Ala Arg Ser Leu Gly Met His Gly Ile Val Phe Asp Asn Gln Ala Asn
            180                 185                 190

Val Phe Arg Gln Leu Arg Asn Ile Phe Gly Asp Pro Ile Arg Arg Gly
        195                 200                 205

Gln Glu Tyr Leu Arg Gly His Ala Gly Lys Leu Glu Ser Ser Thr Asp
```

```
        210            215              220

Asn Gly Leu Ile Phe Glu Glu Asn Phe Thr Gln Leu Ile Ile Tyr Glu
225                     230              235                 240

Leu Thr Gln Asp Arg Thr Leu Ile Ser Leu Ser Glu Cys Pro Arg Thr
                245              250              255

Trp Asn Phe Phe Arg Gly Glu Pro Leu Phe Ser Glu Thr Phe Pro Ala
                260              265              270

Ala Val Ala Thr Thr Ser Val Ala Leu Thr Val Leu Gln Pro Asp Arg
            275              280              285

Ala Leu Val Asn Ser Val Leu Asp Glu Met Leu Glu Tyr Val Asp Ala
        290              295              300

Asp Gly Ile Met Gln Thr Tyr Phe Asp Arg Ser Arg Pro Arg Met Asp
305                 310              315                 320

Pro Phe Val Cys Val Asn Val Leu Ser Leu Phe Tyr Glu Asn Gly Arg
                325              330              335

Gly His Glu Leu Pro Arg Thr Leu Asp Trp Val Tyr Glu Val Leu Leu
                340              345              350

His Arg Ala Tyr His Gly Gly Ser Arg Tyr Tyr Leu Ser Pro Asp Cys
            355              360              365

Phe Leu Phe Phe Met Ser Arg Leu Leu Lys Arg Ala Asp Asp Pro Ala
        370              375              380

Val Gln Ala Arg Leu Arg Pro Leu Phe Val Glu Arg Val Asn Glu Arg
385                 390              395                 400

Val Gly Ala Ala Gly Asp Ser Met Asp Leu Ala Phe Arg Ile Leu Ala
                405              410              415

Ala Ala Ser Val Gly Val Gln Cys Pro Arg Asp Leu Glu Arg Leu Thr
                420              425              430

Ala Gly Gln Cys Asp Asp Gly Gly Trp Asp Leu Cys Trp Phe Tyr Val
            435              440              445

Phe Gly Ser Thr Gly Val Lys Ala Gly Asn Arg Gly Leu Thr Thr Ala
        450              455              460

Leu Ala Val Thr Ala Ile Gln Thr Ala Ile Gly Arg Pro Pro Ser Pro
465                 470              475                 480

Ser Pro Ser Ala Ala Ser Ser Ser Phe Arg Pro Ser Ser Pro Tyr Lys
                485              490              495

Phe Leu Gly Ile Ser Arg Pro Ala Ser Pro Ile Arg Phe Gly Asp Leu
                500              505              510

Leu Arg Pro Trp Arg Lys Met Ser Arg Ser Asn Leu Lys Ser Gln
            515              520              525
```

```
<210> SEQ ID NO 39
<211> LENGTH: 8
<212> TYPE: PRT
<213> ORGANISM: Artificial Sequence
<220> FEATURE:
<223> OTHER INFORMATION: class II synthase motif_mutated_BtHAD

<400> SEQUENCE: 39

Pro Asp Ala Leu Ala Ser Thr Ser
1               5

<210> SEQ ID NO 40
<211> LENGTH: 8
<212> TYPE: PRT
<213> ORGANISM: Artificial Sequence
<220> FEATURE:
<223> OTHER INFORMATION: class II synthase motif_mutated_SmHAD1 + SmHAD2
```

<400> SEQUENCE: 40

Pro Pro Ala Ile Ala Thr Met Ser
1               5

<210> SEQ ID NO 41
<211> LENGTH: 8
<212> TYPE: PRT
<213> ORGANISM: Artificial Sequence
<220> FEATURE:
<223> OTHER INFORMATION: class II synthase motif_mutated_EMD37666

<400> SEQUENCE: 41

Pro Ala Ala Leu Ala Thr Thr Ser
1               5

<210> SEQ ID NO 42
<211> LENGTH: 8
<212> TYPE: PRT
<213> ORGANISM: Artificial Sequence
<220> FEATURE:
<223> OTHER INFORMATION: class II synthase motif_mutated_XP_007369631

<400> SEQUENCE: 42

Pro Ala Ala Val Ala Thr Thr Ser
1               5

<210> SEQ ID NO 43
<211> LENGTH: 7
<212> TYPE: PRT
<213> ORGANISM: Artificial Sequence
<220> FEATURE:
<223> OTHER INFORMATION: QW motif_mutated_BtHAD

<400> SEQUENCE: 43

Gln Asn Val Ala Gly Ser Trp
1               5

<210> SEQ ID NO 44
<211> LENGTH: 7
<212> TYPE: PRT
<213> ORGANISM: Artificial Sequence
<220> FEATURE:
<223> OTHER INFORMATION: QW motif_mutated_SmHAD1+ SmHAD2

<400> SEQUENCE: 44

Gln Asn Ala Ala Gly Ser Trp
1               5

<210> SEQ ID NO 45
<211> LENGTH: 5
<212> TYPE: PRT
<213> ORGANISM: Artificial Sequence
<220> FEATURE:
<223> OTHER INFORMATION: class I synthase motif DDxx(D/E)
<220> FEATURE:
<221> NAME/KEY: MISC_FEATURE
<222> LOCATION: (3)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be D or E

<400> SEQUENCE: 45

Asp Asp Xaa Xaa Xaa
1               5

-continued

```
<210> SEQ ID NO 46
<211> LENGTH: 8
<212> TYPE: PRT
<213> ORGANISM: Artificial Sequence
<220> FEATURE:
<223> OTHER INFORMATION: class II synthase motif PxDxD(T/S)(T/M)S
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be T or S
<220> FEATURE:
<221> NAME/KEY: MISC_FEATURE
<222> LOCATION: (7)..(7)
<223> OTHER INFORMATION: Xaa can be T or M

<400> SEQUENCE: 46

Pro Xaa Asp Xaa Asp Xaa Xaa Ser
1               5

<210> SEQ ID NO 47
<211> LENGTH: 8
<212> TYPE: PRT
<213> ORGANISM: Artificial Sequence
<220> FEATURE:
<223> OTHER INFORMATION: class II synthase motif PDDLDSTS

<400> SEQUENCE: 47

Pro Asp Asp Leu Asp Ser Thr Ser
1               5

<210> SEQ ID NO 48
<211> LENGTH: 8
<212> TYPE: PRT
<213> ORGANISM: Artificial Sequence
<220> FEATURE:
<223> OTHER INFORMATION: class II synthase motif PDDLDTTS

<400> SEQUENCE: 48

Pro Asp Asp Leu Asp Thr Thr Ser
1               5

<210> SEQ ID NO 49
<211> LENGTH: 8
<212> TYPE: PRT
<213> ORGANISM: Artificial Sequence
<220> FEATURE:
<223> OTHER INFORMATION: class II synthase motif PPDIDTMS

<400> SEQUENCE: 49

Pro Pro Asp Ile Asp Thr Met Ser
1               5

<210> SEQ ID NO 50
<211> LENGTH: 8
<212> TYPE: PRT
<213> ORGANISM: Artificial Sequence
<220> FEATURE:
<223> OTHER INFORMATION: class II synthase motif PNDIDTMS

<400> SEQUENCE: 50

Pro Asn Asp Ile Asp Thr Thr Ser
```

-continued 1               5

<210> SEQ ID NO 51
<211> LENGTH: 7
<212> TYPE: PRT
<213> ORGANISM: Artificial Sequence
<220> FEATURE:
<223> OTHER INFORMATION: QW motif
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 51

Gln Xaa Xaa Asp Gly Xaa Trp
1               5

<210> SEQ ID NO 52
<211> LENGTH: 7
<212> TYPE: PRT
<213> ORGANISM: Artificial Sequence
<220> FEATURE:
<223> OTHER INFORMATION: QW motif QNVDGSW

<400> SEQUENCE: 52

Gln Asn Val Asp Gly Ser Trp
1               5

<210> SEQ ID NO 53
<211> LENGTH: 7
<212> TYPE: PRT
<213> ORGANISM: Artificial Sequence
<220> FEATURE:
<223> OTHER INFORMATION: QW motif QCDDGGW

<400> SEQUENCE: 53

Gln Cys Asp Asp Gly Gly Trp
1               5

<210> SEQ ID NO 54
<211> LENGTH: 7
<212> TYPE: PRT
<213> ORGANISM: Artificial Sequence
<220> FEATURE:
<223> OTHER INFORMATION: QW motif QSSDGGW

<400> SEQUENCE: 54

Gln Ser Ser Asp Gly Gly Trp
1               5

<210> SEQ ID NO 55
<211> LENGTH: 7
<212> TYPE: PRT
<213> ORGANISM: Artificial Sequence
<220> FEATURE:
<223> OTHER INFORMATION: QW motif QNEDGSW

<400> SEQUENCE: 55

Gln Asn Glu Asp Gly Ser Trp
1               5

<210> SEQ ID NO 56
<211> LENGTH: 12
<212> TYPE: PRT

```
<213> ORGANISM: Artificial Sequence
<220> FEATURE:
<223> OTHER INFORMATION: conserved motif 1 Lxxxx(W/F)xxYxxG
<220> FEATURE:
<221> NAME/KEY: MISC_FEATURE
<222> LOCATION: (2)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be W or F
<220> FEATURE:
<221> NAME/KEY: MISC_FEATURE
<222> LOCATION: (7)..(8)
<223> OTHER INFORMATION: Xaa can be any naturally occurring amino acid
<220> FEATURE:
<221> NAME/KEY: MISC_FEATURE
<222> LOCATION: (10)..(11)
<223> OTHER INFORMATION: Xaa can be any naturally occurring amino acid

<400> SEQUENCE: 56

Leu Xaa Xaa Xaa Xaa Xaa Xaa Xaa Tyr Xaa Xaa Gly
1               5                   10

<210> SEQ ID NO 57
<211> LENGTH: 12
<212> TYPE: PRT
<213> ORGANISM: Artificial Sequence
<220> FEATURE:
<223> OTHER INFORMATION: conserved motif 1 LRSHIWFNYSMG

<400> SEQUENCE: 57

Leu Arg Ser His Ile Trp Phe Asn Tyr Ser Met Gly
1               5                   10

<210> SEQ ID NO 58
<211> LENGTH: 12
<212> TYPE: PRT
<213> ORGANISM: Artificial Sequence
<220> FEATURE:
<223> OTHER INFORMATION: conserved motif 1 LRSATWAAYECG

<400> SEQUENCE: 58

Leu Arg Ser Ala Thr Trp Ala Ala Tyr Glu Cys Gly
1               5                   10

<210> SEQ ID NO 59
<211> LENGTH: 12
<212> TYPE: PRT
<213> ORGANISM: Artificial Sequence
<220> FEATURE:
<223> OTHER INFORMATION: conserved motif 1 LRTPTWGKYECG

<400> SEQUENCE: 59

Leu Arg Thr Pro Thr Trp Gly Lys Tyr Glu Cys Gly
1               5                   10

<210> SEQ ID NO 60
<211> LENGTH: 12
<212> TYPE: PRT
<213> ORGANISM: Artificial Sequence
<220> FEATURE:
<223> OTHER INFORMATION: conserved motif 1 LQHSSFLAYSCG

<400> SEQUENCE: 60

Leu Gln His Ser Ser Phe Leu Ala Tyr Ser Cys Gly
1               5                   10

<210> SEQ ID NO 61
```

```
<211> LENGTH: 12
<212> TYPE: PRT
<213> ORGANISM: Artificial Sequence
<220> FEATURE:
<223> OTHER INFORMATION: conserved motif 1 LRxxTWxxYECG
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 61

Leu Arg Xaa Xaa Thr Trp Xaa Xaa Tyr Glu Cys Gly
1               5                   10

<210> SEQ ID NO 62
<211> LENGTH: 16
<212> TYPE: PRT
<213> ORGANISM: Artificial Sequence
<220> FEATURE:
<223> OTHER INFORMATION: conserved motif 2 YxDxxRxRVD(P/A)V(V/A)xxN
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be P or A
<220> FEATURE:
<221> NAME/KEY: MISC_FEATURE
<222> LOCATION: (13)..(13)
<223> OTHER INFORMATION: Xaa can be V or A
<220> FEATURE:
<221> NAME/KEY: MISC_FEATURE
<222> LOCATION: (14)..(15)
<223> OTHER INFORMATION: Xaa can be any naturally occurring amino acid

<400> SEQUENCE: 62

Tyr Xaa Asp Xaa Xaa Arg Xaa Arg Val Asp Xaa Val Xaa Xaa Xaa Asn
1               5                   10                  15

<210> SEQ ID NO 63
<211> LENGTH: 16
<212> TYPE: PRT
<213> ORGANISM: Artificial Sequence
<220> FEATURE:
<223> OTHER INFORMATION: conserved motif 2 YFDPLRLRVDPVAATN

<400> SEQUENCE: 63

Tyr Phe Asp Pro Leu Arg Leu Arg Val Asp Pro Val Ala Ala Thr Asn
1               5                   10                  15

<210> SEQ ID NO 64
<211> LENGTH: 16
<212> TYPE: PRT
<213> ORGANISM: Artificial Sequence
<220> FEATURE:
<223> OTHER INFORMATION: conserved motif 2 YFDETRPRVDAVVNVN

<400> SEQUENCE: 64
```

```
Tyr Phe Asp Glu Thr Arg Pro Arg Val Asp Ala Val Val Asn Val Asn
1               5                   10                  15

<210> SEQ ID NO 65
<211> LENGTH: 16
<212> TYPE: PRT
<213> ORGANISM: Artificial Sequence
<220> FEATURE:
<223> OTHER INFORMATION: conserved motif 2 YFDKTRPRVDPVVCVN

<400> SEQUENCE: 65

Tyr Phe Asp Lys Thr Arg Pro Arg Val Asp Pro Val Val Cys Val Asn
1               5                   10                  15

<210> SEQ ID NO 66
<211> LENGTH: 16
<212> TYPE: PRT
<213> ORGANISM: Artificial Sequence
<220> FEATURE:
<223> OTHER INFORMATION: conserved motif 2 YLDVERPRVDPVVIAN

<400> SEQUENCE: 66

Tyr Leu Asp Val Glu Arg Pro Arg Val Asp Pro Val Val Ile Ala Asn
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: conserved motif 2 YLDLERPRVDPVVIAN

<400> SEQUENCE: 67

Tyr Leu Asp Leu Glu Arg Pro Arg Val Asp Pro Val Val Ile Ala Asn
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: conserved motif 2
      Y(F/L)Dx(T/E)RPRVD(P/A)VVx(A/V)N
<220> FEATURE:
<221> NAME/KEY: MISC_FEATURE
<222> LOCATION: (2)..(2)
<223> OTHER INFORMATION: Xaa can be F or L
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be T or E
<220> FEATURE:
<221> NAME/KEY: MISC_FEATURE
<222> LOCATION: (11)..(11)
<223> OTHER INFORMATION: Xaa can be P or A
<220> FEATURE:
<221> NAME/KEY: MISC_FEATURE
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (15)..(15)
<223> OTHER INFORMATION: Xaa can be A or V

<400> SEQUENCE: 68

Tyr Xaa Asp Xaa Xaa Arg Pro Arg Val Asp Xaa Val Val Xaa Xaa Asn
1               5                   10                  15
```

```
<210> SEQ ID NO 69
<211> LENGTH: 13
<212> TYPE: PRT
<213> ORGANISM: Artificial Sequence
<220> FEATURE:
<223> OTHER INFORMATION: conserved motif 3 GTx(Y/F)YxxxExFL(Y/F)
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa can be Y or F
<220> FEATURE:
<221> NAME/KEY: MISC_FEATURE
<222> LOCATION: (6)..(8)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Xaa can be Y or F

<400> SEQUENCE: 69

Gly Thr Xaa Xaa Tyr Xaa Xaa Xaa Glu Xaa Phe Leu Xaa
1               5                   10

<210> SEQ ID NO 70
<211> LENGTH: 13
<212> TYPE: PRT
<213> ORGANISM: Artificial Sequence
<220> FEATURE:
<223> OTHER INFORMATION: conserved motif 3 GTLYYRTPEAFLY

<400> SEQUENCE: 70

Gly Thr Leu Tyr Tyr Arg Thr Pro Glu Ala Phe Leu Tyr
1               5                   10

<210> SEQ ID NO 71
<211> LENGTH: 13
<212> TYPE: PRT
<213> ORGANISM: Artificial Sequence
<220> FEATURE:
<223> OTHER INFORMATION: conserved motif 3 GTLFYYHAESFLY

<400> SEQUENCE: 71

Gly Thr Leu Phe Tyr Tyr His Ala Glu Ser Phe Leu Tyr
1               5                   10

<210> SEQ ID NO 72
<211> LENGTH: 13
<212> TYPE: PRT
<213> ORGANISM: Artificial Sequence
<220> FEATURE:
<223> OTHER INFORMATION: conserved motif 3 GTRYYLSQEDFLF

<400> SEQUENCE: 72

Gly Thr Arg Tyr Tyr Leu Ser Gln Glu Asp Phe Leu Phe
1               5                   10

<210> SEQ ID NO 73
<211> LENGTH: 1755
<212> TYPE: DNA
<213> ORGANISM: Dryopteris fragrans
<220> FEATURE:
```

-continued

<221> NAME/KEY: misc_feature
<223> OTHER INFORMATION: DfHAD_wt_nucleic acid sequence

<400> SEQUENCE: 73

```
atggagttct ctgcctctgc tcctcctcct aggctagcca gtgtcataat attggagcct      60
ctcggcttcc tcctcacacc acactactcc tctcagcttc ccaaaaagct gctccgtcgc     120
ctgttgtgca ctagaatctg gcacaggtat cagcgaggcc gccttcgcct gcgtgacgct     180
gctatgctgc tcgcccagct cccattccta gctgtgtctg atcacccctg ggctctggac     240
aatctcgcaa gcctgctccg ccccacagct gtgcgtgcgg tgccatggat gctgctgctg     300
ctcgacttcc tacgagacga gctccatctg aaggtagtct cgcgcgaccaa ctcctcccca     360 gaagagctgc aagagctgcg ccaccagttt ccggccctct ttgccaaggt cgatgccacc     420
gtttcttcag gcgaggaggg cgtgggcaag ccgtccgtgc gcttcctgca ggctgcgttg     480
gacaaagccg gtgtccacgc gcagcaaacc ttgtatcttg actcttttga cagcttggag     540
accatcatgg ctgcacgctc tcttggcatg catgcactat ctgtagagcc atgccacatt     600
gatgagctca ccgccagggc ctcttccggc cagctaagag atgcacagct tataaggcgt     660
attgtgtgcg ccatgcacgg gccagcagta tctgcagttg tgtcgggcag tatcacatcg     720
tccggcccac agacagcaaa gatcgaggaa ttgccaacag ctgctgatag tcatctccgc     780
agcgcagctc tcacttctgc tcagcagttt ttcctcaaag ttattgctcc acatcgtcct     840
gagaagccat tcgtccagct tccatctctc acctcggagg gcatccgaat atacgacacc     900
tttgcacagt ttgtcatagc cgacctgctc gacgacaccc gcttcctacc catgcaatct     960
cctcctccca atgggctcat cacctttgtt aacccaagcg cgtaccttgc tgatgatata    1020
aagaatggca acagccatat tgtcccgggt gtgcaatttt acgcatccga tgcgtgcact    1080
ctcatcgaca tcccacatga cctagacacc acctccgttg gcttgtcagt actgcacaag    1140
tttggaaagg tggacaagga cacactcaac aaagtgctag acagaatgct cgagcaagtg    1200
agtgaagacg acggcattct gcaggtgtat tttgatgtgg agcgtccgcg catcgatcca    1260
gttgtggtgg caaacacggt gtttctgttc cacttgggaa agagagggca tgaggtggcg    1320
aggagtgaga agtttgtgga gagtgtgctg ctgcagaggg catacgaaga agggacgttg    1380
tattacaacc tgggggaagc attttttggtg agtgtggcga ggctggtgca cgagtttaag    1440
gagcacttta caaggagcgg catgaggagg gcactggagg agaggctaag agagcgggca    1500
agggcgggca tgcaagagag ggatgatgcg ctggcgctag ccatgcgcat tcgtgcatgc    1560
gctttgtgtg gcctggccgg agagggcctc acaaaagcag cagagcagga gcttttgcgc    1620
ctgcagtgca gtccaagggg ctgttggggg tgccaccctt tctatcgcaa tggcagtaat    1680
gtgctcagct ggatcggcag tgaggccctt accactgctt acgctattgc tgcgctacag    1740
cccattgata tttaa                                                     1755
```

<210> SEQ ID NO 74
<211> LENGTH: 591
<212> TYPE: PRT
<213> ORGANISM: Dryopteris fragrans
<220> FEATURE:
<221> NAME/KEY: MISC_FEATURE
<223> OTHER INFORMATION: DfHAD_amino acid sequence

<400> SEQUENCE: 74

```
Met Glu Phe Ser Ala Ser Ala Pro Pro Pro Arg Leu Ala Ser Val Ile
1               5                   10                  15
```

```
Ile Leu Glu Pro Leu Gly Phe Leu Leu Thr Pro His Tyr Ser Ser Gln
            20                  25                  30

Leu Pro Lys Lys Leu Leu Arg Arg Leu Leu Cys Thr Arg Ile Trp His
        35                  40                  45

Arg Tyr Gln Arg Gly Arg Leu Arg Leu Arg Asp Ala Ala Met Leu Leu
    50                  55                  60

Ala Gln Leu Pro Phe Leu Ala Val Ser Asp His Pro Trp Ala Leu Asp
65                  70                  75                  80

Asn Leu Ala Ser Leu Leu Arg Pro Thr Ala Val Arg Ala Val Pro Trp
                85                  90                  95

Met Leu Leu Leu Leu Asp Phe Leu Arg Asp Glu Leu His Leu Lys Val
        100                 105                 110

Val Cys Ala Thr Asn Ser Ser Pro Glu Glu Leu Gln Glu Leu Arg His
        115                 120                 125

Gln Phe Pro Ala Leu Phe Ala Lys Val Asp Ala Thr Val Ser Ser Gly
    130                 135                 140

Glu Glu Gly Val Gly Lys Pro Ser Val Arg Phe Leu Gln Ala Ala Leu
145                 150                 155                 160

Asp Lys Ala Gly Val His Ala Gln Gln Thr Leu Tyr Leu Asp Ser Phe
            165                 170                 175

Asp Ser Leu Glu Thr Ile Met Ala Ala Arg Ser Leu Gly Met His Ala
            180                 185                 190

Leu Ser Val Glu Pro Cys His Ile Asp Glu Leu Thr Ala Arg Ala Ser
        195                 200                 205

Ser Gly Gln Leu Arg Asp Ala Gln Leu Ile Arg Arg Ile Val Cys Ala
    210                 215                 220

Met His Gly Pro Ala Val Ser Ala Val Val Ser Gly Ser Ile Thr Ser
225                 230                 235                 240

Ser Gly Pro Gln Thr Ala Lys Ile Glu Glu Leu Pro Thr Ala Ala Asp
            245                 250                 255

Ser His Leu Arg Ser Ala Ala Leu Thr Ser Ala Gln Gln Phe Phe Leu
            260                 265                 270

Lys Val Ile Ala Pro His Arg Pro Glu Lys Pro Phe Val Gln Leu Pro
        275                 280                 285

Ser Leu Thr Ser Glu Gly Ile Arg Ile Tyr Asp Thr Phe Ala Gln Phe
    290                 295                 300

Val Ile Ala Asp Leu Leu Asp Asp Thr Arg Phe Leu Pro Met Gln Ser
305                 310                 315                 320

Pro Pro Pro Asn Gly Leu Ile Thr Phe Val Asn Pro Ser Ala Tyr Leu
            325                 330                 335

Ala Asp Asp Ile Lys Asn Gly Asn Ser His Ile Val Pro Gly Val Gln
            340                 345                 350

Phe Tyr Ala Ser Asp Ala Cys Thr Leu Ile Asp Ile Pro His Asp Leu
        355                 360                 365

Asp Thr Thr Ser Val Gly Leu Ser Val Leu His Lys Phe Gly Lys Val
    370                 375                 380

Asp Lys Asp Thr Leu Asn Lys Val Leu Asp Arg Met Leu Glu Gln Val
385                 390                 395                 400

Ser Glu Asp Asp Gly Ile Leu Gln Val Tyr Phe Asp Val Glu Arg Pro
            405                 410                 415

Arg Ile Asp Pro Val Val Val Ala Asn Thr Val Phe Leu Phe His Leu
            420                 425                 430

Gly Lys Arg Gly His Glu Val Ala Arg Ser Glu Lys Phe Val Glu Ser
```

-continued

```
            435              440              445

Val Leu Leu Gln Arg Ala Tyr Glu Glu Gly Thr Leu Tyr Tyr Asn Leu
    450              455              460

Gly Glu Ala Phe Leu Val Ser Val Ala Arg Leu Val His Glu Phe Lys
465              470              475              480

Glu His Phe Thr Arg Ser Gly Met Arg Arg Ala Leu Glu Glu Arg Leu
                485              490              495

Arg Glu Arg Ala Arg Ala Gly Met Gln Glu Arg Asp Asp Ala Leu Ala
                500              505              510

Leu Ala Met Arg Ile Arg Ala Cys Ala Leu Cys Gly Leu Ala Gly Glu
                515              520              525

Gly Leu Thr Lys Ala Ala Glu Gln Glu Leu Leu Arg Leu Gln Cys Lys
    530              535              540

Ser Lys Gly Cys Trp Gly Cys His Pro Phe Tyr Arg Asn Gly Ser Asn
545              550              555              560

Val Leu Ser Trp Ile Gly Ser Glu Ala Leu Thr Thr Ala Tyr Ala Ile
                565              570              575

Ala Ala Leu Gln Pro Ile Asp Ile Ile Asp Phe Met Phe Ala Met
                580              585              590
```

```
<210> SEQ ID NO 75
<211> LENGTH: 6
<212> TYPE: PRT
<213> ORGANISM: Artificial Sequence
<220> FEATURE:
<223> OTHER INFORMATION: class II synthase motif DxDxxS
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (4)..(5)
<223> OTHER INFORMATION: Xaa can be any naturally occurring amino acid

<400> SEQUENCE: 75

Asp Xaa Asp Xaa Xaa Ser
1               5

<210> SEQ ID NO 76
<211> LENGTH: 7
<212> TYPE: PRT
<213> ORGANISM: Artificial Sequence
<220> FEATURE:
<223> OTHER INFORMATION: QW motif QxxxxxW
<220> FEATURE:
<221> NAME/KEY: MISC_FEATURE
<222> LOCATION: (2)..(6)
<223> OTHER INFORMATION: Xaa can be any naturally occurring amino acid

<400> SEQUENCE: 76

Gln Xaa Xaa Xaa Xaa Xaa Trp
1               5
```